(12) United States Patent
Meng et al.

(10) Patent No.: US 11,926,643 B2
(45) Date of Patent: Mar. 12, 2024

(54) HETEROCYCLIC GLP-1 AGONISTS

(71) Applicant: Gasherbrum Bio, Inc., South San Francisco, CA (US)

(72) Inventors: Qinghua Meng, Shanghai (CN); Xichen Lin, Shanghai (CN); Haizhen Zhang, Shanghai (CN); Weiqiang Xing, Shanghai (CN); Hui Lei, Shanghai (CN); Andrew Jennings, San Francisco, CA (US)

(73) Assignee: Gasherbrum Bio, Inc., South San Francisco, CA (US)

( * ) Notice: Subject to any disclaimer, the term of this patent is extended or adjusted under 35 U.S.C. 154(b) by 0 days.

(21) Appl. No.: 17/853,755

(22) Filed: Jun. 29, 2022

(65) Prior Publication Data

US 2023/0174565 A1 Jun. 8, 2023

Related U.S. Application Data

(63) Continuation of application No. 17/571,351, filed on Jan. 7, 2022, now Pat. No. 11,492,365, which is a continuation of application No. PCT/CN2021/075488, filed on Feb. 5, 2021.

(30) Foreign Application Priority Data

Feb. 7, 2020 (WO) ................ PCT/CN2020/074537
Aug. 14, 2020 (WO) ................ PCT/CN2020/109304

(51) Int. Cl.
*C07F 9/6561* (2006.01)

(52) U.S. Cl.
CPC .................... *C07F 9/6561* (2013.01)

(58) Field of Classification Search
CPC .................................................. C07F 9/6561
See application file for complete search history.

(56) References Cited

U.S. PATENT DOCUMENTS

| | | |
|---|---|---|
| 10,858,356 B2 | 12/2020 | Yoshino et al. |
| 11,492,365 B2 | 11/2022 | Meng et al. |
| 2004/0009573 A1 | 1/2004 | Strobel et al. |
| 2007/0015812 A1 | 1/2007 | Boehringer et al. |
| 2009/0197863 A1 | 8/2009 | Chu et al. |
| 2011/0190343 A1 | 8/2011 | Gochin et al. |
| 2016/0141517 A1 | 5/2016 | Yang |
| 2018/0092908 A1 | 4/2018 | Stockwell et al. |
| 2019/0300526 A1 | 10/2019 | Fan et al. |
| 2020/0017505 A1 | 1/2020 | Maeba et al. |

FOREIGN PATENT DOCUMENTS

| | | |
|---|---|---|
| CN | 103421006 | 12/2013 |
| CN | 110325530 | 10/2019 |
| CN | 110804059 | 2/2020 |
| CN | 111217796 | 6/2020 |
| CN | 111217842 | 6/2020 |
| EP | 461079 | 12/1991 |
| EP | 3539948 | 9/2019 |
| EP | 3539950 | 9/2019 |
| JP | 08295646 | 11/1996 |
| JP | 2012223714 | 11/2012 |
| JP | 2012224760 | 11/2012 |
| JP | 2019099571 | 6/2019 |
| KR | 2013088577 | 8/2013 |
| WO | WO-95/01961 | 1/1995 |
| WO | WO-97/32848 | 9/1997 |
| WO | WO-98/30569 | 7/1998 |
| WO | WO-99/01457 | 1/1999 |
| WO | WO-2001/003680 | 1/2001 |
| WO | WO-2002/046164 | 6/2002 |
| WO | WO-2002/046183 | 6/2002 |
| WO | WO-2003/000682 | 1/2003 |
| WO | WO-2004/026836 | 4/2004 |
| WO | WO-2004/107958 | 12/2004 |
| WO | WO-2005/040169 | 5/2005 |

(Continued)

OTHER PUBLICATIONS

Paternoster "Dissecting the Physiology and Pathophysiology of Glucagon-Like Peptide-1" Frontiers in Endocrinology Oct. 2018 | vol. 9 | Article 584 1-26.*

Taing "GLP-1(28-36)amide, the Glucagon-like peptide-1 metabolite: friend, foe, or pharmacological folly?" Drug Design, Development and Therapy 2014, 8, 677-688.*

Montrose-Rafizadeh "Pancreatic Glucagon-Like Peptide-1 Receptor Couples to Multiple G Proteins and Activates Mitogen-Activated Protein Kinase Pathways in Chinese Hamster Ovary Cells" Endocrinology 1999, 40(3), 1132-1140.*

Tomas New Insights into Beta-Cell GLP-1 Receptor and CAMP Signaling Journal of Molecular Biology (2020) 432, 1347-1366.*

Bavec "Different role of intracellular loops of glucagon-like peptide-1 receptor in G-protein coupling." Regul Pept 2003, 111:137-144.*

(Continued)

*Primary Examiner* — David K O'Dell

(74) *Attorney, Agent, or Firm* — Sheppard Mullin Richter & Hampton LLP

(57) ABSTRACT

This disclosure relates to GLP-1 agonists of Formula (I): including pharmaceutically acceptable salts and solvates thereof, and pharmaceutical compositions including the same.

Formula (I)

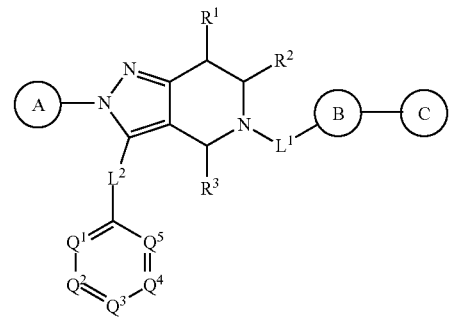

20 Claims, No Drawings

(56) References Cited

FOREIGN PATENT DOCUMENTS

| | | |
|---|---|---|
| WO | WO-2005/066136 | 7/2005 |
| WO | WO-2005/112932 | 12/2005 |
| WO | WO-2005/121138 | 12/2005 |
| WO | WO-2006/024837 | 3/2006 |
| WO | WO-2006/034419 | 3/2006 |
| WO | WO-2006/083869 | 8/2006 |
| WO | WO-2007/054453 | 5/2007 |
| WO | WO-2007/091107 | 8/2007 |
| WO | WO-2008/014219 | 1/2008 |
| WO | WO-2008/053341 | 5/2008 |
| WO | WO-2008/077597 | 7/2008 |
| WO | WO-2008/117061 | 10/2008 |
| WO | WO-2009/019505 | 2/2009 |
| WO | WO-2009/036275 | 3/2009 |
| WO | WO-2009/126691 | 10/2009 |
| WO | WO-2010/037050 | 4/2010 |
| WO | WO-2010/091176 | 8/2010 |
| WO | WO-2012/065065 | 5/2012 |
| WO | WO-2013/151975 | 10/2013 |
| WO | WO-2014/055634 | 4/2014 |
| WO | WO-2014/101120 | 7/2014 |
| WO | WO-2014/105666 | 7/2014 |
| WO | WO-2014/122067 | 8/2014 |
| WO | WO-2015/049624 | 4/2015 |
| WO | WO-2016/038045 | 3/2016 |
| WO | WO-2017/182983 | 10/2017 |
| WO | WO-2017/182984 | 10/2017 |
| WO | WO-2017/182986 | 10/2017 |
| WO | WO-2018/056453 | 3/2018 |
| WO | WO-2018/109607 | 6/2018 |
| WO | WO-2018/178947 | 10/2018 |
| WO | WO-2019/013311 | 1/2019 |
| WO | WO-2019/126424 | 6/2019 |
| WO | WO-2019/158731 | 8/2019 |
| WO | WO-2019/166951 | 9/2019 |
| WO | WO-2019/239319 | 12/2019 |
| WO | WO-2019/239371 | 12/2019 |
| WO | WO-2020/001321 | 1/2020 |
| WO | WO-2020/024232 | 1/2020 |
| WO | WO-2020/089453 | 5/2020 |
| WO | WO-2020/089455 | 5/2020 |
| WO | WO-2020/103815 | 5/2020 |
| WO | WO-2020/135513 | 7/2020 |
| WO | WO-2020/163236 | 8/2020 |
| WO | WO-2020/207474 | 10/2020 |
| WO | WO-2020/263695 | 12/2020 |
| WO | WO-2021/018023 | 2/2021 |
| WO | WO-2021/081207 | 4/2021 |
| WO | WO-2021/096284 | 5/2021 |
| WO | WO-2021/096304 | 5/2021 |
| WO | WO-2021/160127 | 8/2021 |
| WO | WO-2021/219019 | 11/2021 |

OTHER PUBLICATIONS

Hallbrink "Different domains in the third intracellular loop of the GLP-1 receptor are responsible for Galpha(s) and Galpha(i)/ Galpha (o) activation." Biochim Biophys Acta 2001, 1546:79-86.*

Walsh "Eating Disorders" in Harrison's Principles of Internal Medicine (McGraw-Hill Book Company, New York, 2005 Kasper, Dennis L., Harrison, Tinsley Randolph. Eds. pp. 430-433.*

Ramos "Designing drugs that combat kidney damage" Expert Opinion on Drug Discovery (2015), 10(5), 541-556.*

Nauck "GLP-1 receptor agonists in type 1 diabetes: a Magic bullet?" vol. 8, Issue 4, Apr. 2020, p. 262.*

Petit-Demouliere et. al. "Forced swimming test in mice: a review of antidepressant activity." Psychopharmacology 2005, 177, 245-255.*

Miyamoto "Pharmacological treatment of schizophrenia: a critical review of the pharmacology and clinical effects of current and future therapeutic agents" Molecular Psychiatry (2012) 17, 1206-1227.*

Marcotte "Animal models of schizophrenia: a critical review" Psychiatry Neurosci 2001;26(5):395-410.*

DeWeerdt "Parkinson's disease 4 Big Questions" vol. 538, Oct. 2016, S17.*

International Search Report and Written Opinion for PCT/CN2021/075488 dated May 8, 2021, 12 pages.

Kawai et al., "Structural basis for GLP-1 receptor activation by LY3502970, an orally active nonpeptide agonist", Proceedings of the National Academy of Sciences of the United States of America (2020), 117(47), 29959-29967.

Finkbeiner et al., "Phosphine Oxides from a Medicinal Chemist's Perspective: Physicochemical and in Vitro Parameters Relevant for Drug Discovery", Journal of Medicinal Chemistry (2020), 63(13), 7081-7107.

Huang et al., "Discovery of Brigatinib (AP26113), a Phosphine Oxide-Containing, Potent, Orally Active Inhibitor of Anaplastic Lymphoma Kinase", Journal of Medicinal Chemistry (2016), 59(10), 4948-4964.

Bergman et al., Safety, Tolerability, Pharmacokinetics, and Pharmacodynamics of a Liver-Targeting Acetyl-CoA Carboxylase Inhibitor (PF-05221304): A Three-Part Randomized Phase 1 Study, Clinical Pharmacology in Drug Development, 2020, 9(4) 514-526 (with Supporting Information, Figure S1, 1 page).

* cited by examiner

US 11,926,643 B2

HETEROCYCLIC GLP-1 AGONISTS

CROSS REFERENCE TO RELATED APPLICATIONS

This application is a continuation of U.S. patent application Ser. No. 17/571,351, filed on Jan. 7, 2022, now U.S. Pat. No. 11,492,365, which is a continuation of International Patent Application Number PCT/CN2021/075488, filed on Feb. 5, 2021, which claims the benefit of International Patent Application Number PCT/CN2020/109304, filed on Aug. 14, 2020 and International Patent Application Number PCT/CN2020/074537, filed on Feb. 7, 2020, each of which is incorporated herein by reference in its entirety.

TECHNICAL FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take anti-diabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

Accordingly, provided herein are compounds of Formula (I):

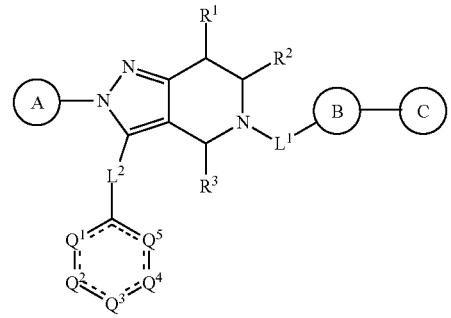

Formula (I)

or a pharmaceutically acceptable salt thereof or a solvate thereof, wherein:
$Q^1$, $Q^2$, $Q^3$, $Q^4$, and $Q^5$ are defined according to (AA) or (BB) below:

AA $Q^1$ and $Q^5$ are independently selected from the group consisting of N, CH, and $CR^{QA}$;
$Q^2$, $Q^3$, and $Q^4$ are independently selected from the group consisting of N, CH, $CR^{QA}$, and $CR^{QB}$, provided that at least one of $Q^2$, $Q^3$, and $Q^4$ is $CR^{QB}$;
each ═ is a single bond or double bond, provided that the ring including $Q^1$-$Q^5$ is aromatic;

BB $Q^1$ is a bond;
$Q^2$, $Q^3$, $Q^4$, and $Q^5$ are independently selected from the group consisting of O, S, N, NH, NR, CH, $CR^{QA}$, and $CR^{QB}$, provided that at least one of $Q^2$, $Q^3$, $Q^4$, and $Q^5$ is $CR^{QB}$;
each ═ is a single bond or double bond, provided that the ring including $Q^1$-$Q^5$ is aromatic;
$R^{QB}$ is P(═O)$R^aR^b$, wherein $R^a$ and $R^b$ are independently selected from the group consisting of $C_{1-6}$ alkyl which is optionally substituted with from 1-6 substituents each independently selected from the group consisting of $C_{1-6}$ alkoxy, $C_{3-6}$ cycloalkyl, and halo; $C_{3-6}$ cycloalkyl optionally substituted with from 1-3 substituents each independently selected from the group consisting of $C_{1-3}$ alkyl and halo; and $C_{6-10}$ aryl optionally substituted with from 1-3 independently selected $C_{1-3}$ alkyl; or
$R^a$ and $R^b$ taken together with the phosphorous atom to which each is attached forms a ring including from 5-8 ring atoms, wherein from 0-2 ring atoms (in addition to the phosphorous attached to $R^a$ and $R^b$) are heteroatoms each independently selected from the group consisting of: O, S, and N, wherein the ring is optionally substituted with from 1-3 independently selected $C_{1-6}$ alkyl;
each $R^{QA}$ is independently selected from the group consisting of: (a) halo; (b) cyano; (c) OH; (d) —NR$^c$R$^d$; (e) C(═O)NR$^c$R$^d$; (f) S(═O)$_{0-2}$R$^e$; (g) $C_{1-6}$ alkyl optionally substituted with from 1-6 independently selected R$^f$; (h) $C_{1-6}$ alkoxy optionally substituted with from 1-6 substituents each independently selected from the group consisting of: hydroxy, halo, and $C_{1-6}$ alkoxy; (i) 3-12 membered heterocyclyl optionally substituted with one or more substituents each independently selected from the group consisting of $C_{1-6}$ alkyl and C(=O)(C$_{1-6}$ alkyl); 0) C$_{6-10}$ aryl optionally substituted with from 1-3 independently selected C(=O)(C$_{1-6}$ alkyl); and (k) 5-10 membered heteroaryl optionally substituted with from 1-6 independently selected R$^g$;

or a pair of R$^{QA}$ on adjacent carbon atoms, taken together with the atom to which each is attached, forms a ring including from 5-8 ring atoms, wherein from 0-2 ring atoms are heteroatoms each independently selected from the group consisting of O, N, and S, wherein said ring is optionally substituted with from 1-2 independently selected R$^h$ groups;

L$^2$ is selected from the group consisting of:

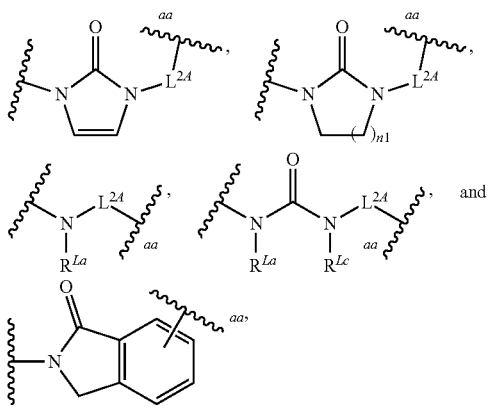

and

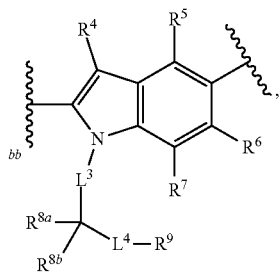

wherein aa represents the point of attachment to the ring containing Q$^1$-Q$^5$;
n1 is an integer from 1-3;
L$^{2A}$ is a bond or C$_{1-10}$ alkylene;
R$^{La}$ is selected from the group consisting of H, C$_{1-6}$ alkyl, and C(=O)(C$_{1-6}$ alkyl);
each of R$^{Lb}$ and R$^{Lc}$ is independently selected from the group consisting of H and C$_{1-6}$ alkyl;
Ring A is C$_{6-10}$ aryl, C$_{5-7}$ cycloalkyl, 5-7 membered heterocyclyl, or 5-10 membered heteroaryl, each of which is optionally substituted with from 1-5 substituents each independently selected from the group consisting of halo, C$_{1-6}$ alkyl, C$_{1-6}$ haloalkyl, and C$_{1-6}$ alkoxy;
R$^1$, R$^2$ and R$^3$ are each independently selected from the group consisting of H and C$_{1-6}$ alkyl which is optionally substituted with from 1-6 substituents each independently selected from the group consisting of halo, —OH, and C$_{1-6}$ alkoxy;
L$^1$ is selected from the group consisting of: —C(=O)—, —CH$_2$—, —CH(C$_{1-6}$ alkyl)-, and —S(=O)$_2$;
Ring B is selected from the group consisting of:

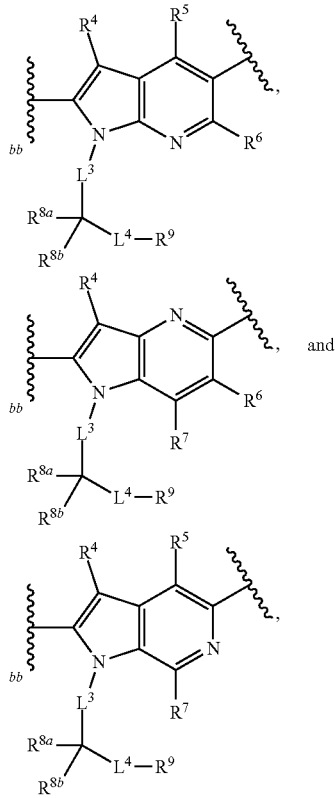

wherein bb represents point of attachment to L;
R$^4$, R$^5$, R$^6$, and R$^7$ are independently selected from the group consisting of: H, halo, and C$_{1-6}$ alkyl;
L$^3$ is a bond or C$_{1-3}$ alkylene;
L$^4$ is a bond or C$_{1-5}$ alkylene;
R$^{8a}$ and R$^{8b}$ are independently selected from the group consisting of: H and C$_{1-6}$ alkyl optionally substituted with one or more substituents independently selected from the group consisting of: halo and C$_{3-15}$ cycloalkyl; or
R$^{8a}$ and R$^{8b}$ taken together with the carbon atom to which each is attached forms a C$_{3-15}$ cycloalkyl ring which is optionally substituted with from 1-3 independently selected C$_{1-6}$ alkyl, wherein the C$_{1-6}$ alkyl is optionally substituted with from 1-6 independently selected R$^f$;
R$^9$ is selected from the group consisting of: C(=O)OH, C(=O)(OC$_{1-6}$ alkyl), C(=O)NR$^{9a}$R$^{9b}$, (IX-1), (IX-2), (IX-3), and (IX-4):

(IX-1)

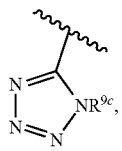

(IX-2)

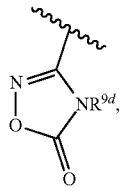

-continued

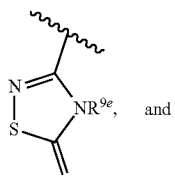
(IX-3)

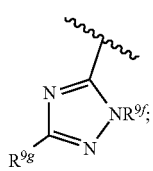
(IX-4)

$R^{9a}$ is H or $C_{1-6}$ alkyl;

$R^{9b}$ is H, $C_{1-6}$ alkyl, C(=O)($C_{1-6}$ alkyl), S(O)$_{0-2}$($C_{1-6}$ alkyl), or cyano;

$R^{9c}$, $R^{9d}$, $R^{9e}$, $R^{9f}$, and $R^{9g}$ are each independently selected from the group consisting of: H; $C_{1-6}$ alkyl optionally substituted with from 1-6 independently selected halo and $C_{1-6}$ alkoxy; and C(=O)($C_{1-6}$ alkyl);

Ring C is selected from the group consisting of 3-12 membered heterocyclyl; $C_{3-15}$ cycloalkyl; and 5-10 membered heteroaryl, each of which is optionally substituted with from 1-3 $R^{Ca}$;

each $R^{Ca}$ is independently selected from the group consisting of: halo, $C_{1-6}$ alkyl, $C_{1-6}$ haloalkyl, $C_{1-6}$ alkoxy, and NR$^c$R$^d$;

or a pair of $R^{Ca}$ on the same or different ring atoms, taken together with the ring atom(s) to which each is attached, forms a carbocyclic ring including from 3-8 ring atoms;

each $R^c$ and $R^d$ are independently selected from the group consisting of: H, $C_{1-6}$ alkyl, C(=O)($C_{1-6}$ alkyl), C(=O)($C_{3-6}$ cycloalkyl), C(=O)O($C_{1-6}$ alkyl), S(O)$_{1-2}$($C_{1-6}$ alkyl), and S(O)$_{1-2}$($C_{3-6}$ cycloalkyl), wherein the $C_{1-6}$ alkyl, C(=O)($C_{1-6}$ alkyl), C(=O)($C_{3-6}$ cycloalkyl), C(=O)O($C_{1-6}$ alkyl), S(O)$_{1-2}$($C_{1-6}$ alkyl), and S(O)$_{1-2}$($C_{3-6}$ cycloalkyl) are each optionally substituted with from 1-6 substituents independently selected from the group consisting of: —OH, halo, and $C_{1-6}$ alkoxy;

$R^e$ is H, $C_{1-6}$ alkyl, or $C_{1-6}$ haloalkyl;

each $R^f$ is independently selected from the group consisting of halo, —OH, NR$^c$R$^d$, $C_{1-6}$ alkoxy, $C_{1-6}$ haloalkoxy, and 3-12 membered heterocyclyl which is optionally substituted with from 1-4 substituents each independently selected from the group consisting of —OH, $C_{1-6}$ alkyl, and 3-12 membered heterocyclyl;

each $R^g$ is independently selected from the group consisting of: $C_{1-6}$ alkyl, $C_{1-6}$ alkoxy, NR$^c$R$^d$, and 3 to 12 membered heterocyclyl optionally substituted with one or more substituents each independently selected from the group consisting of $C_{1-6}$ alkyl and C(=O)$C_{1-6}$ alkyl; and each $R^f$ is independently selected from the group consisting of halo, cyano, $C_{1-6}$ alkyl, $C_{1-6}$ haloalkyl, —OH, NH$_2$, NH($C_{1-3}$ alkyl), N($C_{1-3}$ alkyl)$_2$, $C_{1-3}$ alkoxy, and $C_{1-3}$ haloalkoxy.

Also provided herein are pharmaceutical compositions comprising a compound of Formula (I), or a pharmaceutically acceptable salt or solvate thereof, and a pharmaceutically acceptable excipient.

Also provided herein are methods for treating type 2 diabetes mellitus in a patient in need thereof, the methods comprising administering to the patient a therapeutically effective amount of a compound of Formula (I), or a pharmaceutically acceptable salt or solvate thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula (I), or a pharmaceutically acceptable salt or solvate thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula (I), or a pharmaceutically acceptable salt or solvate thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin A1c (HbA1c), fasting plasma glucose, non-fasting plasma glucose, or any combination thereof. In some embodiments, the level of HbA1c is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 kg/m$^2$. In some embodiments, the patient has a BMI greater than or about 30 kg/m$^2$.

In some embodiments, the methods for the treatment of type 2 diabetes mellitus comprise a reduction in fasting plasma glucose levels. In some embodiments, the fasting plasma glucose levels are reduced to about or below 100 mg/dL.

In some embodiments, the methods for the treatment of type 2 diabetes mellitus comprise a reduction in HbA1c levels. In some embodiments, the HbA1c levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 kg/m$^2$.

In some embodiments, the compound of Formula (I), or a pharmaceutically acceptable salt or solvate thereof, or a pharmaceutical composition thereof, is administered orally.

In some embodiments, the methods of treatment for type 2 diabetes mellitus further comprise administering an additional therapy or therapeutic agent to the patient. In some embodiments, the additional therapy or therapeutic agent is selected from the group consisting of an anti-diabetic agent, an anti-obesity agent, a GLP-1 receptor agonist, an agent to treat non-alcoholic steatohepatitis (NASH), gastric electrical stimulation, dietary monitoring, physical activity, or any combinations thereof. In some embodiments, the anti-diabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the anti-obesity agent is selected from the group consisting of neuropeptide Y receptor type 2 (NPYR2) agonist, a NPYR1 or NPYR5 antagonist, a human proislet peptide (HIP), a cannabinoid receptor type 1 (CB1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASKI) inhibitor, or any combinations thereof. In some embodiments, the compound of Formula (I), or a pharmaceutically acceptable salt or solvate thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula (I), or a pharmaceutically acceptable salt or solvate thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula (I), or a pharmaceutically acceptable salt or solvate thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula (I), or a pharmaceutically acceptable salt or solvate thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the invention will be apparent from the following detailed description and figures, and from the claims.

DETAILED DESCRIPTION

Provided herein are heterocyclic GLP-1 agonists for use in the management of type 2 diabetes mellitus (T2DM) and other conditions where activation of GLP-1 activity is useful.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "halo" or "halogen" means —F (sometimes referred to herein as "fluoro" or "fluoros"), —Cl (sometimes referred to herein as "chloro" or "chloros"), —Br (sometimes referred to herein as "bromo" or "bromos"), and —I (sometimes referred to herein as "iodo" or "iodos").

As used herein, the term "alkyl" refers to saturated linear or branched-chain monovalent hydrocarbon radicals, containing the indicated number of carbon atoms. For example, "$C_{1-6}$ alkyl" refers to saturated linear or branched-chain monovalent hydrocarbon radicals of one to six carbon atoms. Non-limiting examples of alkyl include methyl, ethyl, 1-propyl, isopropyl, 1-butyl, isobutyl, sec-butyl, tert-butyl, 2-methyl-2-propyl, pentyl, neopentyl, and hexyl.

As used herein, the term "alkylene" refers to a divalent alkyl containing the indicated number of carbon atoms. For example, "$C_{1-3}$ alkylene" refers to a divalent alkyl having one to three carbon atoms (e.g., —CH$_2$—, —CH(CH$_3$)—, —CH$_2$CH$_2$—, or —CH$_2$CH$_2$CH$_2$—).

As used herein, the term "alkenyl" refers to a linear or branched mono-unsaturated hydrocarbon chain, containing the indicated number of carbon atoms. For example, "$C_{2-6}$ alkenyl" refers a linear or branched mono unsaturated hydrocarbon chain of two to six carbon atoms. Non-limiting examples of alkenyl include ethenyl, propenyl, butenyl, or pentenyl.

As used herein, the term "alkynyl" refers to a linear or branched di-unsaturated hydrocarbon chain, containing the indicated number of carbon atoms. For example, "$C_{2-6}$ alkynyl" refers to a linear or branched di-unsaturated hydrocarbon chain having two to six carbon atoms. Non-limiting examples of alkynyl include ethynyl, propynyl, butynyl, or pentynyl.

As used herein, the term "cycloalkyl" refers to a saturated or partially saturated cyclic hydrocarbon, containing the indicated number of carbon atoms. For example, "$C_{3-6}$ cycloalkyl" refers to a saturated or partially saturated cyclic hydrocarbon having three to six ring carbon atoms. Non-limiting examples of cycloalkyl include cyclopropyl, cyclobutyl, cyclopentyl, and cyclohexyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

As used herein, the term "heterocyclyl" refers to a mon-, bi-, tri-, or polycyclic nonaromatic ring system containing indicated number of ring atoms (e.g., 3-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heterocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, the term "aryl" refers to a mono-, bi-, tri- or polycyclic hydrocarbon group containing the indicated numbers of carbon atoms, wherein at least one ring in the system is aromatic (e.g., $C_6$ monocyclic, $C_{10}$ bicyclic, or $C_{14}$ tricyclic aromatic ring system). Examples of aryl groups include phenyl, naphthyl, tetrahydronaphthyl, and the like.

As used herein, the term "heteroaryl" refers to a mono-, bi-, tri- or polycyclic group having indicated numbers of ring atoms (e.g., 5-6 ring atoms; e.g., 5, 6, 9, 10, or 14 ring atoms); wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others.

As used herein, the term "haloalkyl" refers to an alkyl radical as defined herein, wherein one or more hydrogen atoms is replaced with one or more halogen atoms. Non-limiting examples include fluoromethyl, difluoromethyl, trifluoromethyl, 2-fluoroethyl, 2,2-difluoroethyl, 2,2,2-trifluoroethyl, chloromethyl, dichloromethyl, chloroethyl, trichloroethyl, bromomethyl, and iodomethyl.

As used herein, the term "alkoxy" refers to an —O-alkyl radical, wherein the radical is on the oxygen atom. For example, "$C_{1-6}$ alkoxy" refers to an —O—($C_{1-6}$ alkyl) radical, wherein the radical is on the oxygen atom. Examples of alkoxy include methoxy, ethoxy, propoxy, isopropoxy, butoxy and tert-butoxy. Accordingly, as used herein, the term "haloalkoxy" refers to an —O-haloalkyl radical, wherein the radical is on the oxygen atom.

As used herein, "" indicates an optional single or double bond, as allowed by valence. As used herein, "" indicates the point of attachment to the parent molecule.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucose-dependent insulin secretion; suppress inappropriately elevated glucagon levels, both in fasting and postprandial states; and slow gastric emptying. Karla et al., Glucagon-like peptide-1 receptor agonists in the treatment of type 2 diabetes: Past, present, and future, *Indian J Endocrinol Metab.* 2016 March-April; 20(2): 254-267. GLP-1 RAs have been shown to treat type 2 diabetes. Examples of GLP-1 RAs include, but are not limited to, albiglutide (TANZEUM®), dulaglutide (LY2189265, TRULICITY®), efpeglenatide, exenatide (BYETTA®, BYDUREON®, Exendin-4), liraglutide (VICTOZA®, NN2211), lixisenatide (LYXUMIA®), semaglutide (OZEMPIC®), tirzepatide, ZP2929, NNC0113-0987, BPI-3016, and TT401. See, also, for example, additional GLP-1 receptor agonists described in U.S. Pat. Nos. 10,370,426; 10,308,700; 10,259,823; 10,208,019; 9,920,106; 9,839,664; 8,129,343; 8,536,122; 7,919,598; 6,414,126; 6,628,343; and RE45313; and International Publication Nos. WO 2019/239319; WO 2019/239371; WO 2020/103815; WO 2020/207474; WO 20202/34726; WO 2020/044266; WO 2020117987; and WO 2020263695.

The term "pharmaceutically acceptable" as used herein indicates that the compound, or salt or composition thereof is compatible chemically and/or toxicologically with the other ingredients comprising a formulation and/or the patient being treated therewith.

The term "therapeutic compound" as used herein is meant to include, without limitation, all compounds of Formula (I), or pharmaceutically acceptable salts or solvates thereof (e.g., a compound of any one of Formulas (IA), (IB), (IC), (ID), and (IE), or a pharmaceutically acceptable salt or solvate thereof), and all compositions (e.g., pharmaceutical compositions) wherein a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is a component of the composition.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof)) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009.

The term "pharmaceutical composition" refers to a mixture of a compound of Formula (I), or a pharmaceutically acceptable salt or solvate thereof (e.g., a compound of any one of Formulas (IA), (IB), (IC), (ID), and (IE) or a pharmaceutically acceptable salt or solvate thereof) as described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing", as used herein, is the prevention of the onset, recurrence or spread, in whole or in part, of the disease or condition as described herein, or a symptom thereof.

The terms "subject", "patient" or "individual", as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the patient is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination of the invention.

The term "pharmaceutical combination", as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulation", as used herein, refers to a regulation or an adjustment (e.g., increase or decrease) and can include, for example agonism, partial agonism or antagonism.

Compounds

In one aspect, provided herein are compounds of Formula (I):

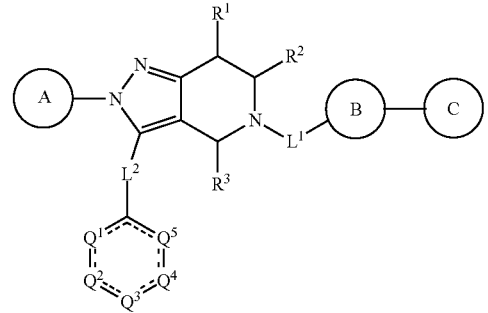

Formula (I)

or a pharmaceutically acceptable salt or solvate thereof, wherein:

$Q^1$, $Q^2$, $Q^3$, $Q^4$, and $Q^5$ are defined according to (AA) or (BB) below:

AA $Q^1$ and $Q^5$ are independently selected from the group consisting of N, CH, and $CR^{QA}$;

$Q^2$, $Q^3$, and $Q^4$ are independently selected from the group consisting of N, CH, $CR^{QA}$, and $CR^{QB}$, provided that at least one of $Q^2$, $Q^3$, and $Q^4$ is $CR^{QB}$;

each ═ is a single bond or double bond, provided that the ring including $Q^1$-$Q^5$ is aromatic;

BB $Q^1$ is a bond;

$Q^2$, $Q^3$, $Q^4$, and $Q^5$ are independently selected from the group consisting of O, S, N, NH, $NR^c$, CH, $CR^{QA}$, and $CR^{QB}$, provided that at least one of $Q^2$, $Q^3$, $Q^4$, and $Q^5$ is $CR^{QB}$;

each ═ is a single bond or double bond, provided that the ring including $Q^1$-$Q^5$ is aromatic;

$R^{QB}$ is P(═O)$R^aR^b$, wherein $R^a$ and $R^b$ are independently selected from the group consisting of $C_{1-6}$ alkyl which is optionally substituted with from 1-6 substituents each independently selected from the group consisting of $C_{1-6}$ alkoxy, $C_{3-6}$ cycloalkyl, and halo; $C_{3-6}$ cycloalkyl optionally substituted with from 1-3 substituents each independently selected from the group consisting of $C_{1-3}$ alkyl and halo; and $C_{6-10}$ aryl optionally substituted with from 1-3 independently selected $C_{1-3}$ alkyl; or $R^a$ and $R^b$ taken together with the phosphorous atom to which each is attached forms a ring including from 5-8 ring atoms, wherein from 0-2 ring atoms (in addition to the phosphorous attached to $R^a$ and $R^b$) are heteroatoms each independently selected from the group consisting of: O, S, and N, wherein the ring is optionally substituted with from 1-3 independently selected $C_{1-6}$ alkyl;

each $R^{QA}$ is independently selected from the group consisting of: (a) halo; (b) cyano; (c) OH; (d) —$NR^cR^d$; (e) $C(=O)NR^cR^d$; (f) $S(=O)_{0-2}R^e$; (g) $C_{1-6}$ alkyl optionally substituted with from 1-6 independently selected Rr; (h) $C_{1-6}$ alkoxy optionally substituted with from 1-6 substituents each independently selected from the group consisting of: hydroxy, halo, and $C_{1-6}$ alkoxy; (i) 3-12 membered heterocyclyl optionally substituted with one or more substituents each independently selected from the group consisting of $C_{1-6}$ alkyl and $C(=O)(C_{1-6}$ alkyl); (j) $C_{6-10}$ aryl optionally substituted with from 1-3 independently selected $C(=O)(C_{1-6}$ alkyl); and (k) 5-10 membered heteroaryl optionally substituted with from 1-6 independently selected $R^g$;

or a pair of $R^{QA}$ on adjacent carbon atoms, taken together with the atom to which each is attached, forms a ring including from 5-8 ring atoms, wherein from 0-2 ring atoms are heteroatoms each independently selected from the group consisting of O, N, and S, wherein said ring is optionally substituted with from 1-2 independently selected $R^h$ groups;

$L^2$ is selected from the group consisting of:

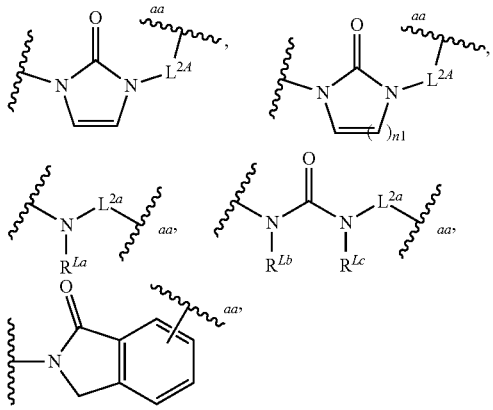

wherein aa represents the point of attachment to the ring containing $Q^1$-$Q^5$;

n1 is an integer from 1-3;

$L^{2A}$ is a bond or $C_{1-10}$ alkylene;

$R^{La}$ is selected from the group consisting of H, $C_{1-6}$ alkyl, and $C(=O)(C_{1-6}$ alkyl);

each of $R^{Lb}$ and $R^{Lc}$ is independently selected from the group consisting of H and $C_{1-6}$ alkyl;

Ring A is $C_{6-10}$ aryl, $C_{5-7}$ cycloalkyl, 5-7 membered heterocyclyl, or 5-10 membered heteroaryl, each of which is optionally substituted with from 1-5 substituents each independently selected from the group consisting of halo, $C_{1-6}$ alkyl, $C_{1-6}$ haloalkyl, and $C_{1-6}$alkoxy;

$R^1$, $R^2$, and $R^3$ are each independently selected from the group consisting of H and $C_{1-6}$ alkyl which is optionally substituted with from 1-6 substituents each independently selected from the group consisting of halo, —OH, and $C_{1-6}$ alkoxy;

$L^1$ is selected from the group consisting of: —C(=O)—, —$CH_2$—, —$CH(C_{1-6}$ alkyl)-, and —$S(=O)_2$;

Ring B is selected from the group consisting of:

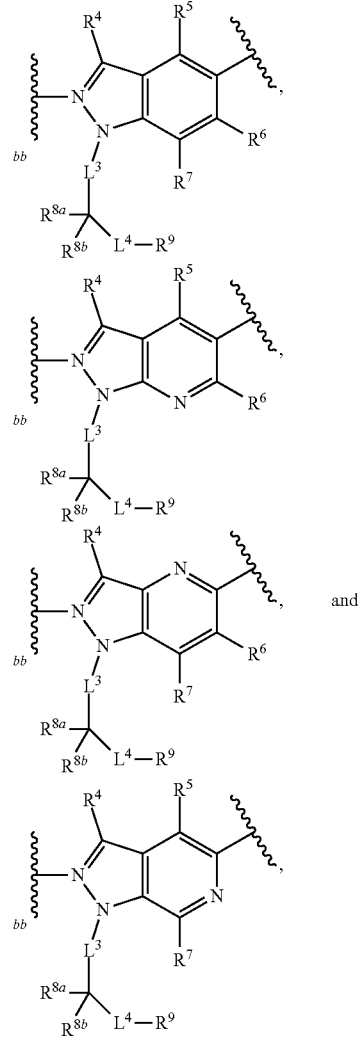

wherein bb represents point of attachment to $L^1$;

$R^4$, $R^5$, $R^6$, and $R^7$ are independently selected from the group consisting of: H, halo, and $C_{1-6}$ alkyl;

$L^3$ is a bond or $C_{1-3}$ alkylene;

$L^4$ is a bond or $C_{1-5}$ alkylene;

$R^{8a}$ and $R^{8b}$ are independently selected from the group consisting of: H and $C_{1-6}$ alkyl optionally substituted with one or more substituents independently selected from the group consisting of: halo and $C_{3-15}$ cycloalkyl; or $R^{8a}$ and $R^{8b}$ taken together with the carbon atom to which each is attached forms a $C_{3-15}$ cycloalkyl ring which is optionally substituted with from 1-3 independently selected $C_{1-6}$ alkyl, wherein the $C_{1-6}$ alkyl is optionally substituted with from 1-6 independently selected $R^f$;

$R^9$ is selected from the group consisting of: $C(=O)OH$, $C(=O)(OC_{1-6}$ alkyl), $C(=O)NR^{9a}R^{9b}$, (IX-1), (IX-2), (IX-3), and (IX-4):

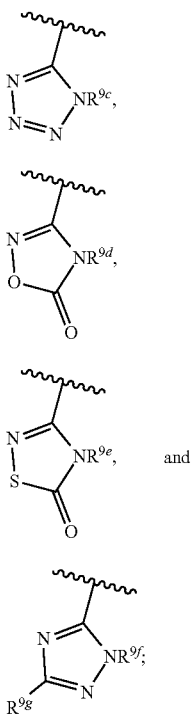

R$^{9a}$ is H or C$_{1-6}$ alkyl;

R$^{9b}$ is H, C$_{1-6}$ alkyl, C(=O)(C$_{1-6}$ alkyl), S(O)$_{0-2}$(C$_{1-6}$ alkyl), or cyano;

R$^{9c}$, R$^{9d}$, R$^{9e}$, R$^{9f}$, and R$^{9g}$ are each independently selected from the group consisting of: H; C$_{1-6}$ alkyl optionally substituted with from 1-6 independently selected halo and C$_{1-6}$ alkoxy; and C(=O)(C$_{1-6}$ alkyl);

Ring C is selected from the group consisting of 3-12 membered heterocyclyl; C$_{3-15}$ cycloalkyl; and 5-10 membered heteroaryl, each of which is optionally substituted with from 1-3 R$^{Ca}$;

each R$^{Ca}$ is independently selected from the group consisting of: halo, C$_{1-6}$ alkyl, C$_{1-6}$ haloalkyl, C$_{1-6}$ alkoxy, and NR$^c$R$^d$;

or a pair of R$^{Ca}$ on the same or different ring atoms, taken together with the ring atom(s) to which each is attached, forms a carbocyclic ring including from 3-8 ring atoms;

each R$^c$ and R$^d$ are independently selected from the group consisting of: H, C$_{1-6}$ alkyl, C(=O)(C$_{1-6}$ alkyl), C(=O)(C$_{3-6}$ cycloalkyl), C(=O)O(C$_{1-6}$ alkyl), S(O)$_{1-2}$(C$_{1-6}$ alkyl), and S(O)$_{1-2}$(C$_{3-6}$ cycloalkyl), wherein the C$_{1-6}$ alkyl, C(=O)(C$_{1-6}$ alkyl), C(=O)(C$_{3-6}$ cycloalkyl), C(=O)O(C$_{1-6}$ alkyl), S(O)$_{1-2}$(C$_{1-6}$ alkyl), and S(O)$_{1-2}$(C$_{3-6}$ cycloalkyl) are each optionally substituted with from 1-6 substituents independently selected from the group consisting of: —OH, halo, and C$_{1-6}$ alkoxy;

R$^e$ is H, C$_{1-6}$ alkyl, or C$_{1-6}$ haloalkyl;

each R$^f$ is independently selected from the group consisting of halo, —OH, NR$^c$R$^d$, C$_{1-6}$ alkoxy, C$_{1-6}$ haloalkoxy, and 3-12 membered heterocyclyl which is optionally substituted with from 1-4 substituents each independently selected from the group consisting of —OH, C$_{1-6}$ alkyl, and 3-12 membered heterocyclyl;

each R$^g$ is independently selected from the group consisting of: C$_{1-6}$ alkyl, C$_{1-6}$ alkoxy, NR$^c$R$^d$, and 3 to 12 membered heterocyclyl optionally substituted with one or more substituents each independently selected from the group consisting of C$_{1-6}$ alkyl and C(=O)C$_{1-6}$ alkyl; and each R$^h$ is independently selected from the group consisting of halo, cyano, C$_{1-6}$ alkyl, C$_{1-6}$ haloalkyl, —OH, NH$_2$, NH(C$_{1-3}$ alkyl), N(C$_{1-3}$ alkyl)$_2$, C$_{1-3}$ alkoxy, and C$_{1-3}$ haloalkoxy.

In some embodiments, provided herein are compounds of Formula (I):

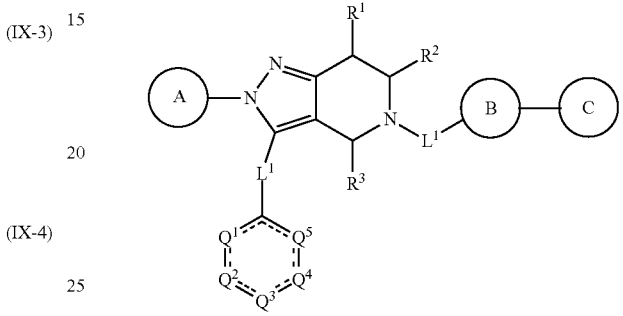

Formula (I)

or a pharmaceutically acceptable salt or solvate thereof, wherein:

Q$^1$, Q$^2$, Q$^3$, Q$^4$, and Q$^5$ are defined according to (AA) or (BB) below:

AA

Q$^1$ and Q$^5$ are independently selected from the group consisting of N, CH, and CR$^{QA}$;

Q$^2$, Q$^3$, and Q$^4$ are independently selected from the group consisting of N, CH, CR$^{QA}$, and CR$^{QB}$, provided that at least one of Q$^2$, Q$^3$, and Q$^4$ is CR$^{QB}$;

each ═ is a single bond or double bond, provided that the ring including Q$^1$-Q$^5$ is aromatic;

BB

Q$^1$ is a bond;

Q$^2$, Q$^3$, Q$^4$, and Q$^5$ are independently selected from the group consisting of O, S, N, NH, NR$^c$, CH, CR$^{QA}$, and CR$^{QB}$, provided that at least one of Q$^2$, Q$^3$, Q$^4$, and Q$^5$ is CR$^{QB}$;

each ═ is a single bond or double bond, provided that the ring including Q$^1$-Q$^5$ is aromatic;

R$^{QB}$ is P(=O)R$^a$R$^b$, wherein R$^a$ and R$^b$ are independently selected from the group consisting of C$_{1-6}$ alkyl which is optionally substituted with from 1-6 substituents each independently selected from the group consisting of C$_{1-6}$ alkoxy, C$_{3-6}$ cycloalkyl, and halo; and C$_{6-10}$ aryl optionally substituted with from 1-3 independently selected C$_{1-3}$ alkyl; or R$^a$ and R$^b$ taken together with the phosphorous atom to which each is attached forms a ring including from 5-8 ring atoms, wherein from 0-2 ring atoms (in addition to the phosphorous attached to R$^a$ and R$^b$) are heteroatoms each independently selected from the group consisting of: O, S, and N, wherein the ring is optionally substituted with from 1-3 independently selected C$_{1-6}$ alkyl;

each R$^{QA}$ is independently selected from the group consisting of: (a) halo; (b) cyano; (c) OH; (d) —NR$^c$R$^d$; (e)

C(=O)NR^cR^d; (f) S(=O)_{0-2}R^e; (g) C_{1-6} alkyl optionally substituted with from 1-6 independently selected Rr; (h) C_{1-6} alkoxy optionally substituted with from 1-6 substituents each independently selected from the group consisting of: hydroxy, halo, and C_{1-6} alkoxy; (i) 3-12 membered heterocyclyl optionally substituted with one or more substituents each independently selected from the group consisting of C_{1-6} alkyl and C(=O)(C_{1-6} alkyl); (j) C_{6-10} aryl optionally substituted with from 1-3 independently selected C(=O)(C_{1-6} alkyl); and (k) 5-10 membered heteroaryl optionally substituted with from 1-6 independently selected R^g;

or a pair of $R^{QA}$ on adjacent carbon atoms, taken together with the atom to which each is attached, forms a ring including from 5-8 ring atoms, wherein from 0-2 ring atoms are heteroatoms each independently selected from the group consisting of O, N, and S, wherein said ring is optionally substituted with from 1-2 independently selected $R^h$ groups;

$L^2$ is selected from the group consisting of:

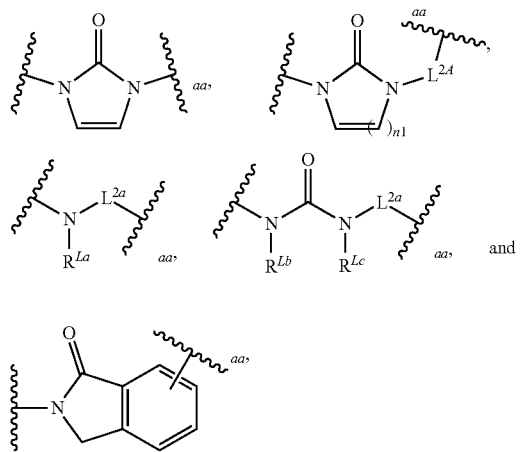

wherein aa represents the point of attachment to the ring containing $Q^1$-$Q^5$;

n1 is an integer from 1-3;

$L^{2A}$ is a bond or $C_{1-10}$ alkylene;

$R^{La}$ is selected from the group consisting of H, $C_{1-6}$ alkyl, and C(=O)($C_{1-6}$ alkyl);

each of $R^{Lb}$ and $R^{Lc}$ is independently selected from the group consisting of H and $C_{1-6}$ alkyl;

Ring A is $C_{6-10}$ aryl, $C_{5-7}$ cycloalkyl, 5-7 membered heterocyclyl, or 5-10 membered heteroaryl, each of which is optionally substituted with from 1-5 substituents each independently selected from the group consisting of halo, $C_{1-6}$ alkyl, $C_{1-6}$ haloalkyl, and $C_{1-6}$ alkoxy;

$R^1$, $R^2$ and $R^3$ are each independently selected from the group consisting of H and $C_{1-6}$ alkyl which is optionally substituted with from 1-6 substituents each independently selected from the group consisting of halo, —OH, and $C_{1-6}$ alkoxy;

$L^1$ is selected from the group consisting of: —C(=O)—, —CH_2—, —CH(C_{1-6} alkyl)-, and —S(=O)_2;

Ring B is selected from the group consisting of:

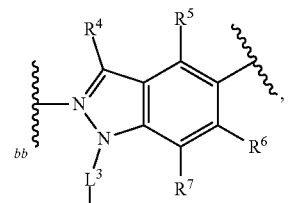

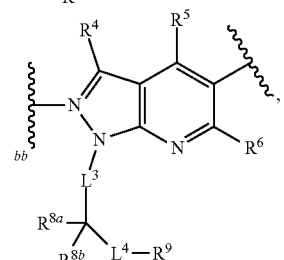

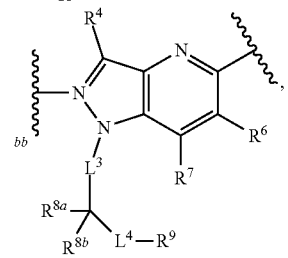 and

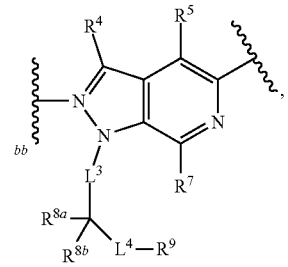

wherein bb represents point of attachment to $L^1$;

$R^4$, $R^5$, $R^6$, and $R^7$ are independently selected from the group consisting of: H, halo, and $C_{1-6}$ alkyl;

$L^3$ is a bond or $C_{1-3}$ alkylene;

$L^4$ is a bond or $C_{1-5}$ alkylene;

$R^{8a}$ and $R^{8b}$ are independently selected from the group consisting of: H and $C_{1-6}$ alkyl optionally substituted with one or more substituents independently selected from the group consisting of: halo and $C_{3-15}$ cycloalkyl; or $R^{8a}$ and $R^{8b}$ taken together with the carbon atom to which each is attached forms a $C_{3-15}$ cycloalkyl ring which is optionally substituted with from 1-3 independently selected $C_{1-6}$ alkyl, wherein the $C_{1-6}$ alkyl is optionally substituted with from 1-6 independently selected $R^i$;

$R^9$ is selected from the group consisting of: C(=O)OH, C(=O)(OC_{1-6} alkyl), C(=O)NR^{9a}R^{9b}, (IX-1), (IX-2), (IX-3), and (IX-4):

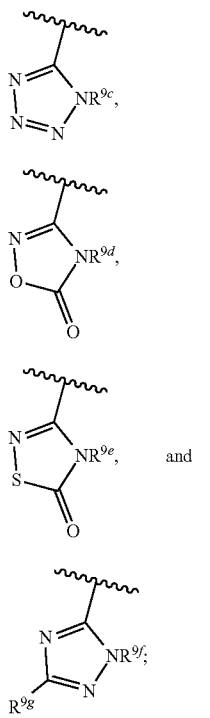

(IX-1)

(IX-2)

(IX-3)

(IX-4)

$R^{9a}$ is H or $C_{1-6}$ alkyl;
$R^{9b}$ is H, $C_{1-6}$ alkyl, C(=O)($C_{1-6}$ alkyl), S(O)$_{0-2}$($C_{1-6}$ alkyl), or cyano;
$R^{9c}$, $R^{9d}$, $R^{9e}$, $R^{9f}$, and $R^{9g}$ are each independently selected from the group consisting of: H; $C_{1-6}$ alkyl optionally substituted with from 1-6 independently selected halo and $C_{1-6}$ alkoxy; and C(=O)($C_{1-6}$ alkyl);
Ring C is selected from the group consisting of 3-12 membered heterocyclyl and 5-10 membered heteroaryl, each of which is optionally substituted with from 1-3 $R^{Ca}$;
each $R^{Ca}$ is independently selected from the group consisting of: halo, $C_{1-6}$ alkyl, $C_{1-6}$ haloalkyl, $C_{1-6}$ alkoxy, and NR$^c$R$^d$;
or a pair of $R^{Ca}$ on the same or different ring atoms, taken together with the ring atom(s) to which each is attached, forms a carbocyclic ring including from 3-8 ring atoms;
each $R^c$ and $R^d$ are independently selected from the group consisting of: H, $C_{1-6}$ alkyl, and C(=O)($C_{1-6}$ alkyl), wherein the $C_{1-6}$ alkyl and C(=O)($C_{1-6}$ alkyl) are each optionally substituted with from 1-6 substituents independently selected from the group consisting of: —OH, halo, and $C_{1-6}$ alkoxy;
$R^e$ is H, $C_{1-6}$ alkyl, or $C_{1-6}$ haloalkyl;
each $R^f$ is independently selected from the group consisting of halo, —OH, NR$^c$R$^d$, $C_{1-6}$ alkoxy, $C_{1-6}$ haloalkoxy, and 3-12 membered heterocyclyl which is optionally substituted with from 1-4 substituents each independently selected from the group consisting of —OH, $C_{1-6}$ alkyl, and 3-12 membered heterocyclyl;
each $R^g$ is independently selected from the group consisting of: $C_{1-6}$ alkyl, $C_{1-6}$ alkoxy, NR$^c$R$^d$, and 3 to 12 membered heterocyclyl optionally substituted with one or more substituents each independently selected from the group consisting of $C_{1-6}$ alkyl and C(=O)$C_{1-6}$ alkyl; and each $R^h$ is independently selected from the group consisting of halo, cyano, $C_{1-6}$ alkyl, $C_{1-6}$ haloalkyl, —OH, NH$_2$, NH($C_{1-3}$ alkyl), N($C_{1-3}$ alkyl)$_2$, $C_{1-3}$ alkoxy, and $C_{1-3}$ haloalkoxy.

Embodiments can include any one or more of the features delineated below and/or in the claims.

In some embodiments, $Q^1$, $Q^2$, $Q^3$, $Q^4$, and $Q^5$ are defined according to (AA).

In certain embodiments, $Q^3$ is CR$^{QB}$. In certain of these embodiments, $Q^4$ is N, CH, or CR$^{QA}$.

In certain embodiments, $Q^4$ is CR$^{QB}$. In certain of these embodiments, $Q^3$ is N, CH, or CR$^{QA}$.

In certain embodiments, $Q^1$ is CH or CR$^{QA}$. In certain embodiments, $Q^1$ is CH.

In certain embodiments, $Q^2$ is CH or CR$^{QA}$. In certain embodiments, $Q^2$ is CH.

In certain embodiments, $Q^5$ is CH or CR$^{QA}$. In certain embodiments, $Q^5$ is CH. In certain other embodiments, $Q^5$ is CR$^{QA}$.

In certain embodiments, $Q^3$ is CR$^{QB}$; and each one of $Q^1$, $Q^2$, $Q^4$, and $Q^5$ is independently CH or CR$^{QA}$. In certain of these embodiments, each one of $Q^1$, $Q^2$, $Q^4$, and $Q^5$ is CH.

In certain embodiments (when $Q^3$ is CR$^{QB}$; and each one of $Q^1$, $Q^2$, $Q^4$, and $Q^5$ is independently CH or CR$^{QA}$), one of $Q^1$, $Q^2$, $Q^4$, and $Q^5$ is CR$^{QA}$; and each remaining one of $Q^1$, $Q^2$, $Q^4$, and $Q^5$ is CH. As a non-limiting example of the foregoing embodiments, $Q^4$ is CR$^{QA}$; and $Q^1$, $Q^2$, and $Q^5$ are CH.

In certain embodiments (when $Q^3$ is CR$^{QB}$; and each one of $Q^1$, $Q^2$, $Q^4$, and $Q^5$ is independently CH or CR$^{QA}$), two of $Q^1$, $Q^2$, $Q^4$, and $Q^5$ are independently selected CR$^{QA}$; and each remaining one of $Q^1$, $Q^2$, $Q^4$, and $Q^5$ is CH.

In certain embodiments, $Q^3$ is CR$^{QB}$; one of $Q^1$, $Q^2$, $Q^4$, and $Q^5$ is N; and each remaining one of $Q^1$, $Q^2$, $Q^4$, and $Q^5$ is independently CH or CR$^{QA}$. In certain of these embodiments, $Q^4$ is N. In certain of the foregoing embodiments, $Q^1$, $Q^2$, and $Q^5$ are CH.

In certain embodiments, $Q^3$ is CR$^{QB}$; and the moiety is selected from the group consisting of:

-continued

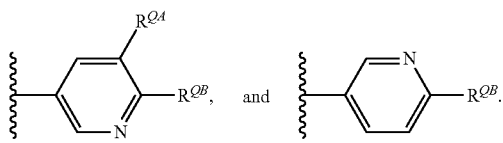 and

In certain embodiments, $Q^3$ is $CR^{QB}$; and the

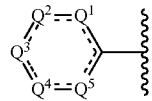

moiety is selected from the group consisting of:

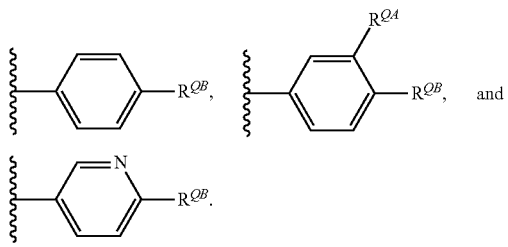

As a non-limiting example, the

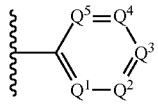

moiety can be

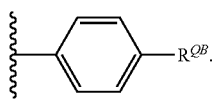

As another non-limiting example, the

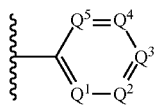

moiety can be

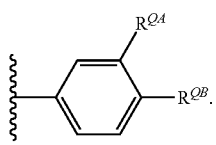

In certain embodiments, $Q^3$ is $CR^{QB}$; and the

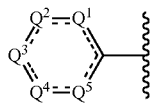

moiety is selected from the group consisting of:

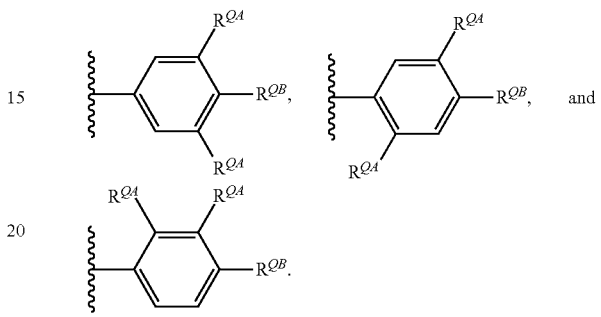

As a non-limiting example, the

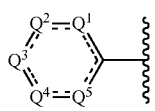

moiety can be

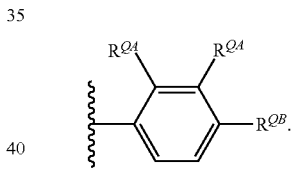

As another non-limiting example, the

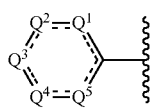

moiety can be

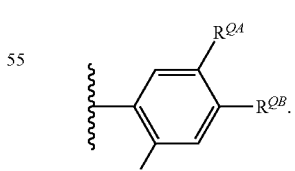

In certain embodiments, $Q^4$ is $CR^{QB}$; and each one of $Q^1$, $Q^2$, $Q^3$, and $Q^5$ is independently CH or $CR^{QA}$. In certain of these embodiments, each one of $Q^1$, $Q^2$, $Q^3$, and $Q^5$ is CH.

In certain embodiments (when $Q^4$ is $CR^{QB}$; and each one of $Q^1$, $Q^2$, $Q^3$, and $Q^5$ is independently CH or $CR^{QA}$), one of $Q^1$, $Q^2$, $Q^3$, and $Q^5$ is $CR^{QA}$; and each remaining one of $Q^1$, $Q^2$, $Q^3$, and $Q^5$ is CH. As a non-limiting example of the foregoing embodiments, $Q^5$ is $CR^{QA}$; and $Q^1$, $Q^2$, and $Q^3$ are CH.

In certain embodiments (when $Q^4$ is $CR^{QB}$; and each one of $Q^1$, $Q^2$, $Q^3$, and $Q^5$ is independently CH or $CR^{QA}$), two of $Q^1$, $Q^2$, $Q^3$, and $Q^5$ are independently selected $CR^{QA}$; and each remaining one of $Q^1$, $Q^2$, $Q^3$, and $Q^5$ is CH. As a non-limiting example of the foregoing embodiments, $Q^2$ and $Q^3$ are independently selected $CR^{Qa}$; and $Q^1$ and $Q^5$ are CH.

In certain embodiments, $Q^4$ is $CR^{QB}$; one of $Q^1$, $Q^2$, $Q^3$, and $Q^5$ is N; and each remaining one of $Q^1$, $Q^2$, $Q^3$, and $Q^5$ is independently CH or $CR^{QA}$.

In certain embodiments, $Q^4$ is $CR^{QB}$; and the

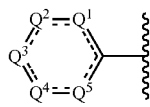

moiety is selected from the group consisting of:

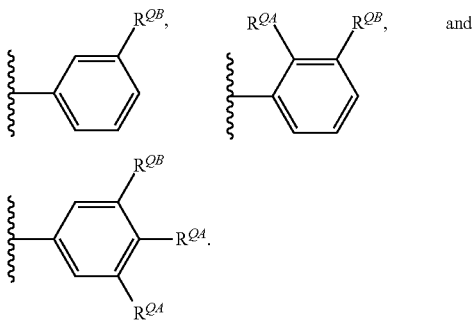

In certain embodiments, $Q^4$ is $CR^{QB}$; and the

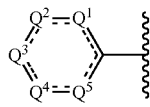

moiety is selected from the group consisting of:

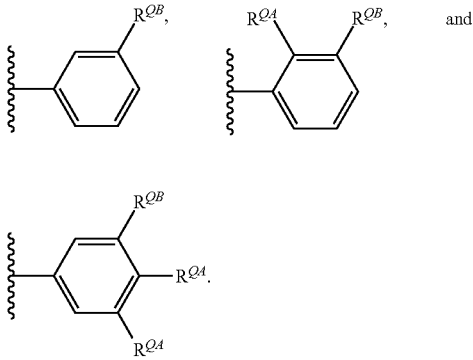

In certain embodiments, the

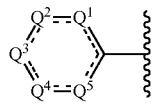

moiety is

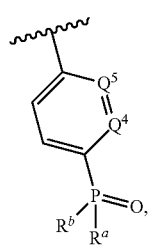

wherein $Q^4$ and $Q^5$ are independently selected from the group consisting of N, CH, and $CR^{QA}$. In certain of these embodiments, each of $Q^4$ and $Q^5$ is CH. In certain other embodiments, $Q^4$ is $CR^{QA}$; and $Q^5$ is CH. In certain other embodiments, $Q^4$ is N; and $Q^5$ is $CR^{QA}$ or CH. In certain embodiments, $Q^5$ is CH.

In certain embodiments, the

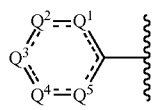

moiety is

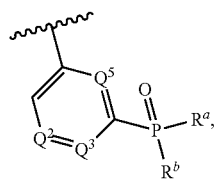

wherein $Q^2$, $Q^3$, and $Q^5$ are independently selected from the group consisting of N, CH, and $CR^{QA}$. In certain of these embodiments, each of $Q^2$, $Q^3$, and $Q^5$ is CH. In certain other embodiments, $Q^5$ is $CR^{QA}$; and each of $Q^2$ and $Q^3$ is CH. In certain other embodiments, $Q^5$ is CH; and $Q^2$ and $Q^3$ are independently selected $CR^{QA}$.

In some embodiments, $R^{QB}$ is $P(=O)R^aR^b$, wherein $R^a$ and $R^b$ are independently selected from the group consisting of $C_{1-6}$ alkyl and $C_{3-6}$ cycloalkyl.

In some embodiments, $R^{QB}$ is $P(=O)R^aR^b$, wherein $R^a$ and $R^b$ are each independently $C_{1-6}$ alkyl. In some embodiments, $R^{QB}$ is $P(=O)R^aR^b$, wherein $R^a$ and $R^b$ are each independently $C_{1-3}$ alkyl.

In certain embodiments, $R^a$ and $R^b$ are the same.

In certain of these embodiments, $R^a$ and $R^b$ are each methyl (i.e., $R^{QB}$ is $P(=O)Me_2$).

In certain embodiments, $R^a$ and $R^b$ are each ethyl (i.e., $R^{QB}$ is $P(=O)Et_2$).

In certain embodiments, $R^a$ and $R^b$ are each propyl, such as isopropyl. For example, $R^{QB}$ can be $P(=O)iPr_2$.

In certain embodiments, $R^{QB}$ is $P(=O)R^aR^b$; $R^a$ and $R^b$ are each independently $C_{1-6}$ alkyl; and $R^a$ and $R^b$ are different. In certain of these embodiments, R$^a$ is C$_{1-3}$ alkyl (e.g., methyl or ethyl); and R$^b$ is C$_{4-6}$ alkyl (e.g., butyl such as tert-butyl). For example, R$^a$ can be methyl; and R$^b$ can be tert-butyl (i.e., R$^{QB}$ can be P(=O)(Me)(tBu)). In certain embodiments, R$^a$ and R$^b$ are independently selected C$_{1-3}$ alkyl, provided that R$^a$ and R$^b$ are different.

In some embodiments, R$^{QB}$ is P(=O)R$^a$R$^b$, wherein R$^a$ and R$^b$ are each independently C$_{3-6}$ cycloalkyl. In certain of these embodiments, R$^a$ and R$^b$ are the same. For example, R$^a$ and R$^b$ can both be cyclopropyl (i.e., R$^{QB}$ can be

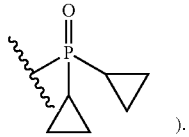 [SMILES: *P(=O)(C1CC1)C1CC1]

).

In some embodiments, R$^{QB}$ is P(=O)R$^a$R$^b$, wherein R$^a$ and R$^b$ taken together with the phosphorous atom to which each is attached forms a ring including from 5-8 ring atoms, wherein from 0-2 ring atoms (in addition to the phosphorous attached to R$^a$ and R$^b$) are heteroatoms each independently selected from the group consisting of: O, S, and N, wherein the ring is optionally substituted with from 1-3 independently selected C$_{1-6}$ alkyl.

In certain of these embodiments, R$^{QB}$ is P(=O)R$^a$R$^b$, wherein R$^a$ and R$^b$ taken together with the phosphorous atom to which each is attached forms a ring including from 5-6 ring atoms, wherein from 0-1 ring atom (in addition to the phosphorous attached to R$^a$ and R$^b$) is a heteroatom selected from the group consisting of: O, S, and N, wherein the ring is optionally substituted with from 1-2 independently selected C$_{1-6}$ alkyl.

As non-limiting examples of the foregoing embodiments, R$^{QB}$ can be

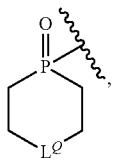

wherein L$^Q$ is a bond, CH$_2$, O, S, NH, or N(C$_{1-6}$ alkyl). For example, R$^{QB}$ can be

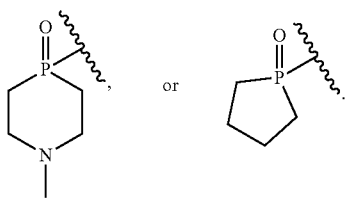

In some embodiments, each R$^{QA}$ is selected from the group consisting of halo, cyano, C$_{1-6}$ alkyl, C$_{1-6}$ alkoxy, OH, and NR$^c$R$^d$.

In some embodiments, each R$^{QA}$ is selected from the group consisting of halo, cyano, OH, and NR$^c$R$^d$.

In some embodiments, one occurrence of R$^{QA}$ is halo. In certain of these embodiments, one occurrence of R$^{QA}$ is —F.

In some embodiments, one occurrence of R$^{QA}$ is —OH.

In some embodiments, one occurrence of R$^{QA}$ is NR$^c$R$^d$.

In certain of these embodiments, one occurrence of R$^{QA}$ is NH(C$_{1-3}$ alkyl) (e.g., NHMe, NHEt, or NHiPr).

In certain embodiments, one occurrence of R$^{QA}$ is NH$_2$.

In certain embodiments, one occurrence of R$^{QA}$ is N(C$_{1-3}$ alkyl)$_2$ (e.g., NMe$_2$).

In certain embodiments, one occurrence of R$^{QA}$ is selected from the group consisting of NHC(=O)(C$_{1-6}$ alkyl), NHC(=O)(C$_{3-6}$ cycloalkyl), NHC(=O)O(C$_{1-6}$ alkyl), NHS(O)$_{1-2}$(C$_{1-6}$ alkyl), and NHS(O)$_{1-2}$(C$_{3-6}$ cycloalkyl).

In certain embodiments, one occurrence of R$^{QA}$ is NHC(=O)(C$_{1-3}$ alkyl), NHC(=O)(C$_{3-6}$ cycloalkyl) (e.g., NHC(=O)(cyclopropyl)), or NHS(O)$_2$(C$_{1-3}$ alkyl) (e.g., NHS(O)$_2$Me).

In some embodiments, one occurrence of R$^{QA}$ is 5-6 membered heterocyclyl optionally substituted with one or more substituents each independently selected from the group consisting of C$_{1-6}$ alkyl and C(=O)(C$_{1-6}$ alkyl). In certain of these embodiments, one occurrence of R$^{QA}$ is morpholinyl.

In some embodiments, one occurrence of R$^{QA}$ is C$_{1-6}$ alkoxy optionally substituted with from 1-6 substituents each independently selected from the group consisting of: hydroxy, halo, and C$_{1-6}$ alkoxy. In certain of these embodiments, one occurrence of R$^{QA}$ is C$_{1-6}$ alkoxy optionally substituted with from 1-6 (e.g., 1-3) independently selected halo. As non-limiting examples of the foregoing embodiments, R$^{QA}$ can be —OMe, —OCF$_3$, or —OCHF$_2$. For example, R$^{QA}$ can be —OMe. For example, R$^{QA}$ can be —OCF$_3$. As another non-limiting example, R$^{QA}$ can be —OCHF$_2$.

In some embodiments, R$^{QA}$ is C$_{1-6}$ alkyl optionally substituted with from 1-6 independently selected R$^f$. In certain of these embodiments, R$^{QA}$ is C$_{1-3}$ alkyl. As a non-limiting example of the foregoing embodiments, R$^{QA}$ can be methyl.

In certain embodiments, one occurrence of R$^{QA}$ is C$_{1-3}$ alkyl substituted with from 1-6 independently selected halo. For example, R$^{QA}$ can be CF$_3$, CHF$_2$, or CH$_2$F (e.g., CF$_3$ or CHF$_2$).

In certain of these embodiments, one occurrence of R$^{QA}$ is C$_{1-3}$ alkyl substituted with NR$^c$R$^d$. For example, R$^{QA}$ can be CH$_2$NHMe.

In certain embodiments, each remaining R$^{QA}$ when present is an independently selected halo, such as —F.

In some embodiments, a pair of R$^{QA}$ on adjacent carbon atoms, taken together with the atom to which each is attached, forms a ring including from 5-6 ring atoms, wherein from 1-2 ring atoms are heteroatoms each independently selected from the group consisting of O, N, and S, wherein said ring is optionally substituted with from 1-2 independently selected R$^h$ groups.

In certain of these embodiments, a pair of R$^{QA}$ on adjacent carbon atoms, taken together with the atom to which each is attached forms:

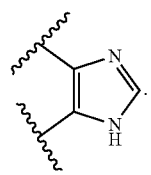 [SMILES: *c1nc[nH]c1*]

In certain embodiments, a pair of R$^{QA}$ on adjacent carbon atoms, taken together with the atom to which each is attached forms:

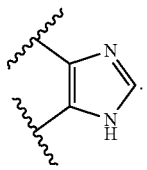 [SMILES: *c1nc[nH]c1*]

In some embodiments, each remaining $R^{QA}$ when present is independently halo, cyano, or $C_{1-3}$ alkyl.

In some embodiments, $L^2$ is

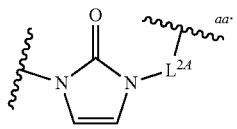

In certain of these embodiments, $L^{2A}$ is a bond. In certain other embodiments, $L^{2A}$ is $CH_2$.

In some embodiments, $L^2$ is

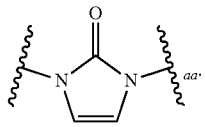 [SMILES: *n1ccn(*)c1=O]

In some embodiments, $L^2$ is

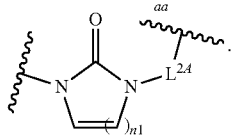

In certain of these embodiments, n1 is 1. In certain other embodiments, n1 is 2 or 3. In certain embodiments, $L^{2A}$ is a bond. In certain other embodiments, $L^{2A}$ is $C_{1-2}$ alkylene.

In some embodiments, $L^2$ is

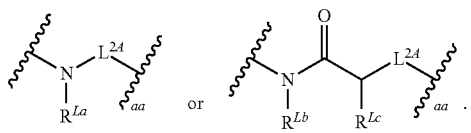

In certain embodiments, $L^{2A}$ is a bond. In certain other embodiments, $L^{2A}$ is $C_{1-2}$ alkylene.

In some embodiments, $L^2$ is

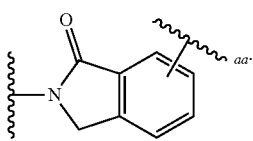

In some embodiments, Ring A is $C_{6-10}$ aryl or 5-10 membered heteroaryl, each of which is optionally substituted with from 1-4 substituents each independently selected from the group consisting of halo, $C_{1-6}$ alkyl, $C_{1-6}$ haloalkyl, and $C_{1-6}$ alkoxy.

In some embodiments, Ring A is phenyl or pyridyl, each of which is optionally substituted with from 2-4 substituents each independently selected from the group consisting of halo, $C_{1-6}$ alkyl, $C_{1-6}$ haloalkyl, and $C_{1-6}$ alkoxy.

In certain of the foregoing embodiments, Ring A is phenyl, which is optionally substituted with from 2-4 substituents each independently selected from the group consisting of halo (e.g., —F) and $C_{1-6}$ alkyl (e.g., $C_{1-3}$ alkyl). As a non-limiting example of the foregoing embodiments, Ring A can be

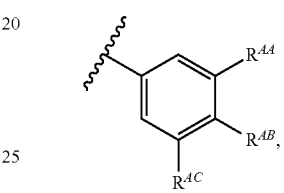

wherein $R^{AA}$, $R^{AB}$, and $R^{AC}$ are independently halo or $C_{1-6}$ alkyl. For example $R^{AA}$ and $R^{AC}$ can be independently selected $C_{1-3}$ alkyl (e.g., methyl); and/or $R^{AB}$ can be halo (e.g., —F).

In certain embodiments, Ring A is pyridyl, which is optionally substituted with from 2-4 substituents each independently selected from the group consisting of halo and $C_{1-6}$ alkyl. For example, Ring A can be 4-pyridyl, which is optionally substituted with from 2-4 substituents each independently selected from the group consisting of halo and $C_{1-6}$ alkyl. As another example, Ring A can be 3-pyridyl, which is optionally substituted with from 2-4 substituents each independently selected from the group consisting of halo and $C_{1-6}$ alkyl. As yet another example, Ring A can be 2-pyridyl, which is optionally substituted with from 2-4 substituents each independently selected from the group consisting of halo and $C_{1-6}$ alkyl.

In some embodiments, $R^1$ is H. In some embodiments, $R^1$ is $C_{1-6}$ alkyl.

In some embodiments, $R^2$ is H. In some embodiments, $R^2$ is $C_{1-6}$ alkyl.

In some embodiments, $R^3$ is H. In some embodiments, $R^3$ is $C_{1-6}$ alkyl (e.g., $C_{1-3}$ alkyl such as methyl).

In certain embodiments, $R^1$, $R^2$, and $R^3$ are H. In certain other embodiments, $R^1$ and $R^2$ are H; and $R^3$ is $C_{1-6}$ alkyl. In certain of these embodiments, $R^3$ is methyl.

In certain embodiments, $R^1$ is H; and $R^2$ and $R^3$ are independently selected $C_{1-6}$ alkyl.

In some embodiments, L is C(=O).

In some embodiments, L is —$CH_2$— or —CH($C_{1-6}$ alkyl)-.

In some embodiments, L is —S(=O)$_2$.

In some embodiments, Ring B is

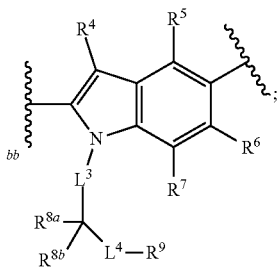

In certain of these embodiments, $R^4$, $R^5$, and $R^6$ are each H or halo. In certain embodiments, $R^4$, $R^5$, and $R^6$ are each H or —F. As a non-limiting example of the foregoing embodiments, $R^4$, $R^5$, and $R^6$ are each H. As another non-limiting example, $R^4$ and $R^5$ are H; and $R^6$ is —F. In certain embodiments, $R^7$ is H. In certain other embodiments, $R^7$ is —F.

In certain embodiments, Ring B is

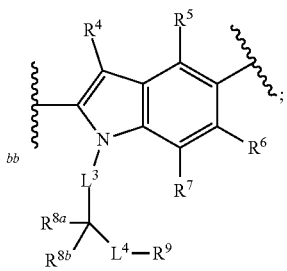

and each of $R^4$, $R^5$, $R^6$, and $R^7$ is H.

In certain other embodiments, Ring B is

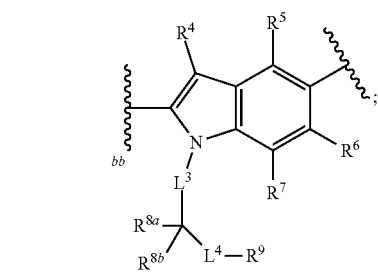

each of $R^4$, $R^5$, and $R^6$ is H; and $R^7$ is —F.

In some embodiments, Ring B is selected from the group consisting of:

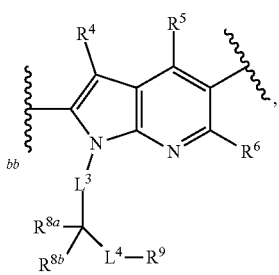

-continued

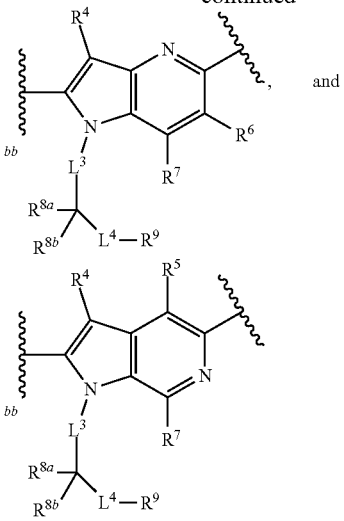

(e.g., Ring B can be

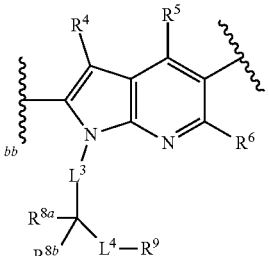

In certain of these embodiments, each of $R^4$, $R^5$, $R^6$, and $R^7$ when present is independently selected from the group consisting of H and halo. For example, each of $R^4$, $R^5$, $R^6$, and $R^7$ when present can be independently selected from the group consisting of —H and —F.

In some embodiments, at least one of $L^3$ and $L^4$ is a bond. In certain of these embodiments, both of $L^3$ and $L^4$ are bonds.

In certain embodiments, $L^3$ is a bond; and $L^4$ is $C_{1-2}$ alkylene.

In certain other embodiments, $L^4$ is a bond; and $L^3$ is $C_{1-2}$ alkylene.

In certain embodiments, $L^3$ and $L^4$ are each independently $C_{1-2}$ alkylene.

In some embodiments, $R^{8a}$ and $R^{8b}$ taken together with the carbon atom to which each is attached forms a $C_{3-8}$ cycloalkyl ring which is optionally substituted with from 1-2 independently selected $C_{1-6}$ alkyl, wherein the $C_{1-6}$ alkyl is optionally substituted with from 1-3 independently selected $R^f$.

In certain embodiments, $R^{8a}$ and $R^{8b}$ taken together with the carbon atom to which each is attached forms a $C_{3-8}$ cycloalkyl ring which is optionally substituted with from 1-2 independently selected $C_{1-6}$ alkyl, wherein the $C_{1-6}$ alkyl is optionally substituted with from 1-3 independently selected $R^f$.

In certain embodiments, $R^{8a}$ and $R^{8b}$ taken together with the carbon atom to which each is attached forms a $C_{3-5}$ cycloalkyl ring which is optionally substituted with from 1-2 independently selected $C_{1-6}$ alkyl.

As a non-limiting example of the foregoing embodiments, $R^{8a}$ and $R^{8b}$ taken together with the carbon atom to which each is attached forms:

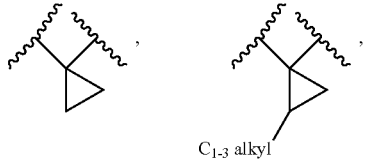

C$_{1-3}$ alkyl

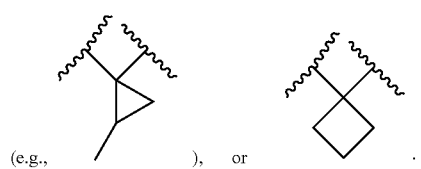

(e.g., ), or .

For example, $R^{8a}$ and $R^{8b}$ taken together with the carbon atom to which each is attached forms:

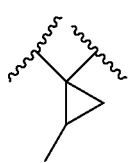

In some embodiments, $R^{8a}$ and $R^{8b}$ are each independently selected from the group consisting of H and $C_{1-6}$ alkyl. For example, $R^{8a}$ and $R^{8b}$ can both be H. As another example, $R^{8a}$ and $R^{8b}$ can be an independently selected $C_{1-6}$ alkyl (e.g., $C_{1-3}$ alkyl). As yet another example, $R^{8a}$ can be H; and $R^{8b}$ can be $C_{1-6}$ alkyl (e.g., $C_{1-3}$ alkyl).

In some embodiments, the $L^3$-C($R^{8a}R^{8b}$)-$L^4$-$R^9$ moiety is:

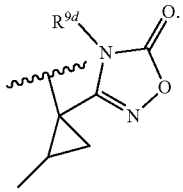

In certain of these embodiments, $R^{9d}$ is H or $C_{1-6}$ alkyl. For example, $R^{9d}$ can be H.

In some embodiments, the $L^3$-C($R^{8a}R^{8b}$)-$L^4$-$R^9$ moiety is:

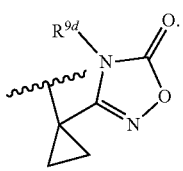

In certain of these embodiments, $R^{9d}$ is H or $C_{1-6}$ alkyl. For example, $R^{9d}$ can be H.

In some embodiments, $R^9$ is

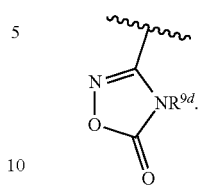

(IX-2)

In certain of these embodiments, $R^{9d}$ is H or $C_{1-6}$ alkyl. For example, $R^{9d}$ can be H.

In some embodiments, $R^9$ is

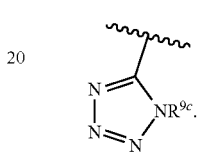

(IX-1)

In some embodiments, $R^9$ is

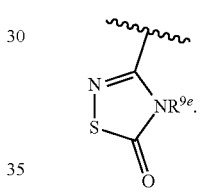

(IX-3)

In some embodiments, $R^9$ is

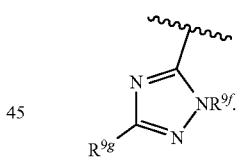

(IX-4)

In some embodiments, $R^9$ is C(=O)OH.
In some embodiments, $R^9$ is C(=O)(OC$_{1-6}$ alkyl).
In some embodiments, $R^9$ is C(=O)NR$^{9a}$R$^{9b}$. In certain of these embodiments, $R^{9a}$ is H. In certain embodiments, $R^{9b}$ is H. In certain embodiments, $R^{9b}$ is $C_{1-6}$ alkyl. In certain embodiments, $R^{9b}$ is selected from the group consisting of: C(=O)($C_{1-6}$ alkyl), S(O)$_{0-2}$($C_{1-6}$ alkyl), and cyano.

In some embodiments, the

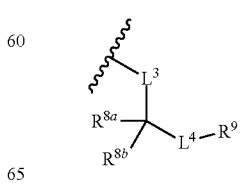

moiety is

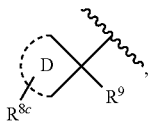

wherein Ring D is a $C_{3-6}$ cycloalkyl; and $R^{8c}$ is selected from the group consisting of H and $C_{1-6}$ alkyl optionally substituted with from 1-3 independently selected $R^f$. Non-limiting examples include:

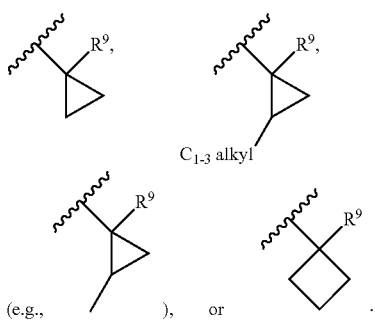

In certain embodiments

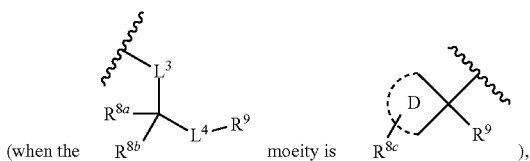

(when the $\begin{smallmatrix}R^{8a}\\R^{8b}\end{smallmatrix}{-}L^4{-}R^9$ moeity is 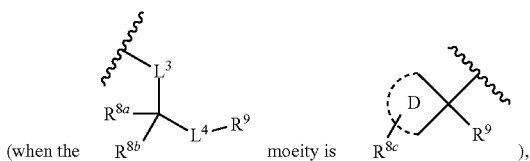 ), $R^9$ is

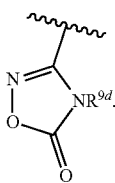
(IX-2)

In certain of these embodiments, $R^{9d}$ is H or $C_{1-6}$ alkyl. For example, $R^{9d}$ can be H.

In some embodiments, Ring C is 3-12 membered heterocyclyl which is optionally substituted with from 1-3 independently selected $R^{Ca}$.

In certain embodiments, Ring C is 4-8 membered heterocyclyl which is optionally substituted with from 1-3 independently selected $R^{Ca}$.

In certain embodiments, Ring C is 5-6 membered heterocyclyl which is optionally substituted with from 1-3 independently selected $R^{Ca}$.

In certain embodiments, Ring C is tetrahydropyranyl which is optionally substituted with from 1-3 independently $R^{Ca}$. For example, Ring C can be selected from the group consisting of:

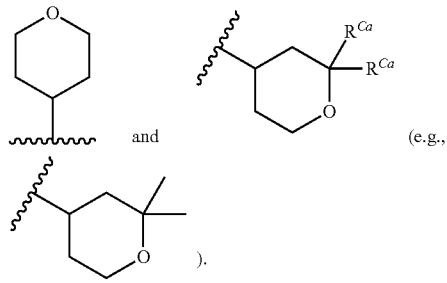

As another non-limiting example, Ring C can be

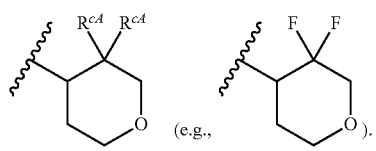

In certain embodiments, Ring C is morpholinyl which is optionally substituted with from 1-3 independently selected $R^{Ca}$. For example, Ring C can be

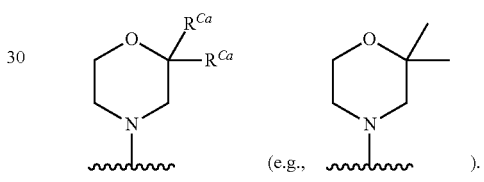

In some embodiments, Ring C is 5-6 membered heteroaryl which is optionally substituted with from 1-3 independently selected $R^{Ca}$.

In some embodiments, Ring C is $C_{3-10}$ cycloalkyl which is optionally substituted with from 1-3 $R^{Ca}$. In some embodiments, Ring C is $C_{3-8}$ cycloalkyl which is optionally substituted with from 1-3 independently selected $R^{Ca}$. For example, Ring C can be

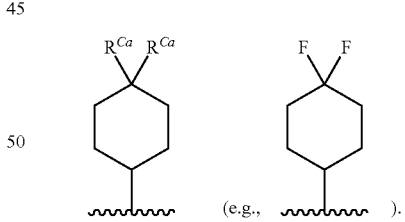

In some embodiments, each $R^{Ca}$ is independently selected from the group consisting of halo, $C_{1-6}$alkyl, $C_{1-6}$ alkoxy, and $NR^cR^d$.

In some embodiments, each $R^{Ca}$ is independently selected from the group consisting of: halo and $C_{1-6}$ alkyl.

In some embodiments, each $R^{Ca}$ is independently $C_{1-6}$ alkyl. For example, each $R^{Ca}$ can be methyl.

In some embodiments, each $R^{Ca}$ is an independently selected halo. For example, each $R^{Ca}$ can be —F.

In some embodiments, a pair of $R^{Ca}$ on the same or different ring atoms, taken together with the ring atom(s) to which each is attached, forms a carbocyclic ring including from 3-6 ring atoms. In certain embodiments, a pair of $R^{Ca}$ on the same ring atom, taken together with the ring atom to which each is attached, forms a carbocyclic ring including from 3-5 ring atoms.

In some embodiments, the compound of Formula (I) is a compound of Formula (IA):

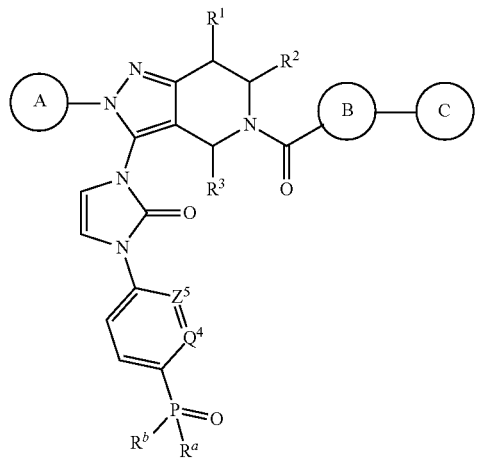

Formula (IA)

wherein $Q^4$ and $Q^5$ are independently selected from the group consisting of: N, CH, and $CR^{QA}$;
or a pharmaceutically acceptable salt or solvate thereof.

In some embodiments of Formula (IA), each of $Q^4$ and $Q^5$ is CH.

In some embodiments of Formula (IA), $Q^4$ is $CR^{QA}$; and $Q^5$ is CH.

In some embodiments of Formula (IA), $Q^4$ is $CR^{QA}$; and $Q^5$ is $CR^{QA}$. In certain of these embodiments, $Q^4$ is $CR^{QA}$; and $Q^5$ is C-halo, such as CF.

In some embodiments of Formula (IA), $Q^4$ is N; and $Q^5$ is $CR^{QA}$ or CH. In certain of these embodiments, $Q^5$ is CH.

In some embodiments, the compound of Formula (I) is a compound of Formula (IB):

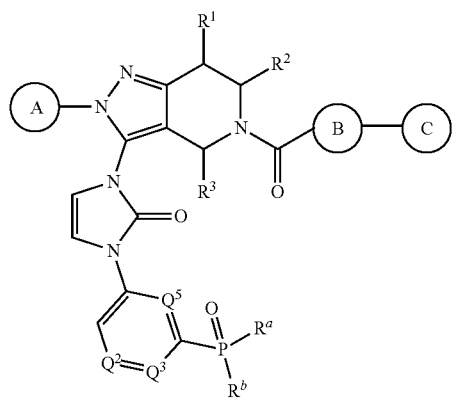

Formula (IB)

wherein $Q^2$, $Q^3$, and $Q^5$ are independently selected from the group consisting of: N, CH, and $CR^{QA}$;
or a pharmaceutically acceptable salt or solvate thereof.

In some embodiments of Formula (IB), each of $Q^2$, $Q^3$, and $Q^5$ is CH.

In some embodiments of Formula (IB), $Q^5$ is $CR^{QA}$; and each of $Q^2$ and $Q^3$ is CH.

In some embodiments of Formula (IB), $Q^5$ is CH; and $Q^2$ and $Q^3$ are independently selected $CR^{QA}$.

In some embodiments of Formula (IA) or (IB), Ring B is

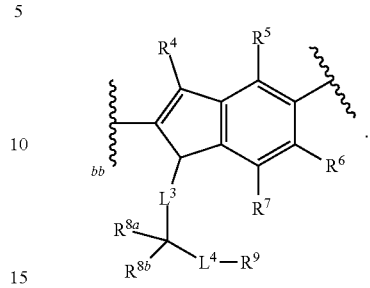

In certain of these embodiments, at least one of $L^3$ and $L^4$ is a bond. As a non-limiting example of the foregoing embodiments, both of $L^3$ and $L^4$ are bonds.

In some embodiments of Formula (IA) or (IB), $R^{8a}$ and $R^{8b}$ taken together with the carbon atom to which each is attached forms a $C_{3-5}$ cycloalkyl ring which is optionally substituted with from 1-2 independently selected $C_{1-6}$ alkyl, wherein the $C_{1-6}$ alkyl is optionally substituted with from 1-3 independently selected $R^f$.

In certain of these embodiments, $R^{8a}$ and $R^{8b}$ taken together with the carbon atom to which each is attached forms a $C_{3-4}$ cycloalkyl ring which is optionally substituted with from 1-2 independently selected $C_{1-6}$ alkyl.

As a non-limiting example of the foregoing embodiments, $R^{8a}$ and $R^{8b}$ taken together with the carbon atom to which each is attached forms:

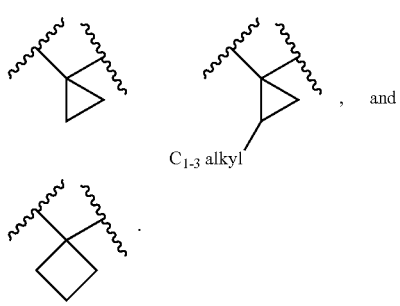

In some embodiments of Formula (IA) or (IB), Ring C is 3-12 membered heterocyclyl which is optionally substituted with from 1-3 independently selected $R^{Ca}$. In certain embodiments, Ring C is 5-6 membered heterocyclyl which is optionally substituted with from 1-3 independently selected $R^{Ca}$. In certain embodiments, Ring C is tetrahydropyranyl which is optionally substituted with from 1-3 independently $R^{Ca}$. As a non-limiting example of the foregoing embodiments, Ring C can be selected from the group consisting of:

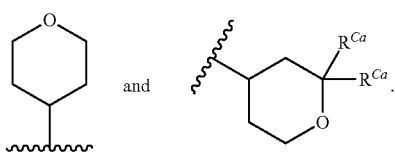

In certain embodiments, Ring C is morpholinyl which is optionally substituted with from 1-3 independently selected $R^{Ca}$. For example, Ring C can be

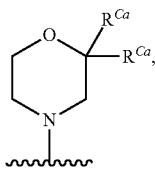

In some embodiments of Formula (IA) or (IB), Ring C is $C_{3-8}$ cycloalkyl which is optionally substituted with from 1-3 $R^{Ca}$. For example, Ring C can be

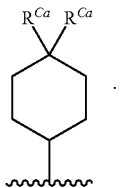

In some embodiments of Formula (IA) or (IB), each $R^{Ca}$ is independently $C_{1-6}$ alkyl. For example, each $R^{Ca}$ can be H. As another non-limiting example, each $R^{Ca}$ is $C_{1-3}$ alkyl (e.g., methyl).

In some embodiments of Formula (IA) or (IB), each $R^{Ca}$ is an independently selected halo (e.g., —F).

In some embodiments of Formula (IA) or (IB), a pair of $R^{Ca}$ on the same or different ring atoms, taken together with the ring atom(s) to which each is attached, forms a carbocyclic ring including from 3-6 ring atoms.

In some embodiments of Formula (IA) or (IB), a pair of $R^{Ca}$ on the same ring atom, taken together with the ring atom to which each is attached, forms a carbocyclic ring including from 3-5 ring atoms.

In some embodiments, the compound of Formula (I) is a compound of Formula (IC):

Formula (IC)

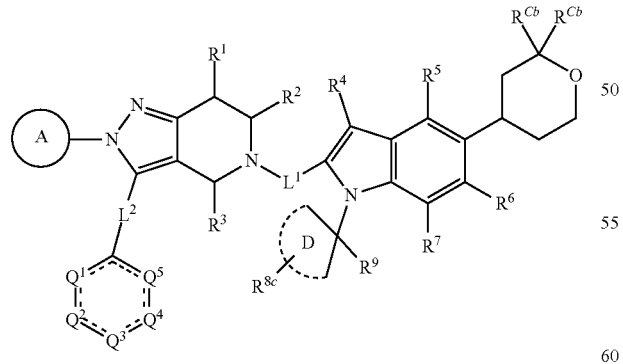

or a pharmaceutically acceptable salt or solvate thereof, wherein:

Ring D is a $C_{3-6}$ cycloalkyl;
$R^{8c}$ is selected from the group consisting of H and $C_{1-6}$ alkyl optionally substituted with from 1-3 independently selected $R^f$; and each $R^{Cb}$ is independently selected from the group consisting of H and $R^{Ca}$.

In some embodiments of Formula (IC), Ring D is cyclopropyl.

In some embodiments of Formula (IC), Ring D is cyclobutyl.

In some embodiments of Formula (IC), $R^{8c}$ is H.

In some embodiments of Formula (IC), $R^{8c}$ is $C_{1-3}$ alkyl. For example, $R^{8c}$ can be methyl.

In some embodiments of Formula (IC), each $R^{Cb}$ is H.

In some embodiments of Formula (IC), each $R^{Cb}$ is independently $C_{1-6}$ alkyl (e.g., $C_{1-3}$ alkyl (e.g., methyl)).

In some embodiments of Formula (IC), $Q^1$, $Q^2$, $Q^3$, $Q^4$, and $Q^5$ are as defined according to (AA).

In some embodiments of Formula (IC), the

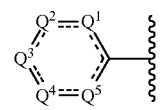

moiety is

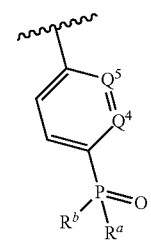

wherein $Q^4$ and $Q^5$ are independently selected from the group consisting of N, CH, and $CR^{QA}$.

In certain of these embodiments, each of $Q^4$ and $Q^5$ is CH.

In certain other embodiments, $Q^4$ is $CR^{QA}$; and $Q^5$ is CH.

In certain embodiments, $Q^4$ is $CR^{QA}$; and $Q^5$ is $CR^{QA}$. In certain of these embodiments, $Q^4$ is $CR^{QA}$; and $Q^5$ is C-halo, such as CF.

In certain other embodiments, $Q^4$ is N; and $Q^5$ is $CR^{QA}$ or CH. In certain of these embodiments, $Q^5$ is CH.

In some embodiments of Formula (IC), the

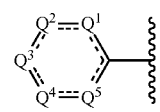

moiety is

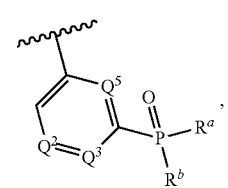

wherein $Q^2$, $Q^3$, and $Q^5$ are independently selected from the group consisting of N, CH, and $CR^{QA}$.

In certain of these embodiments, each of $Q^2$, $Q^3$, and $Q^5$ is CH.

In certain other embodiments, $Q^5$ is $CR^{QA}$; and each of $Q^2$ and $Q^3$ is CH.

In certain other embodiments, $Q^5$ is CH; and $Q^2$ and $Q^3$ are independently selected $CR^{QA}$.

In some embodiments of Formula (IC), $L^1$ is C(=O).

In some embodiments of Formula (IA), (IB), or (IC), $R^a$ and $R^b$ are each independently selected from the group consisting of $C_{1-6}$ alkyl and $C_{3-6}$ cycloalkyl.

In some embodiments of Formula (IA), (IB), or (IC), $R^a$ and $R^b$ are each independently $C_{1-3}$ alkyl. For example, $R^a$ and $R^b$ can be each methyl. As another non-limiting example, $R^a$ and $R^b$ can each be ethyl. As a further non-limiting example, $R^a$ and $R^b$ can each be isopropyl.

In some embodiments of Formula (IA), (IB), or (IC), $R^a$ is methyl; and $R^b$ is tert-butyl.

In some embodiments of Formula (IA), (IB), or (IC), $R^a$ and $R^b$ are independently selected $C_{3-6}$ cycloalkyl. For example, $R^a$ and $R^b$ can both be cyclopropyl.

In some embodiments of Formula (IA), (IB), or (IC), each $R^{QA}$ is selected from the group consisting of: halo; cyano; OH; $NR^cR^d$; $C_{1-6}$ alkyl optionally substituted with from 1-6 independently selected R; $C_{1-6}$ alkoxy optionally substituted with from 1-6 substituents each independently selected from the group consisting of: hydroxy, halo, and $C_{1-6}$ alkoxy; and 3-12 membered heterocyclyl optionally substituted with one or more substituents each independently selected from the group consisting of $C_{1-6}$ alkyl and C(=O)($C_{1-6}$ alkyl).

In certain of these embodiments, each $R^{QA}$ is selected from the group consisting of —F, OH, $NH_2$ NHMe, NHEt, NHiPr, $N(Me)_2$, NHC(=O)(cyclopropyl), $NHS(O)_2Me$, methyl, $CF_3$, $CHF_2$, OMe, $OCF_3$, $OCHF_2$, and morpholinyl.

In certain of these embodiments, $R^{QA}$ is selected from the group consisting of —F, OH, $NH_2$ NHMe, NHEt, NHC(=O)(cyclopropyl), $NHS(O)_2Me$, methyl, OMe, $OCF_3$, and morpholinyl.

In some embodiments of Formula (IA), (IB), or (IC), each $R^{QA}$ is selected from the group consisting of halo, cyano, OH, and $NR^cR^d$.

In certain of these embodiments, each $R^{QA}$ is selected from the group consisting of —F, OH, and NHMe.

In some embodiments of Formula (IA), (IB), or (IC), a pair of $R^{QA}$ on adjacent carbon atoms, taken together with the atom to which each is attached, forms a ring including from 5-6 ring atoms, wherein from 1-2 ring atoms are heteroatoms each independently selected from the group consisting of O, N, and S, wherein said ring is optionally substituted with from 1-2 independently selected $R^h$ groups. For example, a pair of $R^{QA}$ on adjacent carbon atoms, taken together with the atom to which each is attached can form:

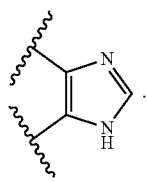 [SMILES: *c1nc[nH]c1*]

As another limiting example, a pair of $R^{QA}$ on adjacent carbon atoms, taken together with the atom to which each is attached can form:

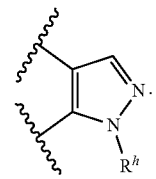

(e.g., $R^h$ is methyl).

In some embodiments of Formula (IA), (IB), or (IC), $L^2$ is

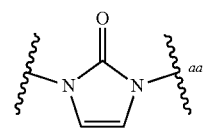

In some embodiments of Formula (IA), (IB), or (IC), Ring A is phenyl or pyridyl, each of which is optionally substituted with from 2-4 substituents each independently selected from the group consisting of halo, $C_{1-6}$ alkyl, $C_{1-6}$ haloalkyl, and $C_{1-6}$ alkoxy.

In some embodiments of Formula (IA), (IB), or (IC), Ring A is phenyl, which is optionally substituted with from 2-4 substituents each independently selected from the group consisting of halo and $C_{1-6}$ alkyl.

As a non-limiting example of the foregoing embodiments, Ring A is

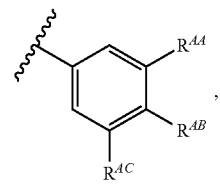

wherein $R^{AA}$, $R^{AB}$, and $R^{AC}$ are independently halo or $C_{1-6}$ alkyl. For example each of $R^{AA}$ and $R^{AC}$ can be independently $C_{1-6}$ alkyl, such as $C_{1-3}$ alkyl (e.g., methyl); and/or $R^{AB}$ can be halo (e.g., —F).

In some embodiments of Formula (IA), (IB), or (IC), $R^1$ and $R^2$ are H.

In some embodiments of Formula (IA), (IB), or (IC), $R^3$ is H.

In some embodiments of Formula (IA), (IB), or (IC), $R^3$ is $C_{1-6}$ alkyl.

In certain embodiments of Formula (IA), (IB), or (IC), $R^1$ and $R^2$ are H; and $R^3$ is $C_{1-6}$ alkyl. For example, $R^3$ can be methyl.

In some embodiments of Formula (IA), (IB), or (IC), $R^4$, $R^5$, and $R^6$ are each H or halo.

In some embodiments of Formula (IA), (IB), or (IC), $R^4$, $R^5$, and $R^6$ are each H or —F. In certain embodiments of Formula (IA), (IB), or (IC), $R^4$, $R^5$, and $R^6$ are each H. In certain embodiments of Formula (IA), (IB), or (IC), $R^4$ and $R^5$ are H; and $R^6$ is —F.

In some embodiments of Formula (IA), (IB), or (IC), $R^7$ is H.

In some embodiments of Formula (IA), (IB), or (IC), $R^7$ is —F.

In some embodiments of Formula (IA), (IB), or (IC), $R^9$ is

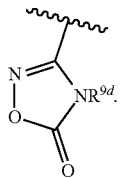
(IX-2)

In certain of these embodiments, $R^{9d}$ is H.

In some embodiments, the compound of Formula (I) is a compound of Formula (ID):

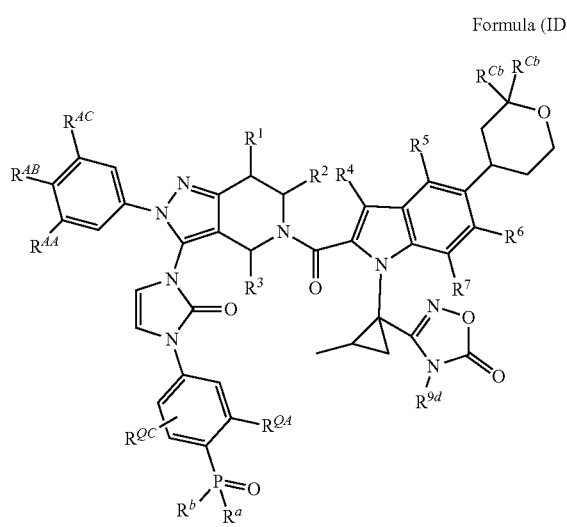

Formula (ID)

or a pharmaceutically acceptable salt or solvate thereof, wherein:
$R^{AA}$, $R^{AB}$, and $R^{AC}$ are independently halo or $C_{1-6}$ alkyl;
$R^{QC}$ is H or halo; and
each $R^{Cb}$ is independently selected from the group consisting of H and $R^{Ca}$.

In some embodiments of Formula (ID), $R^1$ and $R^2$ are H.

In some embodiments of Formula (ID), $R^3$ is $C_{1-3}$ alkyl. In certain of these embodiments, $R^3$ is methyl.

In some embodiments of Formula (ID), $R^4$, $R^5$, $R^6$, and $R^7$ are H.

In some embodiments of Formula (ID), $R^{9d}$ is H.

In some embodiments of Formula (ID), $R^{AA}$ and $R^{AC}$ are independently $C_{1-6}$ alkyl.

In certain of these embodiments, $R^{AA}$ and $R^{AC}$ are methyl.

In some embodiments of Formula (ID), $R^{AB}$ is halo. In certain of these embodiments, $R^{AB}$ is —F.

In some embodiments of Formula (ID), each $R^{Cb}$ is H. In some embodiments of Formula (ID), each $R^{Cb}$ is $C_{1-3}$ alkyl. In certain of these embodiments, each $R^{Cb}$ is methyl.

In some embodiments of Formula (ID), $R^a$ and $R^b$ are independently $C_{1-3}$ alkyl. In certain of these embodiments, $R^a$ and $R^b$ are methyl. In certain embodiments, $R^a$ and $R^b$ are ethyl. In certain embodiments, $R^a$ and $R^b$ are isopropyl.

In some embodiments of Formula (ID), $R^a$ is methyl; and $R^b$ is tert-butyl.

In some embodiments of Formula (ID), $R^a$ and $R^b$ are independently $C_{3-6}$ cycloalkyl. For example, $R^a$ and $R^b$ can both be cyclopropyl.

In some embodiments of Formula (ID), P(=O)$R^aR^b$ is

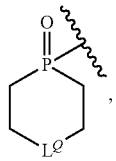

wherein $L^Q$ is a bond, $CH_2$, O, S, NH, or N($C_{1-6}$ alkyl). In certain of these embodiments, P(=O)$R^aR^b$ is

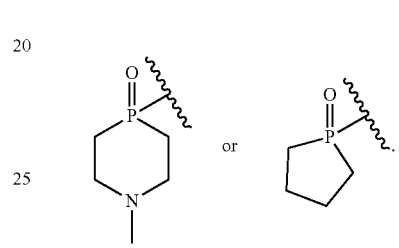

or

In some embodiments of Formula (ID), $R^{QA}$ is —F.

In some embodiments of Formula (ID), $R^{QA}$ is —OH.

In some embodiments of Formula (ID), $R^{QA}$ is $NR^cR^d$. In certain embodiments, $R^{QA}$ is NH($C_{1-3}$ alkyl) (e.g., NHMe or NHEt). In certain embodiments, $R^{QA}$ is $NH_2$. In certain embodiments, $R^{QA}$ is N($C_{1-3}$ alkyl)$_2$ (e.g., $NMe_2$). In certain embodiments, $R^{QA}$ is NHC(=O)($C_{1-3}$ alkyl), NHC(=O)($C_{3-6}$ cycloalkyl), or $NHS(O)_2(C_{1-3}$ alkyl).

In some embodiments of Formula (ID), $R^{QA}$ is 5-6 membered heterocyclyl optionally substituted with one or more substituents each independently selected from the group consisting of $C_{1-6}$ alkyl and C(=O)($C_{1-6}$ alkyl).

In some embodiments of Formula (ID), $R^{QA}$ is $C_{1-6}$ alkoxy optionally substituted with from 1-6 independently selected halo. In certain of these embodiments, $R^{QA}$ is —OMe, —$OCF_3$, or —$OCHF_2$.

In some embodiments of Formula (ID), $R^{QA}$ is $C_{1-3}$ alkyl. In certain of these embodiments, $R^{QA}$ is methyl. In some embodiments of Formula (ID), $R^{QA}$ is $C_{1-3}$ alkyl substituted with from 1-3 independently selected halo. In certain of these embodiments, $R^{QA}$ is —$CF_3$ or —$CHF_2$.

In some embodiments of Formula (ID), $R^{QC}$ is H.

In some embodiments of Formula (ID), $R^{QC}$ is halo. In certain of these embodiments, $R^{QC}$ is —F. In certain embodiments, $R^{QC}$ is meta to P(=O)$R^aR^b$. In certain embodiments, $R^{QC}$ is meta to P(=O)$R^aR^b$ and ortho to $R^{QA}$. In certain embodiments, $R^{QC}$ is —F which is ortho to $R^{QA}$. In certain embodiments, $R^{QC}$ is —F which is meta to P(=O)$R^aR^b$ and ortho to $R^{QA}$.

In some embodiments of Formula (ID), the compound is a compound of Formula (S, S, S)-(ID)

Formula (S, S, S)-(ID)

or a pharmaceutically acceptable salt thereof, wherein $R^3$ is $C_{1-3}$ alkyl.

In some embodiments, the compound of Formula (I) is a compound of Formula (IE):

Formula (IE)

or a pharmaceutically acceptable salt or solvate thereof, wherein:
$R^{AA}$, $R^{AB}$, and $R^{AC}$ are each independently halo or $C_{1-3}$ alkyl;
$R^3$ is H or $C_{1-3}$ alkyl;
$R^{QC}$ is H or halo;
$R^{QD}$ is selected from the group consisting of: (a) H; (b) —$NH_2$; (c) —$NH(C_{1-3}$ alkyl); (d) halo; (e) $C_{1-3}$ alkoxy optionally substituted with from 1-3 independently selected halo; and (f) $C_{1-3}$ alkyl optionally substituted with from 1-3 independently selected halo;
$R^a$ and $R^b$ are each independently selected from the group consisting of $C_{1-4}$ alkyl and $C_{3-6}$ cycloalkyl; or
$R^a$ and $R^b$ taken together with the phosphorous atom to which each is attached form a ring including from 5-8 ring atoms, wherein from 0-1 ring atom (in addition to the phosphorous attached to $R^a$ and $R^b$) is a heteroatom independently selected from the group consisting of: O, S, and N;
$R^{8c}$ is H or $C_{1-3}$ alkyl;
$X^B$ is CH or N; and
each $R^{Cb}$ is independently selected from the group consisting of H and $C_{1-3}$ alkyl.

In some embodiments of Formula (IE), $R^{AA}$ and $R^{AC}$ are each independently $C_{1-3}$ alkyl. For example, $R^{AA}$ and $R^{AC}$ can each be methyl.

In some embodiments of Formula (IE), $R^{AB}$ is halo. For example, $R^{AB}$ can be F.

In some embodiments of Formula (IE), $R^{AA}$ and $R^{AC}$ are each independently $C_{1-3}$ alkyl; and $R^{AB}$ is halo. For example, $R^{AA}$ and $R^{AC}$ can each be methyl; and $R^{AB}$ can be F.

In some embodiments of Formula (IE), $R^3$ is $C_{1-3}$ alkyl. For example, $R^3$ can be methyl.

In some embodiments of Formula (IE), $R^{QD}$ is H.

In some embodiments of Formula (IE), $R^{QD}$ is selected from the group consisting of —$NH_2$ and —$NH(C_{1-3}$ alkyl). For example, $R^{QD}$ can be —$NH_2$. As another non-limiting example, $R^{QD}$ can be —NHMe. As a further non-limiting example, $R^{QD}$ can be —NHEt.

In some embodiments of Formula (IE), $R^{QD}$ is halo. For example, $R^{QD}$ can be —F or —Cl.

In some embodiments of Formula (IE), $R^{QD}$ is $C_{1-3}$ alkoxy optionally substituted with from 1-3 independently selected halo. For example, $R^{QD}$ can be —OMe. As another non-limiting example, $R^{QD}$ can be $OCF_3$. As a further non-limiting example, $R^{QD}$ can be $OCHF_2$.

In some embodiments of Formula (IE), $R^{QD}$ is $C_{1-3}$ alkyl optionally substituted with from 1-3 independently selected halo. For example, $R^{QD}$ can be methyl. As another non-limiting example, $R^{QD}$ can be $CF_3$. As another non-limiting example, $R^3$ can be —$CHF_2$.

In some embodiments of Formula (IE), $R^a$ and $R^b$ are each an independently selected $C_{1-4}$ alkyl. For example, $R^a$ and $R^b$ can each be methyl. As another non-limiting example, $R^a$ and $R^b$ can each be ethyl. As a further non-limiting example, $R^a$ and $R^b$ can each be isopropyl. As a further non-limiting example, $R^a$ can be methyl; and $R^b$ can be tert-butyl.

In some embodiments of Formula (IE), $R^a$ and $R^b$ are each an independently selected $C_{3-6}$ cycloalkyl. For example, $R^a$ and $R^b$ can each be cyclopropyl.

In some embodiments of Formula (IE), $R^a$ and $R^b$ taken together with the phosphorous atom to which each is attached form a ring including from 5-8 ring atoms, wherein from 0-1 ring atom (in addition to the phosphorous attached to $R^a$ and $R^b$) is a heteroatom independently selected from the group consisting of: O, S, and N. For example, $R^a$ and $R^b$ taken together with the phosphorous atom to which each is attached can form.

In some embodiments of Formula (IE), $R^{QC}$ is H.

In some embodiments of Formula (IE), $R^{QC}$ is halo. For example, $R^{QC}$ can be —F. In some embodiments, $R^{QC}$ is ortho to $R^{QD}$. In some embodiments, $R^{QC}$ is para to $R^{QD}$. In some embodiments, $R^{QC}$ is meta to $R^{QD}$.

In some embodiments of Formula (IE), $R^{8c}$ is H. In some embodiments of Formula (IE), $R^{8c}$ is $C_{1-3}$ alkyl. For example, $R^{8c}$ can be methyl.

In some embodiments of Formula (IE), $X^B$ is CH. In some embodiments of Formula (IE), $X^B$ is N.

In some embodiments of Formula (IE), each $R^{Cb}$ is H. In some embodiments of Formula (IE), each $R^{Cb}$ is an independently selected $C_{1-3}$ alkyl. For example, each $R^{Cb}$ can be methyl.

In some embodiments of Formula (IE), $X^B$ is CH; and each $R^{Cb}$ is H. In some embodiments of Formula (IE), $X^B$ is CH; and each $R^{Cb}$ is an independently selected $C_{1-3}$ alkyl (e.g., methyl). In some embodiments of Formula (IE), $X^B$ is N; and each $R^{Cb}$ is H. In some embodiments of Formula (IE), $X^B$ is N; and each $R^{Cb}$ is an independently selected $C_{1-3}$ alkyl (e.g., methyl).

In some embodiments of Formula (IE), the compound is a compound of Formula (S, S, S)-(IE)

Formula (S, S, S)-(IE)

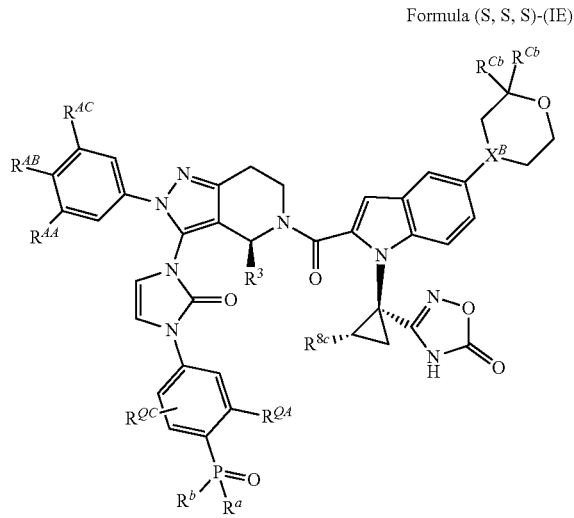

or a pharmaceutically acceptable salt thereof, wherein $R^3$ is $C_{1-3}$ alkyl.

In some embodiments of Formula (IE).

$R^{AA}$ and $R^{AC}$ are methyl;

$R^{AB}$ is —F;

$R^3$ is methyl;

$R^{QC}$ is H or —F;

$R^{QD}$ is selected from the group consisting of: H; —NHMe; —NHEt; —NH$_2$; —OMe; —OCF$_3$; —OCHF$_2$; -Me; —CF$_3$; and —CHF$_2$;

$R^a$ and $R^b$ are independently selected from the group consisting of: methyl, ethyl, isopropyl, tert-butyl, and cyclopropyl;

$R^{8c}$ is H or methyl;

$X^B$ is CH; and each $R^{Cb}$ is independently H or methyl.

In certain of these embodiments, the compound is a compound of Formula Formula (S, S, S)-(IE).

In some embodiments, a compound of Formula (I) is selected from the group consisting of the compounds in Table C1 or a pharmaceutically acceptable salt or solvate thereof.

TABLE C1

| Compound # | Structure |
|---|---|
| 101 | 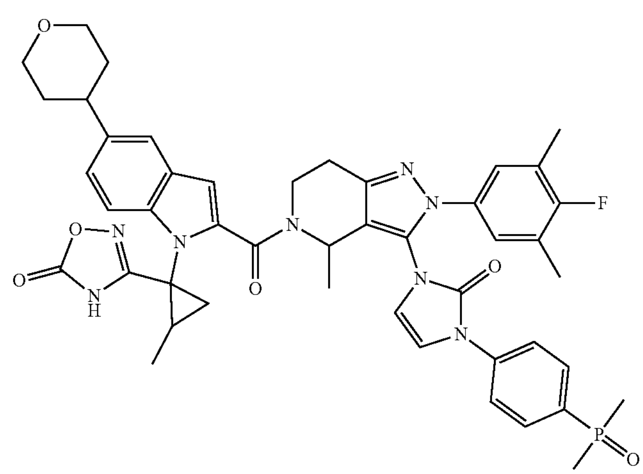 [SMILES: Cc1cc(-n2nc3c(c2-n2ccn(-c4ccc(P(C)(C)=O)cc4)c2=O)C(C)N(C(=O)c2cc4cc(C5CCOCC5)ccc4n2C2(c4noc(=O)[nH]4)CC2C)CC3)cc(C)c1F] |

TABLE C1-continued

| Compound # | Structure |
|---|---|
| 102 | 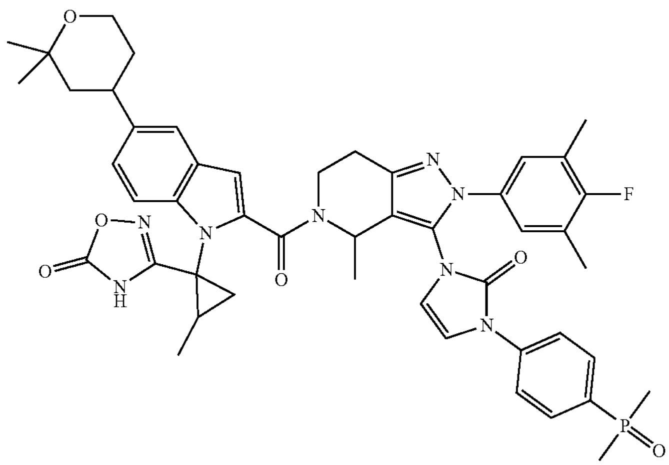 [SMILES: Cc1cc(-n2nc3c(c2-n2ccn(-c4ccc(P(C)(C)=O)cc4)c2=O)C(C)N(C(=O)c2cc4cc(C5CCOC(C)(C)C5)ccc4n2C2(c4noc(=O)[nH]4)CC2C)CC3)cc(C)c1F] |
| 103 | 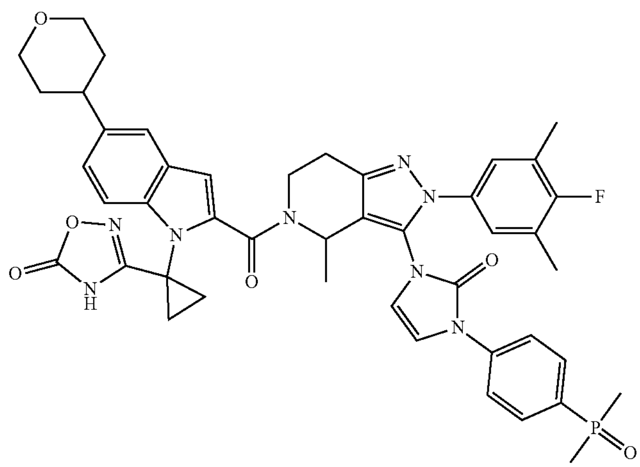 [SMILES: Cc1cc(-n2nc3c(c2-n2ccn(-c4ccc(P(C)(C)=O)cc4)c2=O)C(C)N(C(=O)c2cc4cc(C5CCOCC5)ccc4n2C2(c4noc(=O)[nH]4)CC2)CC3)cc(C)c1F] |
| 104 | 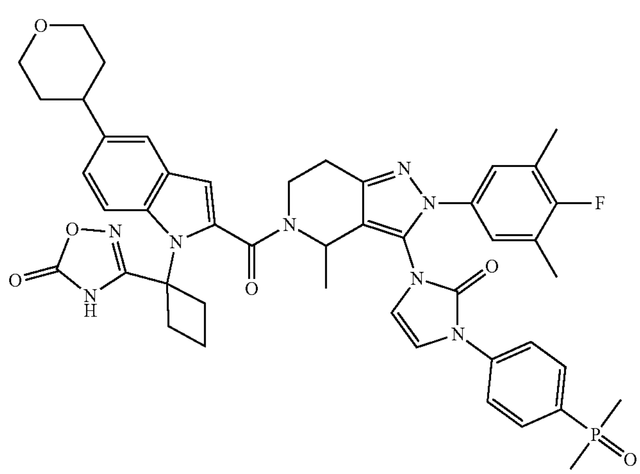 [SMILES: Cc1cc(-n2nc3c(c2-n2ccn(-c4ccc(P(C)(C)=O)cc4)c2=O)C(C)N(C(=O)c2cc4cc(C5CCOCC5)ccc4n2C2(c4noc(=O)[nH]4)CCC2)CC3)cc(C)c1F] |

TABLE C1-continued

| Compound # | Structure |
|---|---|
| 105 | 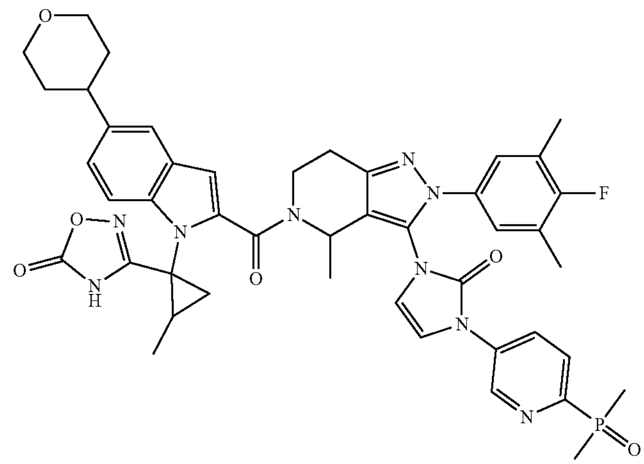 [SMILES: Cc1cc(-n2nc3c(c2-n2ccn(-c4ccc(P(C)(C)=O)nc4)c2=O)C(C)N(C(=O)c2cc4cc(C5CCOCC5)ccc4n2C2(c4noc(=O)[nH]4)CC2C)CC3)cc(C)c1F] |
| 106 | 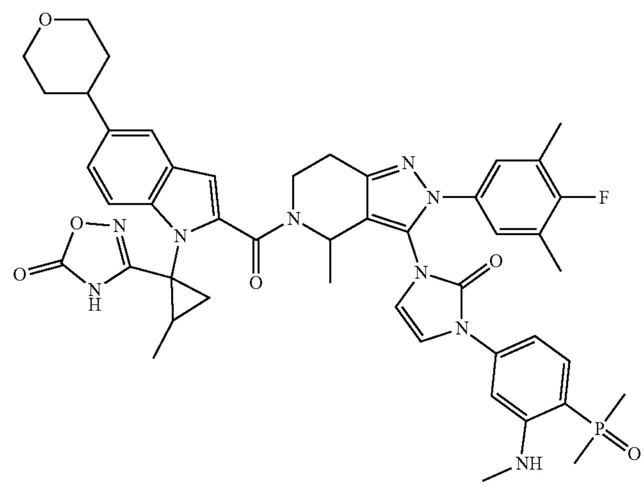 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)ccc1P(C)(C)=O] |
| 107 | 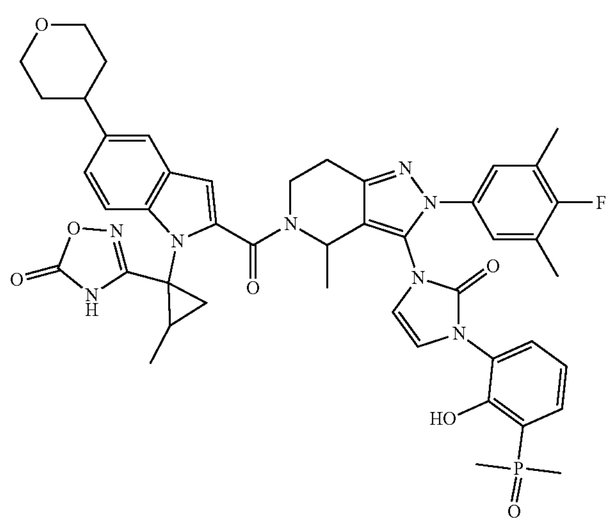 [SMILES: Cc1cc(-n2nc3c(c2-n2ccn(-c4cccc(P(C)(C)=O)c4O)c2=O)C(C)N(C(=O)c2cc4cc(C5CCOCC5)ccc4n2C2(c4noc(=O)[nH]4)CC2C)CC3)cc(C)c1F] |

TABLE C1-continued

| Compound # | Structure |
|---|---|
| 108 | 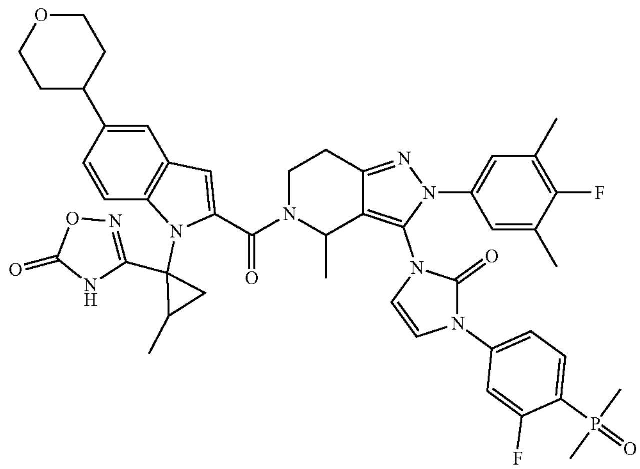 [SMILES: Cc1cc(-n2nc3c(c2-n2ccn(-c4ccc(P(C)(C)=O)c(F)c4)c2=O)C(C)N(C(=O)c2cc4cc(C5CCOCC5)ccc4n2C2(c4noc(=O)[nH]4)CC2C)CC3)cc(C)c1F] |
| 109 | 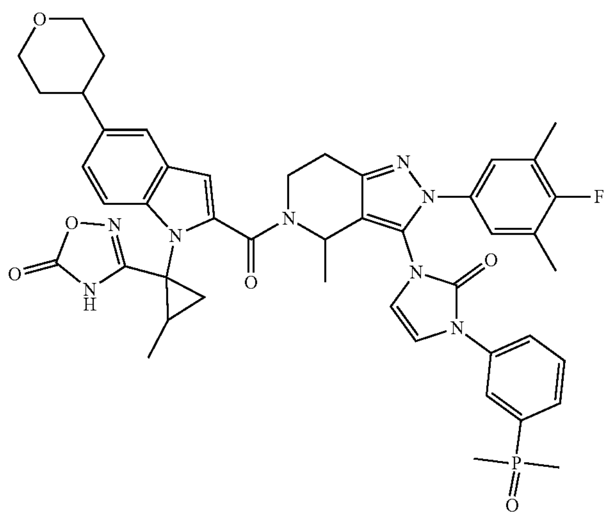 [SMILES: Cc1cc(-n2nc3c(c2-n2ccn(-c4cccc(P(C)(C)=O)c4)c2=O)C(C)N(C(=O)c2cc4cc(C5CCOCC5)ccc4n2C2(c4noc(=O)[nH]4)CC2C)CC3)cc(C)c1F] |
| 110 | 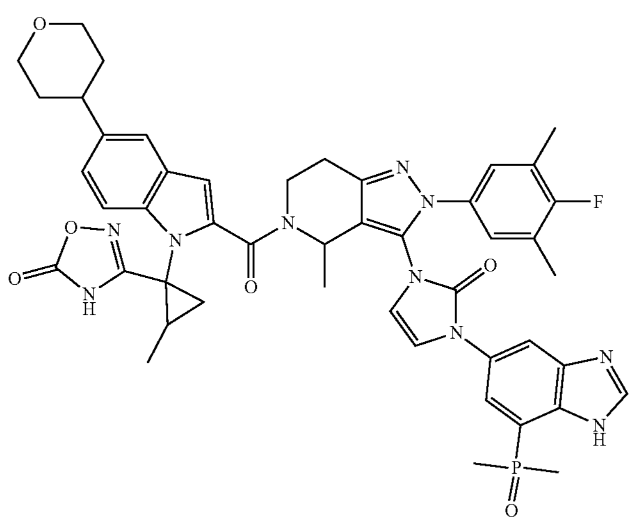 [SMILES: Cc1cc(-n2nc3c(c2-n2ccn(-c4cc(P(C)(C)=O)c5[nH]cnc5c4)c2=O)C(C)N(C(=O)c2cc4cc(C5CCOCC5)ccc4n2C2(c4noc(=O)[nH]4)CC2C)CC3)cc(C)c1F] |

TABLE C1-continued

| Compound # | Structure |
|---|---|
| 111 | 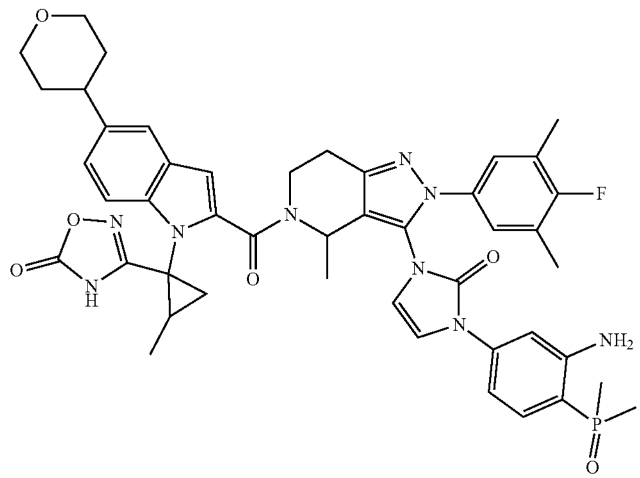 [SMILES: Cc1cc(-n2nc3c(c2-n2ccn(-c4ccc(P(C)(C)=O)c(N)c4)c2=O)C(C)N(C(=O)c2cc4cc(C5CCOCC5)ccc4n2C2(c4noc(=O)[nH]4)CC2C)CC3)cc(C)c1F] |
| 112 | 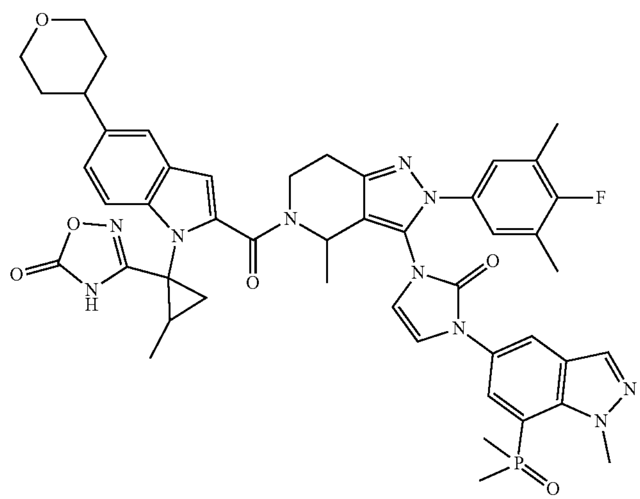 [SMILES: Cc1cc(-n2nc3c(c2-n2ccn(-c4cc(P(C)(C)=O)c5c(cnn5C)c4)c2=O)C(C)N(C(=O)c2cc4cc(C5CCOCC5)ccc4n2C2(c4noc(=O)[nH]4)CC2C)CC3)cc(C)c1F] |
| 113 | 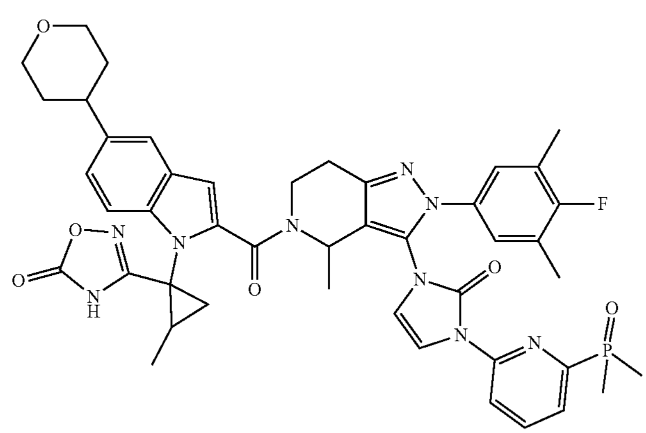 [SMILES: Cc1cc(-n2nc3c(c2-n2ccn(-c4cccc(P(C)(C)=O)n4)c2=O)C(C)N(C(=O)c2cc4cc(C5CCOCC5)ccc4n2C2(c4noc(=O)[nH]4)CC2C)CC3)cc(C)c1F] |

TABLE C1-continued
| Compound # | Structure |
|---|---|
| 114 | 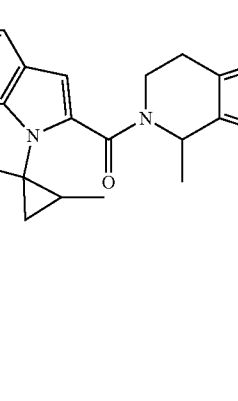 |
| 115 | 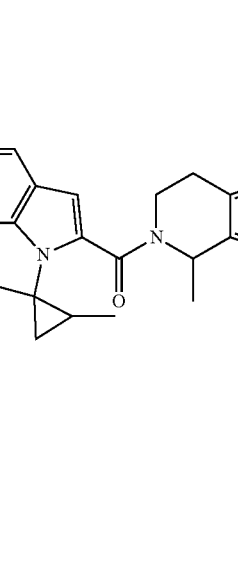 |
| 116 | 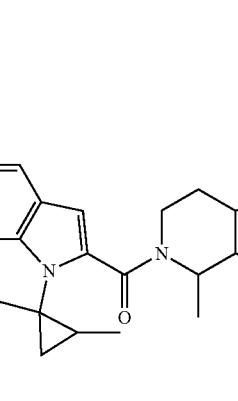 |

TABLE C1-continued

| Compound # | Structure |
|---|---|
| 117 | 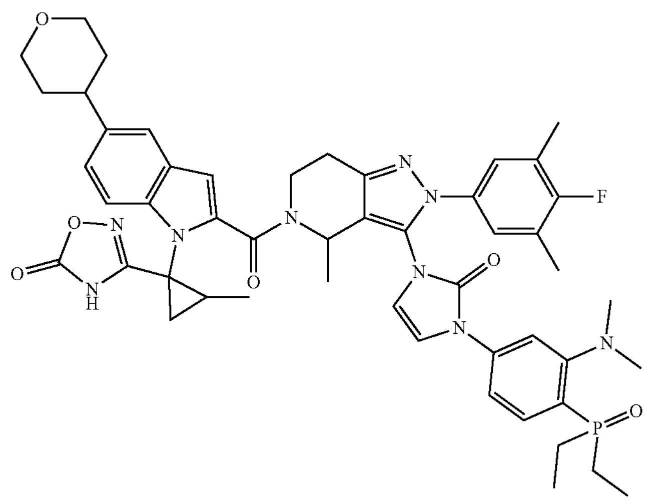 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1N(C)C] |
| 118 | 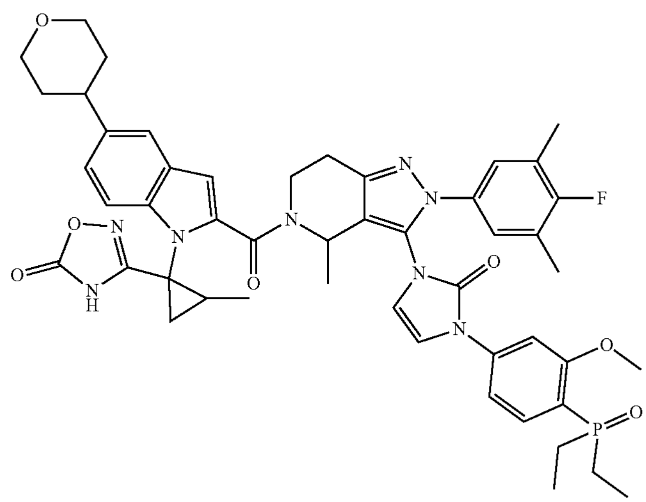 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1OC] |
| 119 | 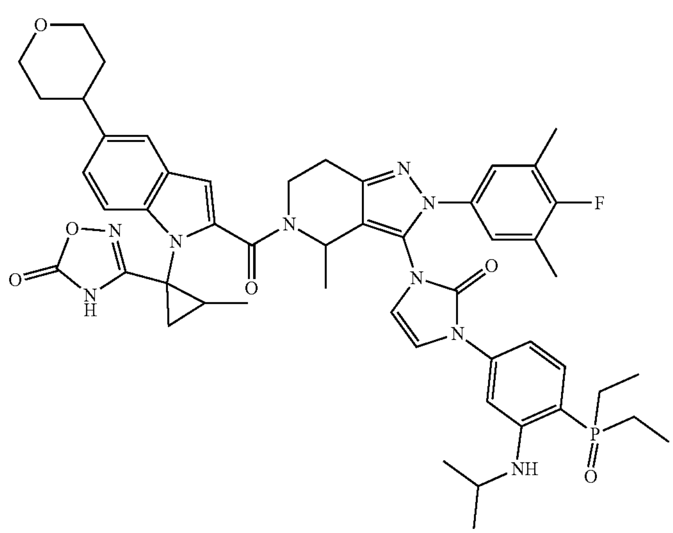 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC(C)C] |

TABLE C1-continued

| Compound # | Structure |
|---|---|
| 120 | 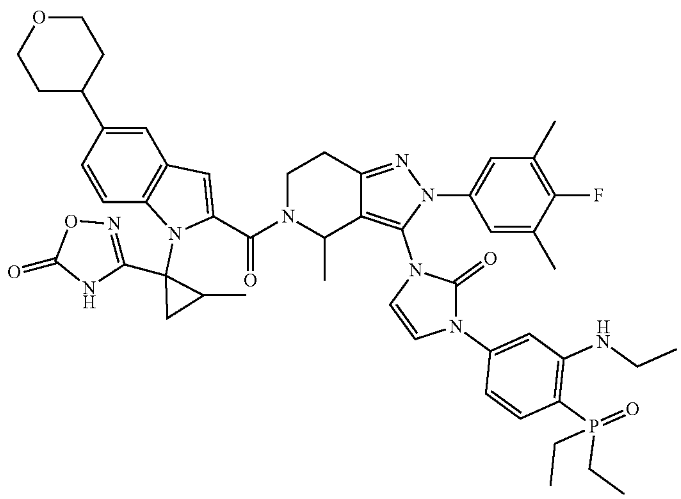 [SMILES: CCNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)ccc1P(=O)(CC)CC] |
| 121 | 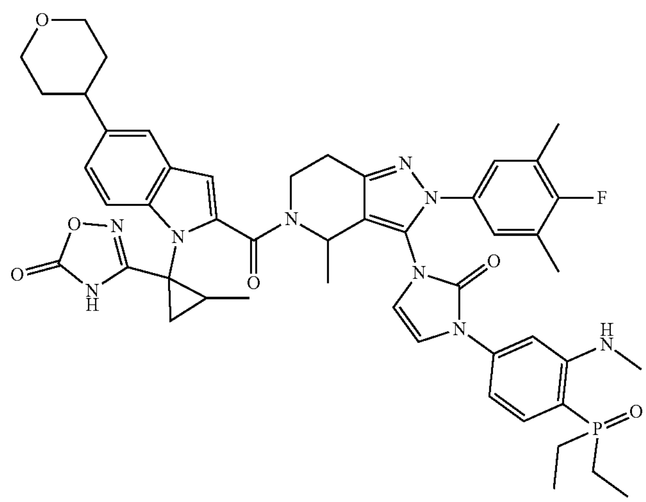 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC] |
| 122 | 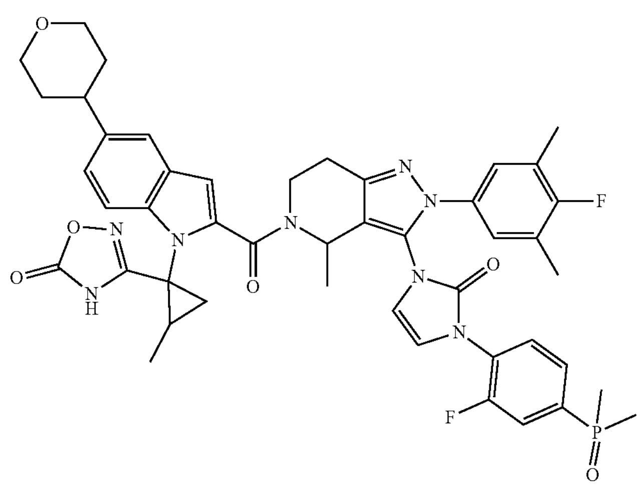 [SMILES: Cc1cc(-n2nc3c(c2-n2ccn(-c4ccc(P(C)(C)=O)cc4F)c2=O)C(C)N(C(=O)c2cc4cc(C5CCOCC5)ccc4n2C2(c4noc(=O)[nH]4)CC2C)CC3)cc(C)c1F] |

TABLE C1-continued
| Compound # | Structure |
|---|---|
| 123 | 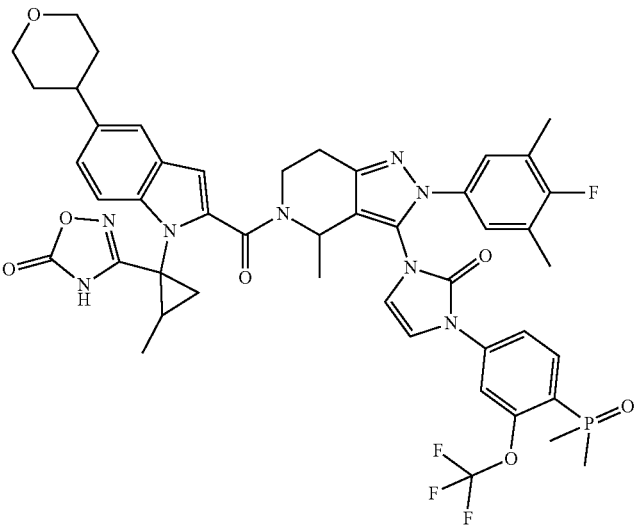 [SMILES: Cc1cc(-n2nc3c(c2-n2ccn(-c4ccc(P(C)(C)=O)c(OC(F)(F)F)c4)c2=O)C(C)N(C(=O)c2cc4cc(C5CCOCC5)ccc4n2C2(c4noc(=O)[nH]4)CC2C)CC3)cc(C)c1F] |
| 124 | 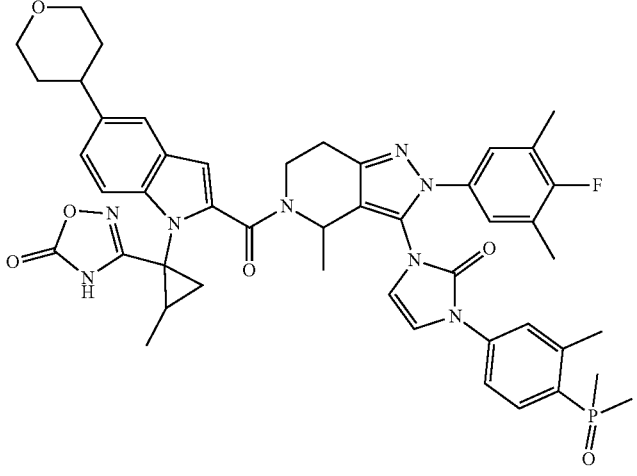 [SMILES: Cc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)ccc1P(C)(C)=O] |
| 125 | 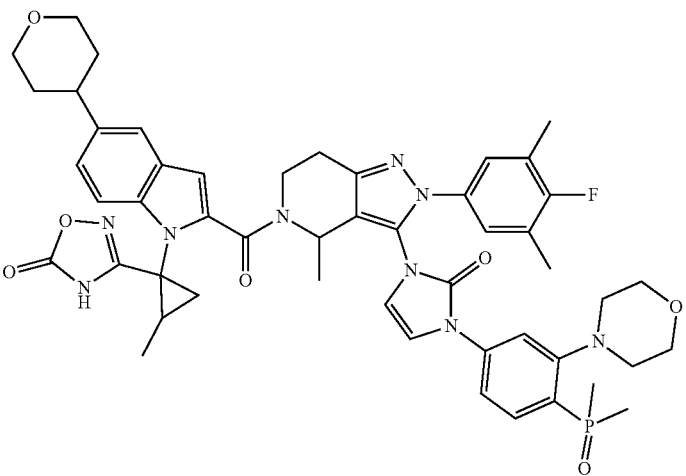 [SMILES: Cc1cc(-n2nc3c(c2-n2ccn(-c4ccc(P(C)(C)=O)c(N5CCOCC5)c4)c2=O)C(C)N(C(=O)c2cc4cc(C5CCOCC5)ccc4n2C2(c4noc(=O)[nH]4)CC2C)CC3)cc(C)c1F] |

TABLE C1-continued

| Compound # | Structure |
|---|---|
| 126 | 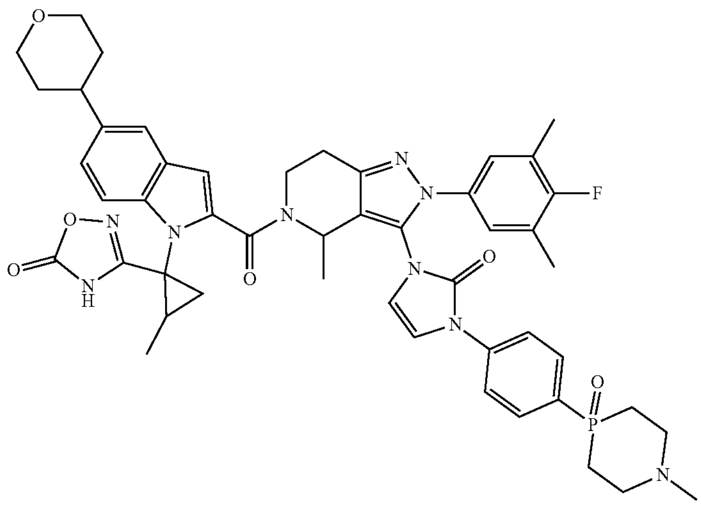 [SMILES: Cc1cc(-n2nc3c(c2-n2ccn(-c4ccc(P5(=O)CCN(C)CC5)cc4)c2=O)C(C)N(C(=O)c2cc4cc(C5CCOCC5)ccc4n2C2(c4noc(=O)[nH]4)CC2C)CC3)cc(C)c1F] |
| 127 | 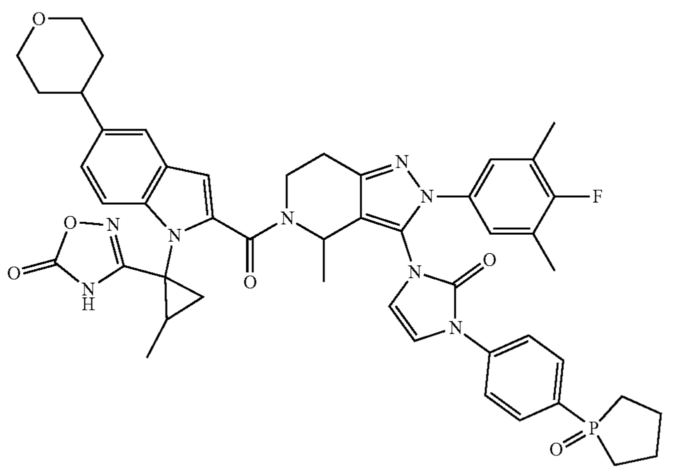 [SMILES: Cc1cc(-n2nc3c(c2-n2ccn(-c4ccc(P5(=O)CCCC5)cc4)c2=O)C(C)N(C(=O)c2cc4cc(C5CCOCC5)ccc4n2C2(c4noc(=O)[nH]4)CC2C)CC3)cc(C)c1F] |
| 128 | 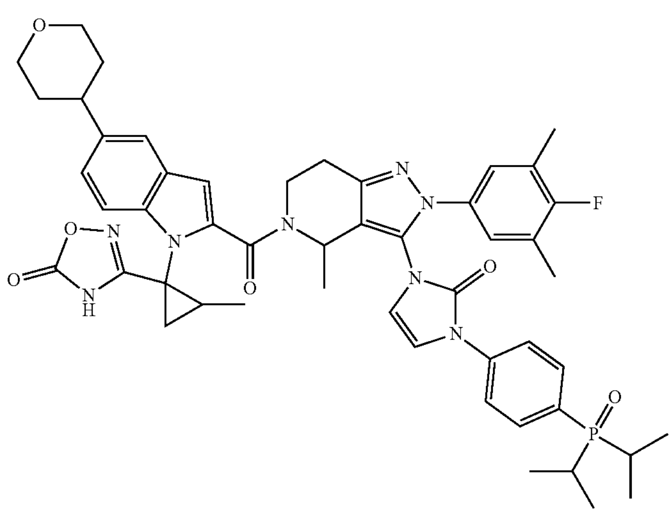 [SMILES: Cc1cc(-n2nc3c(c2-n2ccn(-c4ccc(P(=O)(C(C)C)C(C)C)cc4)c2=O)C(C)N(C(=O)c2cc4cc(C5CCOCC5)ccc4n2C2(c4noc(=O)[nH]4)CC2C)CC3)cc(C)c1F] |

TABLE C1-continued
| Compound # | Structure |
|---|---|
| 129 | 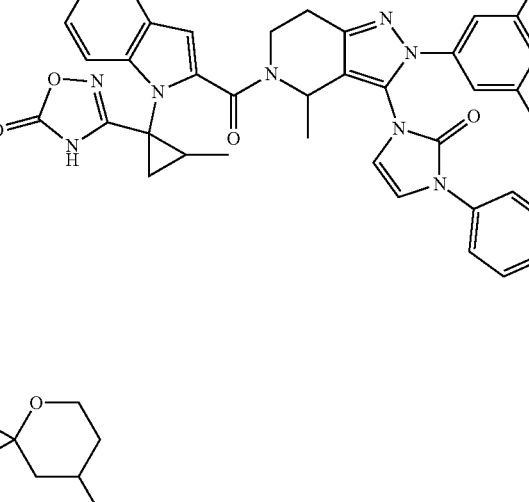 |
| 130 | 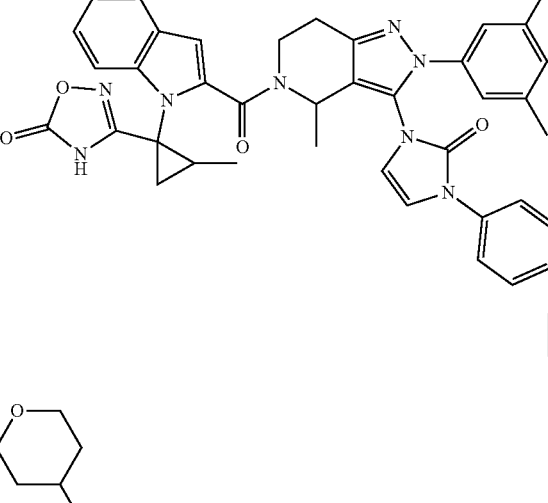 |
| 131 | 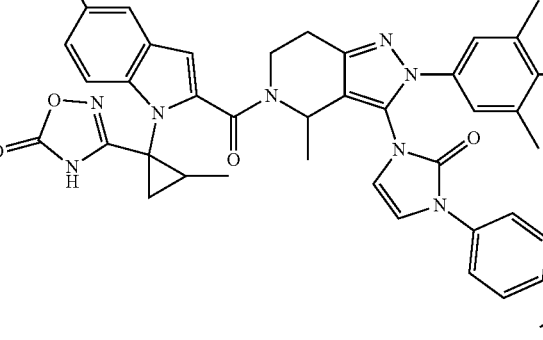 |

TABLE C1-continued
| Compound # | Structure |
|---|---|
| 132 | 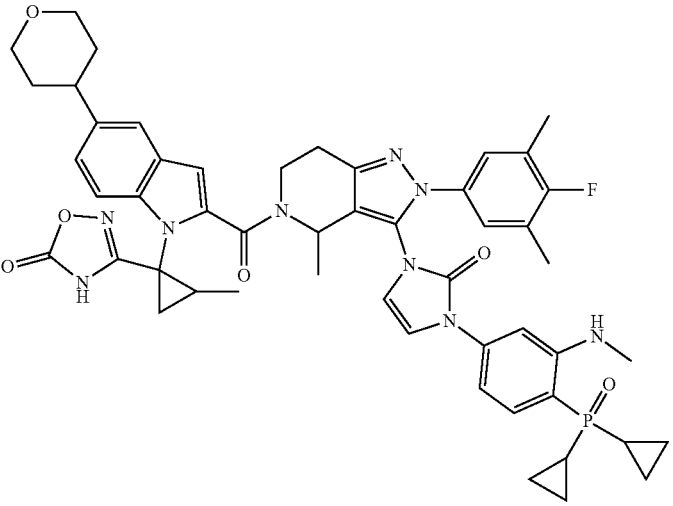 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)ccc1P(=O)(C1CC1)C1CC1] |
| 133 | 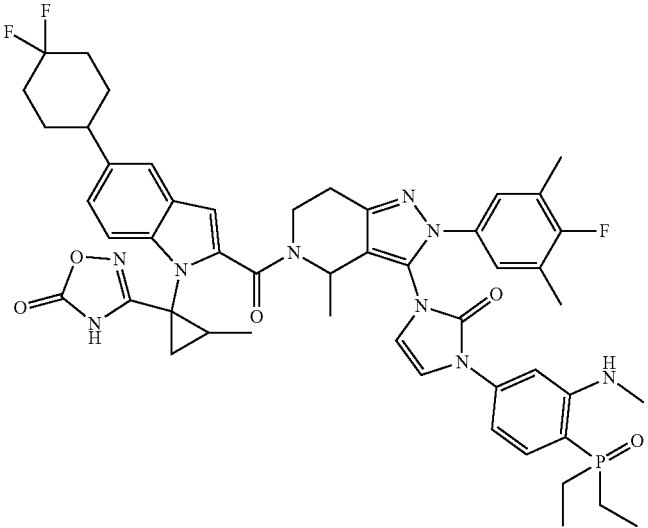 [SMILES: CCP(=O)(CC)c1ccc(-n2ccn(-c3c4c(nn3-c3cc(C)c(F)c(C)c3)CCN(C(=O)c3cc5cc(C6CCC(F)(F)CC6)ccc5n3C3(c5noc(=O)[nH]5)CC3C)C4C)c2=O)cc1NC] |
| 134 | 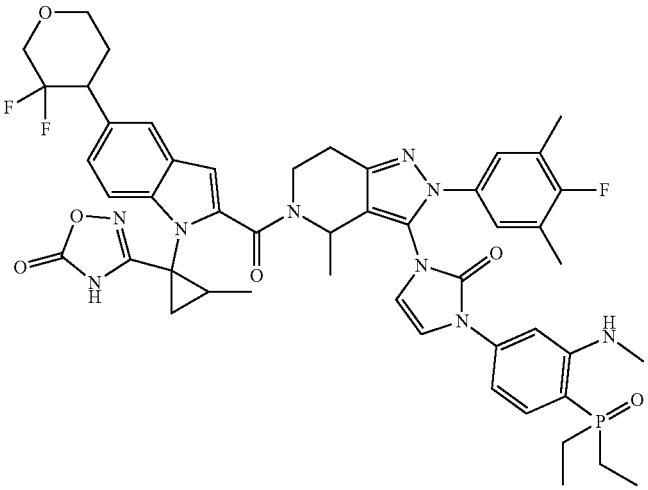 [SMILES: CCP(=O)(CC)c1ccc(-n2ccn(-c3c4c(nn3-c3cc(C)c(F)c(C)c3)CCN(C(=O)c3cc5cc(C6CCOCC6(F)F)ccc5n3C3(c5noc(=O)[nH]5)CC3C)C4C)c2=O)cc1NC] |

TABLE C1-continued
| Compound # | Structure |
|---|---|
| 135 | 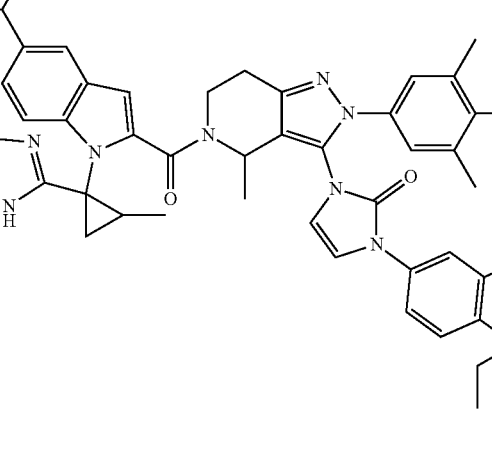 |
| 136 | 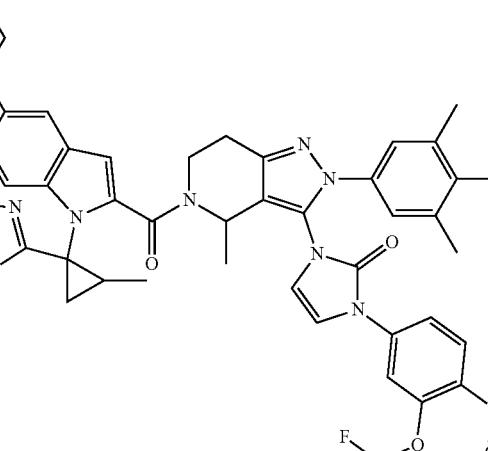 |
| 137 | 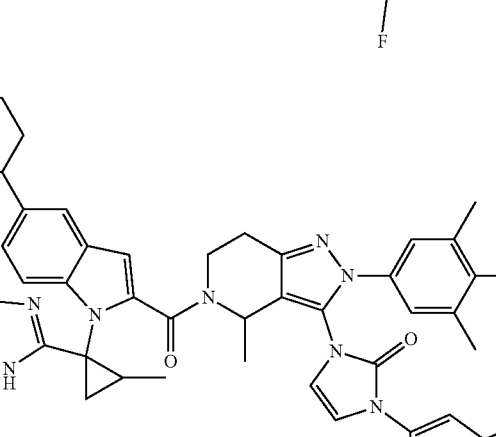 |

TABLE C1-continued

| Compound # | Structure |
|---|---|
| 138 | 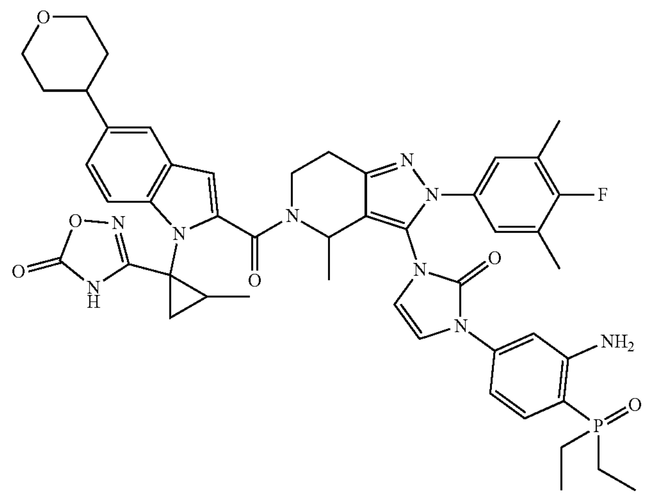 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1N] |
| 139 | 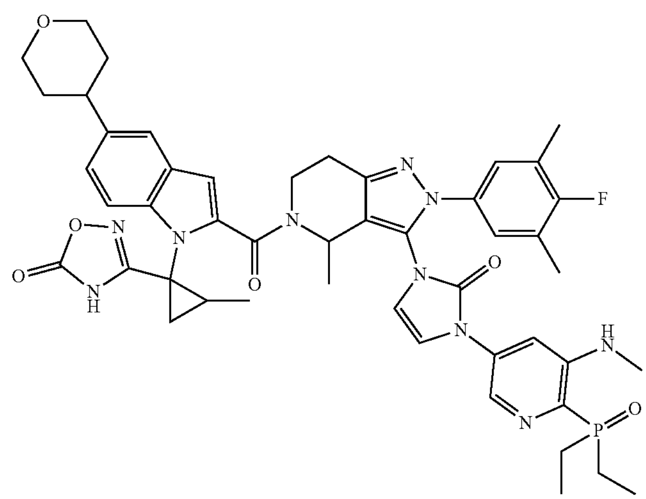 [SMILES: CCP(=O)(CC)c1ncc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC] |
| 140 | 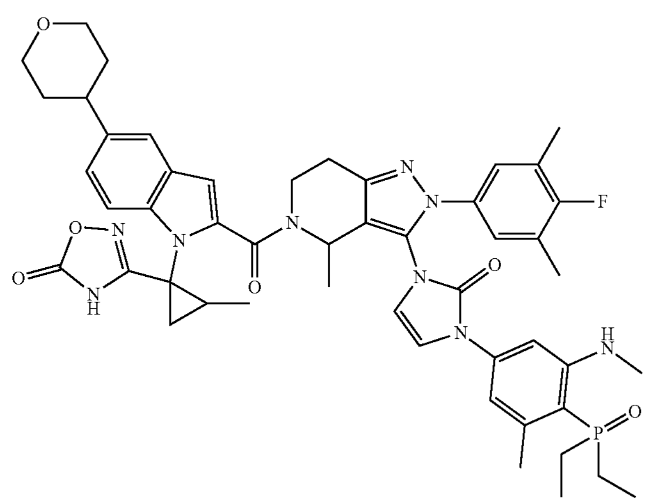 [SMILES: CCP(=O)(CC)c1c(C)cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC] |

TABLE C1-continued

| Compound # | Structure |
|---|---|
| 141 | 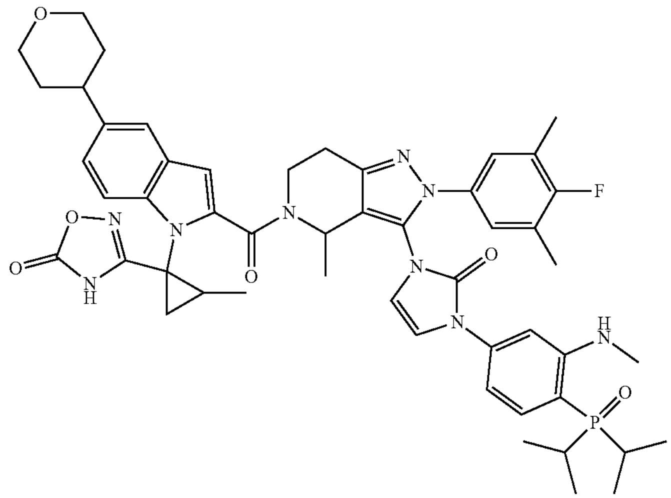 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)ccc1P(=O)(C(C)C)C(C)C] |
| 142 | 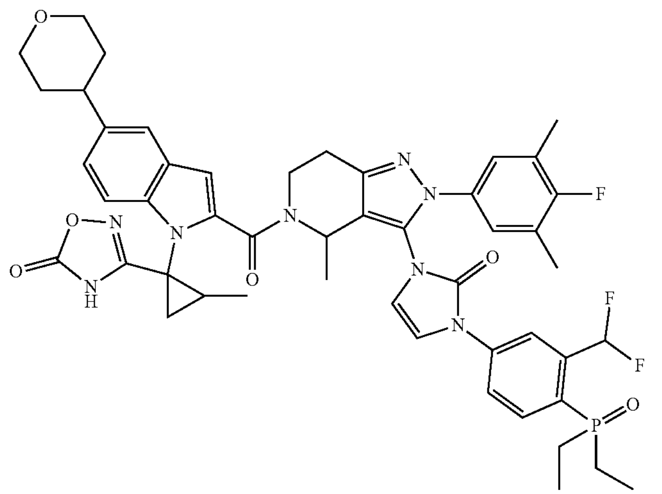 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1C(F)F] |
| 143 | 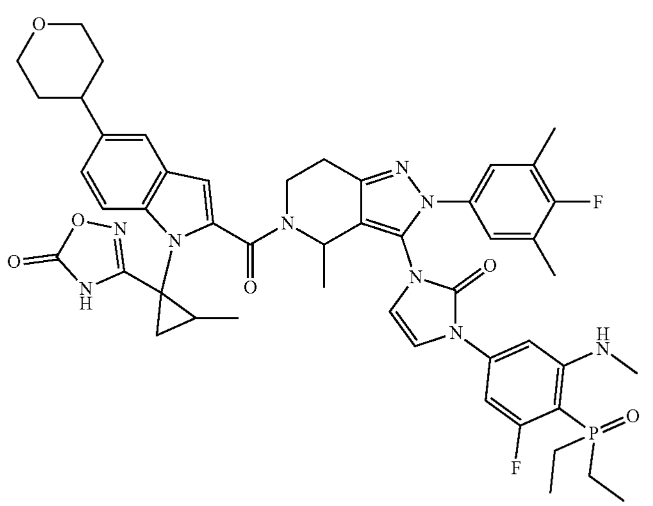 [SMILES: CCP(=O)(CC)c1c(F)cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC] |

TABLE C1-continued
| Compound # | Structure |
|---|---|
| 144 | 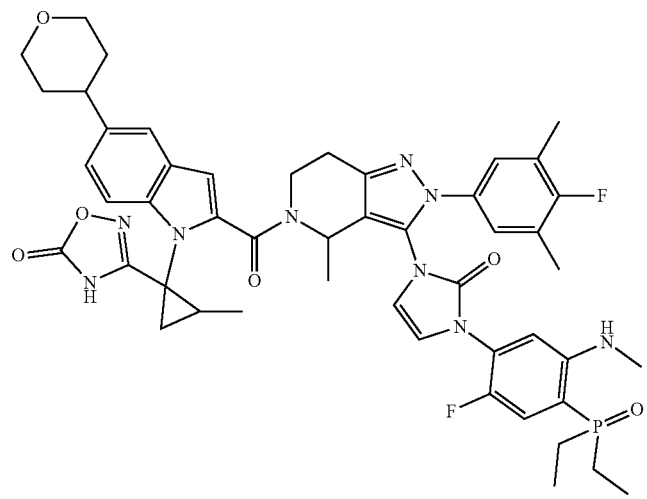 [SMILES: CCP(=O)(CC)c1cc(F)c(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)cc1NC] |
| 145 | 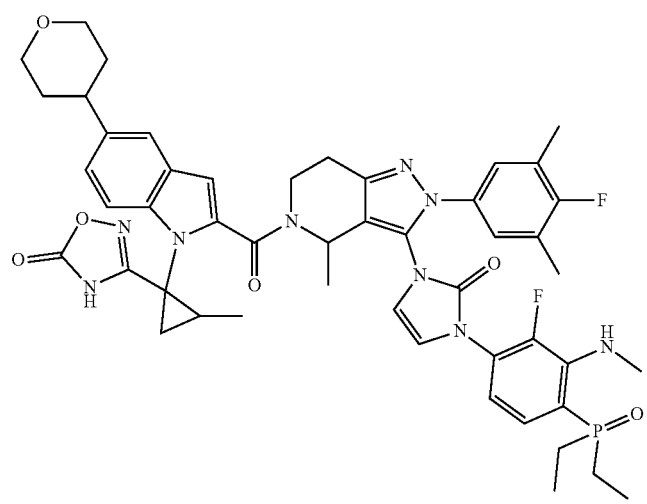 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3C)C4C)c2=O)c(F)c1NC] |
| 146 | 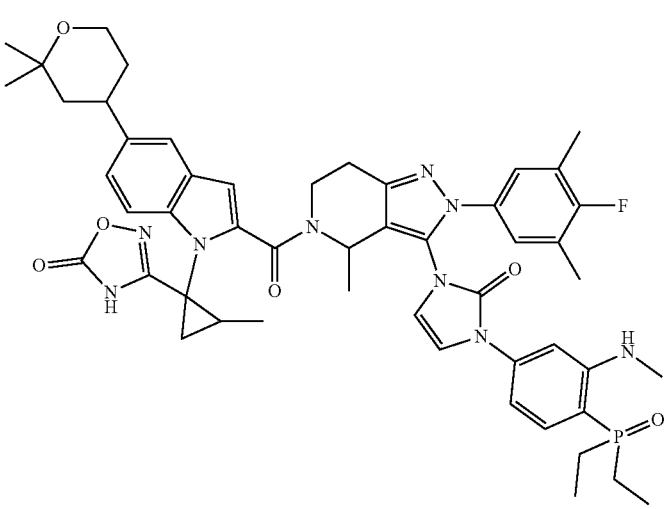 |

TABLE C1-continued
| Compound # | Structure |
|---|---|
| 147 | 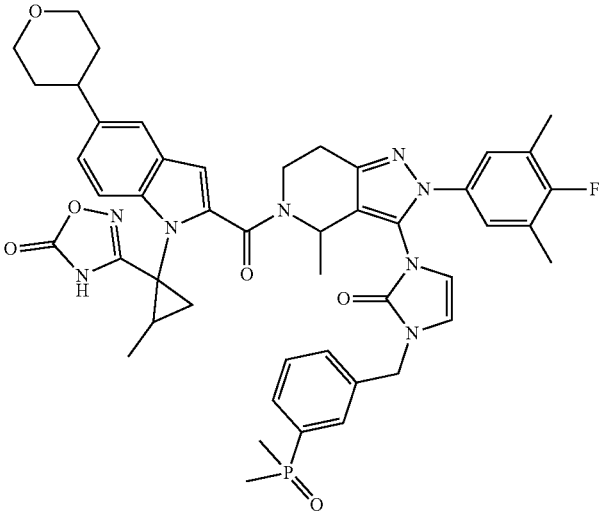 [SMILES: Cc1cc(-n2nc3c(c2-n2ccn(Cc4cccc(P(C)(C)=O)c4)c2=O)C(C)N(C(=O)c2cc4cc(C5CCOCC5)ccc4n2C2(c4noc(=O)[nH]4)CC2C)CC3)cc(C)c1F] |
| 148 | 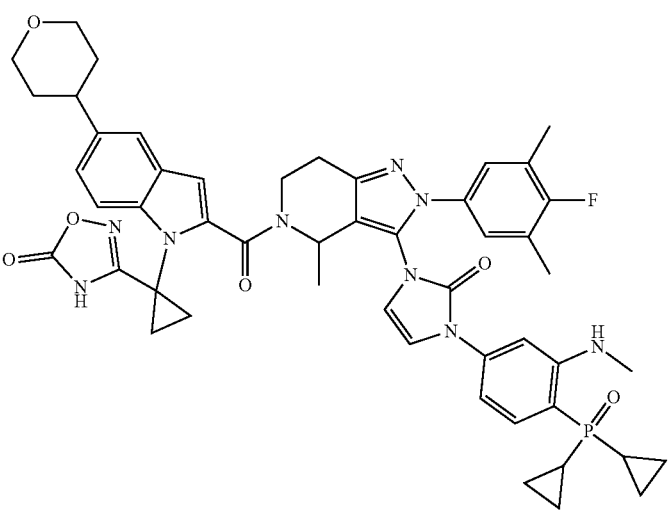 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)C4C)c2=O)ccc1P(=O)(C1CC1)C1CC1] |

TABLE C1-continued
| Compound # | Structure |
|---|---|
| 149 | 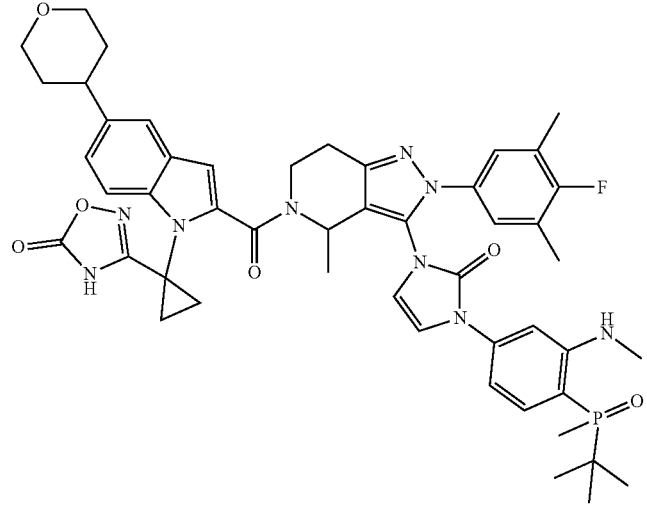 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)C4C)c2=O)ccc1P(C)(=O)C(C)(C)C] |
| 150 | 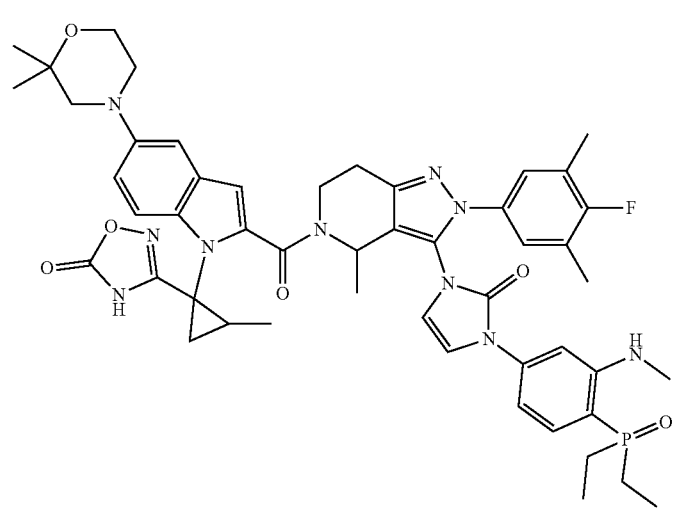 |

In some embodiments, the compound is selected from the group consisting of the compounds in Table C2 or a pharmaceutically acceptable salt or solvate thereof.
TABLE C2
| Compound # | Structure |
|---|---|
| 101a | 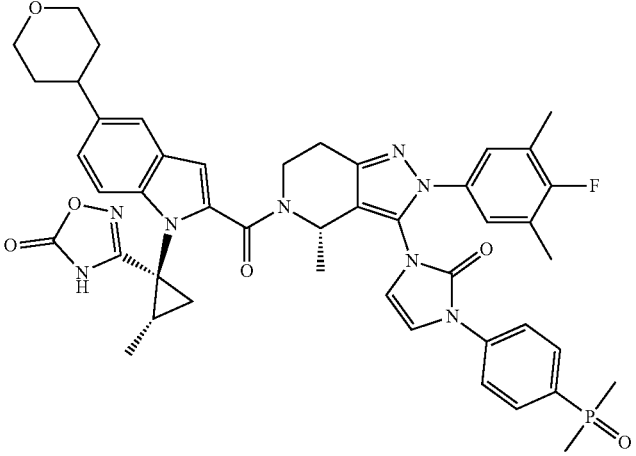 |
| 102a | 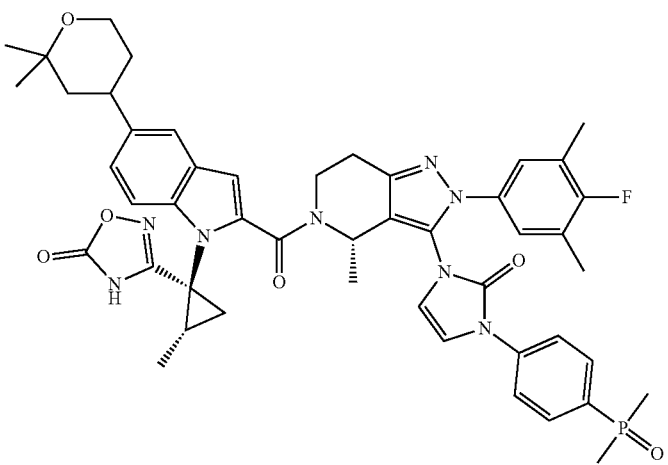 [SMILES: Cc1cc(-n2nc3c(c2-n2ccn(-c4ccc(P(C)(C)=O)cc4)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] |
| 103a | 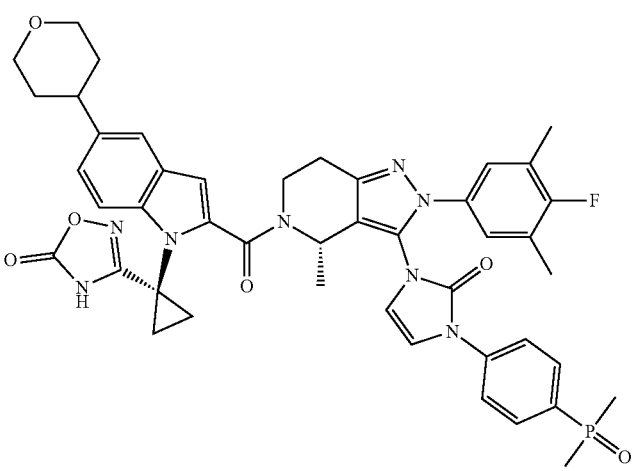 |

TABLE C2-continued

| Compound # | Structure |
| --- | --- |
| 104a | 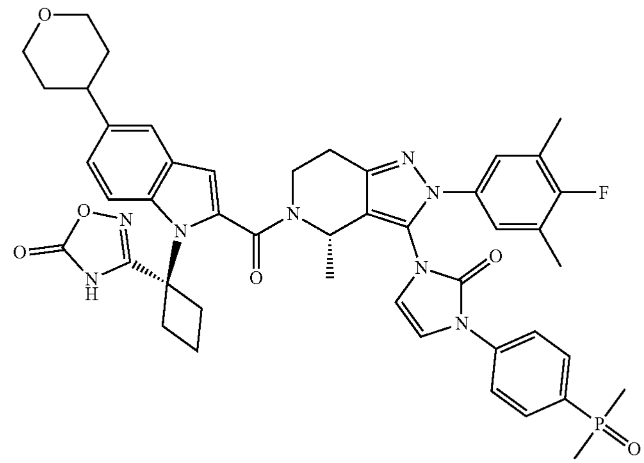 |
| 105a | 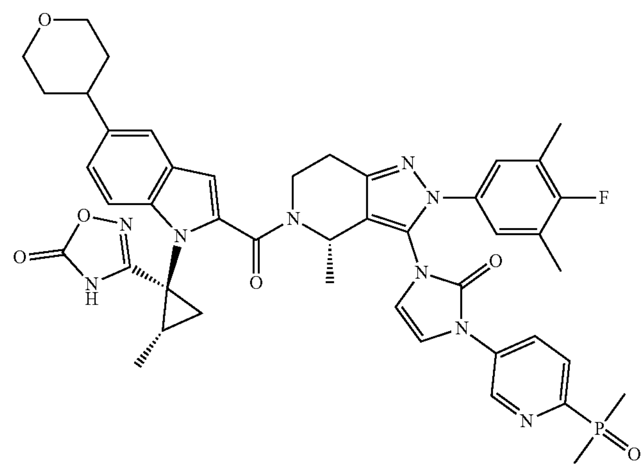 [SMILES: Cc1cc(-n2nc3c(c2-n2ccn(-c4ccc(P(C)(C)=O)nc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 106a | 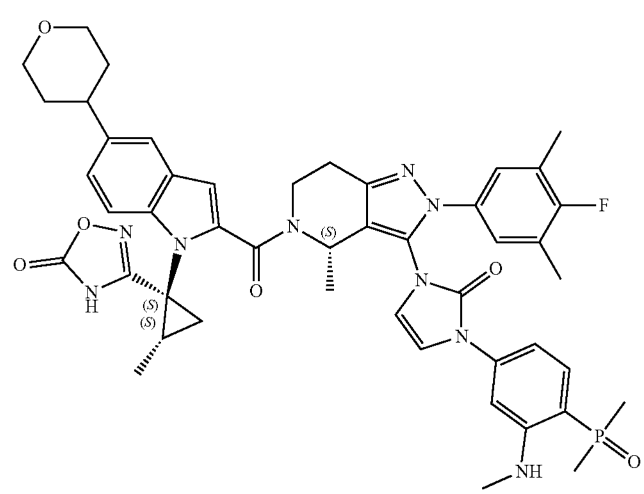 |

TABLE C2-continued

| Compound # | Structure |
|---|---|
| 107a | 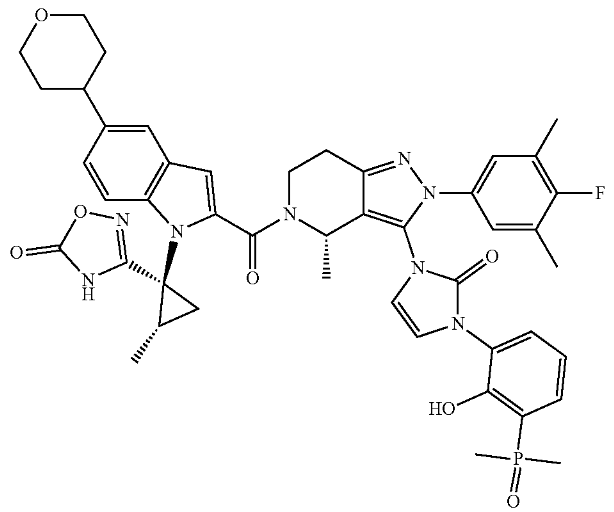 [SMILES: Cc1cc(-n2nc3c(c2-n2ccn(-c4cccc(P(C)(C)=O)c4O)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 108a | 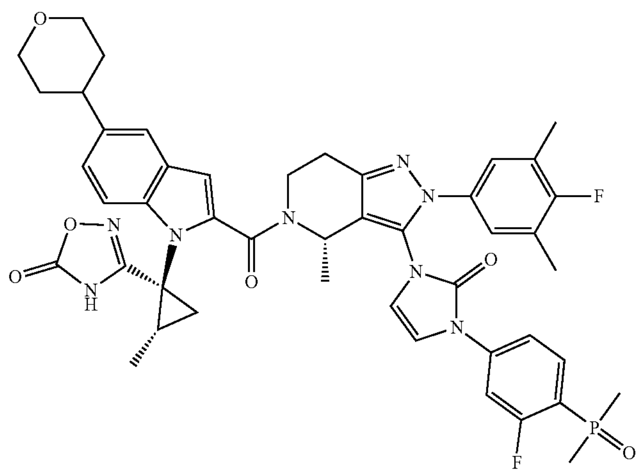 [SMILES: Cc1cc(-n2nc3c(c2-n2ccn(-c4ccc(P(C)(C)=O)c(F)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 109a | 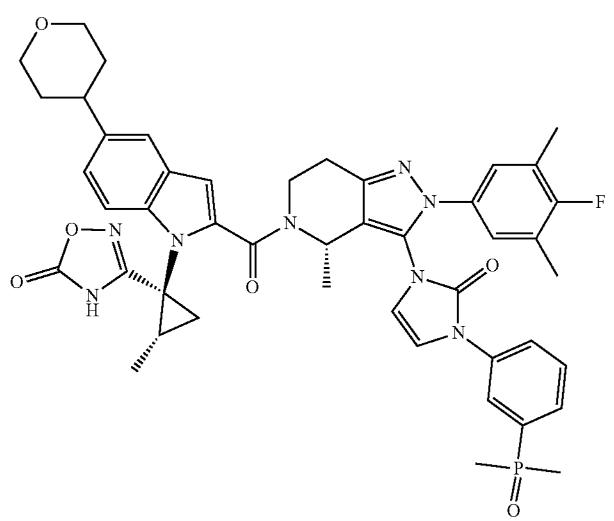 [SMILES: Cc1cc(-n2nc3c(c2-n2ccn(-c4cccc(P(C)(C)=O)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE C2-continued

| Compound # | Structure |
|---|---|
| 110a | 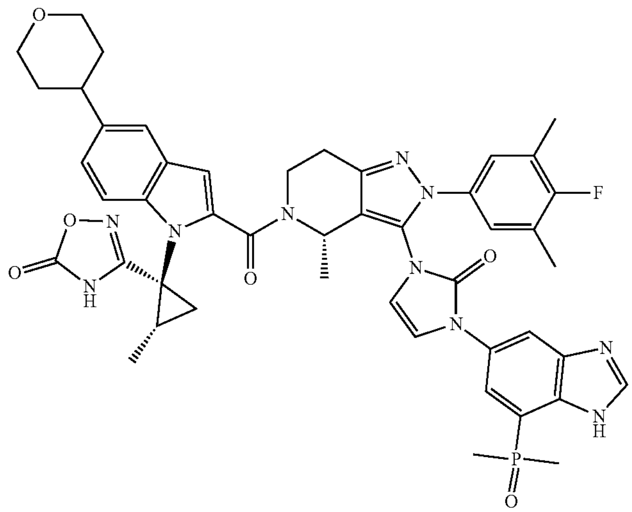 [SMILES: Cc1cc(-n2nc3c(c2-n2ccn(-c4cc(P(C)(C)=O)c5[nH]cnc5c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 111a | 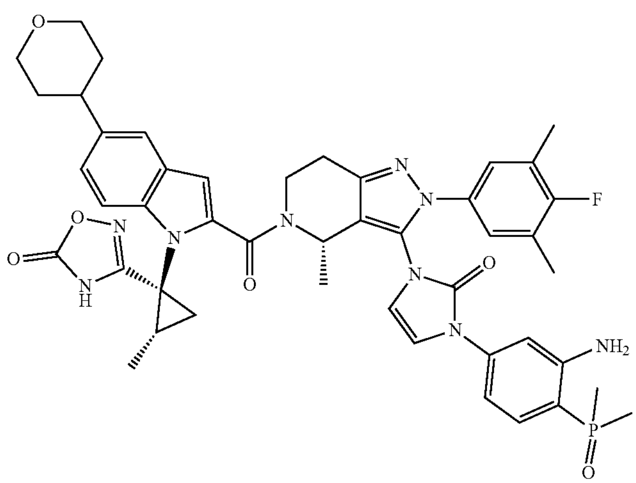 [SMILES: Cc1cc(-n2nc3c(c2-n2ccn(-c4ccc(P(C)(C)=O)c(N)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 112a | 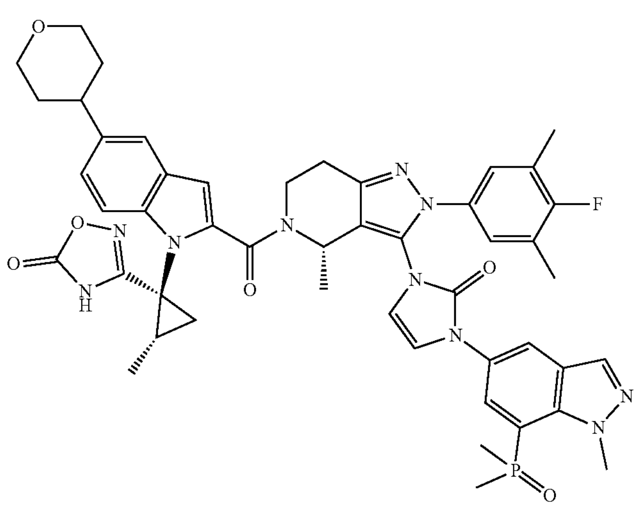 [SMILES: Cc1cc(-n2nc3c(c2-n2ccn(-c4cc(P(C)(C)=O)c5c(cnn5C)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE C2-continued

| Compound # | Structure |
| --- | --- |
| 113a | 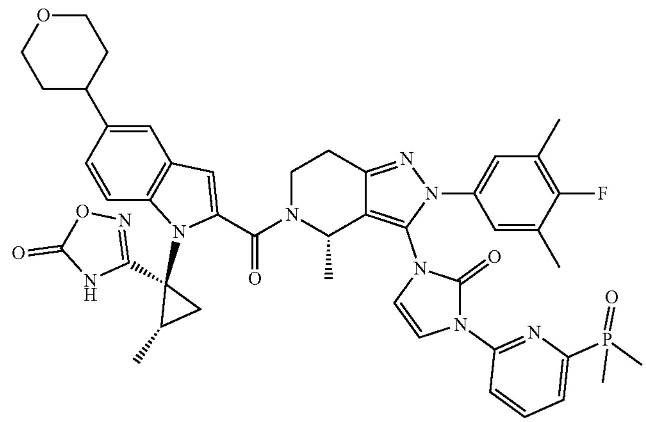 [SMILES: Cc1cc(-n2nc3c(c2-n2ccn(-c4cccc(P(C)(C)=O)n4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 114a | 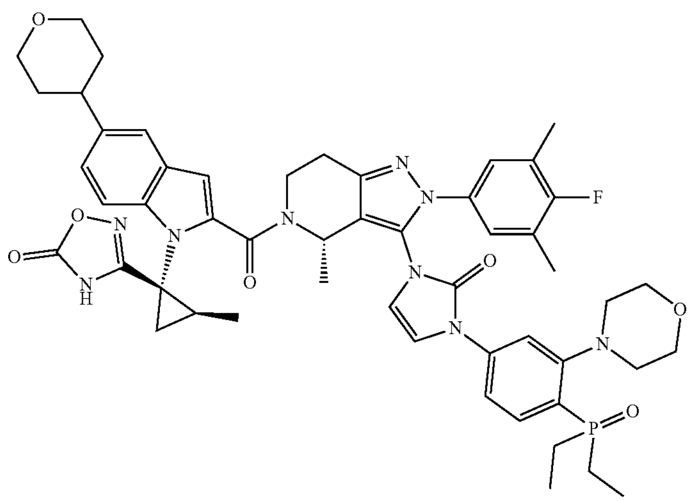 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1N1CCOCC1] |
| 115a | 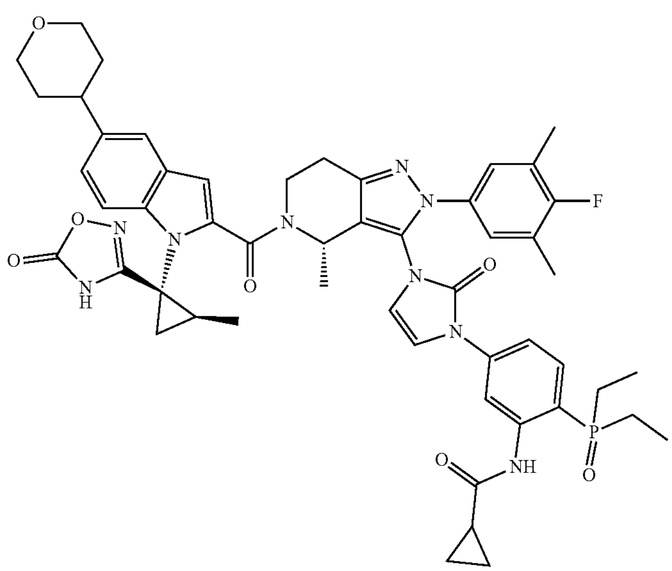 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC(=O)C1CC1] |

TABLE C2-continued
| Compound # | Structure |
|---|---|
| 116a | 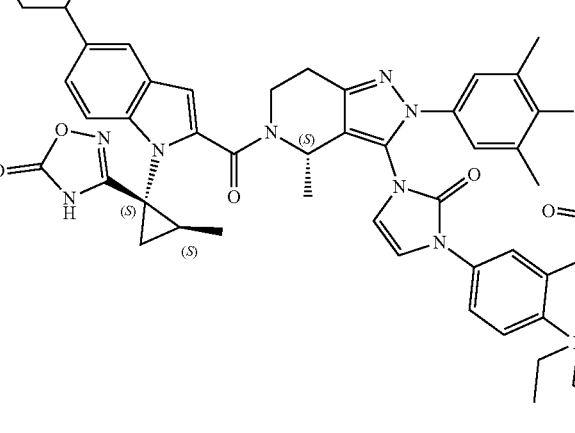 |
| 117a | 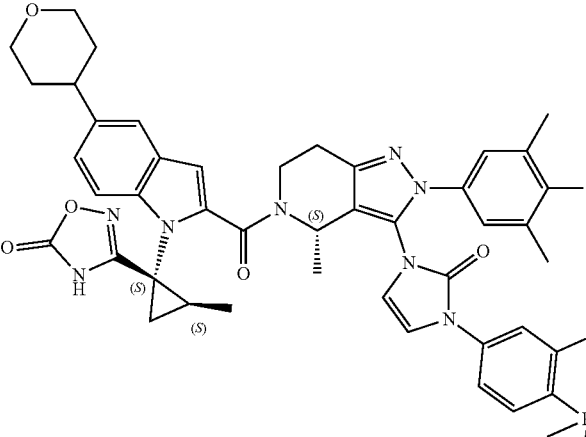 |
| 118a | 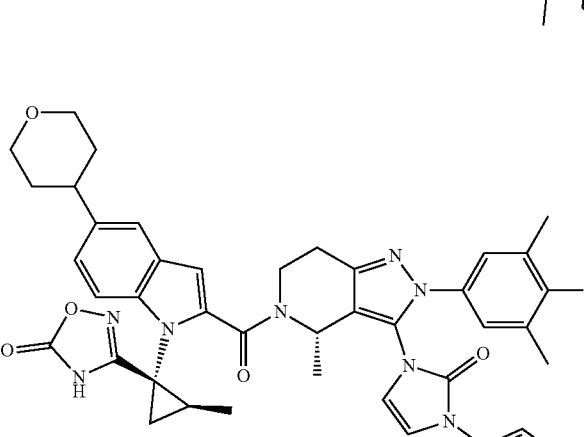 |

TABLE C2-continued

| Compound # | Structure |
|---|---|
| 119a | 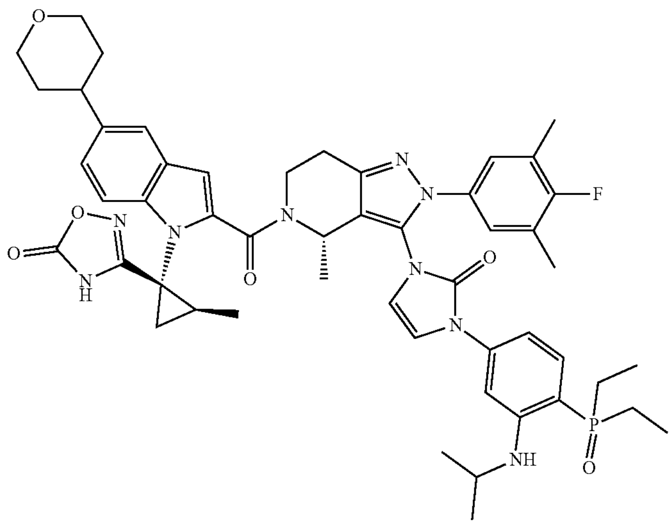 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC(C)C] |
| 120a | 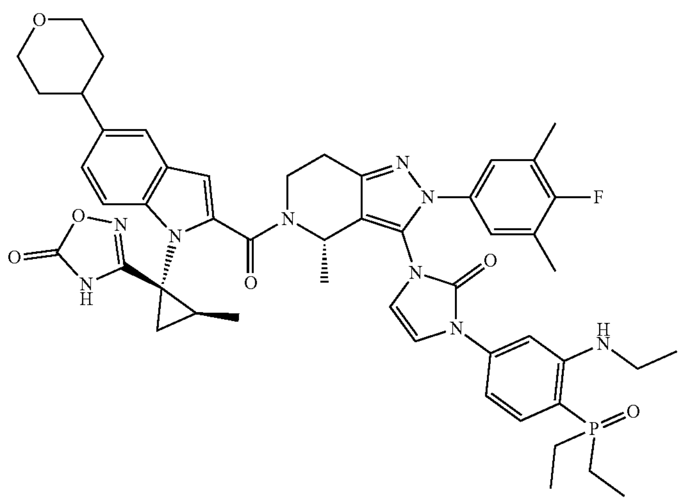 [SMILES: CCNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1P(=O)(CC)CC] |
| 121a | 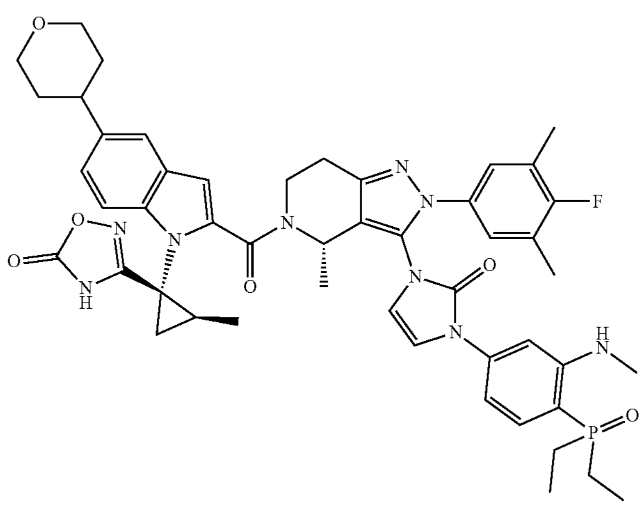 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC] |

TABLE C2-continued
| Compound # | Structure |
|---|---|
| 122a | 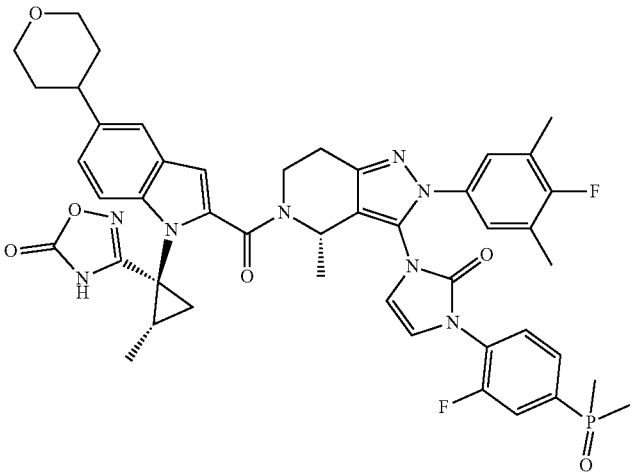 [SMILES: Cc1cc(-n2nc3c(c2-n2ccn(-c4ccc(P(C)(C)=O)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 123a | 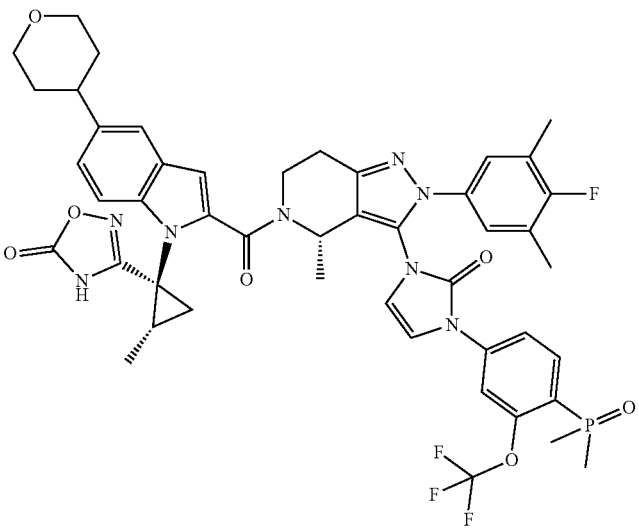 [SMILES: Cc1cc(-n2nc3c(c2-n2ccn(-c4ccc(P(C)(C)=O)c(OC(F)(F)F)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 124a | 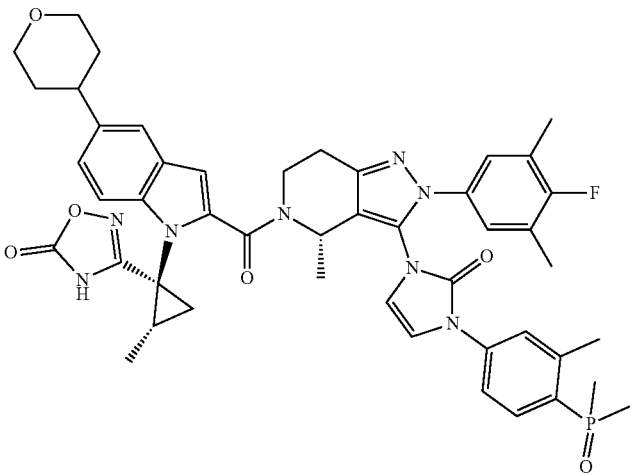 [SMILES: Cc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1P(C)(C)=O] |

TABLE C2-continued

| Compound # | Structure |
|---|---|
| 125a | 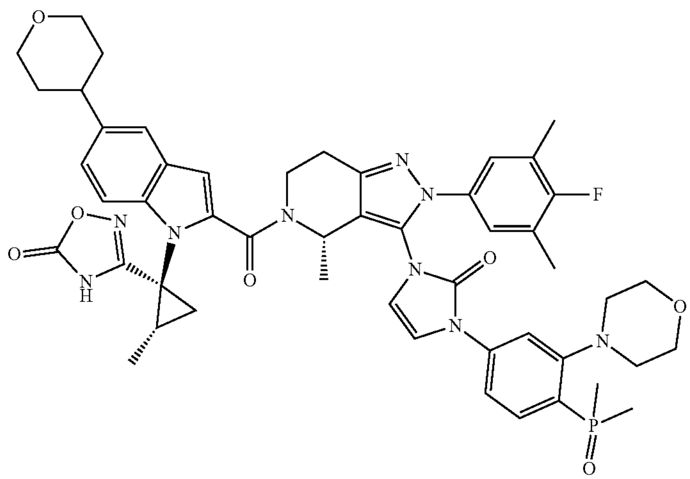 [SMILES: Cc1cc(-n2nc3c(c2-n2ccn(-c4ccc(P(C)(C)=O)c(N5CCOCC5)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 126a | 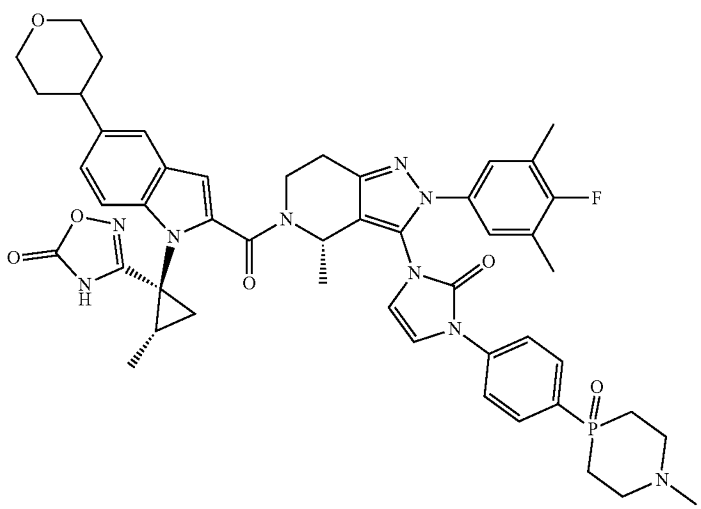 [SMILES: Cc1cc(-n2nc3c(c2-n2ccn(-c4ccc(P5(=O)CCN(C)CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 127a | 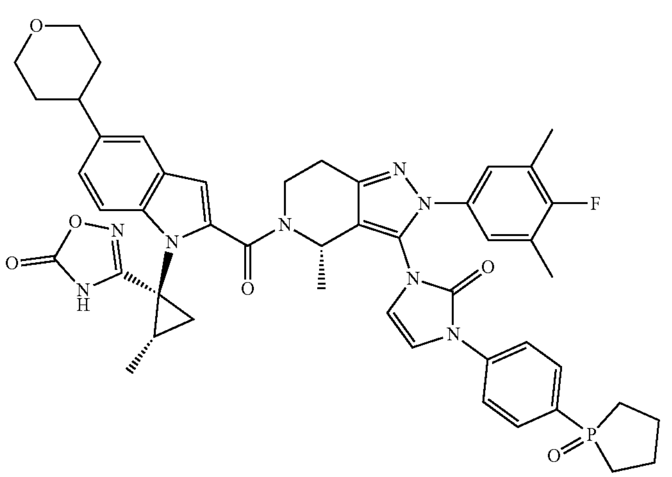 [SMILES: Cc1cc(-n2nc3c(c2-n2ccn(-c4ccc(P5(=O)CCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |

TABLE C2-continued
| Compound # | Structure |
|---|---|
| 128a | 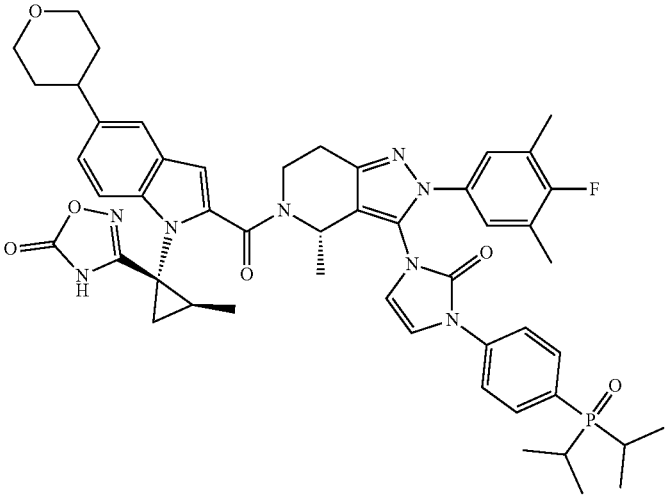 [SMILES: Cc1cc(-n2nc3c(c2-n2ccn(-c4ccc(P(=O)(C(C)C)C(C)C)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 129a | 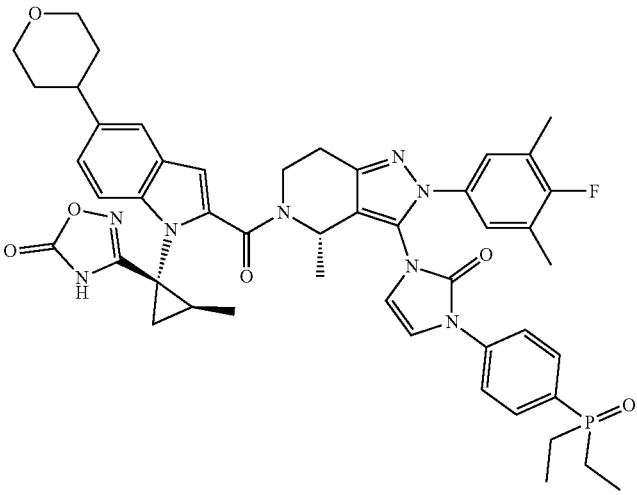 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1] |
| 130a | 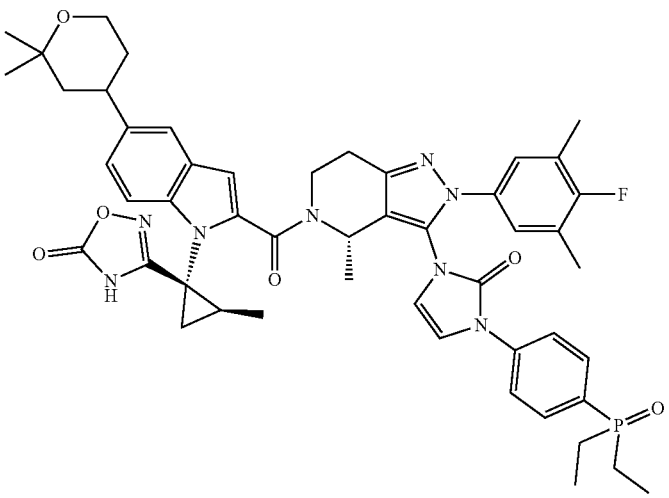 [SMILES: CCP(=O)(CC)c1ccc(-n2ccn(-c3c4c(nn3-c3cc(C)c(F)c(C)c3)CCN(C(=O)c3cc5cc(C6CCOC(C)(C)C6)ccc5n3[C@@]3(c5noc(=O)[nH]5)C[C@@H]3C)[C@H]4C)c2=O)cc1] |

TABLE C2-continued
| Compound # | Structure |
|---|---|
| 130b | 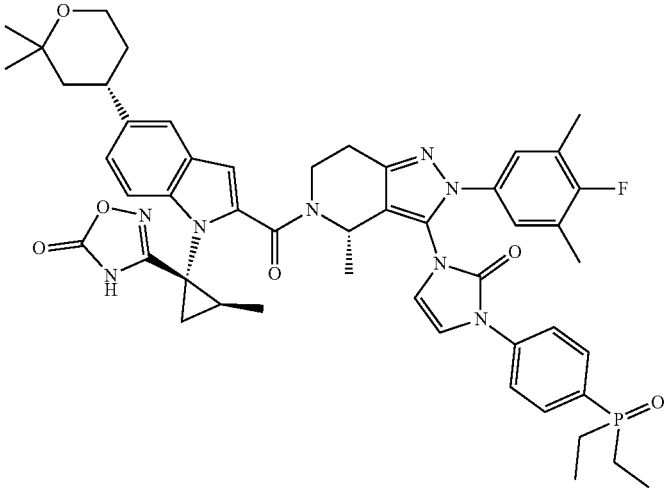 [SMILES: CCP(=O)(CC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1] |
| 131a | 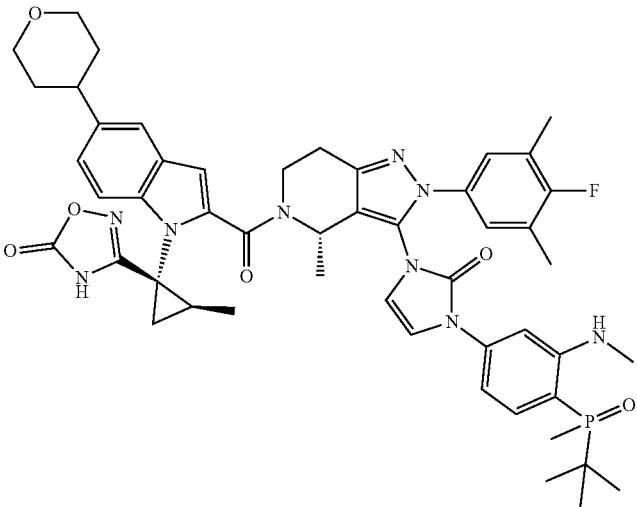 [SMILES: CNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1P(C)(=O)C(C)(C)C] |
| 132a | 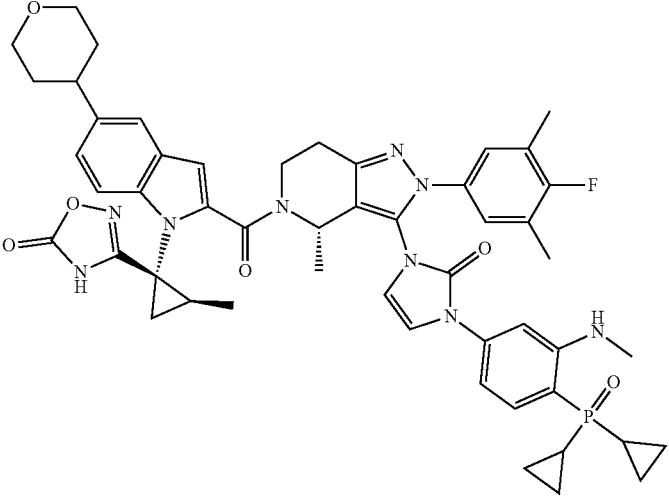 [SMILES: CNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1P(=O)(C1CC1)C1CC1] |

TABLE C2-continued

| Compound # | Structure |
|---|---|
| 133a | 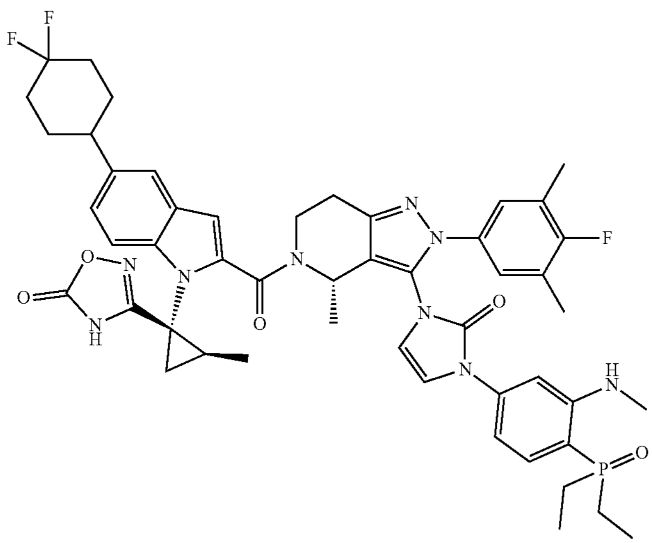 [SMILES: CCP(=O)(CC)c1ccc(-n2ccn(-c3c4c(nn3-c3cc(C)c(F)c(C)c3)CCN(C(=O)c3cc5cc(C6CCC(F)(F)CC6)ccc5n3[C@@]3(c5noc(=O)[nH]5)C[C@@H]3C)[C@H]4C)c2=O)cc1NC] |
| 134a | 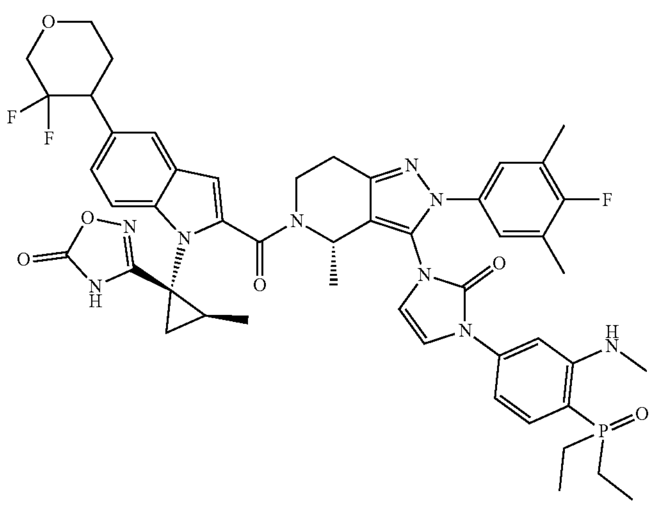 [SMILES: CCP(=O)(CC)c1ccc(-n2ccn(-c3c4c(nn3-c3cc(C)c(F)c(C)c3)CCN(C(=O)c3cc5cc(C6CCOCC6(F)F)ccc5n3[C@@]3(c5noc(=O)[nH]5)C[C@@H]3C)[C@H]4C)c2=O)cc1NC] |
| 135a | 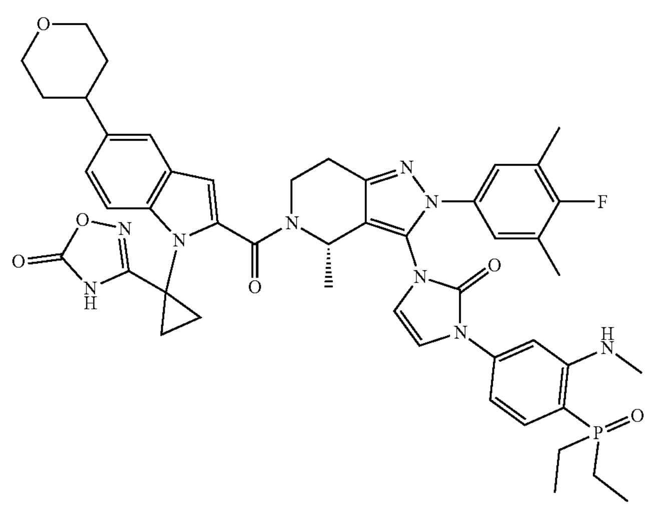 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)[C@H]4C)c2=O)cc1NC] |

TABLE C2-continued
| Compound # | Structure |
|---|---|
| 136a | 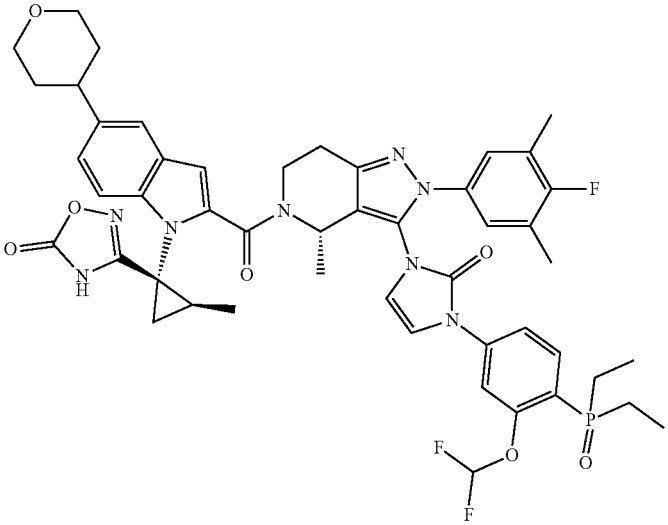 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1OC(F)F] |
| 137a | 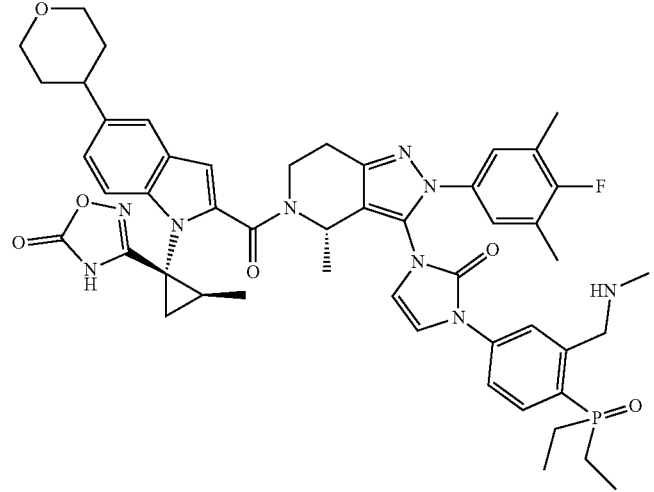 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1CNC] |
| 138a | 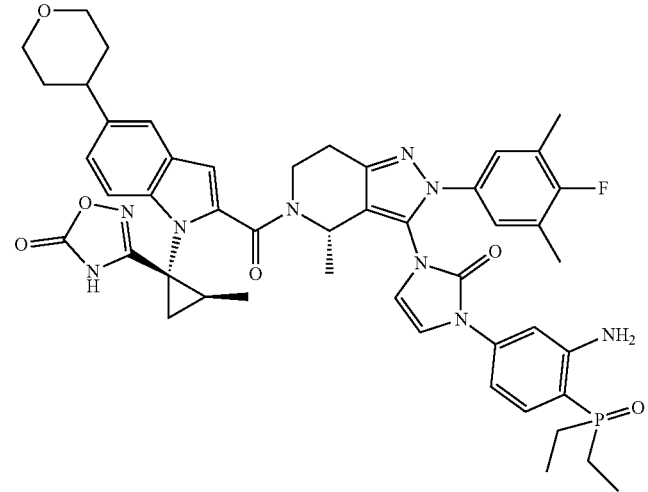 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1N] |

TABLE C2-continued
| Compound # | Structure |
|---|---|
| 139a | 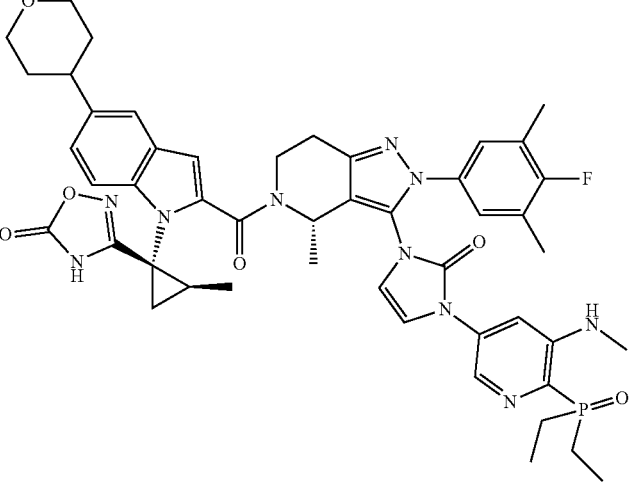 |
| 140a | 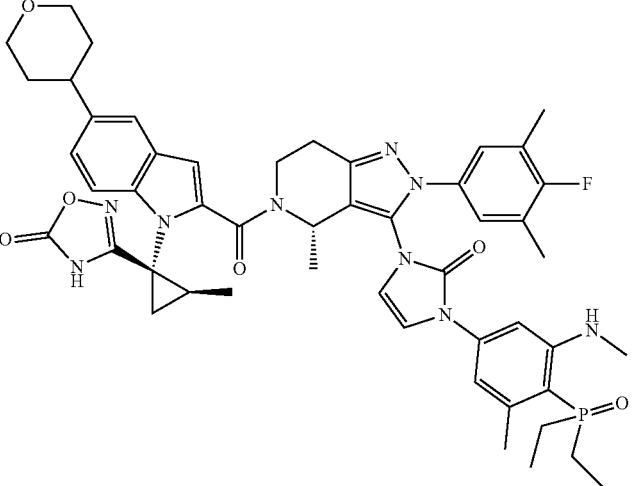 [SMILES: CCP(=O)(CC)c1c(C)cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC] |
| 141a | 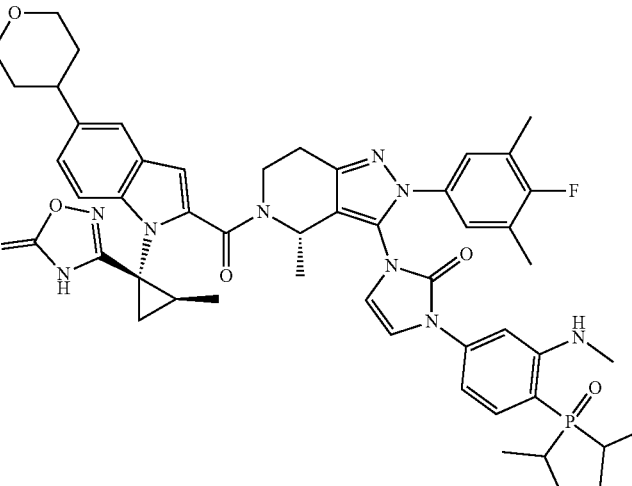 |

TABLE C2-continued
| Compound # | Structure |
|---|---|
| 142a | 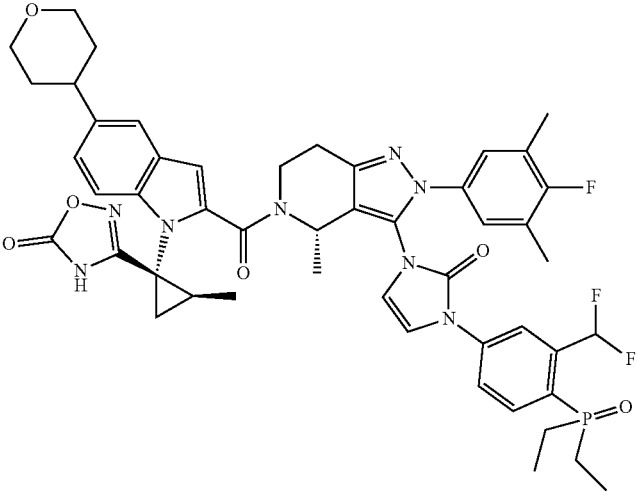 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1C(F)F] |
| 143a | 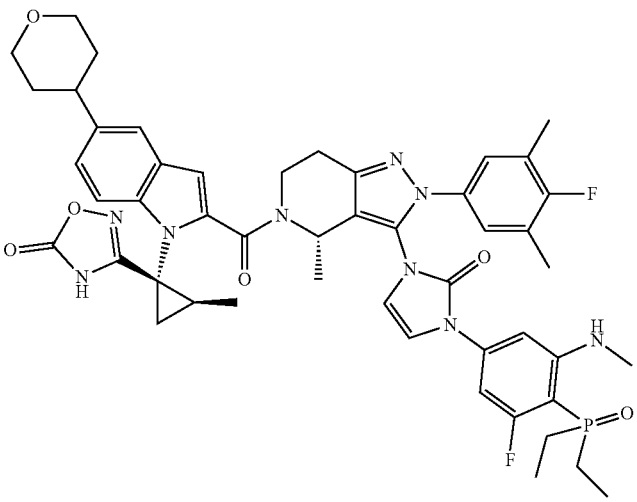 |
| 144a | 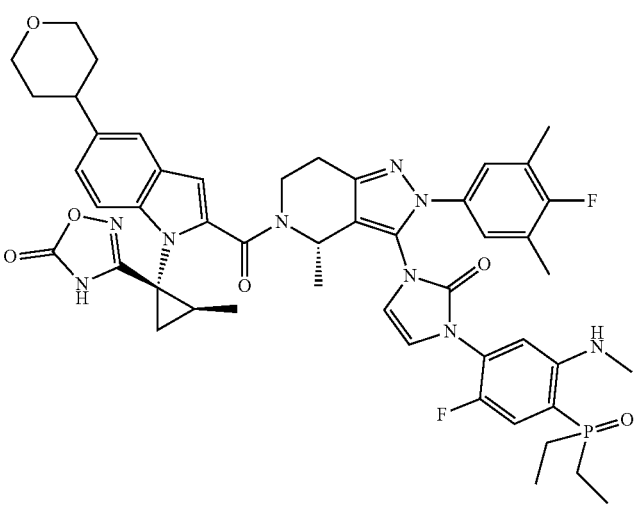 [SMILES: CCP(=O)(CC)c1cc(F)c(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC] |

TABLE C2-continued
| Compound # | Structure |
|---|---|
| 145a | 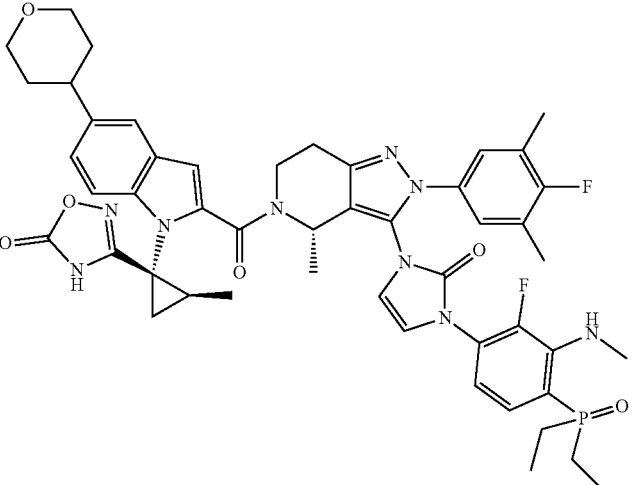 |
| 146a | 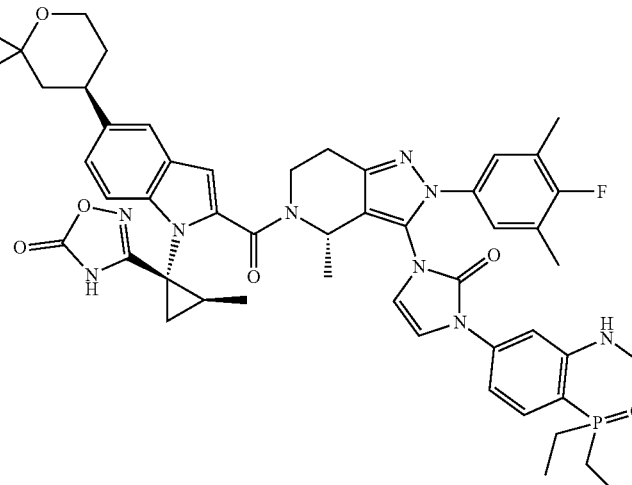 |
| 146b | 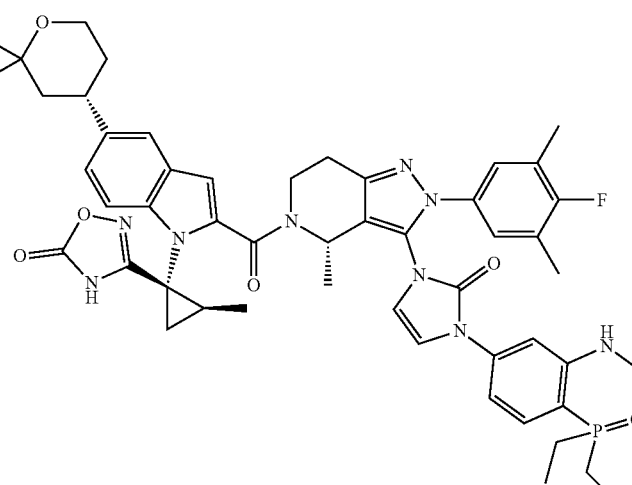 |

TABLE C2-continued

| Compound # | Structure |
|---|---|
| 147a | 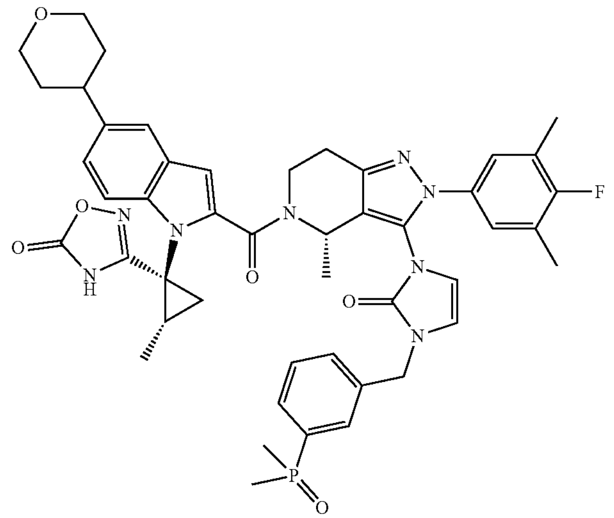 [SMILES: Cc1cc(-n2nc3c(c2-n2ccn(Cc4cccc(P(C)(C)=O)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] |
| 148a | 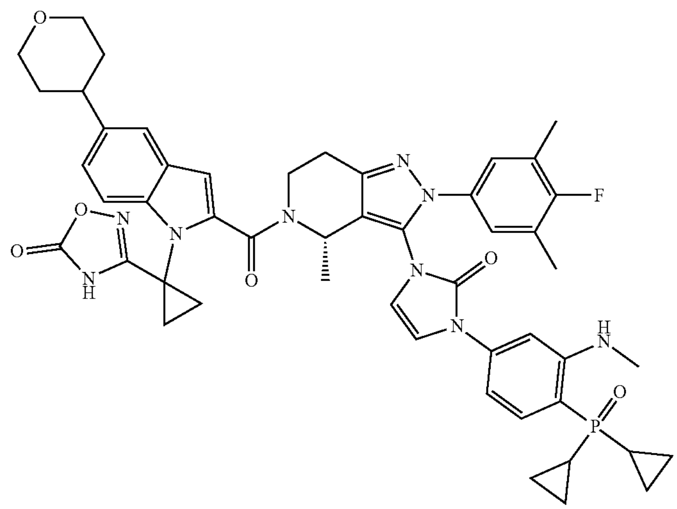 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)[C@H]4C)c2=O)ccc1P(=O)(C1CC1)C1CC1] |
| 149a | 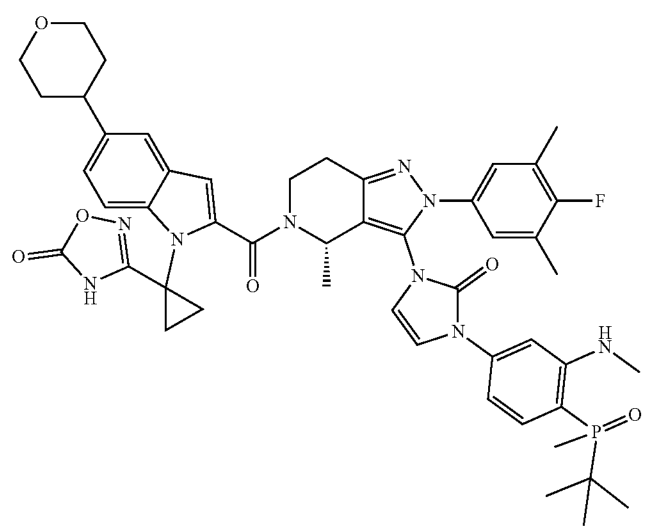 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)[C@H]4C)c2=O)ccc1P(C)(=O)C(C)(C)C] |

TABLE C2-continued

| Compound # | Structure |
|---|---|
| 150a | 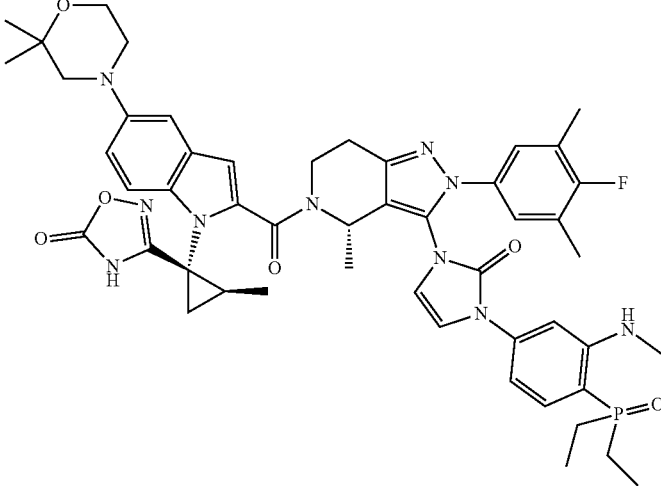 |

The compounds of Formula (I) include pharmaceutically acceptable salts thereof. In addition, the compounds of Formula (I) also include other salts of such compounds which are not necessarily pharmaceutically acceptable salts, and which may be useful as intermediates for preparing and/or purifying compounds of Formula (I) and/or for separating enantiomers of compounds of Formula (I). Non-limiting examples of pharmaceutically acceptable salts of compounds of Formula (I) include trifluoroacetic acid salts.

It will further be appreciated that the compounds of Formula (I) or their salts may be isolated in the form of solvates, and accordingly that any such solvate is included within the scope of the present invention. For example, compounds of Formula (I) and salts thereof can exist in unsolvated as well as solvated forms with pharmaceutically acceptable solvents such as water, ethanol, and the like.

Pharmaceutical Compositions and Administration

When employed as pharmaceuticals, the compounds of Formula (I), including pharmaceutically acceptable salts or solvates thereof can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I), or a pharmaceutically acceptable salt or solvate thereof, in combination with one or more pharmaceutically acceptable excipients (carriers). For example, a pharmaceutical composition prepared using a compound of Formula (I), or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I), or a pharmaceutically acceptable salt or solvate thereof with a pharmaceutically acceptable excipient. Pharmaceutical compositions containing a compound of Formula (I), or a pharmaceutically acceptable salt or solvate thereof as the active ingredient can be prepared by intimately mixing the compound of Formula (I), or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein or a pharmaceutical composition thereof is formulated for ocular administration. In some embodiments, ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments, the dosage for a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), is determined based on a multiple factors including, but not limited to, type, age, weight, sex, medical condition of the patient, severity of the medical condition of the patient, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein is administered as a dosage of about 100 mg/Kg.

In some embodiments, the foregoing dosages of a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is administered to a patient for a period of time followed by a separate period of time where administration of the compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is stopped. In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is administered for a first period and a second period following the first period, with administration stopped during the second period, followed by a third period where administration of the compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) is started and then a fourth period following the third period where administration is stopped. For example, the period of administration of a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), is orally administered to the patient one or more times per day (e.g., one time per day, two times per day, three times per day, four times per day per day or a single daily dose).

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), is administered by parenteral administration to the patient one or more times per day (e.g., 1 to 4 times one time per day, two times per day, three times per day, four times per day or a single daily dose).

In some embodiments, a compound of Formula (I), or a pharmaceutically acceptable salt or solvate thereof (e.g., a compound of any one of Formulas (IA), (IB), (IC), (ID), and (IE), or a pharmaceutically acceptable salt or solvate thereof), is administered by parenteral administration to the patient weekly.

Methods of Treatment

In some embodiments, this disclosure features methods for treating a patient (e.g., a human) having a disease, disorder, or condition in which modulation of GLP-1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt or solvate thereof (e.g., a compound of any one of Formulas (IA), (IB), (IC), (ID), and (IE), or a pharmaceutically acceptable salt or solvate thereof), or a pharmaceutical composition as disclosed herein.

In some embodiments, the disease, disorder, or condition includes, but is not limited to, type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity (including hypothalamic obesity and monogenic obesity), weight gain from use of other agents, idiopathic intracranial hypertension, Wolfram syndrome, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to, type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, kidney disease (e.g., acute kidney disorder, tubular dysfunction, proinflammatory changes to the proximal tubules), adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to, type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of a reduction of blood glucose levels (e.g., reduce blood glucose levels), a reductionc of blood hemoglobin A1c (HbA1c) levels, a promotion of insulin synthesis, a stimulation of insulin secretion, an increase in the mass of Q-cells, a modulation of gastric acid secretion, a modulation of gastric emptying, a decrease in the body mass index (BMI), and/or a decrease in glucagon production (e.g., level). In some embodiments, the compounds and pharmaceutical compositions and methods for treating a patient described herein can reduce blood glucose levels, reduce blood hemoglobin A1c (HbA1c) levels, promote insulin synthesis, stimulate insulin secretion, increase the mass of Q-cells, modulate gastric acid secretion, modulate gastric emptying, decrease the body mass index (BMI), decrease glucagon production (e.g., level), or any combination thereof. In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt or solvate thereof (e.g., a compound of any one of Formulas (IA), (IB), (IC), (ID), and (IE), or a pharmaceutically acceptable salt or solvate thereof), or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt or solvate thereof (e.g., a compound of any one of Formulas (IA), (IB), (IC), (ID), and (IE), or a pharmaceutically acceptable salt or solvate thereof), or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, urine incontinence, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt or solvate thereof (e.g., a compound of any one of a compound of any one of Formulas (IA), (IB), (IC), (ID), and (IE), or a pharmaceutically acceptable salt or solvate thereof, or a pharmaceutically acceptable salt or solvate thereof) or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt or solvate thereof (e.g., a compound of any one of a compound of any one of Formulas (IA), (IB), (IC), (ID), and (IE), or a pharmaceutically acceptable salt or solvate thereof, or a pharmaceutically acceptable salt or solvate thereof), or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt or solvate thereof (e.g., a compound of any one of a compound of any one of Formulas (IA), (IB), (IC), (ID), and (IE), or a pharmaceutically acceptable salt or solvate thereof, or a pharmaceutically acceptable salt or solvate thereof), or a pharmaceutical composition as disclosed herein.

In some embodiments, the compounds and pharmaceutical compositions and methods for treating a patient with a condition, disease, or disorder (e.g., type 2 diabetes mellitus)

described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, hyperlipoproteinemia, glycogen storage diseases, Weber-Christian disease, Wolman disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and can ultimately lead to cirrhosis (Skelly et al., *J Hepatol*

2001; 35: 195-9; Chitturi et al., *Hepatology* 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., *J Gastroenterol Hepatol* 2002; 17 Suppl:S186-90).

Other non-limiting examples of disorders in metabolically important tissues include joint disorders (e.g., osteoarthritis, secondary osteoarthritis), steatosis (e.g., in the liver); fibrosis (e.g., in the liver); cirrhosis (e.g., in the liver); gall stones; gallbladder disorders; gastroesophageal reflux; sleep apnea; hepatitis; fatty liver; bone disorder characterized by altered bone metabolism, such as osteoporosis, including postmenopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease or disorder is a neurological disorder (e.g., neurodegenerative disorder) or a psychiatric disorder. Non-limiting examples of neurological disorders include idiopathic intracranial hypertension (IIH), brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., U.S. Publication No. 20060275288A1.

In some embodiments, the condition, disease or disorder is idiopathic intracranial hypertension. Idiopathic intracranial hypertension is characterized by increased intracranial pressure and papilloedema. See, e.g., Virdee et al. *Ophthalmol Ther.* 2020; 9(4):767-781. In some embodiments, the compounds and pharmaceutical compositions and methods described herein reduce cerebrospinal fluid secretion in a patient with idiopathic intracranial hypertension. In some embodiments, the compounds and pharmaceutical compositions and methods described herein reduce intracranial pressure in a patient with idiopathic intracranial hypertension. In some embodiments, the compounds and pharmaceutical compositions and methods described herein reduce one or more symptoms in a patient with idiopathic intracranial hypertension. Symptoms of idiopathic intracranial hypertension can include severe headaches and visual impairment. In some embodiments, the patient with idiopathic intracranial hypertension is female. In some embodiments, the patient with idiopathic intracranial hypertension is about 20 to about 30 years old. In some embodiments, the patient with idiopathic intracranial hypertension is obese.

In some embodiments, the condition, disease or disorder is Wolfram syndrome. Wolfram syndrome is caused by biallelic mutations of the Wolframin ER transmembrane glycoprotein (Wfs1) gene. See, e.g., Seppa et al. *Sci Rep* 9, 15742 (2019). Wolfram syndrome can first appear as diabetes mellitus, followed by optic nerve atrophy, deafness, and symptoms of neurodegeneration. Patients with Wolfram syndrome can have symptoms of ataxia, sleep apnea, dysphagia, hearing loss, and loss of taste due to brainstem atrophy. In some embodiments, the compounds and pharmaceutical compositions and methods described herein reduce neuroinflammation in a patient with Wolfram syndrome. In some embodiments, the neuroinflammation is reduced in the inferior olive in the patient. In some embodiments, the compounds and pharmaceutical compositions and methods described herein reduce retinal ganglion cell death in a patient with Wolfram syndrome. In some embodiments, the compounds and pharmaceutical compositions and methods described herein reduce axonal degeneration in a patient with Wolfram syndrome. In some embodiments, the compounds and pharmaceutical compositions and methods described herein reduce one or more symptoms (e.g., any of the symptoms described herein) in a patient with Wolfram syndrome.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., U.S. Publication No. 20120021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., U.S. Publication No. 20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking. In some embodiments, the weight gain is induced by the use of steroids or antipsychotics.

In some embodiments, the condition, disease or disorder is an eating disorder, such as hyperphagia, binge eating, bulimia, compulsive eating, or syndromic obesity such as Prader-Willi and Bardet-Biedl syndromes.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the condition, disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the condition, disease or disorder associated with diabetes is related to the hypothalamic-pituitary-gonadal axis.

Pulmonary Disease

In some embodiments, the condition, disease or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the condition, disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of Formula (I) (e.g., a compound of any one of Formulas (IA), (IB), (IC), (ID), and (IE), or a pharmaceutically acceptable salt or solvate thereof), or a pharmaceutically acceptable salt or solvate thereof as described herein can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, and therapeutic agents for dysuria.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), peptide YY or an analogue thereof, cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498, naltrexone), orexin receptor antagonists, melanocortin 4 receptor agonists, 11β-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors (e.g., compounds described in WO 2020/234726, WO 2020/044266, and U.S. Pat. No. 8,859,577), stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin, empagliflozin, canagliflozin, ipragliflozin, tofogliflozin, sergliflozin etabonate, remogliflozin etabonate, or ertugliflozin), SGLT-1 inhibitors, MCR-4 agonists, monoamine reuptake inhibitors, melanocytestimulating hormone analogs, 5HT2c agonists, galanin antagonists, anorectic agents (such as a bombesin agonist), thyromimetic agents, dehydroepiandrosterone or analogs thereof, human agouti-related protein (AGRP) inhibitors, neuromedin U agonists, NFK inhibitors (e.g., HE-3286), PPAR agonists (e.g., GFT-505, DRF-11605, gemfibrozil, fenofibrate, balaglitazone, ciglitazone, darglitazone, englitazone, isaglitazone, pioglitazone, rosiglitazone, CLX-0940, GW-1536, GW-1 929, GW-2433, KRP-297, L-796449, LR-90, MK-0767, and SB-21 9994), phosphotyrosine phosphatase inhibitors (e.g., sodium vanadate, trodusquemin), GPR119 agonists (e.g., PSN-821, MBX-2982, APD597, compounds described in WO 2010/140092, WO 2010/128425, WO 2010/128414, WO 2010/106457), glucokinase activators (e.g., piragliatin, AZD-1656, AZD6370, TTP-355, TTP-399, TTP547, ARRY403, MK-0599, TAK-329, AZD5658 or GKM-001 compounds described in WO 2010/103437, WO 2010/103438, WO 2010/013161, WO 2007/122482, WO 2006/112549, WO 2007/028135, WO 2008/047821, WO 2008/050821, WO 2008/136428 and WO 2008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), melanocortin receptor 4 agonist (e.g., setmelanotide), melanin concentrating hormone receptor 1 antagonist, serotonergic agents (e.g. sibutramine, lorcaserin), farnesoid X receptor (FXR) agonist (e.g., obeticholic acid, tropifexor, cilofexor, LY2562175, Met409, TERN-101, EDP305, compounds described in WO 2020/234726 and WO 2020/044266), phentermine, zonisamide, norepinephrine/dopamine reuptake inhibitor (e.g., buproprion), GDF-15 analog, methionine aminopeptidase 2 (MetAP2) inhibitor (e.g., beloranib or ZGN-1061), diethylpropion, phendimetrazine, benzphetamine, fibroblast growth factor receptor (FGFR) modulator, biotin, a MAS receptor modulator, glucagon receptor agonist, CCKa agonists (e.g., compounds described in WO 2005/116034 and U.S. Publication No. 2005/0287100), and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, glimepiride, tolbutamide, glibenclamide, gliclazide, acetohexamide, glyclopyramide, glybuzole, glyburide, glipizide), thiazolidinedione agents (e.g. rosiglitazone, lobeglitazone, troglitazone, balaglitazone, rivoglitazone, lobeglitazone or pioglitazone), glitazars (e.g., aleglitazar, chiglitazar, saroglitazar, muraglitazar, tesaglitazar), SGLT2 inhibitors (e.g., JNJ-28431754, dapagliflozin, AVE2268, TS-033, YM543, TA-7284, ASP1941, THR1474, TS-071, ISIS388626, LX4211, remogliflozin, empagliflozin, canagliflozin, ipragliflozin, tofogliflozin, sergliflozin etabonate, remogliflozin etabonate, ertugliflozin, compounds described in WO 2010/023594), GPR40 agonists (e.g., a FFAR1/FFA1 agonist, e.g. fasiglifam), α-glucosidase inhibitors (e.g., adiposin, camiglibose, pradimicin-Q, salbostatin, voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, anagliptin (SK-0403), teneligliptin, omarigliptin, B11356, GRC8200, MP-513, PF-00734200, PHX1149, ALS2-0426, TA-6666, TS-021, KRP-104, trelagliptin).

In some embodiments, the one or more additional therapeutic agents include those useful, for example, for treating NAFL and NASH. Non-limiting examples include FXR agonists (e.g., obeticholic acid), PF-05221304, PPAR α/δ agonists (e.g., elafibranor), a synthetic fatty acid-bile conjugate (e.g., aramchol), an anti-lysyl oxidase homologue 2 (LOXL2) monoclonal antibody (e.g., simtuzumab), a caspase inhibitor (e.g., emricasan), a MAPK5 inhibitor (e.g., GS-4997), a galectin 3 inhibitor (e.g., GR-MD-02), a fibroblast growth factor 21 (FGF21) (e.g., BMS-986036), a niacin analogue (e.g., ARJ 3037MO), a leukotriene D4 (LTD4) receptor antagonist (e.g., tipelukast), an acetyl-CoA carboxylase (ACC) inhibitor (e.g., NDI 010976 amd compounds described in WO 2009/144554, WO 2003/072197, WO 2009/144555, and WO 2008/065508), a ketohexokinase (KHK) inhibitor (e.g., compounds described in WO 2020/234726), an apoptosis signal-regulating kinase 1 (ASKI) inhibitor, an ileal bile acid transporter (IBAT) inhibitor, a dual antagonist of chemokine receptor 2 (CCR2) and CCR5 (e.g., cenicriviroc), diacylglyceryl acyltransferase 2 (DGAT2) inhibitor (e.g., compounds described in WO 2020/234726 and U.S. Publication No. 20180051012), a CB1 receptor antagonist, an anti-CB1R antibody, glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone, balaglitazone, rivoglitazone, lobeglitazone), metformin, cysteamine, sulfonylureas, alpha-glucosidase inhibitors, meglitinides, vitamin E, tetrahydrolipstatin, milk thistle protein, antivirals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO 2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and ω-3 fatty acid preparations (e.g., ω-3-fatty acid ethyl esters 90).

In some embodiments, the one or more additional therapeutic agents include those useful, for example, as antihypertensive agents. Non-limiting examples include angiotensin converting enzyme inhibitors (e.g., captopril, zofenopril, fbsinopril, enalapril, ceranopril, cilazopril, delapril, pentopril, quinapril, ramipril, lisinopril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol). Further non-limiting examples of antihypertensive agents include: diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrene, amiloride, spironolactone), alpha adrenergic blockers, beta adrenergic blockers, calcium channel blockers (e.g., diltiazem, verapamil, nifedipine and amlodipine), vasodilators (e.g., hydralazine), renin inhibitors, AT-1 receptor antagonists (e.g., losartan, irbesartan, valsartan), ET receptor antagonists (e.g., sitaxsentan, atrsentan, compounds disclosed in U.S. Pat. Nos. 5,612,359 and 6,043,265), dual ET/AII antagonist (e.g., compounds disclosed in WO 2000/01389), neutral endopeptidase (NEP) inhibitors. If channel blocker ivabradinand, vasopepsidase inhibitors (dual NEP-ACE inhibitors) (e.g., memopatrilat and nitrates).

In some embodiments, the one or more additional therapeutic agents include those useful, for example, as diuretics. Non-limiting examples include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as antithrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran, boroarginine derivatives, boropeptides, heparins, hirudin, and melagatran), FXa inhibitors (e.g., rivaroxaban, apixaban, edoxaban, YM150, compounds described in WO02/06234, WO 2004/048363, WO 2005/030740, WO 2005/058823, and WO 2005/113504) thrombolytic agents (e.g., anistreplase, streptokinase, tenecteplase (TNK), lanoteplase (nPA), urokinase, tisokinase, alteplase, nateplase, monteplase, pamiteplase, factor VIIa inhibitors, PAI-1 inhibitors, alpha2-antiplasmin inhibitors, and anisoylated plasminogen streptokinase activator complex), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-CoA reductase inhibitors (statins, e.g. rosuvastatin pravastatin, pitavastatin, lovastatin, atorvastatin, simvastatin, fluvastatin, itavastatin, ZD-4522), HMG-CoA synthase inhibitors, cholesterol-lowering agents, bile acid sequestrants (e.g., cholestyramine, questran, colestipol, and colesevelam), cholesterol absorption inhibitors (e.g. plant sterols such as phytosterols), cholesteryl ester transfer protein (CETP) inhibitors, inhibitors of the ileal bile acid transport system (IBAT inhibitors), diacylglyceryl acyltransferase 1 (DGAT1) inhibitors (e.g., AZD7687, LCQ908, compounds described in WO 2009/016462, WO 2010/086820), monoacylglycerol O-acyltransferase inhibitors, α-amylase inhibitors (e.g., tendamistat, trestatin, AL-3688), α-glucoside hydrolase inhibitors, SIRT-1 activators, c-Jun N-terminal kinase (INK) inhibitors, a VPAC2 receptor agonist, TGR5 receptor modulators (e.g., compounds described in), GPBAR1 receptor modulators, GPR120 modulators, high affinity nicotinic acid receptor (HM74A) activators, carnitine palmitoyl transferase enzyme inhibitors, mineralocorticoid receptor inhibitors, inhibitors of TORC2, fatty acid synthetase inhibitors, serine palmitoyl transferase inhibitors, GPR81 modulators, GPR39 modulators, GPR43 modulators, GPR41 modulators, GPR105 modulators, Kv1.3 modulators, retinol binding protein 4 modulators, somatostain receptor modulators, PDHK2 modulators, PDHK4 modulators, MAP4K4 inhibitors, IL1 family modulators (e.g., ILI beta modulators), ACAT inhibitors, MTP inhibitors (e.g., diriotapide, mitratapide, and implitapide), lipooxygenase inhibitors, PCSK9 modulators (e.g., alirocumab and evolocumab), RXRalpha modulators, cysteamine, cystamine, an RNA antisense construct to inhibit protein tyrosine phosphatase PTPRU, vitamin B complex, pentraxin proteins, a protein tyrosine phosphatase-1 B (PTP-1 B) inhibitor (e.g., trodusquemine, hyrtiosal extract, and compounds described by Zhang et al. *Drug Discovery Today*. 2007, 12 (9-10): 373-381), ezitimbe, betaine, pentoxifylline, alpha delta-9 desaturase, BCKDK inhibitors, branched-chain alpha keto acid dehydrogenase kinase (BCBK) inhibitors, PNPLA3 inhibitors, FGF1 9 analogs, SCD1 inhibitors, bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone, spironolactone), centrally acting adrenergic drugs, such as central alpha agonists (e.g. clonidine), diuretic agents (e.g. furosemide, torsemide, bemetanide, ethacrynic acid, thiazide-type diuretics (e.g., chlorothiazide, hydrochlorothiazide, benzthiazide, hydroflumethiazide, bendroflumethiazide, methychlorthiazide, polythiazide, trichlormethiazide, indapamide), phthalimidine-type diuretics (e.g., chlorthalidone, metolazone), quinazoline-type diuretics (e.g., quinethazone), potassium-sparing diuretics (e.g., triamterene and amiloride), thyroid receptor agonists (e.g., compounds described in WO 2020/117987), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin), non-steroidal anti-inflammatory drugs (NSAIDS), thromboxane-A2-receptor antagonists (e.g., ifetroban), thromboxane-A2-synthetase inhibitors, PDE inhibitors (e.g., Pletal, dipyridamole)), antagonists of purinergic receptors (e.g., P2Y1 and P2Y12), adenosine diphosphate (ADP) receptor inhibitors (e.g. clopidogrel), phosphodiesterase inhibitors (e.g. cilostazol), glycoprotein IIB/IIA inhibitors (e.g. tirofiban, eptifibatide, and abcixima), adenosine reuptake inhibitors (e.g. dipyridamole), noradrenergic agents (e.g. phentermine), serotonergic agents (e.g. sibutramine, lorcaserin), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in WO 2007/013694, WO 2007/018314, WO 2008/093639 and WO 2008/099794, GPR40 agonists (e.g., fasiglifam or a hydrate thereof, compounds described in WO 2004/041266, WO 2004/106276, WO 2005/063729, WO 2005/063725, WO 2005/087710, WO 2005/095338, WO 2007/013689 and WO 2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor α (PPARα), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., $K^+$ channel openers, mexiletine, propafenone, metoprolol, atenolol, carvadiol, propranolol, sotalol, dofetilide, amiodarone, azimilide, ibutilide, ditiazem, and verapamil), acetylcholine receptor ligands (e.g., ABT-594), endothelin receptor antagonists (e.g., ABT-627), narcotic analgesics (e.g., morphine), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-β), immunomodulators (e.g., glatiramer), TNF-binding proteins (e.g., circulating receptors), immunosuppressants (e.g., mycophenolate), metaglidasen, AMG-131, balaglitazone, MBX-2044, rivoglitazone, aleglitazar, chiglitazar, saroglitazar, muraglitazar, tesaglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide, piroxicam, NO donating agents (e.g., organonitrates), and NO promoting agents (e.g., phosphodiesterase inhibitors).

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin A1c (HbA1c), fasting plasma glucose, non-fasting plasma glucose, or any combination thereof. In some embodiments, the level of HbA1c is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 kg/m$^2$ to greater than or about 100 kg/m$^2$. In some embodiments, the BMI of the patient is greater than or about 30 kg/m$^2$ to greater than or about 90 kg/m$^2$. In some embodiments, the BMI of the patient is greater than or about 40 kg/m$^2$ to greater than or about 80 kg/m$^2$. In some embodiments, the BMI of the patient is greater than or about 50 kg/m$^2$ to greater than or about 70 kg/m$^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First LR. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

EXAMPLES

The invention is further described in the following examples, which do not limit the scope of the invention described in the claims.

Schemes 1-3 delineate exemplary methods for preparing compounds of Formula (I) and intermediates useful for the synthesis of Formula (I) compounds.

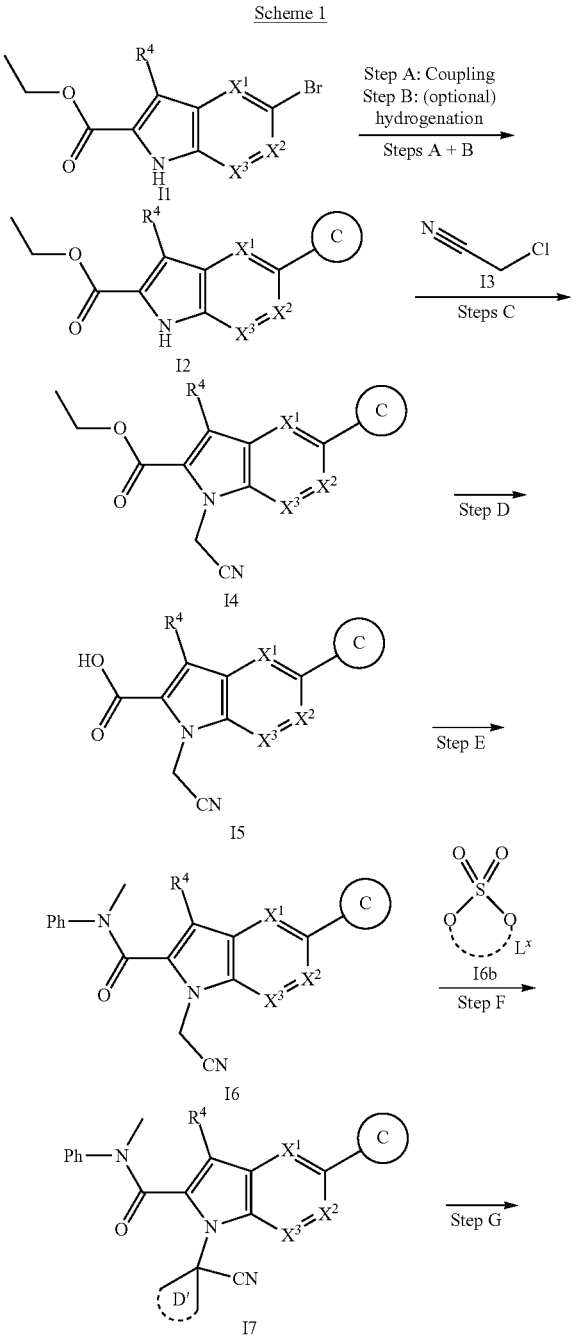

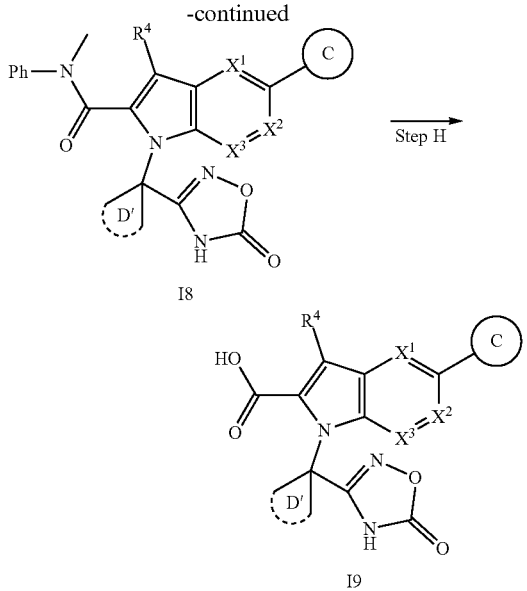

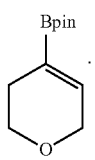

Subsequent reaction of I2 with I3 (e.g., in the presence of NaH in DMF) provides compound I4, whereupon hydrolysis of the ester group under standard conditions (e.g., with LiOH in H$_2$O/THF) affords compound I5. Amide coupling of I5 with NHMePh under standard conditions (e.g., HATU and Hunig's base) provides I6. The reaction of I6 with a reagent I6b (wherein the dashed curve L$^x$ represents a C$_{2-5}$ alkylene optionally substituted with a C$_{1-6}$ alkyl, wherein the C$_{1-6}$ alkyl is optionally substituted with from 1-3 independently selected R$^1$) under basic conditions (e.g., KHMDS, DMPU) then provides I7, wherein Ring D' is a C$_{3-6}$ cycloalkyl which is optionally with a C$_{1-6}$ alkyl, wherein the C$_{1-6}$ alkyl is optionally substituted with from 1-3 independently selected R$^f$. As a non-limiting example, I6b can be

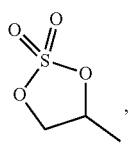

wherein the Ring D' in the corresponding product is

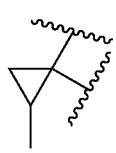

Referring to Scheme 1, ester I1 (wherein R$^4$ is as defined for Formula I;

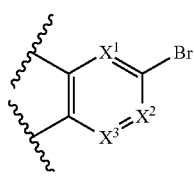

is selected from the group consisting of:

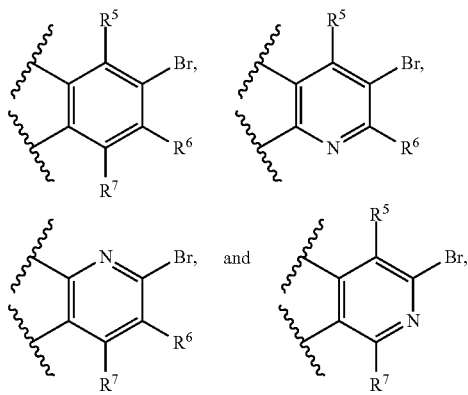

wherein R$^5$, R$^6$, and R$^7$ are as defined for Formula I) is subjected to a metal-catalyzed cross-coupling reaction (e.g., Suzuki coupling using Pd(dppf)ClCH$_2$Cl$_2$ in the presence of potassium carbonate) with an appropriate coupling partner such as a reagent with Formula (Ring C)-Y (wherein Ring C is as defined for Formula I; and Y is B(OH)$_2$ or boronate ester such as BPin) to provide compound I2. Optionally when Ring C is a saturated heterocyclyl, I1 can be coupled with a reagent of Formula (Ring C')-Y wherein Ring C' is a partially saturated heterocyclyl, followed by hydrogenation (e.g., with palladium on carbon) to afford I2. As a non-limiting example, when Ring C is tetrahydropyran-4-yl, I1 can be coupled with (Ring-C')-Y of formula:

Treatment of I7 with a hydroxylamine source (e.g., NH$_2$OH·HCl in EtOH under reflux) followed by reaction with a phosgene equivalent (e.g., CDI (e.g., in the presence of DBU and DMSO at 80° C.)) provides compound I8. Hydrolysis of the amide group in I8 (e.g., with KOH in CH$_3$OCH$_2$CH$_2$OH at e.g., 125° C.) provides compound I9.

Scheme 2

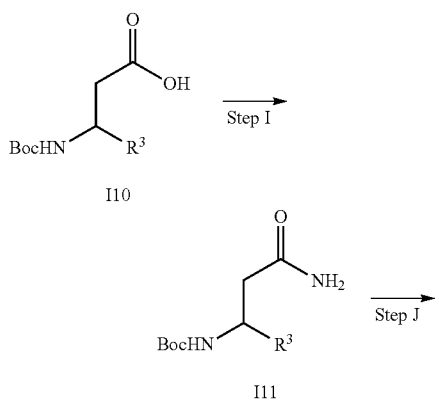

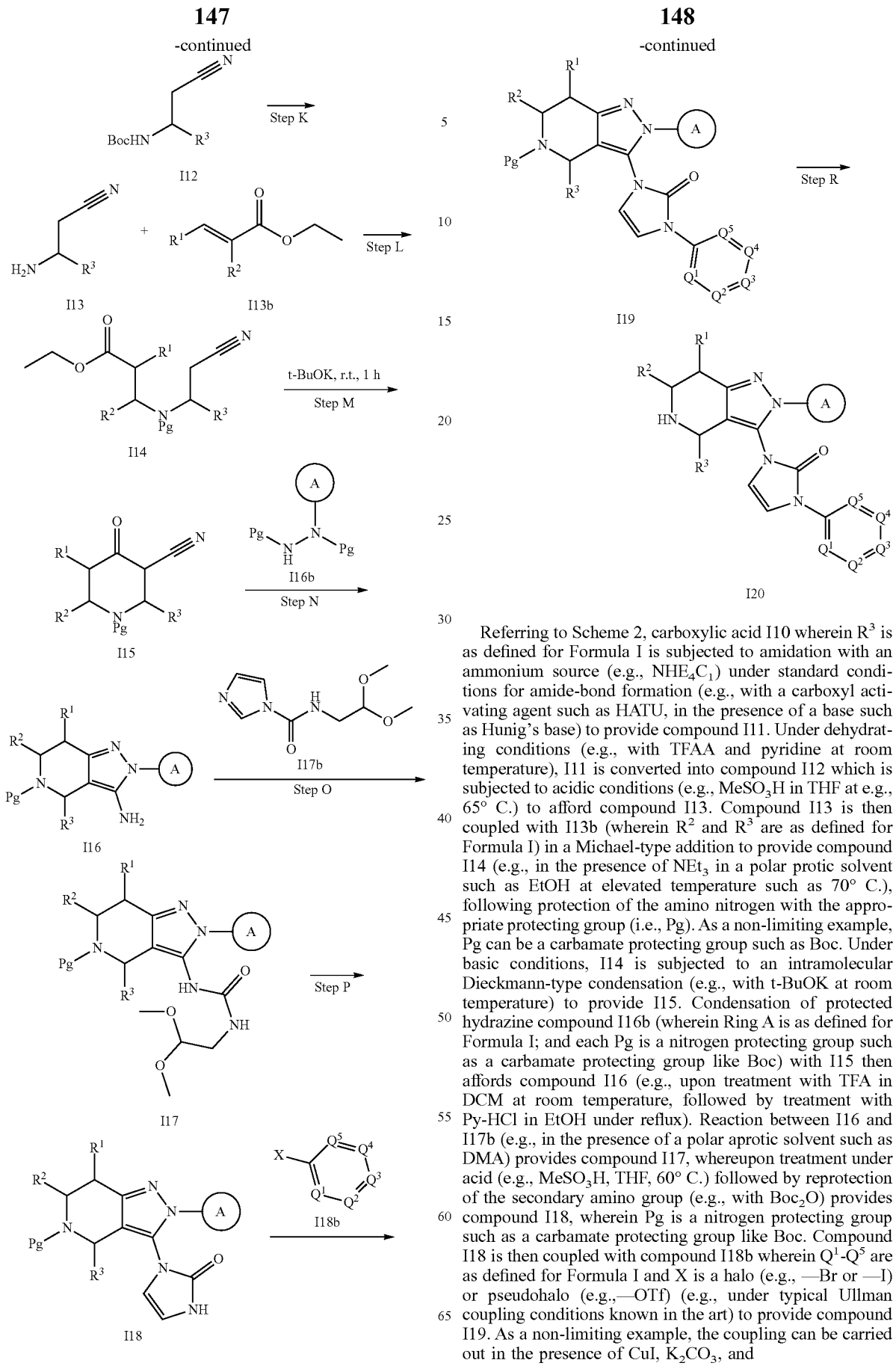

Referring to Scheme 2, carboxylic acid I10 wherein $R^3$ is as defined for Formula I is subjected to amidation with an ammonium source (e.g., $NHE_4C_1$) under standard conditions for amide-bond formation (e.g., with a carboxyl activating agent such as HATU, in the presence of a base such as Hunig's base) to provide compound I11. Under dehydrating conditions (e.g., with TFAA and pyridine at room temperature), I11 is converted into compound I12 which is subjected to acidic conditions (e.g., $MeSO_3H$ in THF at e.g., 65° C.) to afford compound I13. Compound I13 is then coupled with I13b (wherein $R^2$ and $R^3$ are as defined for Formula I) in a Michael-type addition to provide compound I14 (e.g., in the presence of $NEt_3$ in a polar protic solvent such as EtOH at elevated temperature such as 70° C.), following protection of the amino nitrogen with the appropriate protecting group (i.e., Pg). As a non-limiting example, Pg can be a carbamate protecting group such as Boc. Under basic conditions, I14 is subjected to an intramolecular Dieckmann-type condensation (e.g., with t-BuOK at room temperature) to provide I15. Condensation of protected hydrazine compound I16b (wherein Ring A is as defined for Formula I; and each Pg is a nitrogen protecting group such as a carbamate protecting group like Boc) with I15 then affords compound I16 (e.g., upon treatment with TFA in DCM at room temperature, followed by treatment with Py-HCl in EtOH under reflux). Reaction between I16 and I17b (e.g., in the presence of a polar aprotic solvent such as DMA) provides compound I17, whereupon treatment under acid (e.g., $MeSO_3H$, THF, 60° C.) followed by reprotection of the secondary amino group (e.g., with $Boc_2O$) provides compound I18, wherein Pg is a nitrogen protecting group such as a carbamate protecting group like Boc. Compound I18 is then coupled with compound I18b wherein $Q^1$-$Q^5$ are as defined for Formula I and X is a halo (e.g., —Br or —I) or pseudohalo (e.g.,—OTf) (e.g., under typical Ullman coupling conditions known in the art) to provide compound I19. As a non-limiting example, the coupling can be carried out in the presence of CuI, $K_2CO_3$, and

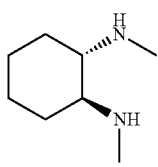

in NMP (e.g., at 130° C.). Removal of the nitrogen protecting group (i.e., Pg) on I19 (e.g., under acidic conditions such as HCl in dioxanes) then provides compound I20.

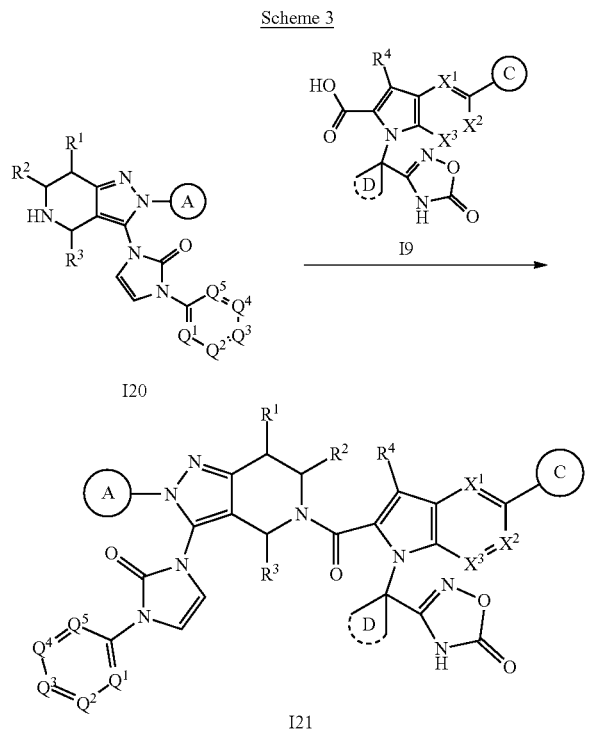

Referring to Scheme 3, coupling of I20 with I9 under standard amide bond forming conditions (e.g., in the presence of a carboxyl activation agent such as HATU (e.g., in a polar aproptic solvent such as DMF)) provides compound I21, which is a compound of Formula I.

It will be apparent to a person of ordinary skill in the art that in the synthetic sequences delineated above (see Schemes 1-3), reactive groups such as $NH_2$, NH, and OH can be protected with appropriate protecting groups, followed by a deprotection steps at appropriate stages of the synthesis. It is also within the purview of a person of ordinary skill in the art to conceive variations of the foregoing methods to synthesize other Formula I compounds. For example, by exchanging I6b with other electrophilic reagents, compounds with other $L^3$-C($R^{8a}R^{8b}$)-$L^4$-$R^9$ groups can be obtained. As another example, by replacing 116 with other appropriate reagents, compounds with other $L^2$ moieties can be obtained.

General Information All NMR spectra were recorded on a Bruker 400 (400 MHz) spectrometer. 1H chemical shifts are reported in S values in ppm with the deuterated solvent as the internal standard. Data are reported as follows: chemical shift, multiplicity (s=singlet, d=doublet, t=triplet, q=quartet, br=broad signal, m=multiplet), coupling constant (Hz), integration. LCMS spectra were obtained on an Agilent series with electrospray ionization unless otherwise indicated.

| Abbreviations | |
|---|---|
| Ac acetyl | m multiplet (spectral); meter(s); milli |
| acac acetylacetonate | M molar (moles per liter); |
| AIBN 2,2'-azobisisobutyronitrile | $M^+$ parent molecular ion |
| aq aqueous | max maximum |
| Ar aryl | Me methyl |
| atm atmosphere(s) | MEM (2-methoxyethoxy)methyl |
| av average | Mes 2,4,6-trimethylphenyl (mesityl) [not methylsulfonyl (mesyl)] |
| 9-BBN 9-borabicyclo[3.3.1]nonyl 9-BBN-H9-borabicyclo[3.3.1]nonane | MHz megahertz |
| Bn, Bzl benzyl | min minute(s); minimum |
| bpy 2,2'-bipyridyl | mM millimolar (millimoles per liter) |
| BOC, Boc tert-butoxycarbonyl | MOM methoxymethyl |
| bp boiling point, | mp melting point |
| br broad (spectral) | Ms methylsulfonyl (mesyl) |
| Bu, n-Bu normal (primary) butyl | MS mass spectrometry |
| s-Bu sec-butyl | MTBE methyl tert-butyl ether |
| t-Bu tert-butyl | MW, mol wt molecular weight |
| Bz benzoyl (not benzyl) | m/z mass-to-charge ratio (not m/e) |
| ° C. degrees Celsius | N normal (equivalents per liter) |
| calcd calculated | NBS N-bromosuccinimide |
| CAN ceric ammonium nitrate | NCS N-chlorosuccinimide |
| cat catalytic | NICS nucleus-independent chemical shift |
| CBZ, Cbz benzyloxycarbonyl (preferred over the abbreviation Z) | nm nanometer(s) |

| Abbreviations | |
|---|---|
| CD circular dichroism | NMO N-methylmorpholine-N-oxide |
| c-Hex, c-C6H11 cyclohexyl | NMP N-methylpyrrolidone |
| CI chemical ionization; configuration interaction | NMR nuclear magnetic resonance |
| CIF crystallographic information file | NOE nuclear Overhauser effect |
| cm centimeter(s) | NOESY nuclear Overhauser effect spectroscopy |
| cod 1,5-cyclooctadiene | Nu nucleophile |
| compd compound | obsd observed |
| concd concentrated | PCC pyridinium chlorochromate |
| concn concentration | PDC pyridinium dichromate |
| COSY correlation spectroscopy | PES photoelectron spectroscopy |
| cot 1,3,5,7-cyclooctatetraene | Ph phenyl |
| Cp cyclopentadienyl | piv pivaloyl |
| m-CPBA meta-chloroperoxybenzoic acid | pm picometer(s) |
| δ chemical shift in parts per million downfield from tetramethylsilane | PMB p-methoxybenzyl |
| d day(s); doublet (spectral); deci | PPA poly(phosphoric acid) |
| d density | ppm part(s) per million |
| DABCO 1,4-diazabicyclo[2.2.2]octane | PPTS pyridinium para-toluenesulfonate |
| dansyl 5-(dimethylamino)-1-naphthalenesulfonyl | Pr propyl |
| DBN 1,5-diazabicyclo[4.3.0]non-5-ene | i-Pr isopropyl |
| DBU 1,8-diazabicyclo[5.4.0]undec-7-ene | PTC phase-transfer catalysis |
| DCC N,N' dicyclohexylcarbodiimide | py pyridine |
| DCE 1,2-dichloroethane | q quartet (spectral) |
| DDQ 2,3-dichloro-5,6-dicyano- 1,4-benzoquinone | QSAR quantitative structure-activity relationship |
| DEAD diethyl azodicarboxylate | RCM ring-closure metathesis |
| DEPT distortionless enhancement by polarization transfer | redox reduction-oxidation |
| DFT density functional theory | rel relative |
| DIBALH diisobutylaluminum hydride | Rf retention factor (in chromatography) |
| DMA dimethylacetamide | ROESY rotating frame Overhauser effect spectroscopy |
| DMAP 4-(N,N-dimethylamino)pyridine | ROMP ring-opening metathesis polymerization |
| DMDO dimethyldioxirane | rt room temperature |
| DME 1,2-dimethoxyethane | s singlet (spectral); second(s) |
| DMF dimethylformamide | SAR structure-activity relationship |
| DMPU 1,3-dimethyl-3,4,5,6-tetrahydro-2(1H)-pyrimidinone | SET single electron transfer |
| DMSO dimethyl sulfoxide | SN1 unimolecular nucleophilic substitution |
| DMT 4,4'-dimethoxytrityl(4,4'-dimethoxyltriphenylmethyl) | SN2 bimolecular nucleophilic substitution |
| DNA deoxyribonucleic acid | SN' nucleophilic substitution with allylic rearrangement |
| DPS tert-butyldiphenylsilyl | SOMO single-occupied molecular orbital |
| dr diastereomeric ratio | t triplet (spectral) |
| ED50 dose effective in 50% of test subjects | t time; temperature in units of degrees Celsius (° C.) |
| EDTA ethylenediaminetetraacetic acid | T absolute temperature in units of kelvins (K) |
| eq equation | TBAB tetrabutylammonium bromide |
| equiv equivalent | TBAC tetrabutylammonium chloride |
| er enantiomeric ratio | TBAF tetrabutylammonium fluoride |
| ESI electrospray ionization | TBS tert-butyldimethylsilyl |
| Et ethyl | TBHP tert-butyl hydroperoxide |
| FID flame ionization detector; free induction decay | TCA trichloroacetic acid |
| Fmoc 9-fluorenylmethoxycarbonyl | TCNE tetracyanoethylene |
| g gram(s); prefix to NMR abbreviation denoting gradient-selected (e.g. gCOSY, gHMQC) | TDDFT time-dependent density functional theory |
| GC gas chromatography | TEAB tetraethylammonium bromide |
| | temp temperature |
| HMBC heteronuclear multiple bond correlation | Tf trifluoromethanesulfonyl (triflyl) |
| HMPA hexamethylphosphoric triamide (hexamethylphosphoramide) | TFA trifluoroacetic acid |
| HMQC heteronuclear multiple quantum correlation | TFAA trifluoroacetic anhydride |
| HOMO highest occupied molecular orbital | THF tetrahydrofuran |
| HPLC high-performance liquid chromatography | THP tetrahydropyran-2-yl |
| HRMS high-resolution mass spectrometry | TIPS triisopropylsilyl |
| HSQC heteronuclear single quantum correlation | TLC thin-layer chromatography |

-continued

| Abbreviations | |
|---|---|
| Hz hertz | TMAI tetramethylammonium iodide |
| J coupling constant (in NMR spectrometry) | TMEDA N,N,N',N+2-tetramethyl-1,2-ethylenediamine |
| k kilo K kelvin(s) (absolute temperature) | TMS trimethylsilyl; tetramethylsilane |
| L liter(s) | Tr triphenylmethyl (trityl) |
| LAH lithium aluminum hydride | tR retention time (in chromatography) |
| LDA lithium diisopropylamide; | Ts para-toluenesulfonyl (tosyl) |
| LHMDS lithium hexamethyldisilazane, lithium bis(trimethylsilyl)amide | UV ultraviolet |
| lit. literature value (abbreviation used with period) | VCD vibrational circular dichroism |
| LTMP lithium 2,2,6,6-tetramethylpiperidide | vol volume |
| LUMO lowest unoccupied molecular orbital | v/v volume per unit volume (volume-to-volume ratio) |
| µ micro | wt weight |
| | w/w weight per unit weight (weight-to-weight ratio) |

Example 1: Synthesis of 3-((1S,2S)-1-(2-((S)-3-(3-(4-(Dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 101a)

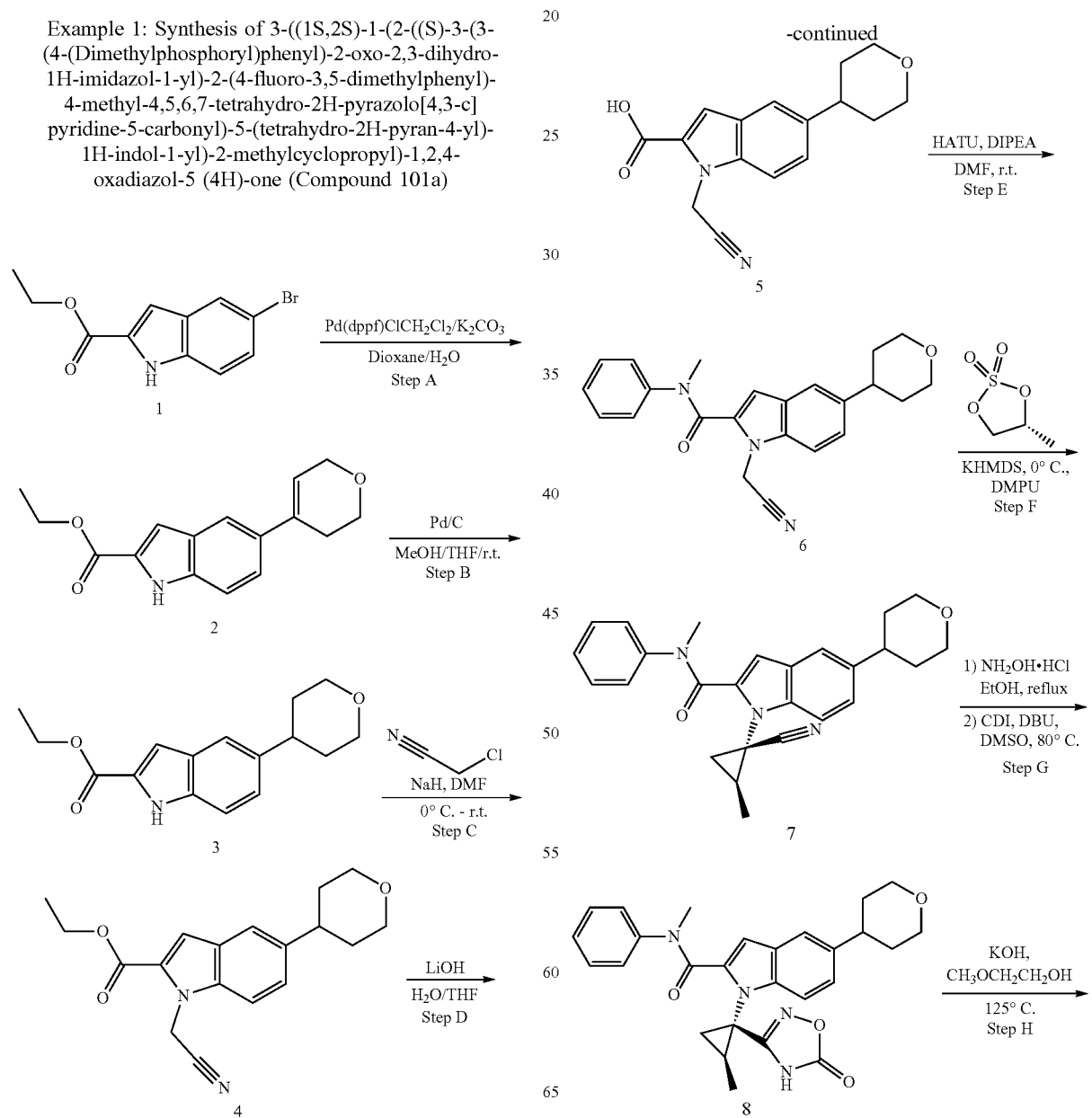

-continued

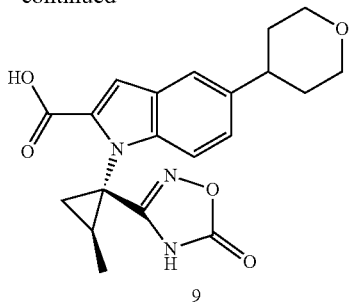

9

Step A: Ethyl 5-(3,6-dihydro-2H-pyran-4-yl)-1H-indole-2-carboxylate

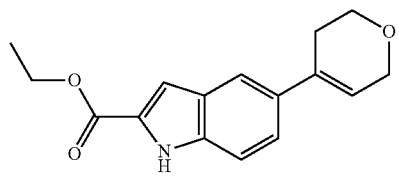 [SMILES: CCOC(=O)c1cc2cc(C3=CCOCC3)ccc2[nH]1]

To a solution of ethyl 5-bromo-1H-indole-2-carboxylate (10.0 g, 37.3 mmol) in dioxane/H$_2$O (240 mL/60 mL) were added 2-(3,6-dihydro-2H-pyran-4-yl)-4,4,5,5-tetramethyl-1,3,2-dioxaborolane (8.60 g, 41.0 mmol), Pd(dppf)Cl$_2$·CH$_2$Cl$_2$ (3.00 g, 3.73 mmol), K$_2$CO$_3$ (15.4 g, 112 mmol). The reaction was evacuated and backfilled with N$_2$ for three times. The reaction mixture was stirred at 80° C. under N$_2$ atmosphere for 2.5 h, after which it was filtered, diluted with DCM, washed with water, dried over Na$_2$SO$_4$, concentrated, and purified by silica gel column (PE/EtOAc=10/1 to 4/1) to give ethyl 5-(3,6-dihydro-2H-pyran-4-yl)-1H-indole-2-carboxylate as a white to yellow solid (7.00 g, 69% yield).

LC-MS: m/z 272.0 (M+H)$^+$ $^1$H NMR (400 MHz, CDCl$_3$) δ: 8.89 (s, 1H), 7.66 (s, 1H), 7.44 (dd, J=8.8, 1.6 Hz, 1H), 7.38 (d, J=8.8 Hz, 1H), 7.21 (dd, J=2.0, 0.8 Hz, 1H), 6.01-6.17 (m, 1H), 4.41 (q, J=7.2 Hz, 2H), 4.35 (q, J=2.8 Hz, 2H), 3.97 (t, J=5.6 Hz, 2H), 2.56-2.62 (m, 2H), 1.42 (t, J=7.2 Hz, 3H).

Step B: Ethyl 5-(tetrahydro-2H-pyran-4-yl)-1H-indole-2-carboxylate

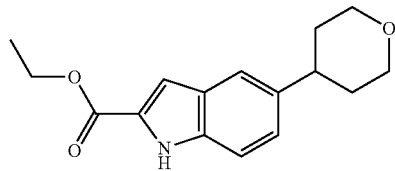 [SMILES: CCOC(=O)c1cc2cc(C3CCOCC3)ccc2[nH]1]

To a solution of ethyl 5-(3,6-dihydro-2H-pyran-4-yl)-1H-indole-2-carboxylate (7.00 g, 25.8 mmol) in MeOH/THF (50 mL/150 mL) was added 10% w/w Pd/C (700 mg). The mixture was stirred at room temperature under H$_2$ atmosphere overnight. The reaction mixture was filtered, concentrated, slurried with MeOH, and filtered to give ethyl 5-(tetrahydro-2H-pyran-4-yl)-1H-indole-2-carboxylate as a white solid (6.00 g, 85% yield).

LC-MS: m/z 274.0 (M+H)$^+$ $^1$H NMR (400 MHz, CDCl$_3$) δ: 8.87 (s, 1H), 7.51 (s, 1H), 7.37 (d, J=8.4 Hz, 1H), 7.21 (dd, J=8.4, 1.6 Hz, 1H), 7.18-7.19 (m, 1H), 4.41 (q, J=7.2 Hz, 2H), 4.11 (dd, J=10.8, 4.0 Hz, 2H), 3.56 (td, J=11.6, 2.8 Hz, 2H), 2.80-2.88 (m, 1H), 1.80-1.90 (m, 4H), 1.42 (t, J=7.2 Hz, 3H).

Step C: Ethyl 1-(cyanomethyl)-5-(tetrahydro-2H-pyran-4-yl)-1H-indole-2-carboxylate

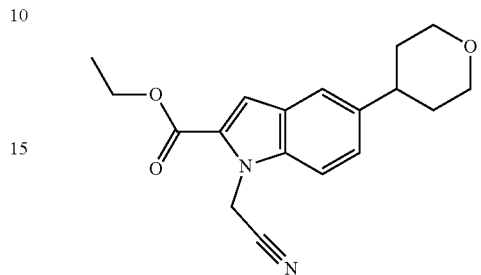

To a solution of ethyl 5-(tetrahydro-2H-pyran-4-yl)-1H-indole-2-carboxylate (6.00 g, 22.0 mmol) in DMF (170 mL) was added NaH (60% in oil) (1.30 g, 33.0 mmol) at 0° C. The mixture was stirred at 0° C. for 0.5 h, and then 2-chloroacetonitrile (3.30 g, 43.9 mmol) was added. The mixture was stirred at room temperature overnight. The reaction was quenched with H$_2$O (100 mL) at 0° C. The suspension was filtered and dried to afford ethyl 1-(cyanomethyl)-5-(tetrahydro-2H-pyran-4-yl)-1H-indole-2-carboxylate as a creamy-white solid (6.30 g, 92% yield).

LC-MS: m/z 313.0 (M+H)$^+$ $^1$H NMR (400 MHz, DMSO-d$_6$) δ: 7.71 (d, J=8.8 Hz, 1H), 7.59 (s, 1H), 7.39 (dd, J=8.8, 1.6 Hz, 1H), 7.36 (d, J=0.8 Hz, 1H), 5.75 (s, 2H), 4.37 (q, J=7.2 Hz, 2H), 3.95-3.98 (m, 2H), 3.42-3.48 (m, 2H), 2.82-2.90 (m, 1H), 1.70-1.75 (m, 4H), 1.36 (t, J=7.2 Hz, 3H).

Step D: 1-(Cyanomethyl)-5-(tetrahydro-2H-pyran-4-yl)-1H-indole-2-carboxylic acid

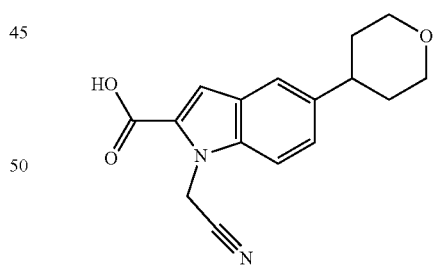

To a solution of ethyl 1-(cyanomethyl)-5-(tetrahydro-2H-pyran-4-yl)-1H-indole-2-carboxylate (4.90 g, 15.7 mmol, 1.0 equiv) in H$_2$O/THF (40 mL/70 mL) was added LiOH (564 mg, 23.6 mmol) at 0° C. The mixture was stirred at room temperature for 3 h. Then THF was removed in vacuo and pH was adjusted to around 4-5 with 1 N HCl solution. The suspension was filtered to afford 1-(cyanomethyl)-5-(tetrahydro-2H-pyran-4-yl)-1H-indole-2-carboxylic acid as off-white solid (4.30 g, 97% yield).

LC-MS: m/z 285.0 (M+H)$^+$ $^1$H NMR (400 MHz, DMSO-d$_6$) δ: 13.3 (s, 1H), 7.68 (d, J=8.4 Hz, 1H), 7.58 (s, 1H), 7.37 (dd, J=8.8, 1.6 Hz, 1H), 7.31 (d, J=0.4 Hz, 1H), 5.76 (s, 2H), 3.95-3.98 (m, 2H), 3.45-3.49 (m, 2H), 2.82-2.90 (m, 1H), 1.71-1.76 (m, 4H).

Step E: 1-(Cyanomethyl)-N-methyl-N-phenyl-5-(tetrahydro-2H-pyran-4-yl)-1H-indole-2-carboxamide

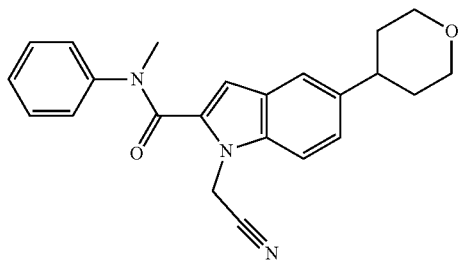 [SMILES: CN(C(=O)c1cc2cc(C3CCOCC3)ccc2n1CC#N)c1ccccc1]

To a solution of 1-(cyanomethyl)-5-(tetrahydro-2H-pyran-4-yl)-1H-indole-2-carboxylic acid (4.70 g, 16.6 mmol) and HATU (9.43 g, 24.8 mmol) in DMF (70 mL) was added DIPEA (8.65 mL, 49.6 mmol) at 0° C. The mixture was stirred at 0° C. for 1 h, and then N-methylaniline (2.68 mL, 24.8 mmol) was added. The mixture was stirred at room temperature overnight, after which it was diluted with water (150 mL) and extracted with EtOAc (100 mL*3). The organic layers was dried over $Na_2SO_4$, concentrated, and purified by silica gel column (PE/EA=6/1 to 4/1) to afford the title compound as a yellow solid (4.30 g, 70% yield).

LC-MS: m/z 374.0 $(M+H)^+$ $^1$H NMR (400 MHz, $CDCl_3$) δ: 7.34-7.38 (m, 2H), 7.29-7.31 (m, 2H), 7.21-7.24 (m, 4H), 5.90 (s, 1H), 5.54 (s, 2H), 4.04-4.07 (m, 2H), 3.47-3.54 (m, 5H), 2.73-2.80 (m, 1H), 1.72-1.84 (m, 4H)

Step F: 1-((1S,2S)-1-Cyano-2-methylcyclopropyl)-N-methyl-N-phenyl-5-(tetrahydro-2H-pyran-4-yl)-1H-indole-2-carboxamide

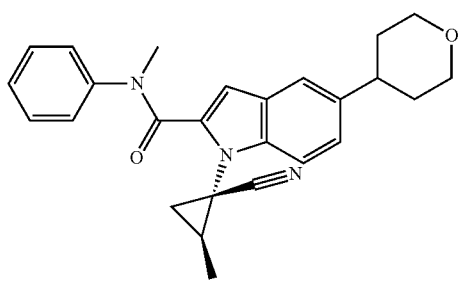 [SMILES: C[C@H]1C[C@]1(C#N)n1c(C(=O)N(C)c2ccccc2)cc2cc(C3CCOCC3)ccc21]

To a solution of 1-(cyanomethyl)-N-methyl-N-phenyl-5-(tetrahydro-2H-pyran-4-yl)-1H-indole-2-carboxamide (2.90 g, 7.80 mmol) and (R)-4-methyl-1,3,2-dioxathiolane 2,2-dioxide (2.70 g, 19.5 mmol) in DMPU (15 mL) was added dropwise KHMDS (1.0 mol/L in THF, 31.2 mL, 31.2 mmol) at 0° C. under $N_2$ atmosphere. The reaction mixture was stirred at 0° C. for 2 h. The reaction mixture was quenched with HCOOH (10 mL), concentrated in vacuo, and purified by flash chromatography (PE/EtOAc=1/1) to afford crude 1-((1S,2S)-1-cyano-2-methylcyclopropyl)-N-methyl-N-phenyl-5-(tetrahydro-2H-pyran-4-yl)-1H-indole-2-carboxamide (3.20 g) as a yellow oil which was used directly for the next step without further purifications.

LC-MS: m/z 414.1 $(M+H)^+$

Step G: N-Methyl-1-((1S,2S)-2-methyl-1-(5-oxo-4,5-dihydro-1,2,4-oxadiazol-3-yl)cyclopropyl)-N-phenyl-5-(tetrahydro-2H-pyran-4-yl)-1H-indole-2-carboxamide

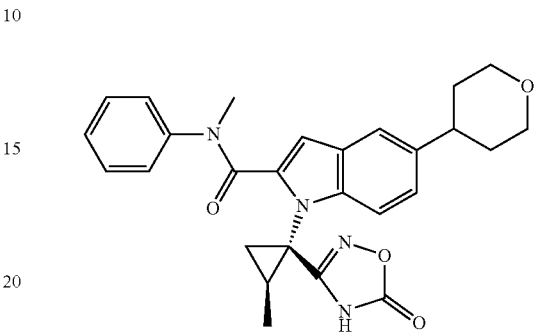

A solution of crude 1-((1S,2S)-1-cyano-2-methylcyclopropyl)-N-methyl-N-phenyl-5-(tetrahydro-2H-pyran-4-yl)-1H-indole-2-carboxamide (3.20 g, 7.80 mmol), $NH_2OH·HCl$ (2.70 g, 39.0 mmol), and $K_2CO_3$ (5.90 g, 43.0 mmol) in EtOH (50 mL) was stirred at 100° C. for 2 h. The reaction mixture was concentrated and diluted with $H_2O$ (100 mL). The suspension was filtered and dried under vacuum. The solid was dissolved in DMSO (10 mL) and then carbonyl diimidazole (2.50 g, 15.6 mmol) and 1,8-diazabicycloundec-7-ene (3.00 g, 19.5 mmol) were added. The resulting mixture was stirred at 80° C. for 1 h. Formic acid (5 mL) was added and then the mixture was concentrated and purified by reversed-phase chromatography (acetonitrile/$H_2O$=7/3, 0.1% formic acid) to obtain N-methyl-1-((1S,2S)-2-methyl-1-(5-oxo-4,5-dihydro-1,2,4-oxadiazol-3-yl)cyclopropyl)-N-phenyl-5-(tetrahydro-2H-pyran-4-yl)-1H-indole-2-carboxamide as a white solid (1.00 g, 27% yield).

LC-MS: m/z 473.1 $(M+H)^+$

Step H: 1-((1S,2S)-2-Methyl-1-(5-oxo-4,5-dihydro-1,2,4-oxadiazol-3-yl)cyclopropyl)-5-(tetrahydro-2H-pyran-4-yl)-1H-indole-2-carboxylic acid

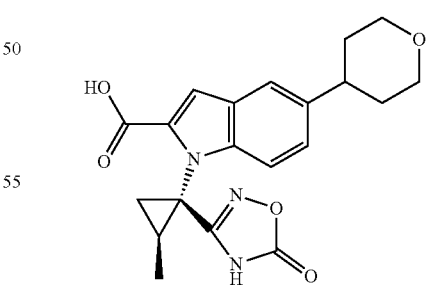

A solution of N-methyl-1-((1S,2S)-2-methyl-1-(5-oxo-4,5-dihydro-1,2,4-oxadiazol-3-yl)cyclopropyl)-N-phenyl-5-(tetrahydro-2H-pyran-4-yl)-1H-indole-2-carboxamide (1.00 g, 2.10 mmol) and KOH (1.20 g, 21.0 mmol) in $CH_3CH_2CH_2OH$ (4 mL) was stirred at 130° C. for 1 h. The reaction mixture was acidified with 5 N HCl solution to pH=3, and a brown precipitate was observed. The solid was collected by filtration, washed with H₂O (5 mL), and dried under reduced pressure to afford 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid as a brown solid (700 mg, 86% yield).
LC-MS: m/z 384.1 (M+H)⁺
¹H NMR (400 MHz, DMSO-d₆) δ: 12.88 (s, 1H), 12.29 (s, 0.4H), 12.02 (s, 0.6H), 7.54 (d, J=4.8 Hz, 1H), 7.37 (t, J=8.0 Hz, 1H), 7.29 (td, J=11.2 Hz, 1.2 Hz, 1H), 7.19 (d, J=4.4 Hz, 1H), 3.94-3.97 (m, 2H), 3.41-3.49 (m, 2H), 2.79-2.88 (m, 1H), 1.89-2.03 (m, 1H), 1.54-1.82 (m, 6H), 1.39 (d, J=6.4 Hz, 1.3H), 1.27 (d, J=6.5 Hz, 1.7H).
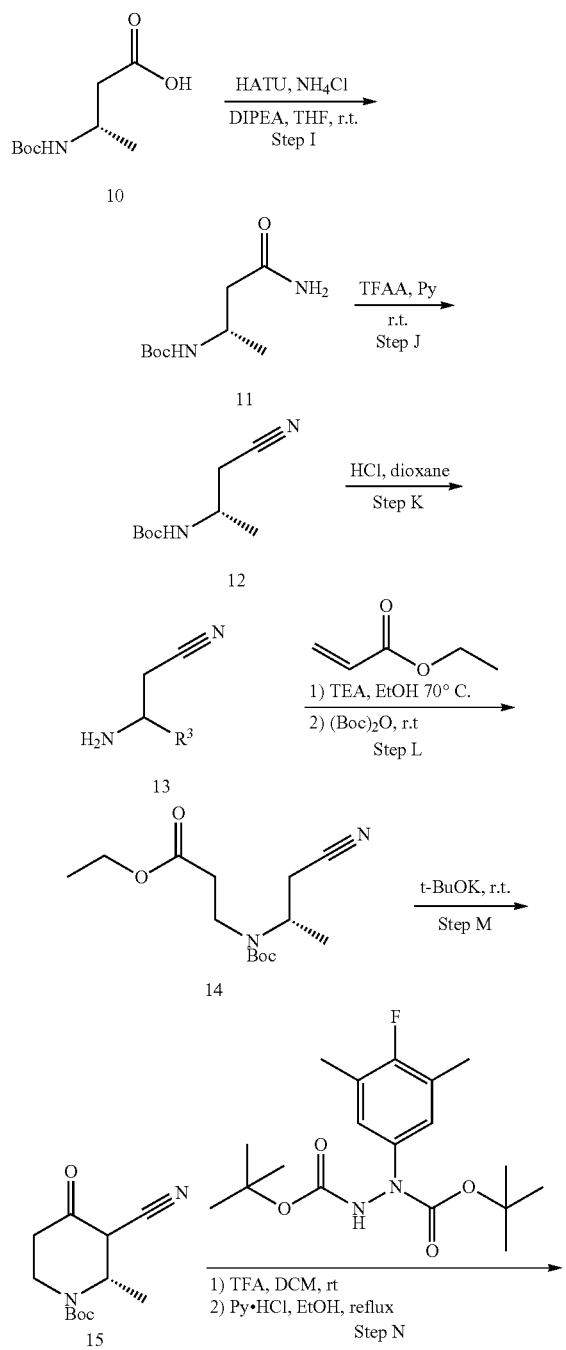
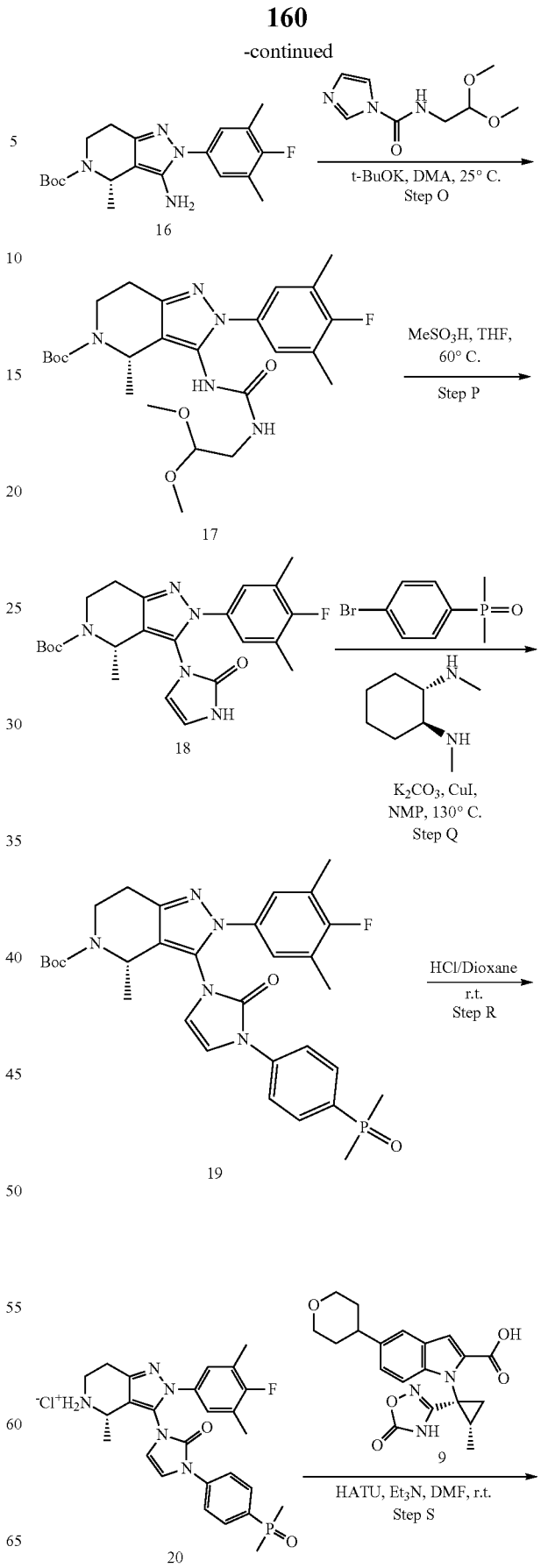

-continued

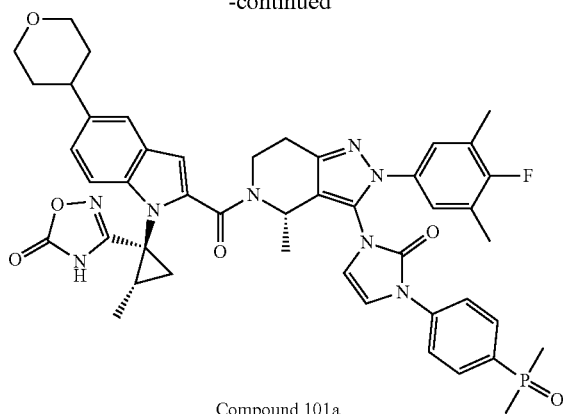

Compound 101a

Step I: (S)-tert-Butyl(4-amino-4-oxobutan-2-yl)carbamate

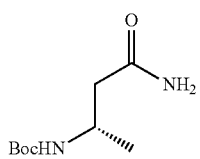

To a mixture of methyl (S)-3-((tert-butoxycarbonyl)amino)butanoic acid (10.0 g, 49.2 mmol) in THF (150 mL) was added HATU (22.5 g, 59.0 mmol), DIPEA (19.0 g, 148 mmol), and NH$_4$Cl (6.60 g, 123 mmol) at 0° C. The reaction mixture was stirred at room temperature overnight under N$_2$, after which it was diluted with EtOAc (150 mL), washed with H$_2$O (50 mL*3), dried over Na$_2$SO$_4$, concentrated in vacuo, and purified by flash chromatography (PE/EtOAc=1/1) to afford (S)-tert-butyl(4-amino-4-oxobutan-2-yl)carbamate as a yellow solid (12.2 g, 100% yield).

$^1$H NMR (400 MHz, DMSO-d$_6$) δ 7.27 (s, 1H), 6.79 (s, 1H), 6.69 (d, J=8.0 Hz, 1H), 3.70-3.84 (m, 1H), 2.23 (dd, J=14.0, 5.6 Hz, 1H), 2.06 (dd, J=14.0, 8.0 Hz, 1H), 1.37 (s, 9H), 1.01 (d, J=6.4 Hz, 3H).

Step J: (S)-tert-Butyl(1-cyanopropan-2-yl)carbamate

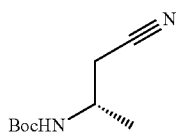

To a mixture of (S)-tert-butyl(4-amino-4-oxobutan-2-yl)carbamate (10.0 g, 49.5 mmol) were added TFAA (6.90 mL, 49.5 mmol) and pyridine (8.00 mL, 99.0 mmol). The mixture was stirred at room temperature for 1 h. The reaction was quenched with H$_2$O (100 mL) and extracted with EtOAc (100 mL*3). The organic layers were washed with brine (100 mL), dried over Na$_2$SO$_4$, concentrated in vacuo and purified by flash chromatography (PE/EtOAc=20/1) to afford (S)-tert-butyl(1-cyanopropan-2-yl)carbamate as a white solid (6.00 g, 65% yield).

$^1$H NMR (400 MHz, DMSO-d$_6$) δ 7.11 (d, J=7.2 Hz, 1H), 3.71-3.74 (m, 1H), 2.57-2.69 (m, 2H), 1.39 (s, 9H), 1.11 (d, J=6.4 Hz, 3H).

Step K: (S)-3-Aminobutanenitrile

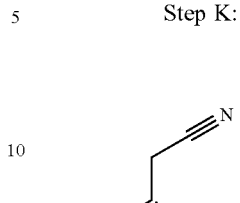

A solution of (S)-tert-butyl(1-cyanopropan-2-yl)carbamate (2.10 g, 11.4 mmol) in 4 N HCl solution in dioxane (20 mL) was stirred at room temperature for 3 h. The reaction mixture was concentrated in vacuo to afford (S)-3-aminobutanenitrile HCl salt as a white solid (1.50 g, 100% yield).

$^1$H NMR (400 MHz, DMSO-d$_6$) δ 8.58 (br. s, 2H), 3.38-3.53 (m, 1H), 2.90-3.06 (m, 2H), 1.27-1.38 (m, 3H).

Step L: (S)-Ethyl 3-((tert-butoxycarbonyl)(1-cyanopropan-2-yl) amino)propanoate

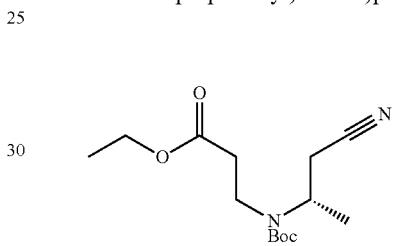

To a solution of (s)-3-aminobutanenitrile (2.80 g, 23.1 mmol, 1.0 equiv) in EtOH (20 mL) was added TEA (3.50 g, 34.6 mmol, 1.5 equiv) and ethyl acrylate (2.33 g, 23.1 mmol, 1.0 equiv) at room temperature. After stirred at 70° C. for 3 h, the reaction mixture was cooled to room temperature and (Boc)$_2$O (6.10 mL, 27.8 mmol, 1.2 equiv) was added. The solution was stirred at room temperature overnight and then diluted with H$_2$O (50 mL). The mixture was extracted with EtOAc (50 mL*3). The organic layers were washed with brine (50 mL), dried over Na$_2$SO$_4$, concentrated and purified by flash chromatography (PE/EtOAc=10/1) to afford (s)-ethyl 3-((tert-butoxycarbonyl)(1-cyanopropan-2-yl) amino)propanoate (4.00 g, 68% yield).

$^1$H NMR (400 MHz, DMSO-d$_6$) δ 4.09-4.18 (m, 3H), 3.40-3.52 (m, 2H), 2.51-2.78 (m, 4H), 1.48 (s, 9H), 1.34-1.36 (m, 3H), 1.25-1.29 (m, 3H).

Step M: tert-Butyl (2S)-3-cyano-2-methyl-4-oxopiperidine-1-carboxylate

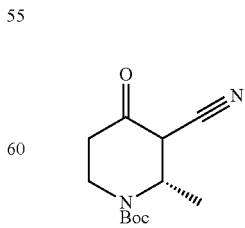

To a solution of (s)-ethyl 3-((tert-butoxycarbonyl)(1-cyanopropan-2-yl) amino)propanoate (3.00 g, 10.6 mmol) in THF (100 mL) was added t-BuOK (1.20 g, 10.6 mmol). The mixture was stirred at room temperature for 1 h and then quenched with 2N HCl solution. The mixture was diluted with H₂O (100 mL) and extracted with EtOAc (100 mL*3). The organic layers were washed with brine, dried over Na₂SO₄, concentrated in vacuo, and purified by flash chromatography (PE/EtOAc=8/1) to afford tert-butyl (2S)-3-cyano-2-methyl-4-oxopiperidine-1-carboxylate (2.60 g, 100% yield).

Step N: tert-Butyl (S)-3-amino-2-(4-fluoro-3, 5-dimethylphenyl)-4-methyl-2, 4, 6, 7-tetrahydro-5H-pyrazolo[4, 3-c]pyridine-5-carboxylate

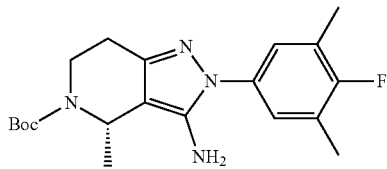 [SMILES: Cc1cc(-n2nc3c(c2N)[C@H](C)N(C(=O)OC(C)(C)C)CC3)cc(C)c1F]

To a solution of di-tert-butyl 1-(4-fluoro-3,5-dimethylphenyl)hydrazine-1, 2-dicarboxylate (4.46 g, 12.6 mmol) in DCM (40 mL) was added TFA (18 mL) and the mixture was stirred at room temperature for 1 h. The reaction mixture was concentrated in vacuo. A EtOH (40 mL) solution of Py'HCl (145 mg, 1.26 mmol) and tert-butyl (2S)-3-cyano-2-methyl-4-oxopiperidine-1-carboxylate (2.40 g, 10.1 mmol) were added. The reaction mixture was stirred at 85° C. for 2 h. The reaction mixture was cooled to room temperature, diluted with saturated NaOH aqueous solution (20 mL) and extracted with DCM (20 mL*3). The combined organic phase was concentrated in vacuo and the residue was purified by flash chromatography (PE/EtOAc=20/1) to afford tert-butyl (S)-3-amino-2-(4-fluoro-3, 5-dimethylphenyl)-4-methyl-2, 4, 6, 7-tetrahydro-5H-pyrazolo[4, 3-c]pyridine-5-carboxylate (2.70 g, 57% yield).

¹H NMR (400 MHz, DMSO-d₆) δ: 7.23 (d, J=6.4 Hz, 2H), 5.20 (br. s, 2H), 5.01-5.12 (m, 1H), 4.02-4.16 (m, 1H), 2.98-3.07 (m, 1H), 2.42-2.46 (m, 2H), 2.25 (d, J=2.0 Hz, 6H), 1.43 (s, 9H), 1.24-1.26 (m, 3H).

Step O: tert-Butyl (S)-3-(3-(2,2-dimethoxyethyl)ureido)-2-(4-fluoro-3,5-dimethylphenyl)-4-methyl-2,4,6,7-tetrahydro-5H-pyrazolo[4,3-c]pyridine-5-carboxylate

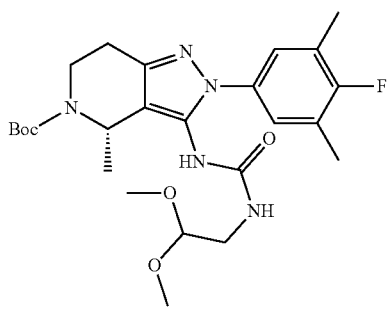 [SMILES: COC(CNC(=O)Nc1c2c(nn1-c1cc(C)c(F)c(C)c1)CCN(C(=O)OC(C)(C)C)[C@H]2C)OC]

To a solution of tert-butyl (S)-3-amino-2-(4-fluoro-3,5-dimethylphenyl)-4-methyl-2,4,6,7-tetrahydro-5H-pyrazolo[4,3-c]pyridine-5-carboxylate (400 mg, 1.10 mmol) and N-(2,2-dimethoxyethyl)-1H-imidazole-1-carboxamide (426 mg, 2.2 mmol) in DMA (20 mL) was added t-BuOK (358 mg, 3.20 mmol) at room temperature. The reaction mixture was stirred at 80° C. for 48 h. The reaction mixture was quenched with H₂O (10 mL), concentrated in vacuo and purified by flash chromatography (PE/EtOAc=1/1) to afford tert-butyl (S)-3-(3-(2,2-dimethoxyethyl)ureido)-2-(4-fluoro-3,5-dimethylphenyl)-4-methyl-2,4,6,7-tetrahydro-5H-pyrazolo[4,3-c]pyridine-5-carboxylate as a yellow solid (181 mg, 33% yield).

LC-MS: m/z 506.4 (M+H)⁺

Step P: tert-Butyl (S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate

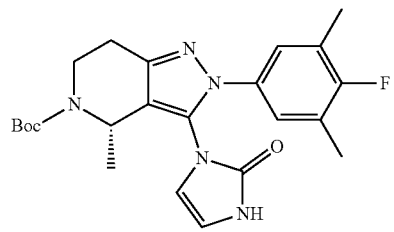 [SMILES: Cc1cc(-n2nc3c(c2-n2cc[nH]c2=O)[C@H](C)N(C(=O)OC(C)(C)C)CC3)cc(C)c1F]

tert-Butyl (S)-3-(3-(2,2-dimethoxyethyl)ureido)-2-(4-fluoro-3,5-dimethylphenyl)-4-methyl-2,4,6,7-tetrahydro-5H-pyrazolo[4,3-c] pyridine-5-carboxylate (181 mg, 0.360 mmol) was suspended in THF (10 mL). Methanesulfonic acid (35.0 mg, 0.360 mmol) was added at external temperature 60° C. The mixture was stirred for 2 h. Water (10 mL) was added to the reaction solution and then the mixture was extracted with EtOAc (10 mL*3). The organic layer was washed with brine, dried over Na₂SO₄, concentrated under reduced pressure and purified by silica gel column chromatography (PE/EtOAc=1/1) to give tert-butyl (S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c] pyridine-5-carboxylate as yellow solid (139 mg, 88% yield).

LC-MS: m/z 442.3 (M+H)⁺

Step Q: tert-Butyl(S)-3-(3-(4-(dimethylphosphoryl)phenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate

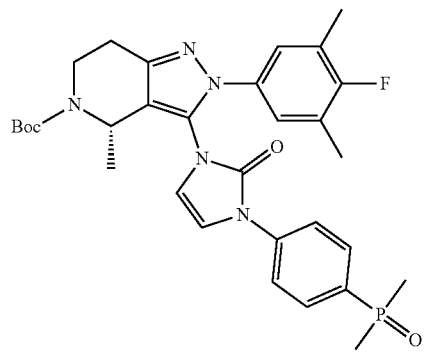 [SMILES: Cc1cc(-n2nc3c(c2-n2ccn(-c4ccc(P(C)(C)=O)cc4)c2=O)[C@H](C)N(C(=O)OC(C)(C)C)CC3)cc(C)c1F]

To a mixture of tert-Butyl (S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (139 mg, 0.320 mmol), (4-bromophenyl) dimethylphosphine oxide (110 mg, 0.470 mmol), (1S, 2S)-1-N,2-N-dimethylcyclohexane-1,2-diamine (67.0 mg, 0.470 mmol), and potassium carbonate (88.0 mg, 0.640 mmol) in N-methyl pyrrolidone (15 mL) was added copper (I) iodide (90.0 mg, 0.470 mmol) at room temperature. The mixture was degassed and recharged with $N_2$ for three times. Then the mixture was stirred at 130° C. for 3 h under $N_2$ atmosphere. The reaction mixture was purified by silica gel chromatography to give tert-butyl (S)-3-(3-(4-(dimethylphosphoryl)phenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate as a yellow solid (76.0 mg, 41% yield).

LC-MS: m/z 594.4 (M+H)$^+$

Step R: (S)-3-(3-(4-(Dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridin-5-ium chloride

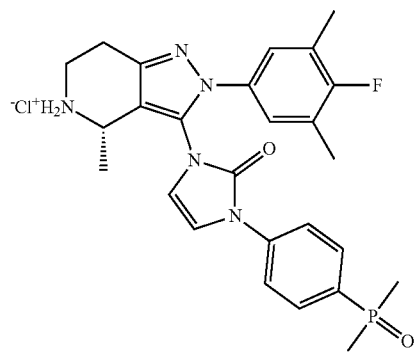

A mixture of tert-butyl (S)-3-(3-(4-(dimethylphosphoryl)phenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate (76.0 mg, 0.130 mmol) and 4 N HCl solution in dioxane (50 ml) was stirred at room temperature for 16 h. The mixture was concentrated under reduced pressure to give the title compound (S)-3-(3-(4-(dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridin-5-ium chloride as a yellow solid (54.0 mg, 34% yield).

LC-MS: m/z 494.2 (M+H)$^+$

Step S: 3-((1S,2S)-1-(2-((S)-3-(3-(4-(Dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one

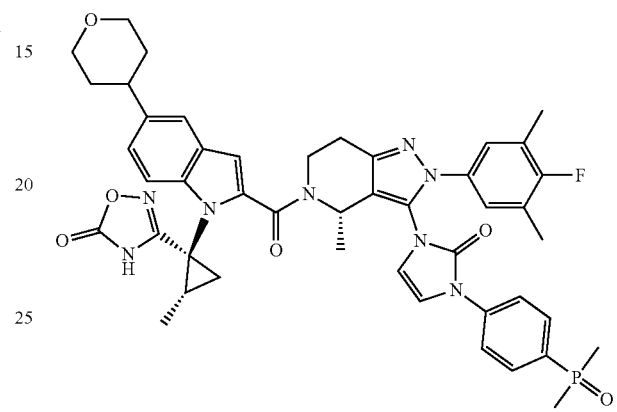

A solution of (S)-3-(3-(4-(Dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridin-5-ium chloride (54.0 mg, 0.110 mmol), 1-((1S, 2S)-2-methyl-1-(5-oxo-4,5-dihydro-1,2,4-oxadiazol-3-yl) cyclopropyl)-5-(tetrahydro-2H-pyran-4-yl)-1H-indole-2-carboxylic acid (46.0 mg, 0.120 mmol), HATU (125 mg, 0.320 mmol) and $Et_3N$ (220 mg, 2.20 mmol) in DMF (4 ml) was stirred at room temperature for 16 h. The mixture was treated with water (30 ml) and extracted with EtOAc (10 mL*3). The organic layer was washed with brine, dried over $Na_2SO_4$, concentrated under reduced pressure, and purified by pre-HPLC to give compound 3-((1S,2S)-1-(2-((S)-3-(3-(4-(dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one as a yellow solid (29.0 mg, 33% yield).

LC-MS: m/z 859.2 (M+H)$^+$

1H NMR (400 MHz, DMSO-d$_6$, 80° C.) δ: 7.79-7.90 (m, 4H), 7.35-7.45 (m, 2H), 7.10-7.30 (m, 4H), 6.95 (br, 1H), 6.57 (br, 1H), 5.41-5.52 (m, 1H), 4.37 (t, J=8.4 Hz, 1H), 3.96 (d, J=10.4 Hz, 2H), 3.85 (dd, J=9.2, 6.0 Hz, 1H), 3.47 (td, J=10.8, 3.6 Hz, 2H), 2.98-3.01 (m, 1H), 2.75-2.83 (m, 2H), 2.65-2.75 (m, 1H), 2.18 (d, J=1.2 Hz, 6H), 1.71-1.76 (s, 4H), 1.56-1.70 (m, 8H), 1.15-1.40 (m, 6H).

Example 2: Synthesis of 3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 121a)
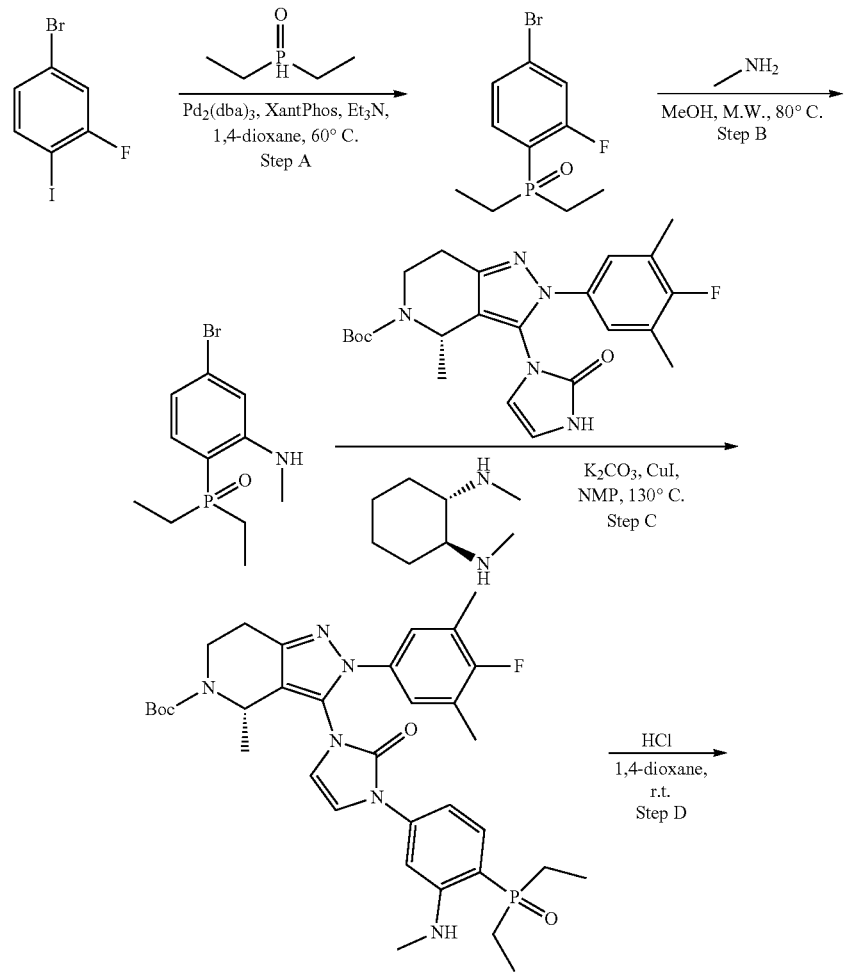
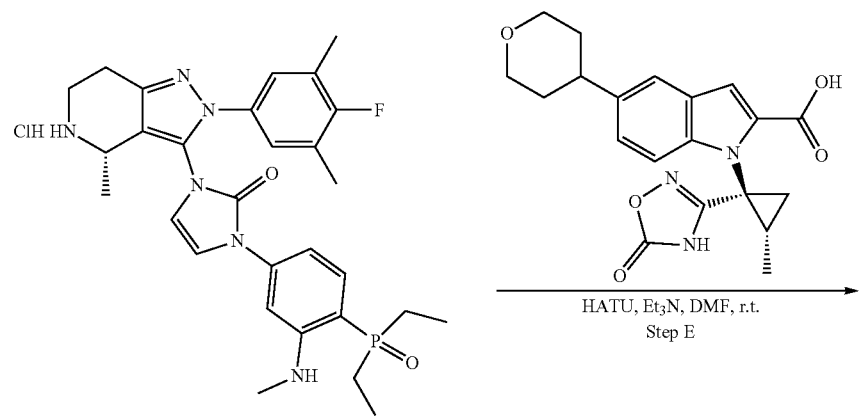

-continued

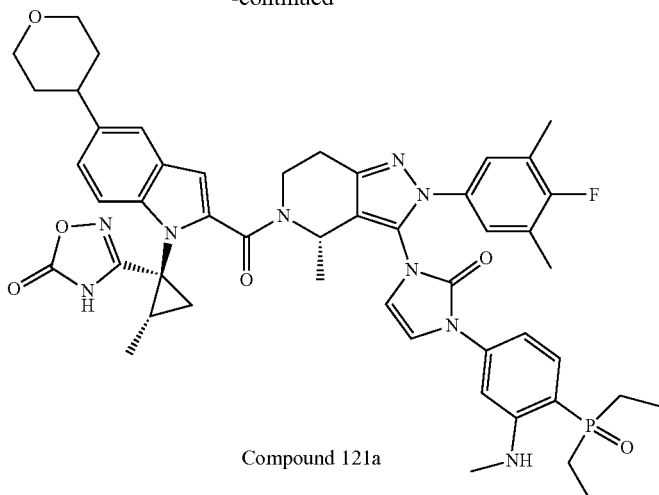

Compound 121a

Step A: (4-bromo-2-fluorophenyl)diethylphosphine oxide

The mixture of 4-bromo-2-fluoro-1-iodobenzene (2.00 g, 6.60 mmol), diethylphosphine oxide (775 mg, 7.30 mmol), Pd$_2$(dba)$_3$ (302 mg, 0.330 mmol) and XantPhos (382 mg, 0.660 mmol) in 40 mL of 1,4-dioxane was sparged with argon. Then triethylamine (1.30 g, 13.2 mmol) was added. The mixture was heated at 60° C. for 12 h under an atmosphere of argon. LCMS showed the reaction was completed. The mixture was concentrated, and the residue was diluted with ethyl acetate (100 mL) and washed with water (50 mL). The organic layer was dried and concentrated. The residue was purified with silica gel column chromatography (PE/EA/methanol=1:2:0.1) to provide (4-bromo-2-fluorophenyl)diethylphosphine oxide (1.50 g, 5.37 mmol, 80.6% yield) as a pale white solid.

LCMS: m/z=279.0, 281.0 (M+H)$^+$.

$^1$H NMR (400 MHz, DMSO-d$_6$) δ 7.63-7.73 (m, 3H), 1.95-2.08 (m, 2H), 1.80-1.92 (m, 2H), 0.80-1.10 (m, 6H).

Step B: (4-bromo-2-(methylamino)phenyl)diethylphosphine oxide

To a mixture of (4-bromo-2-fluorophenyl)diethylphosphine oxide (360 mg, 1.29 mmol) in 2 mL of methanol was added methylamine (9.8 M in methanol, 4 mL, 39.2 mmol). The mixture was heated at 80° C. for 3 h in a microwave reactor. LCMS showed most of the starting material was consumed. The mixture was concentrated, diluted with ethyl acetate (50 mL), and washed with water (30 mL). The organic layer was dried and concentrated. The resulting residue was purified with silica gel column chromatography (PE/EA/methanol=1:2:0.1) to provide (4-bromo-2-(methylamino)phenyl)diethylphosphine oxide (179 mg, 0.617 mmol, 47.9% yield) as a white solid.

LCMS: m/z=290.0, 292.0 (M+H)$^+$.

$^1$H NMR (600 MHz, DMSO-d$_6$) δ 7.75-7.76 (m, 1H), 7.11 (dd, J=13.2, 8.4 Hz, 1H), 6.63-6.80 (m, 2H), 2.71 (d, J=5.4 Hz, 3H), 1.88-1.94 (m, 4H), 0.90-1.05 (m, 6H).

Step C: tert-butyl (S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate The mixture of (4-bromo-2-(methylamino)phenyl)diethylphosphine oxide (310 mg, 1.07 mmol), tert-butyl (S)-2-(4-fluoro-3,5-dimethylphenyl)-4-methyl-3-(2-oxo-2,3-dihydro-1H-imidazol-1-yl)-2,4,6,7-tetrahydro-5H-pyrazolo[4,3-c]pyridine-5-carboxylate (428 mg, 0.970 mmol), CuI (278 mg, 1.46 mmol), potassium carbonate (268 mg, 1.94 mmol), and (1S,2S)—N$^1$,N$^2$-dimethylcyclohexane-1,2-diamine (208 mg, 1.46 mmol) in NMP (25 mL) was heated at 130° C. for 3 h under an atmosphere of argon. LCMS showed the reaction was completed. The mixture was added ethyl acetate (100 mL) and washed with water (50 mL*3). The organic layer was dried and concentrated. The residue was purified with silica gel column chromatography (PE/EA/methanol=1:4:0.3) to provide tert-butyl (S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-2,4,6,7-tetrahydro-5H-pyrazolo[4,3-c]pyridine-5-carboxylate (530 mg, 0.810 mmol, 84.0% yield) as a pale yellow solid.

LCMS: m/z=651.3 (M+H)$^+$.

$^1$H NMR (600 MHz, DMSO-d$_6$) δ 7.73 (q, J=4.8 Hz, 1H), 7.35 (d, J=3.0 Hz, 1H), 7.26 (dd, J=13.2, 8.4 Hz, 1H), 7.11 (d, J=6.6 Hz, 2H), 6.98 (s, 1H), 6.89 (d, J=7.8 Hz, 1H), 6.86 (s, 1H), 5.12 (br. s, 1H), 4.13-4.34 (m, 1H), 3.02-3.19 (m, 1H), 2.69-2.74 (m, 4H), 2.61-2.69 (m, 1H), 2.19 (s, 6H), 1.89-1.95 (m, 4H), 1.43 (s, 9H), 1.17-1.18 (m, 3H), 0.95-1.05 (m, 6H).

Step D: (S)-1-(4-(diethylphosphoryl)-3-(methylamino)phenyl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one hydrochloride To a mixture of tert-butyl (S)-3-(3-(4-(diethylphosphoryl)-3-(methylamino)phenyl)-2-oxo-2,3-dihydro-1H-imidazol-1-yl)-2-(4-fluoro-3, 5-dimethylphenyl)-4-methyl-2,4,6,7-tetrahydro-5H-pyrazolo[4,3-c]pyridine-5-carboxylate (520 mg, 0.800 mmol) in 1,4-dioxane (6 mL) was added hydrogen chloride (4 M in 1,4-dioxane, 12 mL, 48.0 mmol). The mixture was stirred at room temperature for 3 h. LCMS showed the reaction was completed. The mixture was concentrated, and the residue was dispersed in 40 mL of ethyl ether. The resulting solid was collected and dried in vacuo to provide (S)-1-(4-(diethylphosphoryl)-3-(methylamino)phenyl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one hydrochloride (430 mg, 0.730 mmol, 91.7% yield) as a pale yellow solid.

LCMS: m/z=551.2 (M+H)+.

1H NMR (400 MHz, DMSO-d6) δ 10.14 (s, 1H), 9.46-9.53 (m, 1H), 7.39 (d, J=3.2 Hz, 1H), 7.27 (dd, J=12.8, 8.4 Hz, 1H), 7.13 (d, J=6.4 Hz, 2H), 6.93 (d, J=3.2 Hz, 1H), 6.90 (dt, J=8.4, 2.0 Hz, 1H), 6.86-6.87 (m, 1H), 4.55-4.59 (m, 2H), 3.58-3.62 (m, 1H), 3.28-3.33 (m, 1H), 3.03-3.10 (m, 1H), 2.90-3.05 (m, 1H), 2.73 (s, 3H), 2.20 (d, J=2.0 Hz, 6H), 1.88-1.97 (m, 4H), 1.36 (d, J=6.8 Hz, 3H), 0.90-1.05 (m, 6H).

Step E: 3-((1S,2S)-1-(2-((S)-3-(3-(4-(diethylphosphoryl)-3-(methylamino) phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one To a mixture of 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (272 mg, 0.710 mmol) and DMF (7 mL) in a 50 mL flask (flask A) were added HATU (810 mg, 2.13 mmol) and triethylamine (1.45 g, 14.3 mmol). The mixture was stirred at room temperature for 10 mins. In another 50 mL flask (flask B), (S)-1-(4-(diethylphosphoryl)-3-(methylamino)phenyl)-3-(2-(4-fluoro-3, 5-dimethylphenyl)-4-methyl-4,5,6,7-tetrahydro-2H-pyrazolo[4,3-c]pyridin-3-yl)-1,3-dihydro-2H-imidazol-2-one hydrochloride (420 mg, 0.710 mmol) and triethylamine (2.90 g, 28.7 mmol) in 7 mL of DMF was stirred at room temperature for 10 mins. Then the mixture in flask B was added into flask A dropwise. The resulting mixture was stirred at room temperature for 12 h. LCMS showed most of the starting material was consumed. The mixture was diluted with DCM (100 mL) and washed with water (50 mL*3). The organic layer was dried and concentrated. The residue was purified with Prep-HPLC (0.01% hydrochloric acid in water and acetonitrile) to provide 3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (290 mg) as a white solid.

LCMS: m/z=916.4 (M+H)+.

1H NMR (400 MHz, DMSO-d6, 80° C.) δ 11.58 (br. s, 1H), 7.66 (br. s, 1H), 7.52 (s, 1H), 7.42 (d, J=8.4 Hz, 1H), 7.05-7.30 (m, 5H), 6.70-6.95 (m, 4H), 5.56 (br. s, 1H), 4.45 (br. s, 1H), 3.95-3.99 (m, 2H), 3.40-3.70 (m, 3H), 2.83-2.90 (m, 3H), 2.60-2.80 (m, 3H), 2.22 (d, J=1.6 Hz, 6H), 1.88-1.96 (m, 4H), 1.58-1.80 (m, 7H), 1.43 (br. s, 3H), 1.17 (br. s, 3H), 0.95-1.10 (m, 6H).

The following compounds were synthesized using similar methods as described in Example 2 for Compound 121a.

3-((1S,2S)-1-(2-((S)-3-(3-(3-(dimethylphosphoryl)-2-hydroxyphenyl)-2-oxo-2,3-dihydro-1H-imidazol-1-yl)-2-(4-fluoro-3, 5-dimethylphenyl)-4-methyl-4,5, 6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 107a)

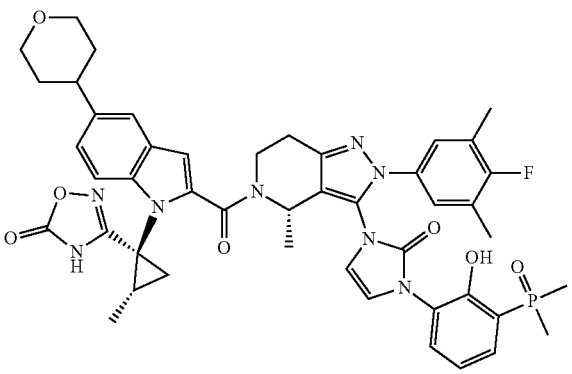 [SMILES: Cc1cc(-n2nc3c(c2-n2ccn(-c4cccc(P(C)(C)=O)c4O)c2=O)[C@H](C)N(C(=O)c2cc4cc(C5CCOCC5)ccc4n2[C@@]2(c4noc(=O)[nH]4)C[C@@H]2C)CC3)cc(C)c1F]

1H NMR (400 MHz, DMSO-d6, 80° C.) δ 11.84 (br. s, 1H), 11.60 (br. s, 1H), 7.51-7.56 (m, 2H), 7.35-7.45 (m, 2H), 7.27 (dd, J=8.4, 1.2 Hz, 1H), 7.17 (d, J=6.0 Hz, 2H), 7.02 (br. s, 1H), 6.80-6.95 (m, 2H), 6.72 (br. s, 1H), 5.60 (br. s, 1H), 4.44 (br. s, 1H), 3.95-4.04 (m, 2H), 3.40-3.70 (m, 3H), 2.84-2.92 (m, 2H), 2.25 (d, J=1.6 Hz, 6H), 1.55-1.90 (m, 14H), 1.47 (s, 3H), 1.19 (s, 3H). LC-MS: m/z 875.2 (M+H)+

3-((1S,2S)-1-(2-((S)-3-(3-(4-(diethylphosphoryl)-3-methoxyphenyl)-2-oxo-2,3-dihydro-1H-imidazol-1-yl)-2-(4-fluoro-3, 5-dimethylphenyl)-4-methyl-4,5,6, 7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 118a)

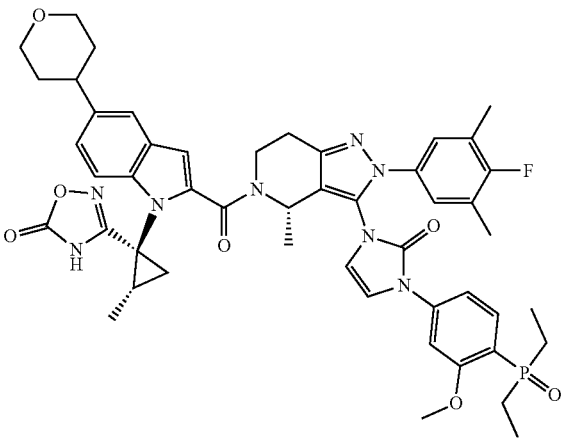 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1OC]

1H NMR (400 MHz, DMSO-d6, 80° C.) δ: 11.58 (br. s, 1H), 7.77 (t, J=8.8 Hz, 1H), 7.53 (s, 1H), 7.33-7.44 (m, 4H), 7.27 (dd, J=8.8, 1.6 Hz, 1H), 7.16 (d, J=6.4 Hz, 2H), 6.87-6.90 (m, 2H), 5.55 (br. s, 1H), 4.49 (br. s, 1H), 3.97-4.00 (m, 2H), 3.84 (s, 3H), 3.43-3.65 (m, 3H), 2.98-3.16 (m, 1H), 2.81-2.97 (m, 2H), 2.23 (d, J=2.0 Hz, 6H), 1.83-2.00 (m, 4H), 1.58-1.82 (m, 7H), 1.40-1.50 (br. s, 3H), 1.09-1.30 (m, 3H), 0.90-1.00 (m, 6H). LC-MS: m/z 917.4 (M+H)+.

3-((1S,2S)-1-(2-((S)-3-(3-(4-(diethylphosphoryl)-3-(ethylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 120a)

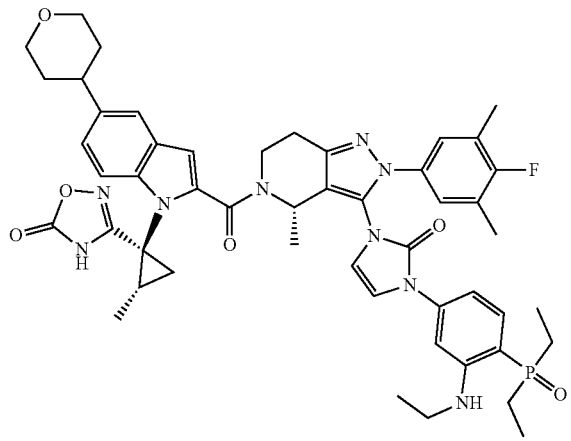 [SMILES: CCNc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1P(=O)(CC)CC]

¹H NMR (400 MHz, DMSO-d₆, 80° C.) δ 11.57 (br. s, 1H), 7.53 (s, 1H), 7.43 (d, J=8.4 Hz, 1H), 7.27 (dd, J=8.8, 1.6 Hz, 1H), 7.18-7.22 (m, 2H), 7.15 (d, J=6.0 Hz, 2H), 6.84-6.89 (m, 4H), 5.56 (br. s, 1H), 4.45 (br. s, 1H), 3.97-4.00 (m, 2H), 3.61-3.44 (m, 3H), 3.08-3.11 (m, 3H), 2.85-2.94 (m, 2H), 2.22 (d, J=2.0 Hz, 6H), 1.88-1.97 (m, 4H), 1.71-1.81 (m, 6H), 1.64 (br. s, 1H), 1.44 (s, 3H), 1.17 (t, J=7.0 Hz, 6H), 1.07 (t, J=7.6 Hz, 3H), 1.01 (t, J=7.6 Hz, 3H). LCMS: m/z=466.0 (M/2+H)⁺.

3-((1S,2S)-1-(2-((S)-3-(3-(6-(dimethylphosphoryl)pyridin-2-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 113a)

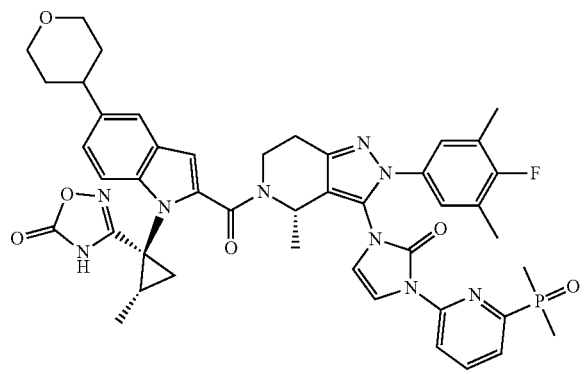 [SMILES: Cc1cc(-n2nc3c(c2-n2ccn(-c4cccc(P(C)(C)=O)n4)c2=O)[C@H](C)N(C(=O)c2cc4cc(C5CCOCC5)ccc4n2[C@@]2(c4noc(=O)[nH]4)C[C@@H]2C)CC3)cc(C)c1F]

¹H NMR (400 MHz, DMSO-d₆, 80° C.) δ 11.62 (br. s, 1H), 8.31 (br. s, 1H), 8.06 (br. s, 1H), 7.82 (t, J=6.0 Hz, 1H), 7.59-7.65 (m, 1H), 7.52 (s, 1H), 7.42-7.45 (m, 1H), 7.25-7.29 (m, 1H), 7.16-7.19 (m, 2H), 6.88 (s, 1H), 6.73 (s, 1H), 5.59 (br. s, 1H), 4.48 (br. s, 1H), 3.97-4.00 (m, 2H), 3.46-3.59 (m, 3H), 3.01-3.11 (m, 1H), 2.84-2.92 (m, 2H), 2.21 (d, J=1.8 Hz, 6H), 1.61-1.79 (m, 12H), 1.56 (br. s, 1H), 1.43 (br. s, 3H), 1.17 (br. s, 3H). LC-MS: m/z 860.2 (M+H)⁺

3-((1S,2S)-1-(2-((S)-3-(3-(4-(diethylphosphoryl)-3-(isopropylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 119a)

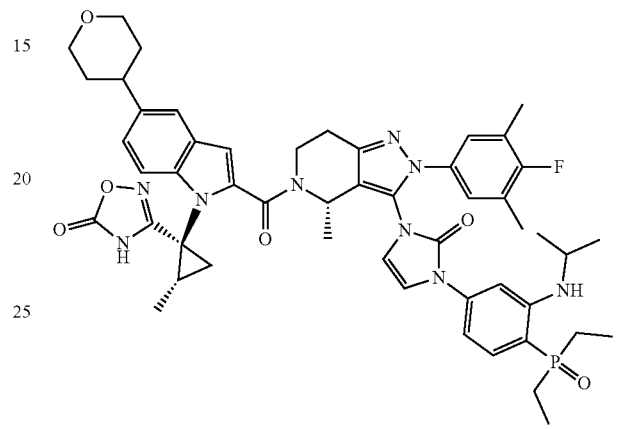

¹H NMR (400 MHz, DMSO-d₆, 80° C.) δ 11.58 (br. s, 1H), 7.53 (s, 1H), 7.43 (d, J=8.4 Hz, 1H), 7.27 (dd, J=8.4, 1.6 Hz, 1H), 7.18-7.21 (m, 2H), 7.15 (d, J=8.4 Hz, 2H), 6.80-6.93 (m, 4H), 5.55 (br. s, 1H), 4.46 (br. s, 1H), 3.97-4.00 (m, 2H), 3.46-3.57 (m, 5H), 3.07 (br. s, 1H), 2.84-2.91 (m, 2H), 2.22 (d, J=2.0 Hz, 6H), 1.88-1.96 (m, 4H), 1.72-1.78 (m, 6H), 1.64 (s, 1H), 1.44 (s, 3H), 1.15-1.17 (m, 9H), 1.00-1.10 (m, 6H). LC-MS: m/z 944.4 (M+H)⁺

3-((1S,2S)-1-(2-((S)-3-(3-(4-(dimethylphosphoryl)-3-morpholinophenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 125a)

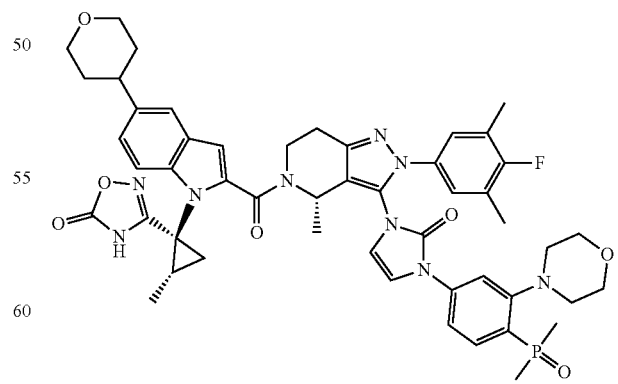

¹H NMR (400 MHz, DMSO-d₆, 80° C.) δ 11.61 (br. s, 1H), 7.81-7.87 (m, 1H), 7.76 (br. s, 1H), 7.62-7.66 (m, 1H), 7.52 (s, 1H), 7.43 (d, J=8.6 Hz, 1H), 7.36 (s, 1H), 7.27 (dd, J=8.4, 1.6 Hz, 1H), 7.16 (d, J=6.0 Hz, 2H), 6.88-6.91 (m,

2H), 5.56 (br. s, 1H), 4.47 (br. s, 1H), 3.97-3.99 (m, 2H), 3.74-3.79 (m, 4H), 3.50 (dd, J=11.2, 3.2 Hz, 4H), 2.80-3.10 (m, 6H), 2.22 (d, J=1.6 Hz, 6H), 1.65-1.78 (m, 13H), 1.44 (s, 3H), 1.18 (s, 3H). LC-MS: m/z 944.4 (M+H)+

3-((1S,2S)-1-(2-((S)-3-(3-(4-(dimethylphosphoryl)-3-(trifluoromethoxy)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 123a)

¹H NMR (400 MHz, DMSO-d₆, 80° C.) δ: 11.58 (br. s, 1H), 9.06 (s, 1H), 8.22 (br. s, 1H), 8.01 (s, 1H), 7.51 (s, 1H), 7.41 (d, J=8.8 Hz, 1H), 7.37 (s, 1H), 7.25 (dd, J=8.8, 1.6 Hz, 1H), 7.13 (d, J=6.4 Hz, 2H), 6.94 (br. s, 1H), 6.86 (br. s, 1H), 5.55 (br. s, 1H), 4.46 (br. s, 1H), 3.93-4.02 (m, 2H), 3.44-3.61 (m, 3H), 2.97-3.16 (m, 1H), 2.82-2.90 (m, 2H), 2.20 (d, J=2.0 Hz, 6H), 1.56-1.81 (m, 13H), 1.42-1.43 (m, 3H), 1.16 (s, 3H). LC-MS: m/z 860.2 (M+H)+

3-((1S,2S)-1-(2-((S)-3-(3-(4-(dimethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 106a)

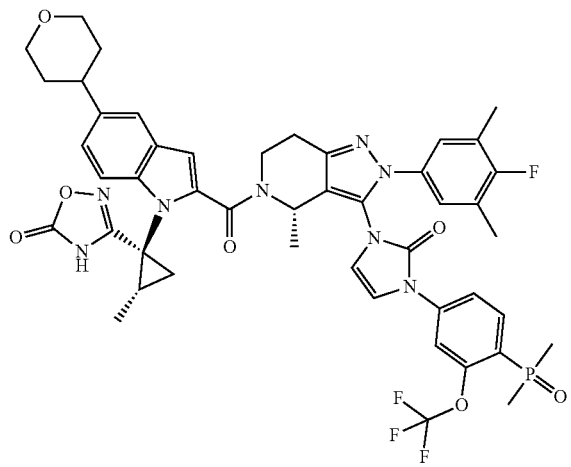 [SMILES: Cc1cc(-n2nc3c(c2-n2ccn(-c4ccc(P(C)(C)=O)c(OC(F)(F)F)c4)c2=O)[C@H](C)N(C(=O)c2cc4cc(C5CCOCC5)ccc4n2[C@@]2(c4noc(=O)[nH]4)C[C@@H]2C)CC3)cc(C)c1F]

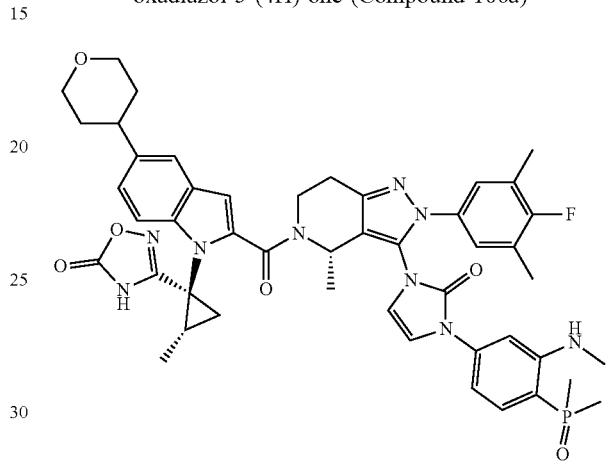

¹H NMR (400 MHz, DMSO-d₆, 80° C.) δ 7.96-8.01 (m, 2H), 7.76 (br. s, 1H), 7.50 (s, 1H), 7.42 (d, J=8.4 Hz, 1H), 7.36-7.39 (m, 1H), 7.25 (d, J=8.4 Hz, 1H), 7.15 (d, J=6.4 Hz, 2H), 6.99 (s, 1H), 6.80 (br. s, 1H), 5.56 (br. s, 1H), 4.44 (br. s, 1H), 3.97-4.00 (m, 2H), 3.46-3.52 (m, 3H), 3.12-3.14 (m, 2H), 2.83-2.91 (m, 1H), 2.21 (d, J=1.6 Hz, 6H), 1.61-1.78 (m, 13H), 1.41 (s, 3H), 1.18 (s, 3H). LC-MS: m/z 943.3 (M+H)+.

3-((1S,2S)-1-(2-((S)-3-(3-(6-(dimethylphosphoryl)pyridin-3-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl-1,2,4-oxadiazol-5 (4H)-one (Compound 105a)

¹H NMR (400 MHz, DMSO-d₆, 80° C.) δ: 11.59 (br. s, 1H), 7.53 (s, 1H), 7.43 (d, J=8.4 Hz, 1H), 7.23-7.33 (m, 3H), 7.15 (d, J=6.0 Hz, 2H), 6.86 (br. s, 4H), 5.57 (br. s, 1H), 4.46 (br. s, 1H), 3.97-3.99 (m, 2H), 3.49-3.58 (m, 3H), 2.85-2.94 (m, 3H), 2.74 (br. s, 3H), 2.22 (d, J=1.6 Hz, 6H), 1.64-1.77 (m, 13H), 1.44 (s, 3H), 1.18 (s, 3H). LC-MS: m/z 888.2 (M+H)+

3-((1S,2S)-1-(2-((S)-3-(3-(4-(dimethylphosphoryl)-3-fluorophenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 108a)

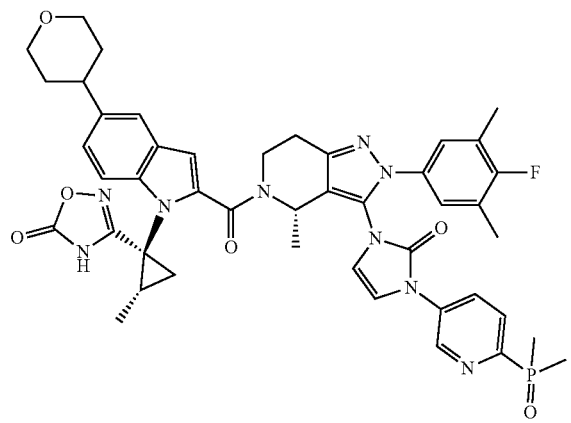 [SMILES: Cc1cc(-n2nc3c(c2-n2ccn(-c4ccc(P(C)(C)=O)nc4)c2=O)[C@H](C)N(C(=O)c2cc4cc(C5CCOCC5)ccc4n2[C@@]2(c4noc(=O)[nH]4)C[C@@H]2C)CC3)cc(C)c1F]

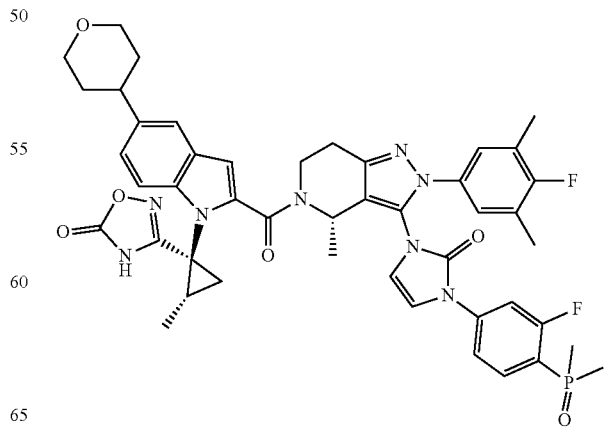

¹H NMR (400 MHz, DMSO-d₆, 80° C.) δ: 11.58 (br. s, 1H), 7.70-7.80 (m, 3H), 7.50 (s, 1H), 7.41 (d, J=8.4 Hz, 1H), 7.35 (br. s, 1H), 7.25 (dd, J=8.8, 1.6 Hz, 1H), 7.12 (d, J=6.0 Hz, 2H), 6.93 (s, 1H), 6.86 (s, 1H), 5.55 (br. s, 1H), 4.44 (br. s, 1H), 3.95-3.98 (m, 2H), 3.44-3.56 (m, 3H), 2.98-3.08 (m, 1H), 2.82-2.89 (m, 2H), 2.20 (d, J=2.0 Hz, 6H), 1.59-1.78 (m, 13H), 1.41 (s, 3H), 1.15 (s, 3H). LC-MS: m/z 877.2 (M+H)⁺

3-((1S,2S)-1-(2-((S)-3-(3-(3-(dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 109a)

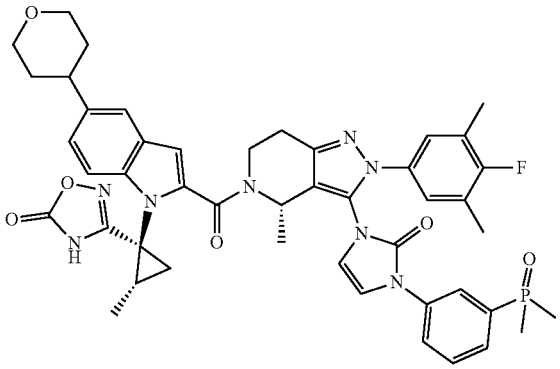 [SMILES: Cc1cc(-n2nc3c(c2-n2ccn(-c4cccc(P(C)(C)=O)c4)c2=O)[C@H](C)N(C(=O)c2cc4cc(C5CCOCC5)ccc4n2[C@@]2(c4noc(=O)[nH]4)C[C@@H]2C)CC3)cc(C)c1F]

¹H NMR (400 MHz, DMSO-d₆, 80° C.) δ: 11.58 (br. s, 1H), 7.95 (d, J=9.6 Hz, 1H), 7.78 (br. s, 1H), 7.62-7.69 (m, 1H), 7.58 (br. s, 1H), 7.50 (s, 1H), 7.41 (d, J=8.4 Hz, 1H), 7.20-7.30 (m, 2H), 7.14 (d, J=6.0 Hz, 2H), 6.86 (br. s, 2H), 5.55 (br. s, 1H), 4.46 (br. s, 1H), 3.93-4.03 (m, 2H), 3.56 (br. s, 1H), 3.44-3.50 (m, 2H), 3.05 (br. s, 1H), 2.81-2.89 (m, 2H), 2.20 (d, J=1.6 Hz, 6H), 1.82-1.57 (m, 13H), 1.43 (s, 3H), 1.15 (s, 3H).
LC-MS: m/z 859.2 (M+H)⁺

3-((1S,2S)-1-(2-((S)-3-(3-(4-(diethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 129a)

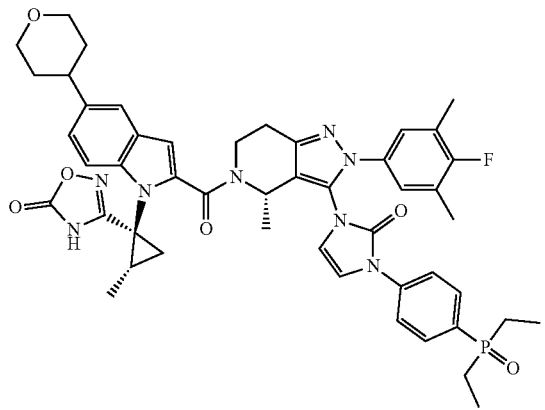 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1]

¹H NMR (400 MHz, DMSO-d₆, 80° C.) δ: 11.56 (br. s, 1H), 7.75-7.78 (m, 4H), 7.51 (s, 1H), 7.41 (d, J=8.4 Hz, 1H), 7.24-7.26 (m, 2H), 7.13 (d, J=6.0 Hz, 2H), 6.86-6.87 (m, 2H), 5.54 (br. s, 1H), 4.44 (br. s, 1H), 3.95-3.98 (m, 2H), 3.55 (br. s, 1H), 3.47 (td, J=11.2, 3.2 Hz, 2H), 3.11-3.15 (m, 1H), 2.82-2.89 (m, 2H), 2.20 (d, J=1.6 Hz, 6H), 1.99-1.81 (m, 4H), 1.71-1.76 (m, 6H), 1.60-1.70 (m, 1H), 1.41 (s, 3H), 1.15 (s, 3H), 1.02-0.91 (m, 6H). LCMS: m/z=444.2 (M/2+H)⁺.

3-((1S,2S)-1-(2-((S)-3-(3-(4-(diisopropylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-11H-indol-1-yl)-2-methylcyclopropyl)-1,2,4-oxadiazol-5 (4H)-one (Compound 128a)

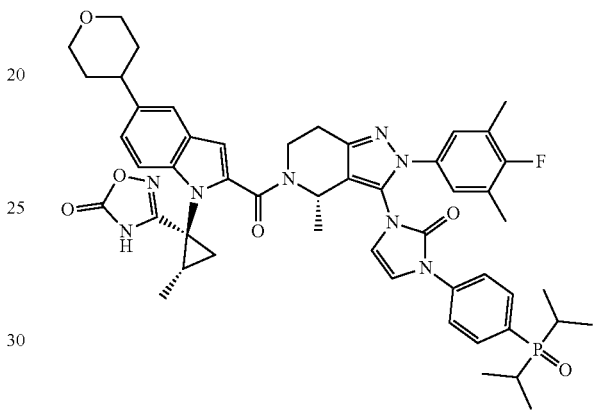

¹H NMR (400 MHz, DMSO-d₆, 80° C.) δ: 11.57 (br. s, 1H), 7.73-7.79 (m, 4H), 7.51 (s, 1H), 7.42 (d, J=8.4 Hz, 1H), 7.28 (s, 1H), 7.25 (dd, J=8.8, 1.6 Hz, 1H), 7.14 (d, J=6.0 Hz, 2H), 6.86 (br. s, 2H), 5.56 (br. s, 1H), 4.46 (br. s, 1H), 3.95-3.98 (m, 2H), 3.53-3.57 (m 1H), 3.47 (td, J=11.2, 3.2 Hz, 2H), 2.97-3.16 (m, 1H), 2.81-2.94 (m, 2H), 2.27-2.36 (m, 2H), 2.20 (d, J=1.6 Hz, 6H), 1.70-1.76 (m, 6H), 1.63-1.65 (m, 1H), 1.42-1.43 (m 3H), 1.07-1.15 (m, 9H), 0.85-1.00 (m, 6H). LC-MS: m/z 915.3 (M+H)⁺

3-((1S,2S)-1-(2-((S)-3-(3-(4-(dimethylphosphoryl)-3-methylphenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 124a)

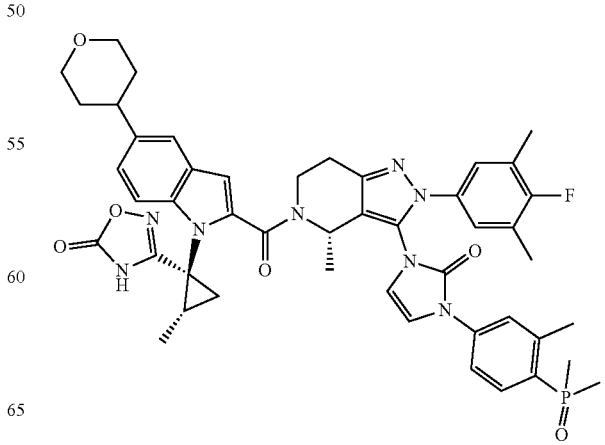

¹H NMR (400 MHz, DMSO-d₆, 80° C.) δ: 11.56 (br. s, 1H), 7.64-7.69 (m, 1H), 7.57 (br. s, 2H), 7.51 (s, 1H), 7.41 (d, J=8.8 Hz, 1H), 7.22-7.28 (m, 2H), 7.12 (d, J=6.4 Hz, 2H), 6.86 (br. s, 2H), 5.54 (br. s, 1H), 4.44 (br. s, 1H), 3.94-3.98 (m, 2H), 3.54 (br. s, 1H), 3.47 (td, J=11.2, 3.2 Hz, 2H), 3.11-3.15 (m, 1H), 2.83-2.89 (m, 2H), 2.61 (s, 3H), 2.20 (d, J=1.6 Hz, 6H), 1.68-1.75 (m, 13H), 1.41-1.42 (br. s, 3H), 1.15 (br. s, 3H).
LC-MS: m/z 873.2 (M+H)⁺

3-((1S,2S)-1-(2-((S)-3-(3-(4-(dimethylphosphoryl)-2-fluorophenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 122a)

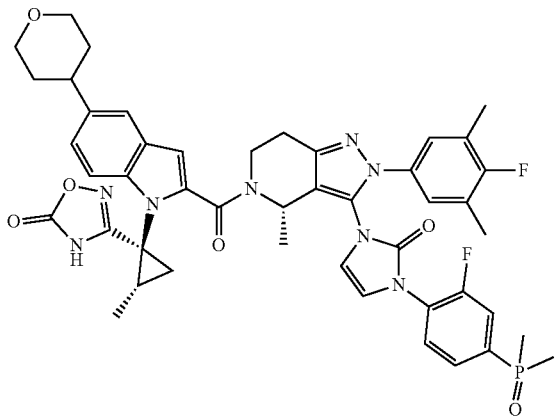 [SMILES: Cc1cc(-n2nc3c(c2-n2ccn(-c4ccc(P(C)(C)=O)cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F]

¹H NMR (400 MHz, DMSO-d₆, 80° C.) δ: 11.57 (br. s, 1H), 7.60-7.80 (m, 3H), 7.51 (s, 1H), 7.41 (d, J=8.8 Hz, 1H), 7.25 (dd, J=8.8, 1.6 Hz, 1H), 7.13 (d, J=6.4 Hz, 2H), 6.98 (s, 1H), 6.75-6.95 (m, 2H), 5.56 (br. s, 1H), 4.43 (br. s, 1H), 3.95-3.98 (m, 2H), 3.56 (br. s, 1H), 3.47 (td, J=11.2, 3.6 Hz, 2H), 3.11-3.15 (m, 1H), 2.92-2.81 (m, 2H), 2.23 (d, J=1.6 Hz, 6H), 1.67-1.74 (m, 13H), 1.44-1.45 (m 3H), 1.17 (s, 3H).
LC-MS: m/z 877.2 (M+H)⁺

3-((1 S,2S)-1-(2-((S)-3-(3-(4-(diethylphosphoryl)-3-(dimethylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one HCl salt (Compound 117a)

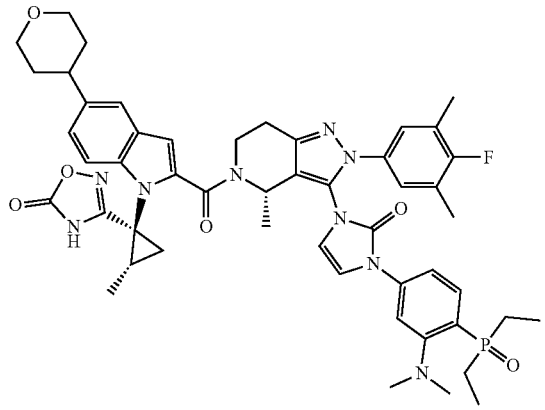 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1N(C)C]

¹H NMR (400 MHz, DMSO-d₆, 80° C.) δ: 11.58 (br. s, 1H), 7.97 (br. s, 1H), 7.85 (br. s, 2H), 7.50 (s, 1H), 7.40-7.42 (m, 2H), 7.25 (dd, J=8.4, 1.2 Hz, 1H), 7.14 (d, J=6.4 Hz, 2H), 6.93 (br. s, 1H), 6.86 (br. s, 1H), 5.56 (br. s, 1H), 4.46 (br. s, 1H), 3.95-3.97 (m, 2H), 3.55 (br. s, 1H), 3.42-3.51 (m, 3H), 2.84-2.89 (m, 8H), 2.19-2.24 (m, 6H), 2.04-2.14 (m, 4H), 1.60-1.80 (m, 7H), 1.42 (br. s, 3H), 1.15 (br. s, 3H), 1.04-0.95 (m, 6H).
LC-MS: m/z 930.4 (M+H)⁺

3-((1S,2S)-1-(2-((S)-3-(3-(4-(diethylphosphoryl)-3-morpholinophenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 114a)

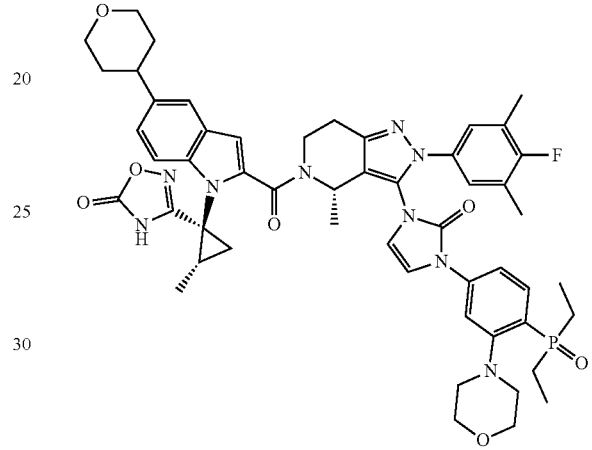

¹H NMR (400 MHz, DMSO-d₆, 80° C.) δ: 11.56 (br. s, 1H), 7.79-7.84 (m, 2H), 7.67 (br. s, 1H), 7.50 (s, 1H), 7.41 (d, J=8.4 Hz, 1H), 7.35 (br. s, 1H), 7.25 (dd, J=8.4, 1.6 Hz, 1H), 7.14 (d, J=6.0 Hz, 2H), 6.90 (br. s, 1H), 6.85 (br. s, 1H), 5.52 (br. s, 1H), 4.44 (br. s, 1H), 3.94-3.98 (m, 2H), 3.77-3.70 (m, 4H), 3.56 (br. s, 1H), 3.47 (td, J=10.8, 3.2 Hz, 2H), 3.02-3.08 (m, 1H), 2.82-2.88 (m, 6H), 2.20 (d, J=2.0 Hz, 6H), 1.95-2.12 (m, 4H), 1.60-1.75 (m, 7H), 1.42 (br. s, 3H), 1.15 (br. s, 3H), 0.92-1.02 (m, 6H). LC-MS: m/z 972.4 (M+H)⁺.

3-((1S,2S)-1-(2-((S)-3-(3-(3-amino-4-(dimethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 111a)

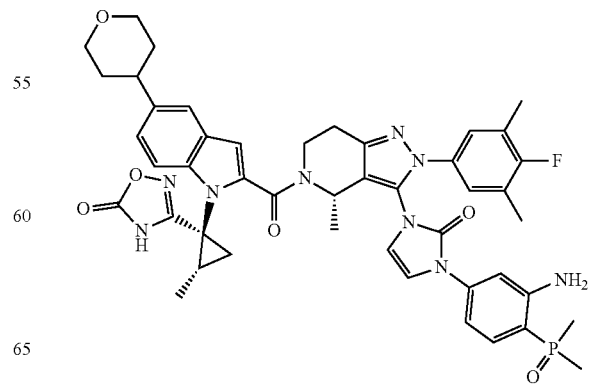

¹H NMR (400 MHz, DMSO-d₆, 80° C.) δ: 11.55 (br. s, 1H), 7.51 (s, 1H), 7.41 (d, J=8.4 Hz, 1H), 7.21-7.25 (m, 2H), 7.11 (d, J=6.0 Hz, 2H), 7.05 (d, J=1.6 Hz, 1H), 6.99 (br. s, 1H), 6.70-6.90 (m, 3H), 5.53 (br. s, 1H), 4.44 (br. s, 1H), 3.94-3.97 (m, 2H), 3.56 (br. s, 1H), 3.44-3.49 (m, 3H), 2.90-2.83 (m, 2H), 2.20 (d, J=1.6 Hz, 6H), 1.69-1.80 (m, 6H), 1.67 (br. s, 3H), 1.61-1.62 (m, 4H), 1.35-1.45 (m, 3H), 1.16 (br. s, 3H). LC-MS: m/z 874.2 (M+H)⁺.

3-((1S,2S)-1-(2-((S)-3-(3-(4-(dimethylphosphoryl) phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(2,2-dimethyltetrahydro-2H-pyran-4-yl)-1H-indol-1-yl)-2-methylcyclopropyl)-1,2,4-oxadiazol-5(4H)-one (Compound 102a)

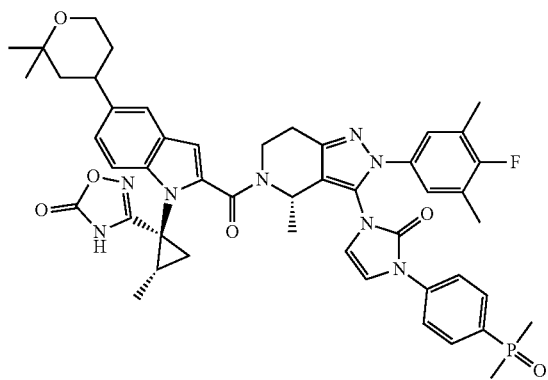 [SMILES: Cc1cc(-n2nc3c(c2-n2ccn(-c4ccc(P(C)(C)=O)cc4)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F]

¹H NMR (400 MHz, DMSO-d₆, 80° C.) δ: 11.58 (s, 1H), 7.80-7.81 (m, 4H), 7.50 (s, 1H), 7.40 (d, J=8.4 Hz, 1H), 7.23-7.28 (m, 2H), 7.13 (d, J=6.4 Hz, 2H), 6.86-6.88 (m, 2H), 5.57 (br. s, 1H), 4.44 (br. s, 1H), 3.65-3.75 (m, 2H), 3.55 (br. s, 1H), 3.00-3.03 (m, 2H), 2.80-2.95 (m, 1H), 2.20 (d, J=1.6 Hz, 6H), 1.62-1.72 (m, 12H), 1.47-1.56 (m, 2H), 1.41-1.42 (m, 3H), 1.27 (br. s, 3H), 1.15-1.18 (m, 5H). LC-MS: m/z 887.3 (M+H)⁺.

(S)-3-(1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)cyclopropyl)-1,2,4-oxadiazol-5(4H)-one (Compound 135a)

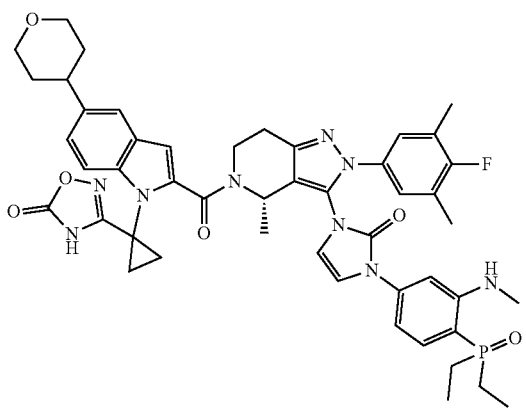 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)[C@H]4C)c2=O)cc1NC]

¹H NMR (400 MHz, DMSO-d₆, 80° C.) δ: 11.81 (br. s, 1H), 7.49-7.50 (m, 2H), 7.23-7.25 (m, 3H), 7.15 (d, J=6.0 Hz, 2H), 6.81-6.92 (m, 3H), 6.79 (s, 1H), 5.54 (br. s, 1H), 4.49 (br. s, 1H), 3.98-4.00 (m, 2H), 3.44-3.55 (m, 3H), 2.82-2.92 (m, 4H), 2.74 (s, 3H), 2.22 (d, J=2.0 Hz, 6H), 1.90-1.95 (m, 4H), 1.75-1.79 (m, 7H), 1.54 (br. s, 1H), 1.39 (d, J=6.4 Hz, 3H), 0.95-1.10 (m, 6H). LC-MS: m/z 901.8 (M+H)⁺.

3-((1S,2S)-1-(2-((S)-3-(3-(4-(diethylphosphoryl)-3-(difluoromethoxy)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5(4H)-one (Compound 136a)

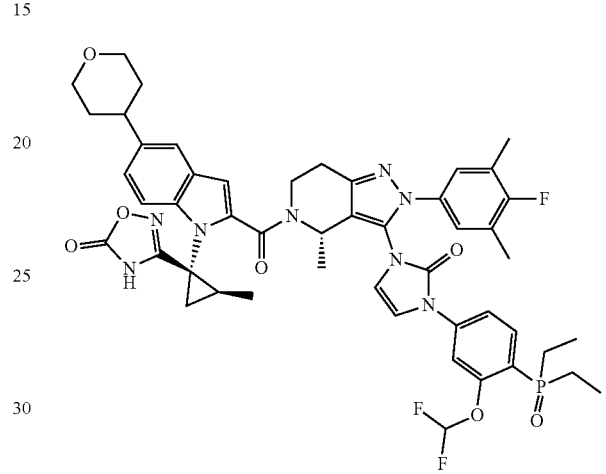

¹H NMR (400 MHz, DMSO-d₆, 80° C.) δ 11.57 (s, 1H), 7.92 (br. s, 1H), 7.70 (br. s, 2H), 7.53 (s, 1H), 7.43 (d, J=8.0 Hz, 1H), 7.20-7.36 (m, 3H), 7.16 (d, J=6.4 Hz, 2H), 6.96 (br. s, 1H), 6.88 (br. s, 1H), 5.57 (br. s, 1H), 4.47 (s, 1H), 3.95-4.05 (m, 2H), 3.42-3.65 (m, 3H), 2.88-2.92 (m, 3H), 2.22 (s, 6H), 1.84-2.09 (m, 4H), 1.60-1.82 (m, 7H), 1.44 (br. s, 3H), 1.18 (br. s, 3H), 0.91-1.05 (m, 6H). LC-MS: m/z 952.9 (M+H)⁺.

3-((1S,2S)-1-(2-((S)-3-(3-(3-amino-4-(diethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5(4H)-one (Compound 138a)

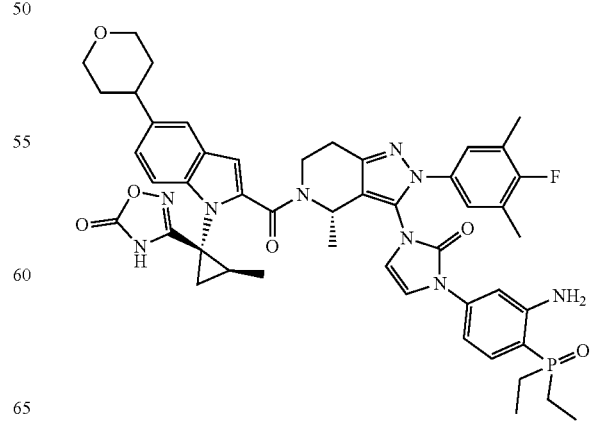

¹H NMR (400 MHz, DMSO-d₆, 80° C.) δ 11.39 (br. s, 1H), 7.50 (s, 1H), 7.41 (d, J=8.8 Hz, 1H), 7.24 (d, J=8.0 Hz, 1H), 7.11-7.19 (m, 2H), 7.08 (s, 1H), 6.99 (s, 1H), 6.77-6.82 (m, 2H), 6.32 (s, 2H), 5.55 (br. s, 1H), 4.42 (br. s, 1H), 3.96 (d, J=10.8 Hz, 2H), 3.40-3.55 (m, 3H), 2.95-3.01 (m, 1H), 2.82-2.89 (m, 2H), 2.20 (s, 6H), 1.85-1.94 (m, 4H), 1.70-1.75 (m, 6H), 1.62 (br. s, 1H), 1.39 (br. s, 3H), 1.10-1.25 (m, 3H), 1.08-0.97 (m, 6H). LC-MS: m/z 452.0 (M/2+H)⁺.

3-((1S,2S)-1-(2-((S)-3-(3-(6-(diethylphosphoryl)-5-(methylamino)pyridin-3-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 139a)

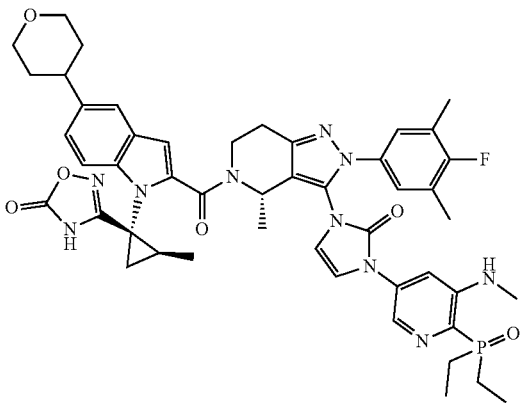 [SMILES: CCP(=O)(CC)c1ncc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC]

¹H NMR (400 MHz, DMSO-d₆, 80° C.) δ 11.55 (s, 1H), 8.24 (s, 1H), 7.52 (s, 1H), 7.43 (d, J=8.4 Hz, 1H), 7.34 (s, 1H), 7.26 (d, J=8.0 Hz, 2H), 7.15 (d, J=6.0 Hz, 2H), 6.88-6.95 (m, 2H), 5.57 (br. s, 1H), 4.46 (br. s, 1H), 3.90-4.10 (m, 2H), 3.43-3.62 (m, 3H), 2.84-2.92 (m, 3H), 2.75 (br. s, 3H), 2.22 (s, 6H), 1.88-2.01 (m, 5H), 1.56-1.80 (m, 7H), 1.44 (s, 3H), 1.10-1.30 (m, 3H), 0.90-1.09 (m, 6H). LCMS: m/z=917.4 (M+H)⁺.

3-((1S,2S)-1-(2-((S)-3-(3-(4-(diethylphosphoryl)-3-methyl-5-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 140a)

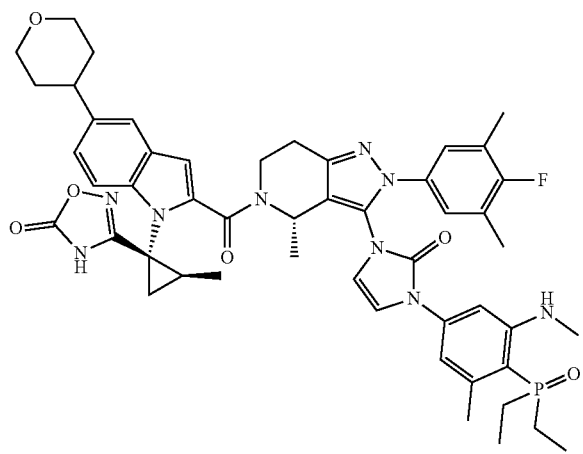 [SMILES: CCP(=O)(CC)c1c(C)cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC]

¹H NMR (400 MHz, DMSO-d₆, 80° C.) δ 11.59 (s, 1H), 7.52 (s, 1H), 7.42 (d, J=8.4 Hz, 1H), 7.27 (d, J=8.4 Hz, 1H), 7.20 (s, 1H), 7.14 (d, J=5.6 Hz, 2H), 6.67-7.00 (m, 4H), 5.55 (br. s, 1H), 4.46 (br. s, 1H), 3.98 (d, J=10.8 Hz, 2H), 3.53-3.45 (m, 3H), 2.87-2.91 (m, 3H), 2.67 (br. s, 3H), 2.27 (br. s, 3H), 2.23 (s, 6H), 1.95-2.07 (m, 4H), 1.60-1.81 (m, 7H), 1.44 (s, 3H), 1.12-1.30 (m, 3H), 1.13-0.99 (m, 6H). LC-MS: m/z 466.0 (M/2+H)⁺.

3-((1S,2S)-1-(2-((S)-3-(3-(4-(diisopropylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 141a)

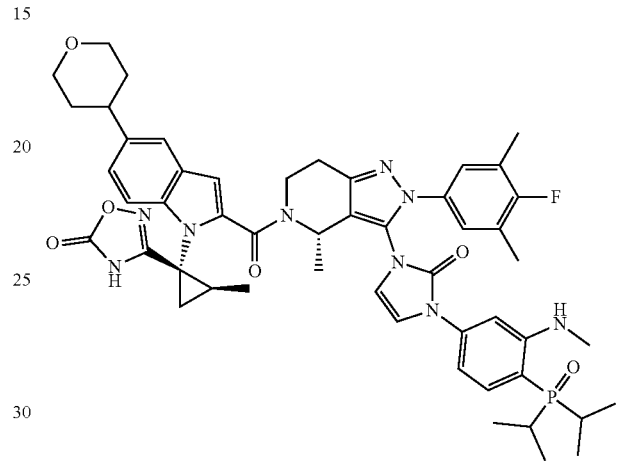

¹H NMR (400 MHz, DMSO-d₆, 80° C.) δ 11.56 (br. s, 1H), 7.53 (s, 1H), 7.43 (d, J=8.4 Hz, 1H), 7.27 (dd, J=8.8, 1.6 Hz, 1H), 7.24 (s, 1H), 7.00-7.20 (m, 3H), 6.87 (br. s, 4H), 5.57 (br. s, 1H), 4.47 (br. s, 1H), 3.94-4.03 (m, 2H), 3.54 (br. s, 1H), 3.49 (td, J=11.2, 4.0 Hz, 2H), 2.83-2.91 (m, 3H), 2.71 (br. s, 3H), 2.38-2.27 (m, 2H), 2.22 (d, J=2.0 Hz, 6H), 1.72-1.77 (m, 6H), 1.64 (br. s, 1H), 1.44 (br. s, 3H), 0.97-1.20 (m, 9H), 0.95-1.20 (m, 6H). LC-MS: m/z 473.2 (M/2+H)⁺.

3-((1S,2S)-1-(2-((S)-3-(3-(4-(diethylphosphoryl)-3-(difluoromethyl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 142a)

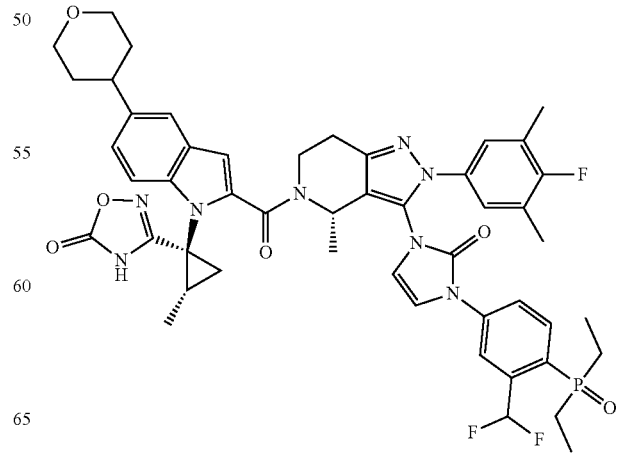

¹H NMR (400 MHz, DMSO-d₆, 80° C.) δ 11.60 (br. s, 1H), 7.77-8.27 (m, 4H), 7.53 (s, 1H), 7.30-7.50 (m, 2H), 7.27 (d, J=8.8 Hz, 1H), 7.16 (d, J=8.0 Hz, 2H), 6.95 (s, 1H), 6.88 (s, 1H), 5.58 (br. s, 1H), 4.46 (br. s, 1H), 3.96-4.03 (m, 2H), 3.46-3.60 (m, 3H), 2.84-2.91 (m, 3H), 2.22 (d, J=1.6 Hz, 6H), 1.99-2.08 (m, 4H), 1.64-1.77 (m, 7H), 1.44 (br. s, 3H), 1.10-1.30 (m, 3H), 0.80-1.05 (m, 6H). LC-MS: m/z 937.2 (M+H)⁺.

3-((1S,2S)-1-(2-((S)-3-(3-(4-(diethylphosphoryl)-3-fluoro-5-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 143a)

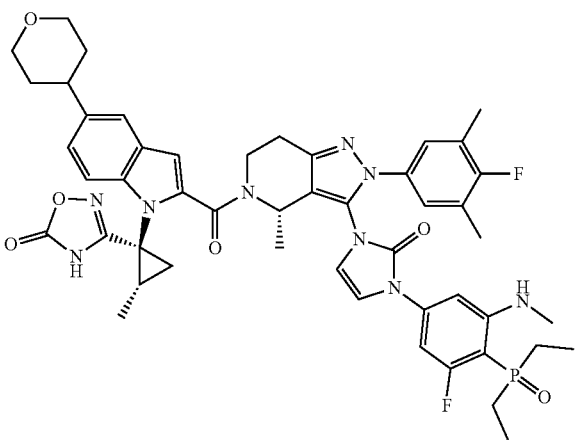 [SMILES: CCP(=O)(CC)c1c(F)cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC]

¹H NMR (400 MHz, DMSO-d₆, 80° C.) δ: 8.39 (br. s, 1H), 7.52 (s, 1H), 7.42 (d, J=8.4 Hz, 1H), 7.25-7.32 (m, 2H), 7.13 (d, J=6.0 Hz, 2H), 6.86 (s, 2H), 6.71 (s, 2H), 5.54 (br. s, 1H), 4.45 (br. s, 1H), 3.97 (d, J=10.8 Hz, 2H), 3.45-3.51 (m, 3H), 2.85-2.95 (m, 3H), 2.71 (s, 3H), 2.21 (s, 6H), 1.85-1.99 (m, 4H), 1.60-1.79 (m, 7H), 1.42 (m, 3H), 1.15 (br. s, 3H), 1.02-1.15 (m, 6H). LC-MS: m/z 934.4 (M+H)⁺

3-((1S,2S)-1-(2-((S)-3-(3-(4-(diethylphosphoryl)-2-fluoro-5-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 144a)

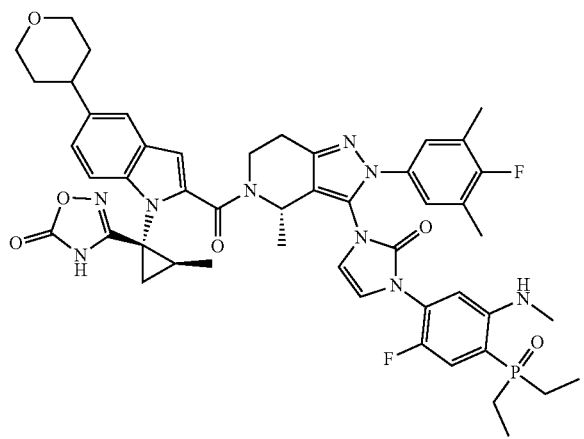 [SMILES: CCP(=O)(CC)c1cc(F)c(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC]

¹H NMR (400 MHz, DMSO-d₆, 80° C.) δ 11.60 (br. s, 1H), 7.53 (s, 1H), 7.43 (d, J=8.8 Hz, 1H), 7.22-7.30 (m, 2H), 7.16 (d, J=6.4 Hz, 2H), 6.97 (br. s, 1H), 6.88 (br. s, 1H), 6.82 (br. s, 1H), 6.62 (br. s, 1H), 5.57 (br. s, 1H), 4.47 (br. s, 1H), 3.97-4.00 (m, 2H), 3.55 (br. s, 1H), 3.46-3.53 (m, 2H), 2.98-3.03 (m, 1H), 2.88-2.91 (m, 2H), 2.72 (br. s, 3H), 2.25 (d, J=1.6 Hz, 6H), 1.94-2.03 (m, 4H), 1.73-1.78 (m, 6H), 1.64 (br. s, 3H), 1.47 (s, 3H), 1.12-1.30 (m, 3H), 1.00-1.10 (m, 6H). LC-MS: m/z 934.3 (M+H)⁺.

3-((1S,2S)-1-(2-((S)-3-(3-(4-(diethylphosphoryl)-2-fluoro-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 145a)

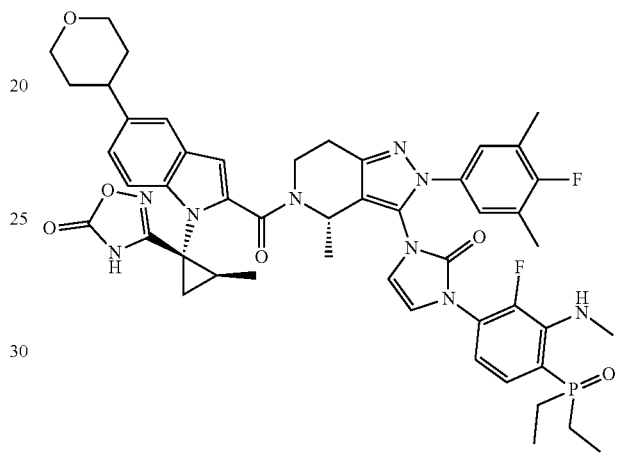

¹H NMR (400 MHz, DMSO-d6, 80° C.) δ 11.58 (br. s, 1H), 7.53 (s, 1H), 7.43 (d, J=8.0 Hz, 1H), 7.27 (d, J=8.0 Hz, 1H), 7.15 (d, J=8.0 Hz, 2H), 7.06-7.12 (m, 1H), 6.74-6.93 (m, 4H), 5.57 (br. s, 1H), 4.45 (br. s, 1H), 3.98 (d, J=12.0 Hz, 2H), 3.42-3.55 (m, 3H), 2.88-2.94 (m, 6H), 2.25 (s, 6H), 1.94-2.00 (m, 4H), 1.64-1.75 (m, 7H), 1.45 (br. s, 3H), 1.15-1.31 (m, 4H), 1.01-1.10 (m, 6H). LC-MS: m/z 934.2 (M+H)⁺.

3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-((R)-2,2-dimethyltetrahydro-2H-pyran-4-yl)-1H-indol-1-yl)-2-methylcyclopropyl)-1,2,4-oxadiazol-5 (4H)-one (Compound 146a)

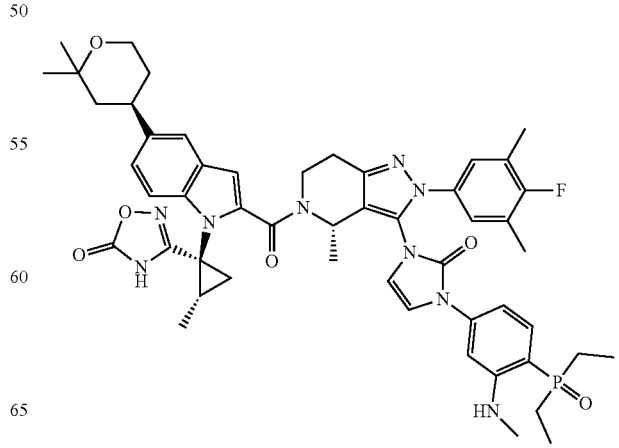

¹H NMR (400 MHz, DMSO-d₆, 80° C.) δ 11.57 (br. s, 1H), 7.68 (br. s, 1H), 7.52 (s, 1H), 7.42 (d, J=8.4 Hz, 1H), 7.21-7.27 (m, 3H), 7.15 (d, J=6.0 Hz, 2H), 6.86 (br. s, 4H), 5.56 (br. s, 1H), 4.48 (br. s, 1H), 3.74 (d, J=7.2 Hz, 2H), 3.58 (s, 1H), 2.99-3.02 (m, 1H), 2.86-2.93 (m, 2H), 2.65-2.80 (m, 3H), 2.23 (s, 6H), 1.88-1.97 (m, 4H), 1.69-1.77 (m, 4H), 1.59-1.67 (m, 2H), 1.50-1.58 (m, 1H), 1.44 (br. s, 3H), 1.30 (br. s, 3H), 1.27 (br. s, 1H), 1.21 (s, 3H), 1.15-1.25 (m, 2H), 0.99-1.08 (m, 6H). LC-MS: m/z 473.0 (M/2+H)⁺.

3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-((S)-2,2-dimethyltetrahydro-2H-pyran-4-yl)-1H-indol-1-yl)-2-methylcyclopropyl)-1,2,4-oxadiazol-5 (4H)-one (Compound 146b)

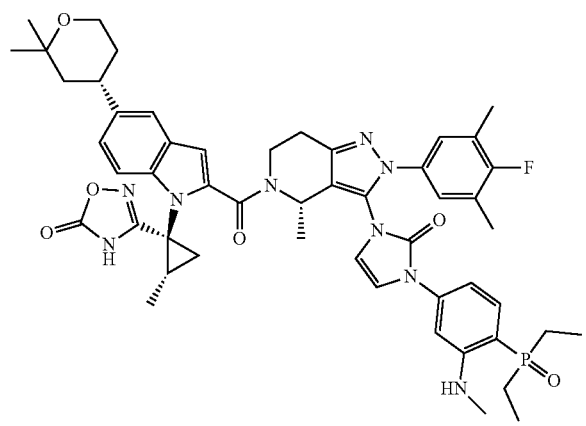 [SMILES: CCP(=O)(CC)c1ccc(-n2ccn(-c3c4c(nn3-c3cc(C)c(F)c(C)c3)CCN(C(=O)c3cc5cc([C@H]6CCOC(C)(C)C6)ccc5n3[C@@]3(c5noc(=O)[nH]5)C[C@@H]3C)[C@H]4C)c2=O)cc1NC]

¹H NMR (400 MHz, DMSO-d₆, 80° C.) δ 11.59 (br. s, 1H), 7.52 (s, 1H), 7.41 (d, J=8.4 Hz, 1H), 7.25 (d, J=8.8 Hz, 1H), 7.18-7.24 (m, 2H), 7.15 (d, J=6.0 Hz, 2H), 6.86 (br. s, 4H), 5.55 (br. s, 1H), 4.45 (br. s, 1H), 3.73 (d, J=8.0 Hz, 2H), 3.56 (br. s, 1H), 2.95-3.05 (m, 2H), 2.85-2.95 (m, 1H), 2.72 (br. s, 3H), 2.22 (s, 6H), 1.88-1.96 (m, 4H), 1.51-1.77 (m, 7H), 1.44 (br. s, 3H), 1.29 (s, 3H), 1.20 (s, 3H), 1.17 (br. s, 3H), 0.95-1.10 (m, 6H). LC-MS: m/z 944.4 (M+H)⁺

3-((1S,2S)-1-(2-((S)-3-(3-(3-(dimethylphosphoryl)benzyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 147a)

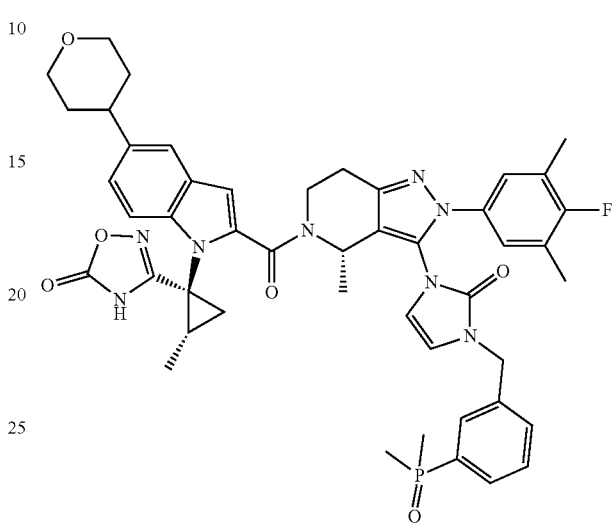

¹H NMR (400 MHz, DMSO-d₆, 80° C.) δ 11.56 (br. s, 1H), 7.66-7.75 (m, 2H), 7.53 (s, 1H), 7.40-7.50 (m, 2H), 7.20-7.38 (m, 2H), 7.08 (d, J=6.0 Hz, 2H), 6.87 (br. s, 1H), 6.77 (br. s, 1H), 6.59 (br. s, 1H), 5.50 (br. s, 1H), 4.82 (br. s, 2H), 4.43 (br. s, 1H), 3.96-3.99 (m, 2H). 3.45-3.54 (m, 3H), 2.83-2.91 (m, 2H), 2.16 (d, J=0.8 Hz, 6H), 1.72-1.77 (m, 6H), 1.61-1.65 (m, 8H), 1.36 (br. s, 3H), 1.17 (br. s, 3H). LCMS: m/z=873.3 (M+H)⁺.

Example 3: Synthesis of N-(2-(diethylphosphoryl)-5-(3-((S)-2-(4-fluoro-3,5-dimethylphenyl)-4-methyl-5-(1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carbonyl)-4,5,6,7-tetrahydro-2H-pyrazolo[4,3-c]pyridin-3-yl)-2-oxo-2,3-dihydro-1H-imidazol-1-yl)phenyl)cyclopropanecarboxamide (Compound 115a)

-continued

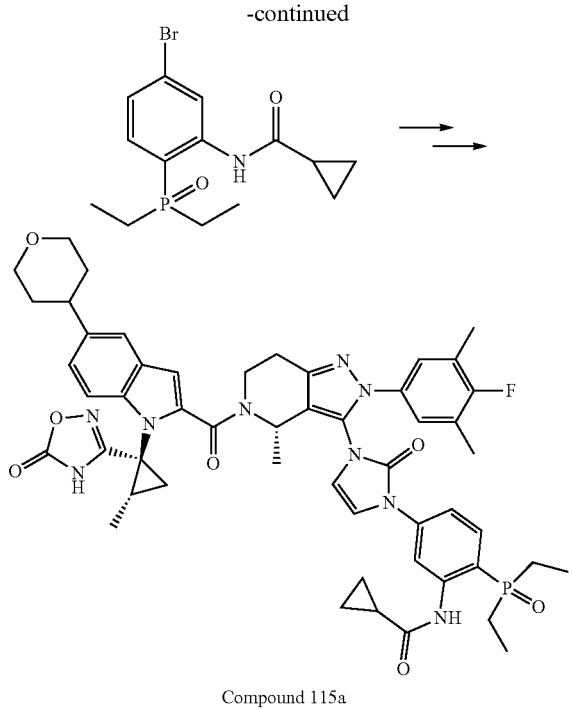

Compound 115a

Step A: (2-amino-4-bromophenyl)diethylphosphine oxide

To a solution of 5-bromo-2-iodoaniline (1.00 g, 3.36 mmol) in dioxane (10 mL) were added Pd$_2$(dba)$_3$ (154 mg, 0.168 mmol), Xantphos (194 mg, 0.336 mmol), TEA (680 mg, 6.71 mmol and diethylphosphine oxide (356 mg, 3.36 mmol) at room temperature. The resulting mixture was stirred at 60° C. for 12 hours under N$_2$ atmosphere. The reaction mixture was diluted with water (20 mL) and extracted with ethyl acetate (3×30 mL). The combined organic phase was washed with brine (30 mL), dried over anhydrous Na$_2$SO$_4$ and concentrated. The residue was purified by flash chromatography (eluted with DCM/MeOH=10/1) to afford the title compound (2-amino-4-bromophenyl)diethylphosphine oxide as brown oil (1.10 g, overweight, 100% yield).

LC-MS: m/z 276.0, 278.0 (M+H)$^+$ $^1$H NMR (400 MHz, CDCl$_3$) δ: 6.75-6.81 (m, 3H), 5.63 (br. s, 2H), 1.84-2.01 (m, 4H), 1.12-1.20 (m, 6H).

Step B: N-(5-bromo-2-(diethylphosphoryl)phenyl)cyclopropanecarboxamide

To a solution of (2-amino-4-bromophenyl)diethylphosphine oxide (200 mg, 0.730 mmol) in DCM (5 mL) were added TEA (221 mg, 2.19 mmol) and cyclopropanecarbonyl chloride (114 mg, 1.09 mmol) at room temperature. The resulting mixture was stirred at room temperature for 12 hours. The reaction mixture was quenched with water (15 mL). The resulting mixture was extracted with DCM (3×15 mL). The combined organic phase was washed with brine (30 mL), dried over anhydrous Na$_2$SO$_4$ and concentrated. The residue was purified by flash chromatography (eluted with PE/EA=1/2) to afford the title compound N-(5-bromo-2-(diethylphosphoryl)phenyl)cyclopropanecarboxamide as yellow oil (120 mg, 48% yield).

LC-MS: m/z 344.0, 346.0 (M+H)$^+$.

$^1$H NMR (400 MHz, CDCl$_3$) δ: 11.85 (s, 1H), 8.94-8.96 (m, 1H), 7.20 (dt, J=8.0, 2.0 Hz, 1H), 6.93-6.98 (m, 1H), 1.89-2.07 (m, 4H), 1.59-1.63 (m, 1H), 1.14-1.22 (m, 6H), 1.04-1.08 (m, 2H), 0.82-0.87 (m, 2H).

N-(2-(diethylphosphoryl)-5-(3-((S)-2-(4-fluoro-3,5-dimethylphenyl)-4-methyl-5-(1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carbonyl)-4,5,6,7-tetrahydro-2H-pyrazolo[4,3-c]pyridin-3-yl)-2-oxo-2,3-dihydro-1H-imidazol-1-yl)phenyl)cyclopropanecarboxamide (Compound 115a) was Synthesized Following the Methods Described in Example 2

$^1$H NMR (400 MHz, DMSO-d$_6$ 80° C.) δ 12.01 (s, 1H), 11.59 (br. s, 1H), 8.79 (s, 1H), 7.52-7.56 (m, 2H), 7.30-7.50 (m, 2H), 7.27 (dd, J=5.6, 1.6 Hz, 1H), 7.00-7.25 (m, 3H), 6.88 (s, 2H), 5.56 (br. s, 1H), 4.47 (br. s, 1H), 3.97-3.99 (m, 2H), 3.45-3.52 (m, 3H), 3.12-3.14 (m, 1H), 2.83-2.91 (m, 2H), 2.22 (d, J=2.0 Hz, 6H), 2.01-2.11 (m, 4H), 1.72-1.78 (m, 6H), 1.64-1.67 (m, 1H), 1.53-1.58 (m, 1H), 1.43 (br. s, 3H), 1.17-1.27 (m, 3H), 1.02-1.10 (m, 6H), 0.84-0.91 (m, 4H). LC-MS: m/z 970.4 (M+H)$^+$.

The following compound was synthesized using similar methods as described in Example 2 for Compound 115a.

N-(2-(diethylphosphoryl)-5-(3-((S)-2-(4-fluoro-3,5-dimethylphenyl)-4-methyl-5-(1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carbonyl)-4,5,6,7-tetrahydro-2H-pyrazolo[4,3-c]pyridin-3-yl)-2-oxo-2,3-dihydro-1H-imidazol-1-yl)phenyl)methanesulfonamide (Compound 116a)

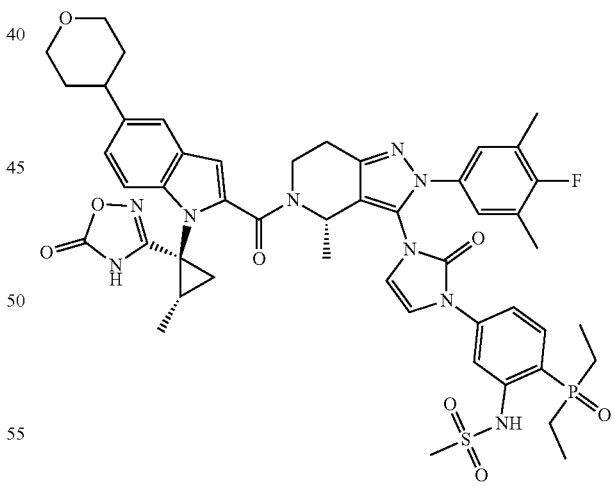

$^1$H NMR (400 MHz, DMSO-d$_6$, 80° C.) δ 11.51-11.62 (m, 2H), 7.93 (s, 1H), 7.53-7.59 (m, 2H), 7.42-7.44 (m, 2H), 7.26-7.28 (m, 2H), 7.15-7.16 (m, 2H), 6.87-6.92 (m, 2H), 5.56 (br. s, 1H), 4.46 (br. s, 1H), 3.97-4.00 (m, 2H), 3.46-3.52 (m, 3H), 2.99-3.20 (m, 2H), 2.87-2.91 (m, 2H), 2.22 (d, J=2.0 Hz, 6H), 2.04-2.12 (m, 5H), 1.65-1.77 (m, 8H), 1.44 (br. s, 3H), 1.18 (br. s, 3H), 1.00-1.10 (m, 6H). LC-MS: m/z 980.3 (M+H)$^+$

Example 4

3-((1S,2S)-1-(2-((S)-3-(3-(7-(dimethylphosphoryl)-1H-benzo[d]imidazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 110a)

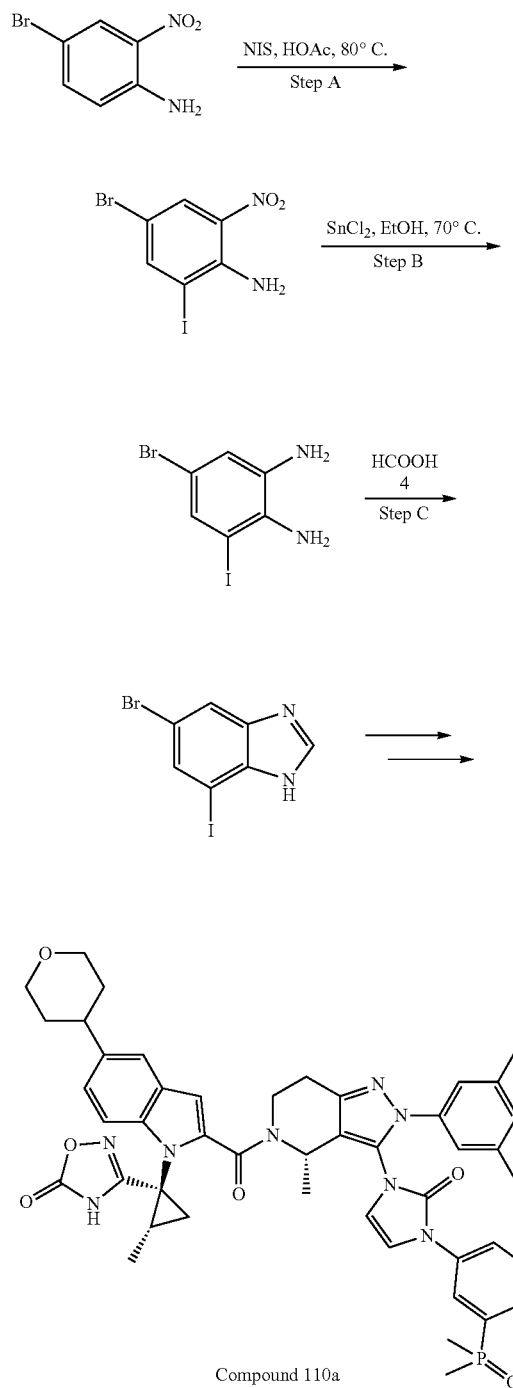

Compound 110a

Step A: 4-bromo-2-iodo-6-nitroaniline

To a solution of 4-bromo-2-nitroaniline (4.40 g, 20.2 mmol) in AcOH (30 mL) was added NIS (8.80 g, 40.4 mmol). The resulting mixture was stirred at 80° C. for 2 hours under $N_2$ atmosphere. The reaction mixture was cooled to room temperature, diluted with water (60 mL), and extracted with DCM (3×50 mL). The combined organic phase was washed with brine (50 mL), dried over anhydrous $Na_2SO_4$ and concentrated. The residue was purified by flash chromatography (eluted with PE/EtOAc=5/1) to afford the title compound 4-bromo-2-iodo-6-nitroaniline as a yellow solid (6.00 g, 88% yield). $^1$H NMR (400 MHz, $CDCl_3$) δ 8.31 (d, J=2.4 Hz, 1H), 8.01 (d, J=2.4 Hz, 1H), 6.67 (s, 2H).

Step B: 5-bromo-3-iodobenzene-1,2-diamine

To a solution of 4-bromo-2-iodo-6-nitroaniline (3.00 g, 8.70 mmol) in EtOH (30 mL) was added $SnCl_2$ (6.00 g, 43.5 mmol). The resulting mixture was stirred at 80° C. for 3 hours. The reaction mixture was quenched with water (10 mL) and yellow solid appeared. The mixture was filtered, and the filter cake was dried to give 5-bromo-3-iodobenzene-1,2-diamine as a yellow solid (2.60 g, crude). The crude product was used directly in next step without purification. LC-MS: m/z 312.8, 314.8 $(M+H)^+$

Step C: 5-bromo-7-iodo-1H-benzo[d]imidazole

A solution of 5-bromo-3-iodobenzene-1,2-diamine (3.50 g, 11.2 mmol) in HCOOH (20 mL) was stirred at 100° C. for 3 hours under $N_2$ atmosphere. The reaction was concentrated to remove excess HCOOH. Then water was added, and the mixture was extracted with EA. The combined organic phase was washed with brine (30 mL), dried over anhydrous $Na_2SO_4$ and concentrated. The residue was purified via silica column to afford the crude title compound 5-bromo-7-iodo-1H-benzo[d]imidazole as a yellow solid (2.60 g, 72% yield). LC-MS: m/z 322.8, 324.8 $(M+H)^+$ 3-((1S,2S)-1-(2-((S)-3-(3-(7-(dimethylphosphoryl)-1H-benzo[d]imidazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 110a) was Synthesized Using the Methods as Described in Example 2

$^1$H NMR (400 MHz, DMSO-$d_6$) δ 11.59 (br. s, 1H), 8.10-8.46 (m, 1H), 7.74 (br. s, 1H), 7.52 (s, 1H), 7.42 (d, J=8.8 Hz, 1H), 7.29 (d, J=7.6 Hz, 1H), 7.16-7.21 (m, 4H), 6.85-6.88 (m, 3H), 5.59 (br. s, 1H), 4.46 (br. s, 1H), 3.96-3.98 (m, 2H), 3.54-3.63 (m, 1H), 3.45-3.54 (m, 2H), 3.02-3.11 (m, 1H), 2.87-2.91 (m, 2H), 2.24 (s, 6H), 1.83-1.74 (m, 13H), 1.47 (s, 3H), 1.10-1.25 (m, 3H). LC-MS: m/z 450.6 $(M/2+H)^+$

The following compound was synthesized using similar method as described in Example 4 for Compound 110a.

3-((1S,2S)-1-(2-((S)-3-(3-(7-(dimethylphosphoryl)-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 112a)

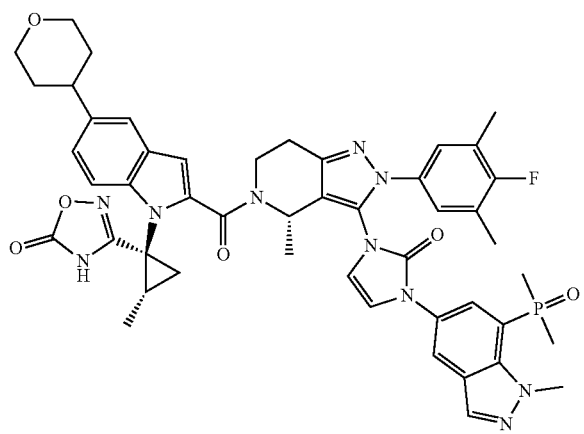 [SMILES: Cc1cc(-n2nc3c(c2-n2ccn(-c4cc(P(C)(C)=O)c5c(cnn5C)c4)c2=O)[C@H](C)N(C(=O)c2cc4cc(C5CCOCC5)ccc4n2[C@@]2(c4noc(=O)[nH]4)C[C@@H]2C)CC3)cc(C)c1F]

¹H NMR (400 MHz, DMSO-d₆) δ 11.60 (br. s, 1H), 8.23 (s, 1H), 8.16 (br. s, 1H), 7.81 (d, J=15.2 Hz, 1H), 7.52 (s, 1H), 7.43 (d, J=8.4 Hz, 1H), 7.26-7.28 (m, 2H), 7.17 (d, J=6.4 Hz, 2H), 6.88 (br. s, 2H), 5.60-5.63 (m, 1H), 4.53 (s, 3H), 4.46-4.58 (m, 1H), 3.96-3.99 (m, 2H), 3.51-3.58 (m, 1H), 3.45-3.50 (m, 2H), 3.02-3.07 (m, 1H), 2.88-2.91 (m, 2H), 2.23 (d, J=1.6 Hz, 6H), 1.62-2.00 (m, 13H), 1.47 (br. s, 3H), 1.17 (br. s, 3H).

LC-MS: m/z 913.4 (M+H)⁺

Example 5

3-((1S,2S)-1-(2-((S)-2-(4-fluoro-3,5-dimethylphenyl)-4-methyl-3-(3-(4-(1-oxidophospholan-1-yl)phenyl)-2-oxo-2,3-dihydro-1H-imidazol-1-yl)-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 127a)

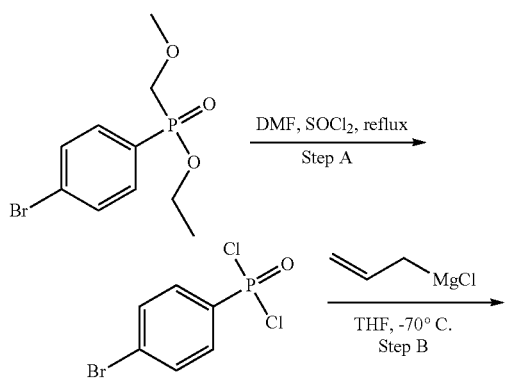

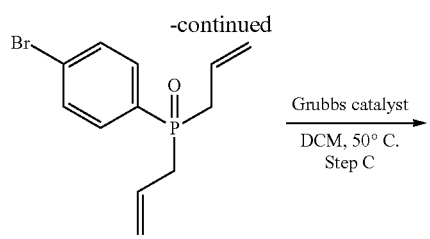

Step A: (4-bromophenyl)phosphonic dichloride

To a mixture of diethyl (4-bromophenyl)phosphonate (4.00 g, 13.6 mmol) and DMF (948 mg, 13.0 mmol) was added thionyl chloride (49.2 g, 413 mmol). The mixture was heated to reflux for 48 hours. The reaction mixture was concentrated, and the residue was dried in vacuo to afford crude (4-bromophenyl)phosphonic dichloride as a yellow oil (3.88 g), which was used in next step directly.

Step B: diallyl(4-bromophenyl)phosphine oxide

To a solution of (4-bromophenyl)phosphonic dichloride (3.88 g) in dry THF (10 mL) at −70° C. was added allylmagnesium chloride (1.0 M in THF, 42.6 mL, 42.6 mmol) dropwise. The mixture was stirred at −70° C. for 1.5 hours. LCMS showed the reaction was completed. The mixture was quenched with saturated NH₄Cl aqueous solution (50 mL) at −70° C. Then the mixture was warmed to room temperature and extracted with EtOAc (3×30 mL). The organic layer was dried and concentrated. The residue was purified with silica column chromatography (eluted with PE/EtOAc=1/3) to afford the title compound diallyl(4-bromophenyl)phosphine oxide as a yellow solid (1.80 g, 46% yield for two steps).

LC-MS: m/z 285.2, 287.0 (M+H)$^+$.

$^1$H NMR (400 MI Hz, DMSO-d$_6$) δ 7.72-7.75 (m, 2H), 7.63-7.69 (m, 2H), 5.58-5.70 (m, 2H), 5.06-5.10 (m, 4H), 2.82-2.98 (m, 4H).

Step C: 1-(4-bromophenyl)-2,5-dihydrophosphole 1-oxide

To a solution of diallyl(4-bromophenyl)phosphine oxide (400 mg, 1.58 mmol) in dichloromethane (40 mL) was added Grubbs catalyst (2$^{nd}$ generation, 70.0 mg, 0.08 mmol). The mixture was stirred at 50° C. for 12 h under Ar atmosphere. LCMS showed the reaction was completed. The mixture was concentrated, and the residue was purified with silica column chromatography (eluted with PE/EA/methanol=1/4/0.1) to afford the title compound 1-(4-bromophenyl)-2,5-dihydrophosphole 1-oxide as a pale white solid (154 mg, 38% yield).

LC-MS: m/z 257.0, 259.0 (M+H)$^+$.

$^1$H NMR (400 MHz, DMSO-d$_6$) δ 7.76 (dd, J=8.4, 2.0 Hz, 2H), 7.64 (dd, J=10.8, 8.4 Hz, 2H), 6.03 (d, J=28.8 Hz, 2H), 2.60-2.77 (m, 4H).

Step D: 1-(4-bromophenyl)phospholane 1-oxide

To a solution of 1-(4-bromophenyl)-2,5-dihydrophosphole 1-oxide (154 mg, 0.600 mmol) in EtOAc (8 mL) was added platinum dioxide (15.0 mg, 0.0660 mmol). The mixture was stirred at room temperature under H$_2$ atmosphere for 4 hours. LCMS showed the reaction was completed. The solid was filtered and the filtrate was concentrated. The residue was purified with silica column chromatography (eluted with PE/EA/methanol=1/4/0.2) to afford the title compound 1-(4-bromophenyl)phospholane 1-oxide as a pale white solid (107 mg, 69% yield).

LC-MS: m/z 259.0, 261.0 (M+H)$^+$.

$^1$H NMR (400 MHz, DMSO-d$_6$) δ: 7.73-7.76 (m, 2H), 7.66-7.71 (m, 2H), 1.93-2.07 (m, 4H), 1.77-1.90 (m, 4H).

3-((1S,2S)-1-(2-((S)-2-(4-fluoro-3,5-dimethylphenyl)-4-methyl-3-(3-(4-(1-oxidophospholan-1-yl)phenyl)-2-oxo-2,3-dihydro-1H-imidazol-1-yl)-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 127a) was Synthesized Using Methods Described in Example 2

$^1$H NMR (400 MHz, DMSO-d$_6$, 80° C.) δ 11.58 (br. s, 1H), 7.81 (br. s, 4H), 7.52 (s, 1H), 7.43 (d, J=8.8 Hz, 1), 7.26-7.28 (m, 2H), 7.15 (d, J=6.4 Hz, 2H), 6.88 (br. s, 2H), 5.55 (br. s, 1H), 4.48 (br. s, 1), 3.96-3.99 (m, 2H), 3.45-3.65 (m, 3H), 3.18-3.24 (m, 1H), 2.84-2.91 (m, 2H), 2.21 (d, J=2.0 Hz, 6H), 1.60-2.08 (m, 15H), 1.44 (d, J=4.8 Hz, 3H), 1.17 (s, 3H). LC-MS: m/z 885.3 (M+H)$^+$.

Example 6

3-((1S,2S)-1-(2-((S)-2-(4-fluoro-3,5-dimethylphenyl)-4-methyl-3-(3-(4-(1-methyl-4-oxido-1,4-azaphosphinan-4-yl)phenyl)-2-oxo-2,3-dihydro-1H-imidazol-1-yl)-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one HCl salt (Compound 126a)

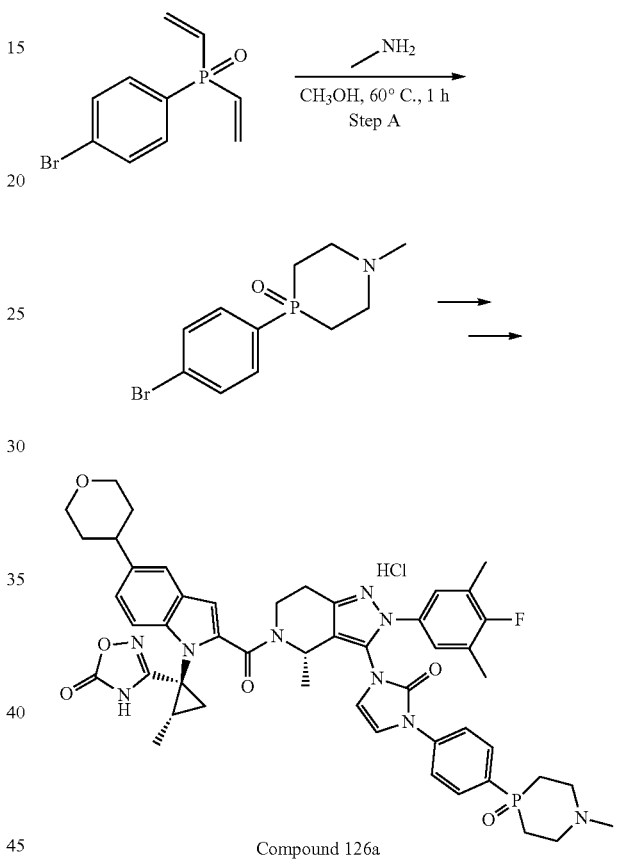

Compound 126a

Step A:
4-(4-bromophenyl)-1-methyl-1,4-azaphosphinane 4-oxide

To a solution of (4-bromophenyl)divinylphosphine oxide (585 mg, 2.28 mmol) in methanol (10 mL) was added methanamine (0.98 M in methanol, 2.79 mL, 2.74 mmol) dropwise. The mixture was stirred at 60° C. for 1 hour. LCMS showed the reaction was completed. The mixture was concentrated and the residue was purified with silica column chromatography (eluted with DCM/methanol=10/1) to afford the title compound 4-(4-bromophenyl)-1-methyl-1,4-azaphosphinane 4-oxide as a yellow solid (278 mg, 42% yield).

LC-MS: m/z 288.0, 290.0 (M+H)$^+$.

$^1$H NMR (400 MHz, DMSO-d$_6$) δ 7.72-7.77 (m, 4H), 2.68-2.78 (m, 4H), 2.19-2.29 (m, 5H), 1.84-1.99 (m, 2H).

3-((1S,2S)-1-(2-((S)-2-(4-fluoro-3,5-dimethylphenyl)-4-methyl-3-(3-(4-(1-methyl-4-oxido-1,4-azaphosphinan-4-yl)phenyl)-2-oxo-2,3-dihydro-1H-imidazol-1-yl)-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one HCl salt (Compound 126a) was Synthesized Using Methods Described in Example 2

¹H NMR (400 MHz, DMSO-d₆, 80° C.) δ 11.62 (br. s, 2H), 7.92 (br. s, 4H), 7.52 (s, 1H), 7.43 (d, J=8.4 Hz, 1H), 7.33 (br. s, 1H), 7.28 (dd, J=8.4, 1.2 Hz, 1H), 7.15 (d, J=6.0 Hz, 2H), 6.87-6.93 (m, 2H), 5.56 (br. s, 1H), 4.46 (br. s, 1H), 3.94-3.99 (m, 2H), 3.59-3.81 (m, 4H), 3.43-3.52 (m, 3H), 3.00-3.40 (m, 1H), 2.80-2.92 (m, 7H), 2.21-2.32 (m, 8H), 1.65-1.77 (m, 7H), 1.43 (br. s, 3H), 1.17 (br. s, 3H). LC-MS: m/z 914.4 (M+H)⁺.

The following compounds were synthesized using similar methods as described in Example 2 for Compound 121a.

3-((1S,2S)-1-(2-((S)-3-(3-(4-(diethylphosphoryl)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-((S)-2,2-dimethyltetrahydro-2H-pyran-4-yl)-1H-indol-1-yl)-2-methylcyclopropyl)-1,2,4-oxadiazol-5 (4H)-one (Compound 130b)

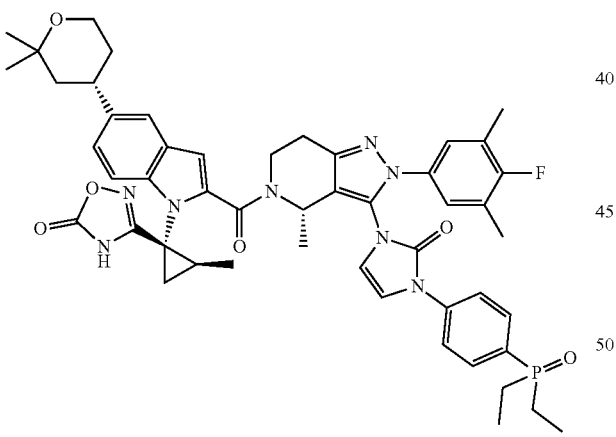

¹HNMR (400 MHz, DMSO-d₆, 80° C.) δ 11.47 (br. s, 1H), 7.79-7.80 (br. s, 4H), 7.52 (s, 1H), 7.43 (d, J=8.4 Hz, 1H), 7.29 (s, 1H), 7.26 (d, J=8.4 Hz, 1H), 7.16 (d, J=6.4 Hz, 2H), 6.91 (br. s, 1H), 6.85 (br. s, 1H), 5.57 (br. s, 1H), 4.44 (br. s, 1H), 3.73-3.75 (m, 2H), 3.56 (br. s, 1H), 2.96-3.04 (m, 2H), 2.82-2.95 (m, 1H), 2.22 (d, J=1.6 Hz, 6H), 1.82-2.04 (m, 4H), 1.52-1.76 (m, 7H), 1.35-1.50 (m, 3H), 1.25-1.35 (m, 3H), 1.18-1.21 (m, 6H), 0.92-1.05 (m, 6H). LC-MS: m/z 915.4 (M+H)⁺.

Example 7

3-((1S,2S)-1-(2-((S)-3-(3-(4-(dicyclopropylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 132a)

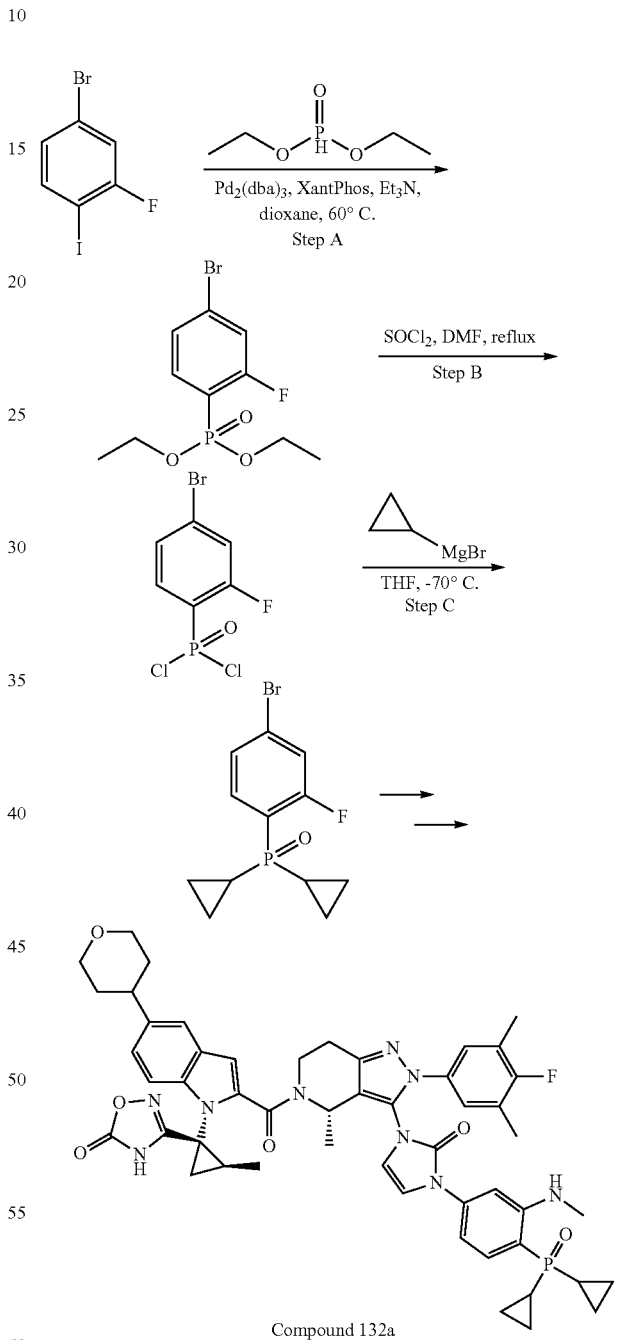

Compound 132a

Step A: diethyl (4-bromo-2-fluorophenyl)phosphonate

The mixture of 4-bromo-2-fluoro-1-iodobenzene (2.02 g, 6.70 mmol), diethyl phosphonate (1.11 g, 8.04 mmol), Pd₂(dba)₃ (311 mg, 0.34 mmol), XantPhos (388 mg, 0.67 mmol), and triethylamine (1.36 g, 13.4 mmol) in 1,4-dioxane (27 mL) was stirred at 60° C. overnight under Argon atmosphere. After cooled to room temperature, the mixture was concentrated and the residue was diluted with EtOAc (100 mL), washed with water (50 mL). The organic layer was dried and concentrated. The residue was purified by silica gel column chromatography (PE/EA=2/1) to afford the title compound diethyl (4-bromo-2-fluorophenyl)phosphonate as a yellow oil (1.40 g, 67% yield).

LC-MS: m/z 311.0, 313.0 (M+H)⁺.

Step B: (4-bromo-2-fluorophenyl)phosphonic dichloride

To a mixture of diethyl (4-bromo-2-fluorophenyl)phosphonate (1.40 g, 4.50 mmol) in thionyl chloride (49.2 g, 414 mmol) was added dry DMF (1.42 g, 19.4 mmol) dropwise. The mixture was heated to reflux for 72 hours. The mixture was concentrated and dried in vacuo to get (4-bromo-2-fluorophenyl)phosphonic dichloride as a colorless oil (1.50 g, crude), which was used in next step directly in the next steps without further purification.

Step C: (4-bromo-2-fluorophenyl)dicyclopropylphosphine oxide

To a mixture of (4-bromo-2-fluorophenyl)phosphonic dichloride (1.50 g, crude) in dry THF (10 mL) at −70° C. was added cyclopropylmagnesium bromide (2.0 M in THF, 5.13 mL, 10.3 mmol) dropwise. The mixture was stirred at −70° C. for 2 hours. LCMS showed the reaction was completed. The mixture was quenched with saturated NH₄Cl aqueous solution (50 mL) at −70° C. Then the mixture was warmed to room temperature and extracted with EtOAc (3×50 mL). The organic layer was dried and concentrated. The residue was purified with silica column chromatography (eluted with PE/EtOAc=1/2) to afford the title compound (4-bromo-2-fluorophenyl)dicyclopropylphosphine oxide as a yellow solid (420 mg, 27% yield).

¹HNMR (400 MHz, CDCl₃) δ 7.69-7.75 (m, 1H), 7.44 (d, J=8.0 Hz, 1H), 7.31-7.35 (m, 1H), 1.15-1.24 (m, 2H), 1.01-1.12 (m, 2H), 0.71-0.97 (m, 6H).

3-((1S,2S)-1-(2-((S)-3-(3-(4-(dicyclopropylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 132a) was Synthesized Using the Methods as Described in Example 2

¹H NMR (400 MHz, DMSO-d₆, 80° C.) δ: 10.95 (br. s, 1H), 7.49 (s, 2H), 7.41 (d, J=8.4 Hz, 1H), 7.22-7.24 (m, 3H), 7.13 (d, J=5.6 Hz, 2H), 6.82-6.84 (m, 3H), 5.54 (br. s, 1H), 4.41 (br. s, 1H), 3.96 (d, J=10.8 Hz, 2H), 3.44-3.50 (m, 3H), 2.81-2.89 (m, 3H), 2.62-2.78 (m, 3H), 2.20 (s, 6H), 1.62-1.74 (m, 7H), 1.40 (br. s, 3H), 1.17-1.25 (m, 5H), 0.71-0.93 (m, 6H), 0.57-0.70 (m, 2H). LC-MS: m/z 940.4 (M+H)⁺.

The following compounds were synthesized using similar methods as described in Example 2 for Compound 121a.

(S)-3-(1-(2-(3-(3-(4-(dicyclopropylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)cyclopropyl)-1,2,4-oxadiazol-5 (4H)-one (Compound 148a)

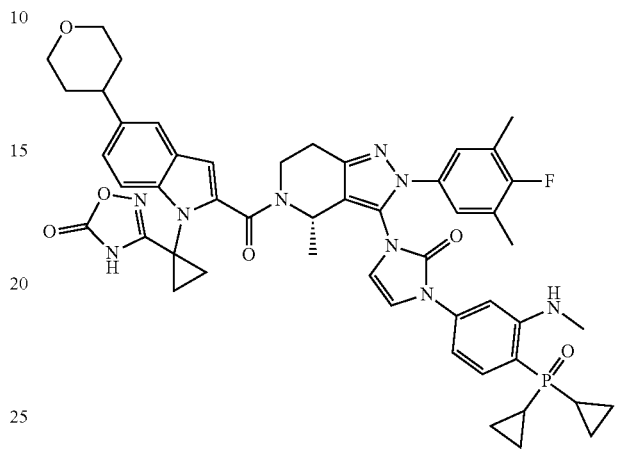

¹HNMR (400 MHz, DMSO-d₆, 80° C.) δ 7.45-7.50 (m, 3H), 7.18-7.20 (m, 3H), 7.13 (d, J=6.4 Hz, 2H), 6.81-6.88 (m, 2H), 6.71 (s, 1H), 5.51 (br. s, 1H), 4.47 (br. s, 1H), 3.96 (d, J=10.8 Hz, 2H), 3.43-3.51 (m, 3H), 2.90-2.85 (m, 2H), 2.77-2.81 (m, 1H), 2.70 (s, 3H), 2.20 (s, 6H), 1.65-1.73 (m, 6H), 1.40-1.55 (br. s, 1H), 1.35 (d, J=6.4 Hz, 3H), 1.15-1.30 (m, 3H), 0.72-0.92 (m, 6H), 0.58-0.69 (m, 2H). LC-MS: m/z 926.4 (M+H)⁺

3-((1S,2S)-1-(2-((4S)-3-(3-(4-(tert-butyl(methyl)phosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)-2-methylcyclopropyl)-1,2,4-oxadiazol-5 (4H)-one (Compound 131a)

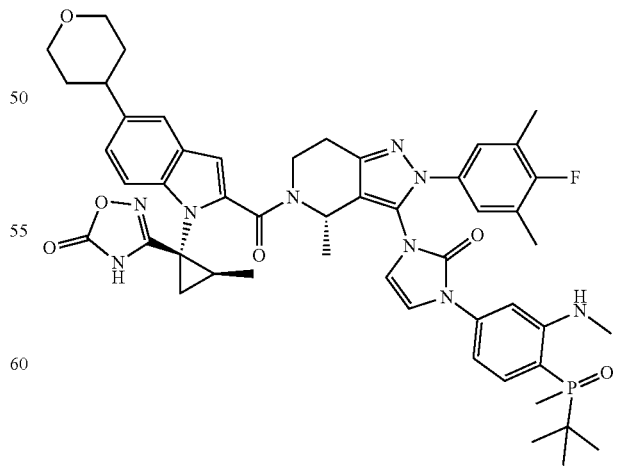

¹H NMR (400 MHz, DMSO-d₆, 80° C.) δ11.57 (br. s, 1H), 7.77 (br. s, 1H), 7.53 (s, 1H), 7.28 (d, J=1.6 Hz, 1H), 7.14-7.26 (m, 5H), 6.87 (br. s, 4H), 5.56 (br, s, 1H), 4.48 (br. s, 1H), 3.97-4.00 (m, 2H), 3.46-3.57 (m, 3H), 2.83-2.91 (m, 3H), 2.72 (br. s, 3H), 2.22 (d, J=−2.0 Hz, 6H), 1.64-1.75 (m, 10H), 1.45 (s, 3H), 1.17 (s, 3H), 1.08 (d, J=14.4 Hz, 9H). LCMS: m/z=930.4 (M+H)+.

3-(1-(2-((4S)-3-(3-(4-(tert-butyl(methyl)phosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)cyclopropyl)-1,2,4-oxadiazol-5 (4H)-one (Compound 149a)

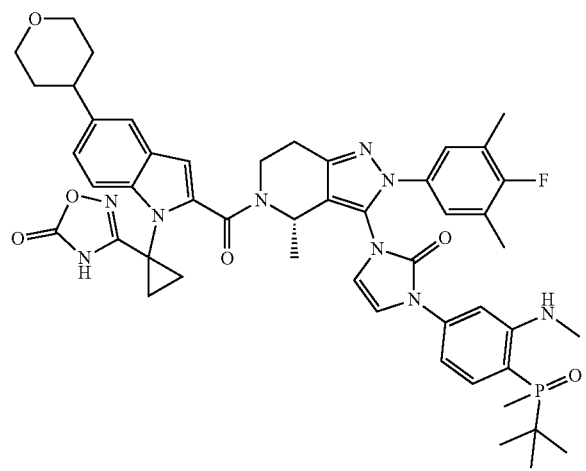 [SMILES: CNc1cc(-n2ccn(-c3c4c(nn3-c3cc(C)c(F)c(C)c3)CCN(C(=O)c3cc5cc(C6CCOCC6)ccc5n3C3(c5noc(=O)[nH]5)CC3)[C@H]4C)c2=O)ccc1P(C)(=O)C(C)(C)C]

¹HNMR (400 MHz, DMSO-d₆, 80° C.) δ11.76 (br. s, 1H), 7.48-7.51 (m, 2H), 7.14H-7.26 (m, 5H), 6.79-6.87 (m, 4H), 5.54 (br. s, 1H), 4.48 (br. s, 1H), 3.97-4.00 (m, 2H), 3.46-3.53 (m, 3H), 2.83-2.91 (m, 3H), 2.72 (s, 3H), 2.22 (d, J=1.6 Hz, 6H), 1.69-1.82 (m, 10H), 1.52-1.54 (m, 1H), 1.39 (d, J=−6.4 Hz, 3H), 1.08 (d, J=11.8 Hz, 9H). LCMS: m/z=916.4 (M+H)+.

Example 8

3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(4,4-difluorocyclohexyl)-1H-indol-1-yl)-2-methylcyclopropyl)-1,2,4-oxadiazol-5 (4H)-one (Compound 133a)

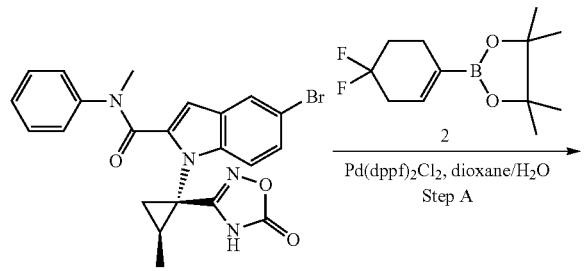

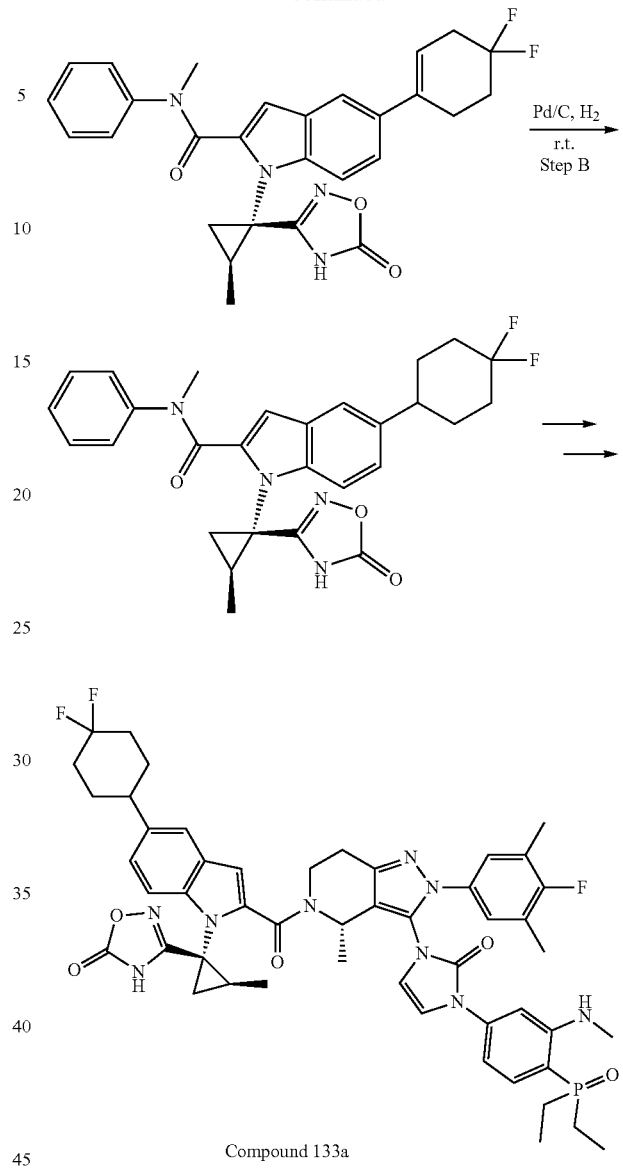

Compound 133a

Step A: 5-(4,4-difluorocyclohex-1-en-1-yl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide To a solution of 5-bromo-N-methyl-1-((1S,2S)-2-methyl-1-(5-oxo-4,5-dihydro-1,2,4-oxadiazol-3-yl)cyclopropyl)-N-phenyl-1H-indole-2-carboxamide (400 mg, 0.86 mmol) and 2-(4,4-difluorocyclohex-1-en-1-yl)-4,4,5,5-tetramethyl-1,3,2-dioxaborolane (629.4 mg, 2.58 mmol) in dioxane/H₂O=5/1 (20 mL) was added K₂CO₃ (237 mg. 1.72 mmol) and Pd(dppf)Cl₂ (70.1 mg, 0.0860 mmol) at room temperature. The resulting mixture was stirred at 80° C. for 16 hours under N₂ atmosphere. The reaction solution was concentrated. The residue was purified by silica gel with PE/EA=3/1 to 2/1 to afford 5-(4,4-difluorocyclohex-1-en-1-yl)-N-methyl-1-((1S,2S)-2-methyl-1-(5-oxo-4,5-dihydro-1,2,4-oxadiazol-3-yl)cyclopropyl)-N-phenyl-1H-indole-2- carboxamide as a yellow glue (360 mg, 83% yield). ¹HNMR (400 MHz, CDCl₃) δ 11.19 (s, 1H), 7.54 (d, J=8.4 Hz, 1H), 7.32-7.36 (m, 5H), 7.15 (s, 2H), 5.89 (s, 1H), 5.78 (s, 1H), 3.56 (s, 3H), 2.64-2.71 (m, 3H), 2.10-2.20 (m, 2H), 1.92 (t, J=7.2 Hz, 1H), 1.78-1.83 (m, 2H), 1.48 (dd, J=9.2, 6.8 Hz, 1H), 1.28 (d, J=6.8 Hz, 3H). LC-MS: m/z 505.2 (M+H)⁺.

Step B: 5-(4,4-difluorocyclohexyl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide To a solution of 5-(4,4-difluorocyclohex-1-en-1-yl)-N-methyl-1-((1S,2S)-2-methyl-1-(5-oxo-4,5-dihydro-1,2,4-oxadiazol-3-yl)cyclopropyl)-N-phenyl-1H-indole-2-carboxamide (360 mg, 0.71 mmol) in ethyl acetate (10 mL) was added Pd/C (10%, 64 mg) at room temperature under Ar. Then the resulting solution was stirred at room temperature for 16 hours under H₂. The reaction was filtered, and the filtrate was concentrated. The crude product was purified by pre-HPLC (HCOOH/CH₃CN/H₂O) to give 5-(4,4-difluorocyclohexyl)-N-methyl-1-((1 S,2S)-2-methyl-1-(5-oxo-4,5-dihydro-1,2,4-oxadiazol-3-yl)cyclopropyl)-N-phenyl-1H-indole-2-carboxamide as white solid (50 mg, 14% yield).

LC-MS: m/z 507.2 (M+H)⁺

3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(4,4-difluorocyclohexyl)-1H-indol-1-yl)-2-methylcyclopropyl)-1,2,4-oxadiazol-5 (4H)-one (Compound 133a) was synthesized Using the Methods as Described in Example 2

¹HNMR (400 MHz, DMSO-d₆, 80° C.) δ11.57 (br. s, 1H), 7.52 (s, 1H), 7.40 (d, J=8.8 Hz, 1H), 7.12-7.25 (m, 5H), 6.84 (br. s, 4H), 5.55 (br. s, 1H), 4.43 (br. s, 1H), 3.54 (br. s, 1H), 3.17 (br. s, 1H), 2.70-2.89 (m, 5H), 2.24-2.31 (m, 1H), 2.20 (s, 6H), 1.86-2.12 (m, 10H), 1.62-1.78 (m, 5H), 1.35-1.50 (m, 3H), 1.15-1.25 (m, 3H), 1.01 (dt, J=7.6, 16.4 Hz, 6H). LC-MS: m/z 950.4 (M+H)⁺.

Example 9

3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(2,2-dimethylmorpholino)-1H-indol-1-yl)-2-methylcyclopropyl)-1,2,4-oxadiazol-5 (4H)-one (Compound 150a)

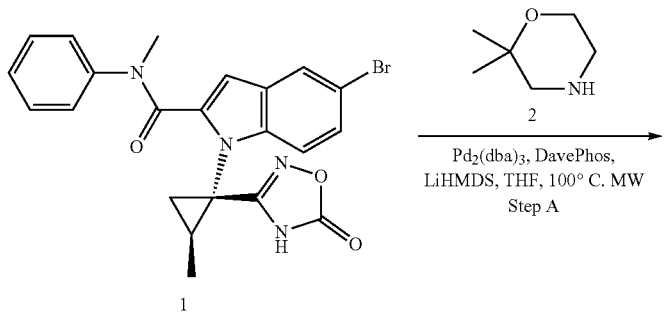

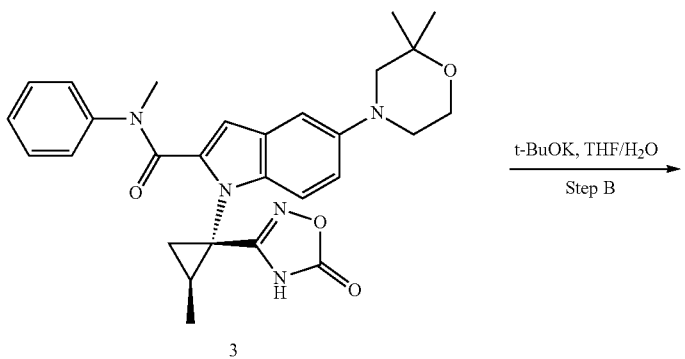

-continued

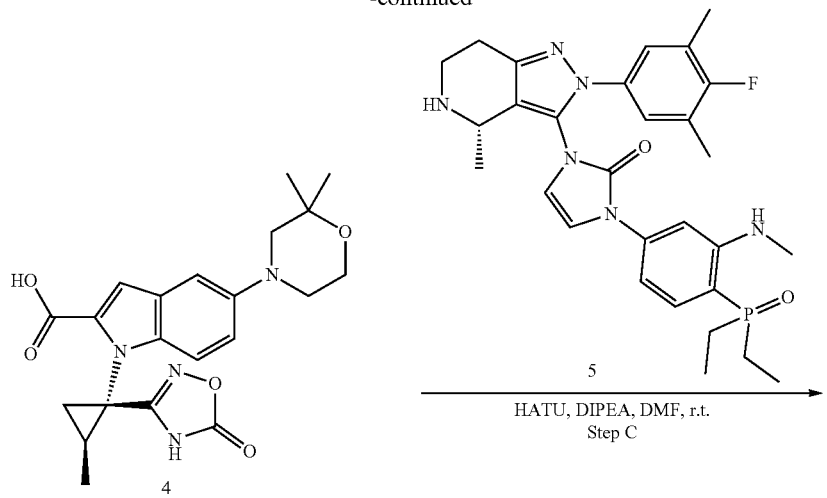

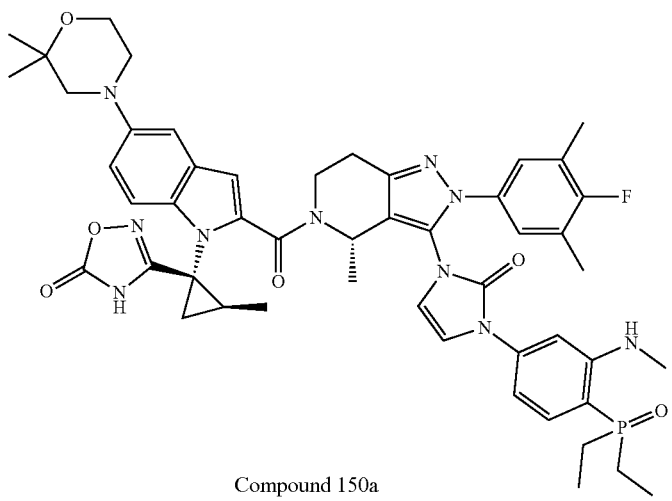

Compound 150a

Step A: 5-(2,2-dimethylmorpholino)-N-methyl-1-((1S,2S)-2-methyl-1-(5-oxo-4,5-dihydro-1,2,4-oxadiazol-3-yl)cyclopropyl)-N-phenyl-1H-indole-2-carboxamide To the mixture of 5-bromo-N-methyl-1-((1S,2S)-2-methyl-1-(5-oxo-4,5-dihydro-1,2,4-oxadiazol-3-yl)cyclopropyl)-N-phenyl-1H-indole-2-carboxamide (585 mg, 1.25 mmol), 2,2-dimethylmorpholine (173 mg, 1.50 mmol), $Pd_2(dba)_3$ (115 mg, 0.13 mmol) and Davephos (98 mg, 0.25 mmol) in THF (20 mL) was added LiHMDS (2.8 mL, 2.75 mmol) under $N_2$ atmosphere. The mixture was stirred at 100° C. via microwave irradiation for 4 hours. To the mixture was added 1M HCl (10 mL) and extracted with EA (30 mL). The organic layers were washed with saturated $NaHCO_3$ aq (10 mL), brine (10 mL), dried over $Na_2SO_4$, concentrated and purified by flash chromatography (eluted with DCM/MeOH=60/1) to afford the title compound 5-(2,2-dimethylmorpholino)-N-methyl-1-((1 S,2S)-2-methyl-1-(5-oxo-4,5-dihydro-1,2,4-oxadiazol-3-yl)cyclopropyl)-N-phenyl-1H-indole-2-carboxamide as a yellow solid (341 mg, 54% yield).
LC-MS: m/z 502.2 $(M+H)^+$ Step B: 5-(2,2-dimethylmorpholino)-1-((1S,2S)-2-methyl-1-(5-oxo-4,5-dihydro-1,2,4-oxadiazol-3-yl)cyclopropyl)-1H-indole-2-carboxylic acid To a solution of 5-(2,2-dimethylmorpholino)-N-methyl-1-((1S,2S)-2-methyl-1-(5-oxo-4,5-dihydro-1,2,4-oxadiazol-3-yl)cyclopropyl)-N-phenyl-1H-indole-2-carboxamide (341 mg, 0.68 mmol) in THF (16 mL) was added t-BuOK (2.3 g, 20.5 mmol), followed by $H_2O$ (116 mg). The mixture was stirred at room temperature overnight. The mixture was concentrated, and pH was adjusted to 4-5 using 1N HCl aq. solution. The mixture was extracted with DCM (3×20 mL), dried over $Na_2SO_4$, concentrated, and purified by reversed phase to afford the title compound 5-(2,2-dimethylmorpholino)-1-((1S,2S)-2-methyl-1-(5-oxo-4,5-dihydro-1,2,4-oxadiazol-3-yl)cyclopropyl)-1H-indole-2-carboxylic acid as a white solid (225 mg, 80% yield).
LC-MS: m/z 411.2 $(M-H,\text{ negative mode})^+$.

Step C: 3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(2,2-dimethylmorpholino)-1H-indol-1-yl)-2-methylcyclopropyl)-1,2,4-oxadiazol-5 (4H)-one To the mixture of (S)-1-(4-(diethylphosphoryl)-3-(methylamino)phenyl)-3-(2-(4-fluoro-3,5-dimethylphenyl)-4-methyl-4,5,6,7-tetrahydro-2H-pyrazolo[4,3-c]pyridin-3-yl)-1,3-dihydro-2H-imidazol-2-one (118 mg, 0.210 mmol), 5-(2,2-dimethylmorpholino)-1-((1S,2S)-2-methyl-1-(5-oxo-4,5-dihydro-1,2,4-oxadiazol-3-yl)cyclopropyl)-1H-indole-2-carboxylic acid (80 mg, 0.190 mmol) and HATU (221 mg, 0.580 mmol) in DMF (4 mL) was added DIEA (150 mg, 1.16 mmol). The mixture was stirred at room temperature overnight. To the mixture was added water (30 mL) and extracted with DCM (3×20 mL). The organic layer was washed with brine, dried over $Na_2SO_4$, concentrated and purified by prep-HPLC to afford 3-((1S,2S)-1-(2-((S)-3-(3-(4-(diethylphosphoryl)-3-(methylamino)phenyl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(2,2-dimethylmorpholino)-1H-indol-1-yl)-2-methylcyclopropyl)-1,2,4-oxadiazol-5 (4H)-one as a white solid (71.0 mg, 35% yield). $^1$HNMR (400 MHz, DMSO-$d_6$, 80° C.) δ 11.58 (br. s, 1H), 7.35 (d, J=8.8 Hz, 1H), 7.07-7.21 (m, 6H), 6.83 (br. s, 3H), 6.77 (br. s, 1H), 5.50 (br. s, 1H), 4.43 (br. s, 1H), 3.74-3.82 (m, 2H), 3.54 (br. s, 2H), 2.98-3.03 (m, 2H), 2.85-2.95 (m, 3H), 2.71 (br. s, 3H), 2.20 (s, 6H), 1.85-1.96 (m, 4H), 1.65-1.72 (m, 1H), 1.60 (br. s, 1H), 1.42 (br. s, 3H), 1.20-1.32 (m, 7H), 1.14 (br. s, 3H), 0.95-1.07 (m, 6H). LC-MS: m/z 473.2 $(M/2+H)^+$.

Example A: cAMP Assays

Activation of GLP-1 receptor is known to stimulate cyclic AMP (cAMP) production in cells which indicates primary coupling to the $G_{\alpha s}$ subunit of the G protein heterotrimeric complex. Evidence suggests signaling through $G_{\alpha s}$ induced cAMP stimulation elicits the desired pharmacological response regarding insulin release from pancreatic β-cells.

Method 1: To optimize functional activity directed toward $G_{\alpha s}$ coupling, a CHO-K1 cell line developed by DiscoverX stably expressing the GLP-1 Receptor is used. Cells expressing GLP-1 receptor are plated in a 384-well microtiter plates and incubated overnight at 37° C. with 5% $CO_2$ to allow the cells to attach and grow. Media is then aspirated from the cells and replaced with 15 μL Hanks Balanced Salt Solution (HBSS)/5 mM Hepes: 0.5 mM IBMX 0.1% BSA (pH 7.4) [Stimulation Buffer]. Plated cells are resuspended in Stimulation buffer and five microliters (5 μL) of the suspension is added to previously generated compound sample stocks at 4× final concentration in Stimulation Buffer are then added to the cells and allowed to incubate at 37° C. for 30 or 60 minutes.

After incubation the assay signal is generated using a europium chelate-labeled cAMP tracer which competes with cAMP for binding sites on a cAMP-specific monoclonal antibody labeled with ULight™ dye. When antibodies are bound to the Eu-labeled cAMP tracer FRET transfer between the Eu chelate and ULIght™ labeled antibodies is detected. Free cAMP produced from stimulated cells competes with the Eu-cAMP tracer for binding to the ULight-mAb causing a decrease in the TR-FRET signal in a dose dependent manner.

The method for detection of cAMP using using the Eu-chelate technology requires incubation with Eu-cAMP tracer solution+ULight-anti-cAMP solution for one hour at room temperature. Microplates are read following signal generation with a PerkinElmer Envision instrument utilizing TR-FRET signal detection. Percentage activity is calculated using the following formula:

% Activity=100%×(mean RLU of test sample−mean RLU of vehicle control)/(mean RLU of MAX control−mean RLU of vehicle control))

Method 2: To optimize functional activity directed toward $G_{\alpha s}$ coupling, a CHO-K1 cell line developed by DiscoverX stably expressing the GLP-1 Receptor is used. Cells expressing GLP-1 receptor are plated in a 384-well microtiter plates and incubated overnight at 37° C. with 5% $CO_2$ to allow the cells to attach and grow. Media is then aspirated from the cells and replaced with 15 μL 2:1 Hanks Balanced Salt Solution (HBSS)/10 mM Hepes: cAMP XS+Ab reagent. Five microliters (5 μL) of previously generated compound sample stocks at 4× final concentration in assay buffer are then added to the cells and allowed to incubate at 37° C. for 30 or 60 minutes.

After incubation the assay signal is generated using enzyme fragment complementation (EFC). In EFC, the enzyme B-galactosidase is split into two complementary portions (EA and ED). The fragment ED is fused to cAMP and in the assay format competes with endogenous cAMP for binding to a cAMP specific antibody. Activated B-Gal is formed when exogenous EA fragment binds to free ED-cAMP (not bound to cAMP specific antibody). Activated enzyme levels are detected through conversion of B-gal chemiluminescent substrate which generates a detectable luminescence signal and read on standard microtiter plate.

The methodology for detection of cAMP using EFC requires incubation with 20 μL of cAMP XS+ED/CL lysis cocktail for one hour followed by incubation with 20 μL cAMP XS+EA reagent for three hours at room temperature. Microplates are read following signal generation with a PerkinElmer Envision instrument utilizing chemiluminescent signal detection. Compound activity is analyzed using CBIS data analysis suite (ChemInnovation, CA). Percentage activity is calculated using the following formula:

% Activity=100%×(mean RLU of test sample−mean RLU of vehicle control)/(mean RLU of MAX control−mean RLU of vehicle control))

Method 3: Activation of GLP-1 receptor is known to stimulate cyclic AMP (cAMP) production in cells which indicates primary coupling to the $G_{\alpha s}$ subunit of the G protein heterotrimeric complex. Evidence suggests signaling through $G_{\alpha s}$ induced cAMP stimulation elicits the desired pharmacological response regarding insulin release from pancreatic β-cells.

To optimize functional activity directed toward $G_{\alpha s}$ coupling, a HEK293/CRE-Luc cell line developed by HDB stably expressing the GLP-1 Receptor was used. 200× concentration of compound working solutions were prepared (Agilent Technologies Bravo) with 1/2 log serial dilution in 384-well Echo LDV plate (Labcyte, Cat #LP-0200). 50 nL/well 200× concentration of compound working solutions were moved to 384-well white low volume plate (Greiner, Cat #784075) using Labcyte ECHO550. 1×10$^5$ cells/mL HEK293/GLP1R/CRE-LUC(HD Biosciences) cell suspensions prepared with assay buffer [DPBS containing 0.5 mM IBMX(Sigma, Cat #15879) and 0.1% BSA(GEN-VIEW, Cat #FA016-100 g)], 10 μL cell suspensions were added to each well of previous generated assay plate which already contains 50 nL compound at 200× concentration using ThermoFisher Multidrop Combi (1000 cells/well). Seal the plate and incubate at 37° C. with 5% $CO_2$ for 30 min.

After incubation the cAMP assay signal was generated using cAMP dynamic 2 Kit (Cisbio). 5 μL cAMP-d2 working solution was added to each well, followed with 5 μL Anti-cAMP antibody-cryptate working solution added to each well using ThermoFisher Multidrop Combi. Incubate at room temperature for 1 hour protected from light. Read the fluorescence at 665 nm and 615 nm with Reader PerkinElmer EnVision.

% Activity=100%×(mean RLU of test sample−mean RLU of vehicle control)/(mean RLU of MAX control−mean RLU of vehicle control))

Table 1 shows the biological activity of compounds in GLP-1R agonist cAMP stimulation assay ($EC_{50}$) [nM] (Method 3)

| Compound Number | GLP1R cAMP Stimulation DR: $EC_{50}$ (nM) [Species: Human, Assay Cell Line: HDB] | GLP1R cAMP Stimulation DR: $pEC_{50}$ (M) [Species: Human, Assay Cell Line: HDB] |
| --- | --- | --- |
| 101a | B | B |
| 102a | A | A |
| 105a | B | B |
| 106a | A | A |
| 107a | C | B |
| 108a | C | B |
| 109a | B | B |
| 110a | D | B |
| 111a | A | A |
| 112a | D | B |
| 113a | C | B |
| 114a | C | B |
| 115a | C | B |
| 116a | C | B |
| 117a | C | B |
| 118a | A | A |
| 119a | C | B |
| 120a | A | A |
| 121a | A | A |
| 122a | A | A |
| 123a | C | B |
| 124a | A | A |
| 125a | C | B |
| 126a | B | B |
| 127a | A | A |
| 128a | A | A |
| 129a | A | A |
| 130b | A | A |
| 131a | B | B |
| 132a | B | B |
| 133a | B | B |
| 135a | A | A |
| 136a | C | B |
| 138a | A | A |
| 139a | A | A |
| 140a | D | B |
| 141a | A | A |
| 142a | A | A |
| 143a | B | B |
| 144a | A | A |
| 145a | A | A |
| 146a | A | A |
| 146b | A | A |
| 147a | D | C |
| 148a | A | A |
| 149a | B | B |
| 150a | B | B |

Notes:
$EC_{50}$ ranges: A: $0 < EC_{50} \leq 0.1$; B: $0.1 < EC_{50} \leq 0.2$; C: $0.2 < EC_{50} \leq 0.5$; D: $0.5 < EC_{50} < 5$
$pEC_{50}$ ranges: A: $pEC_{50} \geq 10$; B: $9 \leq pEC_{50} < 10$; C: $8 \leq pEC_{50} < 9$ Example B Rat Pharmacokinetics (PK) Studies Pharmacokinetics (PK) study was conducted on male Sprague Dawley (SD) rats by two delivery routes: intravenous (IV) and/or oral gavage (PO). Rats in IV route (n=3) were free access to food and water. Rat in PO route (n=3) were fasted overnight and fed at 4 hours post dosing. Test article was formulated in solution for IV route and solution or suspension for PO route, respectively. On the day of experiment, test article was administered via vein (e.g. foot dorsal vein) injection (commonly at 0.2 to 1 mg/kg and 2 mL/kg) for IV route or via oral gavage (commonly at 5 to 100 mg/kg and 10 mL/kg) for PO route, respectively. Blood samples were collected via serial bleeding at ~8 time points from 0.083 to 24 hrs post dose. Approximately 150 μL of blood/time point was collected into $K_2EDTA$ tube via tail vein. Blood samples were put on wet ice and centrifuged to obtain plasma samples and plasma samples were submitted to LC-MS/MS for sample analysis. Pharmacokinetics parameters, including clearance (IV), area under the curve (AUC) and oral bioavailability (F %), etc. were calculated by non-compartmental model using WinNonlin.

Exemplary compounds of Formula (I) (e.g., certain compounds of Formula (IE)) were tested using the protocol above. The compounds tested exhibited plasma clearance (L/hr/kg) in the range of 0.20 to 1.60 (e.g., between 0.20 to 0.80 (e.g., between 0.30 to 0.50); or between 1.00 to 1.60 (e.g., between 1.20 to 1.60)); and volume of distribution (L/Kg) in the range of between 0.40 to 0.70 (L/Kg).

Example C Glucose Tolerance Test in Non-Human Primate (NHP)

Cynomolgus monkeys (2.5-6.0 kg) were individually housed in stainless steel cages for the duration of the study under a controlled environment that was set to maintain a temperature of 18-26° C. and relative humidity of 30-70%, a minimum of 10 air changes/hour. A time-controlled lighting system was used (light 7:00 AM-7:00 PM) to provide a regular 12-hour light/i 2-hour dark diurnal cycle. The monkeys were provided with 3 meals per day consisting of 100 g of proprietary normal diet in the morning 9:00-10:00, one regular fruit (150 g) in the afternoon 14:00-15:00, and 100 g of proprietary normal diet in the afternoon 16:00-17:00. Drinking water was provided ad libitum. All animals were conducted baseline ivGTT and then selected animals assigned into pre-set groups base on the baseline ivGTT insulin AUC and their body weights.

The general study outline is presented in the table below:

| Day: | | | | | | | | | | | | | | | | |
|---|---|---|---|---|---|---|---|---|---|---|---|---|---|---|---|---|
| −7 | −6 | −5 | −4 | −3 | −2 | −1 | 1 | 2 | 3 | 4 | 5 | 6 | 7 | 8 | 9 | |
| Acclimation Phase | | | | | | | Treatment Phase | | | | | | | | | |

Prior to the start of the study, animals were acclimatized for 1 week. On day 1, all animals were dosed with vehicle via IV injection for 5 min prior to IV glucose challenge. On day 9, all animals were dosed with either vehicle or compound via IV injection for 5 min prior to IV glucose challenge.

The ivGTT was conducted on day 1 and day 9, respectively. The overnight fasted animals were anaesthetized (Zoletil 50, intramuscularly, 5 mg/kg initial dose, and then maintenance dose at 2.5-5 mg/kg if needed).

5 min after the compound or vehicle dosing, the animals were intravenously injected with 50% glucose at a dose of 0.5 g/kg (1 mL/kg) for 30 seconds via the saphenous vein or the appropriate peripheral vein. The whole blood samples (1.2 mL) were collected into EDTA-K2 tubes from a peripheral vein at the following time-points: −6 (prior to compound dosing) and 1, 3, 5, 10, 20, 40 and 60 mins after glucose challenge.

The collected blood samples were stored under wet-ice and then centrifuged at 3500 rpm, 4° C. for 10 min within 60 min. The collected plasma samples (0.5 mL each) were stored in a freezer set to maintain −80° C. until analysis for glucose, insulin and C-peptide.

For test compound groups, approximately 1.0 mL of whole blood was collected into EDTA-K2 tubes from saphenous or cephalic vein at each time point of IVGTT on day 9. The collected blood samples were maintained on wet ice until centrifugation. Plasma was separated by centrifugation at 3500 rpm, 4° C. for 10 minutes within 60 minutes of collection. Statistical analysis of the data was completed using GraphPad Prism (version 9, GraphPad Software Inc, La Jolla, CA).

Exemplary compounds of Formula (I) (e.g., certain compounds of Formula (IE)) were tested using the protocol above. Specifically, a test compound was iv injected into healthy NHPs at the dose selected from 0.03 to 0.30 mg/kg (e.g., dosed at 0.05 mg/kg). Following the procedures described above, a 2.0 to 6.0 fold (e.g., 3.0 to 5.0 fold) insulin secretion was induced in ivGTT, and a 10% to 40% (e.g., 30% to 40%) increase in glucose clearance rate was observed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

20. The method of claim 1, wherein the compound is:
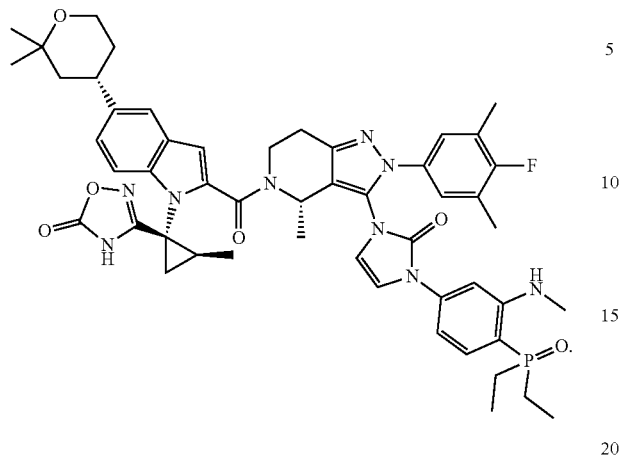

What is claimed is:

1. A method of treating type 2 diabetes mellitus in a patient in need thereof, the method comprising administering to the patient a therapeutically effective amount of a compound selected from:

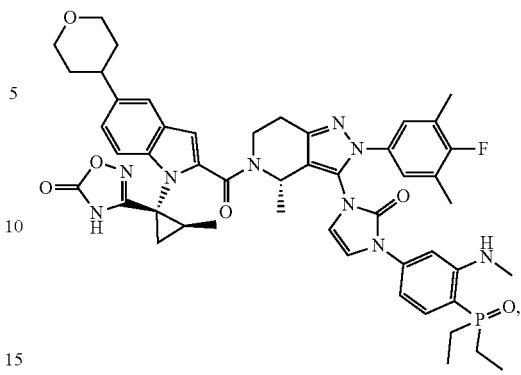

121a

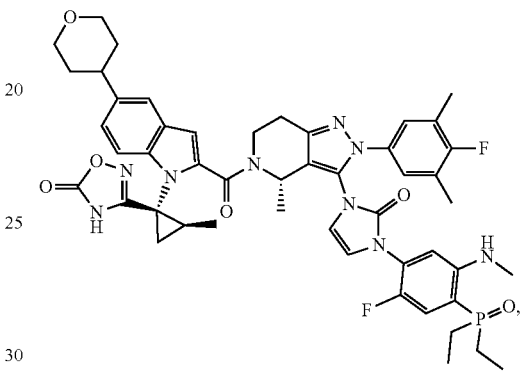

144a

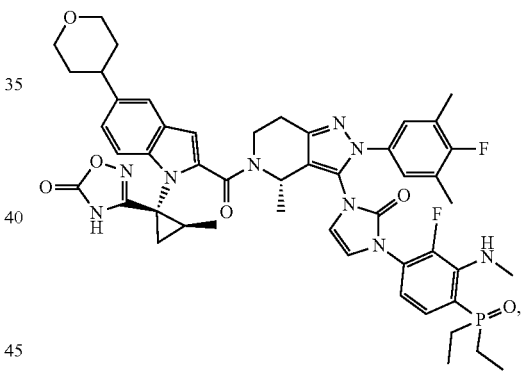

145a

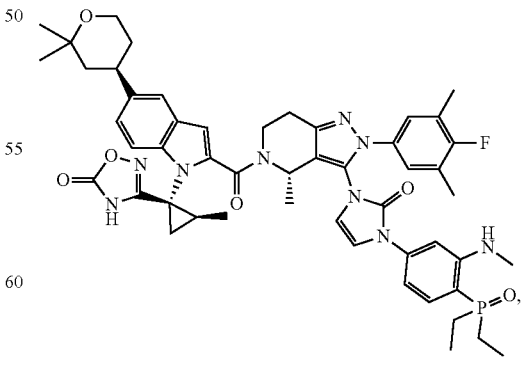

146a and

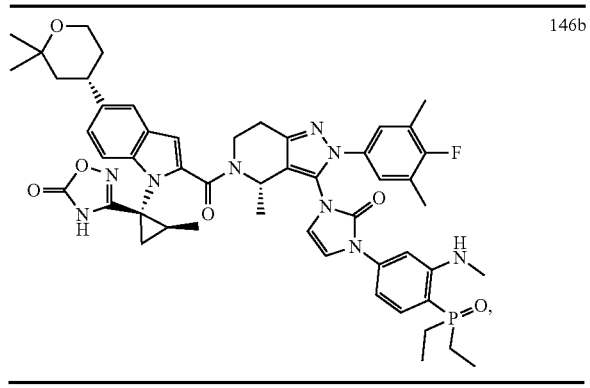

or a pharmaceutically acceptable salt thereof.

2. The method of claim 1, wherein the compound is administered orally.

3. The method of claim 1, further comprising administering an additional therapy or therapeutic agent to the patient.

4. The method of claim 3, wherein the additional therapy or therapeutic agent is an anti-diabetic agent, an anti-obesity agent, a GLP-1 receptor agonist, an agent to treat non-alcoholic steatohepatitis (NASH), gastric electrical stimulation, dietary monitoring, physical activity, or a combination thereof.

5. The method of claim 4, wherein the anti-diabetic agent is a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or a combination thereof.

6. The method of claim 5, wherein the biguanide is metformin.

7. The method of claim 4, wherein the anti-obesity agent is neuropeptide Y receptor type 2 (NPYR2) agonist, a NPYR1 or NPYR5 antagonist, a human proislet peptide (HIP), a cannabinoid receptor type 1 (CB1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, a sodium-glucose cotransporter 1 (SGLT-1) inhibitor, or a combination thereof.

8. The method of claim 4, wherein the GLP-1 receptor agonist is selected from the group consisting of liraglutide, exenatide, dulaglutide, albiglutide, taspoglutide, lixisenatide, semaglutide, or a combination thereof.

9. The method of claim 4, wherein the agent to treat NASH is selected from the group consisting of an FXR agonist, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, a peroxisome proliferator-activated receptor (PPAR) agonist, a diacylglyceryl acyltransferase 2 (DGAT2) inhibitor, or a combination thereof.

10. The method of claim 9, wherein the acetyl-CoA carboxylase (ACC) inhibitor is PF-05221304.

11. The method of claim 1, wherein the compound is:

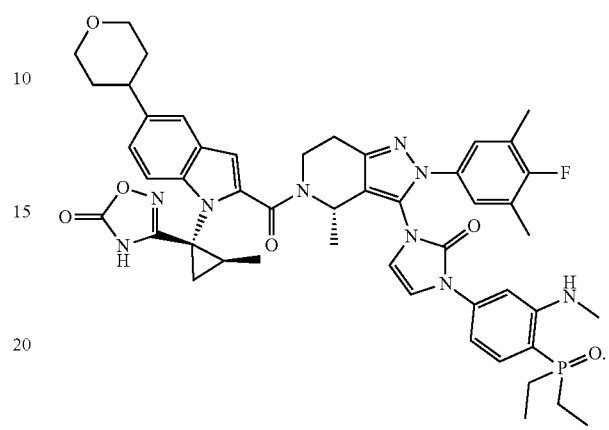

or a pharmaceutically acceptable salt thereof.

12. The method of claim 1, wherein the compound is:

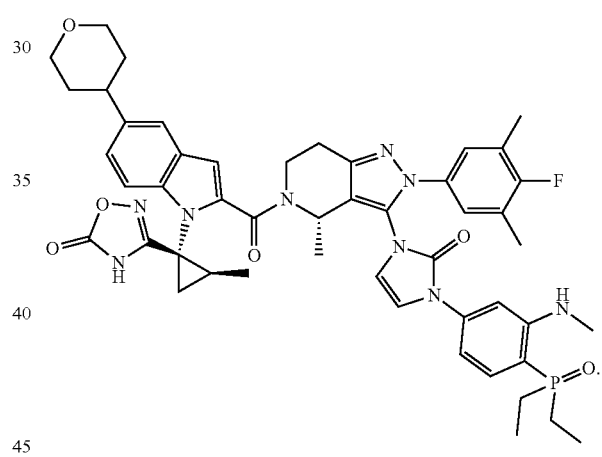

13. The method of claim 1, wherein the compound is:

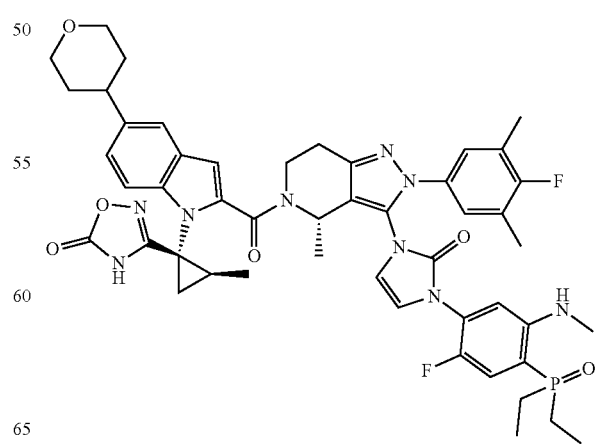

or a pharmaceutically acceptable salt thereof.

14. The method of claim 1, wherein the compound is:

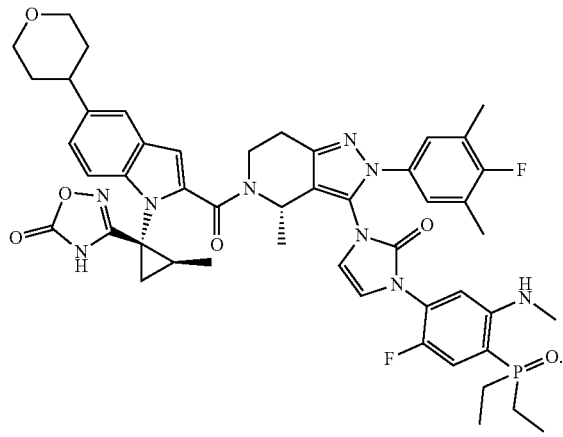

15. The method of claim 1, wherein the compound is:

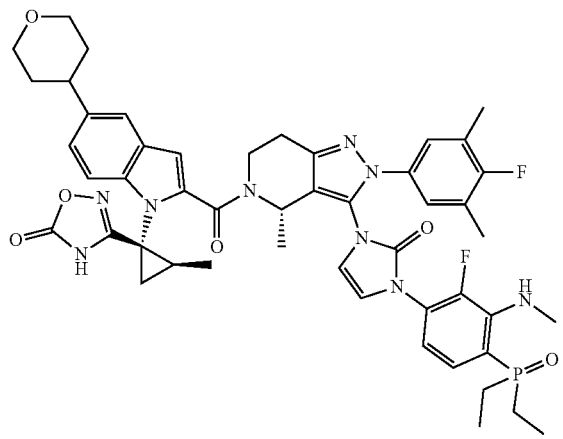 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1NC]

or a pharmaceutically acceptable salt thereof.

16. The method of claim 1, wherein the compound is:

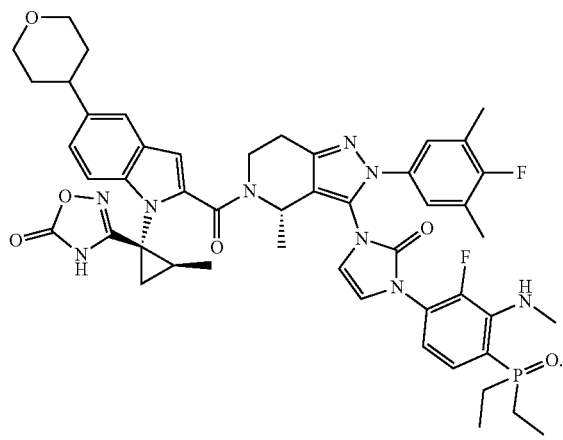 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)c(F)c1NC]

17. The method of claim 1, wherein the compound is:

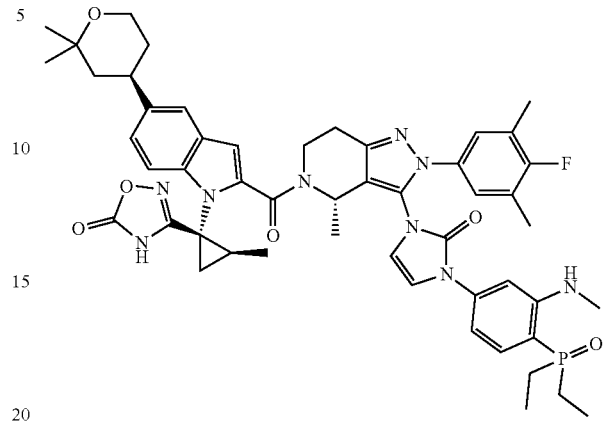

or a pharmaceutically acceptable salt thereof.

18. The method of claim 1, wherein the compound is:

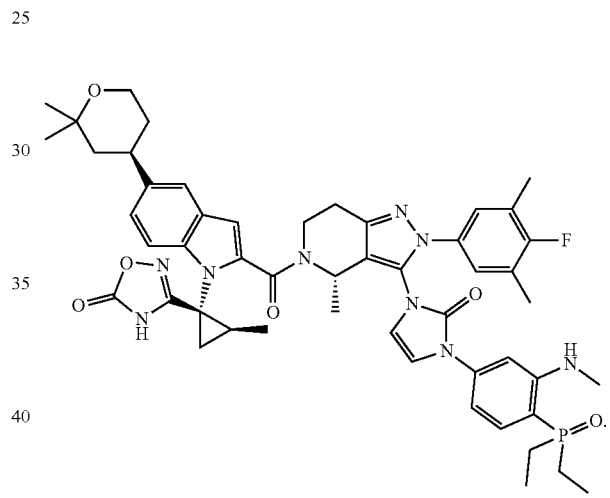

19. The method of claim 1, wherein the compound is:

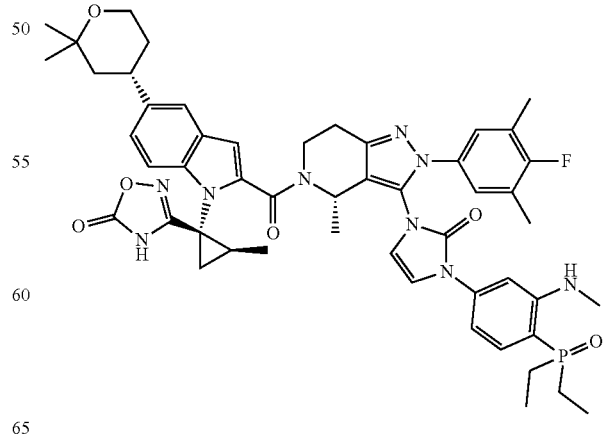

or a pharmaceutically acceptable salt thereof.